United States Patent
Kawazoe et al.

(10) Patent No.: US 10,308,613 B2
(45) Date of Patent: Jun. 4, 2019

(54) FLUOROALKYLATING AGENT

(71) Applicant: KUMIAI CHEMICAL INDUSTRY CO., LTD., Taito-ku, Tokyo (JP)

(72) Inventors: Kentaro Kawazoe, Tokyo (JP); Kotaro Yoshioka, Tokyo (JP)

(73) Assignee: KUMIAI CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 15/314,999

(22) PCT Filed: Jun. 24, 2015

(86) PCT No.: PCT/JP2015/068127
§ 371 (c)(1),
(2) Date: Nov. 30, 2016

(87) PCT Pub. No.: WO2015/199109
PCT Pub. Date: Dec. 30, 2015

(65) Prior Publication Data
US 2017/0197920 A1   Jul. 13, 2017

(30) Foreign Application Priority Data
Jun. 26, 2014   (JP) .................. 2014-131688

(51) Int. Cl.
| | | |
|---|---|---|
| *C07D 235/10* | (2006.01) | |
| *C07C 29/38* | (2006.01) | |
| *C07C 31/38* | (2006.01) | |
| *C07C 319/14* | (2006.01) | |
| *C07C 323/12* | (2006.01) | |
| *C07C 67/343* | (2006.01) | |
| *C07C 319/20* | (2006.01) | |
| *C07D 213/30* | (2006.01) | |
| *C07D 333/16* | (2006.01) | |
| *C07B 61/00* | (2006.01) | |

(52) U.S. Cl.
CPC ............ *C07D 235/10* (2013.01); *C07C 29/38* (2013.01); *C07C 31/38* (2013.01); *C07C 67/343* (2013.01); *C07C 319/14* (2013.01); *C07C 319/20* (2013.01); *C07C 323/12* (2013.01); *C07D 213/30* (2013.01); *C07D 333/16* (2013.01); *C07B 61/00* (2013.01)

(58) Field of Classification Search
CPC .................................................. C07D 235/10
See application file for complete search history.

(56) References Cited

U.S. PATENT DOCUMENTS

| | | |
|---|---|---|
| 2003/0114508 A1 | 6/2003 | Matsuhisa et al. |
| 2015/0087833 A1 | 3/2015 | Domon et al. |

FOREIGN PATENT DOCUMENTS

| | | |
|---|---|---|
| CN | 102229569 A | 11/2011 |
| WO | WO 96/33168 A1 | 10/1996 |
| WO | WO 01/60803 A1 | 8/2001 |
| WO | WO 2012/129384 A2 | 9/2012 |
| WO | WO 2013/157229 A1 | 10/2013 |

OTHER PUBLICATIONS

Kagawa, et al. Document No. 128:263877, retrieved from STN; Mar. 14, 1998.*
Krasovskiy, et al. Document No. 140:339252, retrieved from STN; Oct. 10, 2003.*
Liu, et al. Document No. 156:74620, retrieved from STN; Dec. 19, 2011.*
Liu, et al. Document No. 155:637801, retrieved from STN; Nov. 7, 2011.*
Wang, et al. Document No. 156:421357, retrieved from STN; Feb. 7, 2012.*
Cherkupally et al., "Alkoxide-induced nucleophilic trifluoromethylation using diethyl trifluoromethylphosphonate," Tetrahedron Letters, 2010, 51:252-255.

(Continued)

*Primary Examiner* — Shawquia Jackson
(74) *Attorney, Agent, or Firm* — Foley & Lardner LLP

(57) ABSTRACT

Problem to be Solved

It is intended to provide an industrially preferable fluoroalkylating agent and use thereof.

Solution

The present invention provides a fluoroalkylating agent represented by the general formula (1) wherein $R^1$ is a C1 to C8 fluoroalkyl group; $R^2$ and $R^3$ are each independently a C1 to C12 alkyl group or the like; $Y^1$ to $Y^4$ are each independently a hydrogen atom, a halogen atom, or the like; and $X^-$ is a monovalent anion.

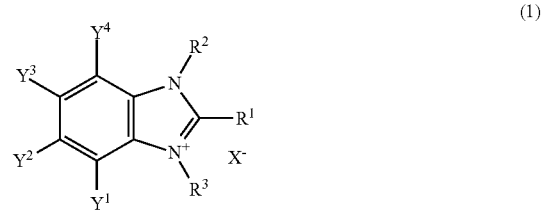

(1)

A compound of the general formula (3): $R^4$—S—$R^1$ having an introduced C1 to C8 fluoroalkyl group is easily obtained by reacting a compound of the general formula (2): $R^4$—S—Z wherein $R^4$ is a hydrocarbon group or the like; and Z is a leaving group, with the compound of the general formula (1).

8 Claims, No Drawings

(56) References Cited

OTHER PUBLICATIONS

Chernega et al., "Molecular structures and reactivity of trifluoromethyltris(dialkylamino)phosphonium bromides," Journal of Fluorine Chemistry, 1995, 70:271-275.
Eapen et al., "Synthesis of some benzimidazoles containing 2-perfluoro substituents," Journal of Fluorine Chemistry, 1981, 18:243-257.
File Registry on STN, RN 64085-79-6, ED Entered STN: Nov. 16, 1984.
Krasovsky et al., Synthesis of $CF_3$-containing β-hetaryl-substituted enones, Russian Chemical Bulletin, International Edition, Aug. 2003, 52(8):1791-1796.
Kuznetsov et al., "Heterocyclic Derivatives of Substituted 1,4-Naphthoquinones, VI. Derivatives of naphtho(2,3-d)imidazole-4,9-dione," Russian Journal of Organic Chemistry, 1967, 3(2):393-402, with English translation.
Kuznetsov et al., "Heterocyclic Ring-Substituted Naphtho[2,3-d]imidazole-4,9-diones and Their Quaternary Salts," Russian Journal of General Chemistry, 1967, 37(8):1802-1809.
Larina et al., "Investigation of Benzimidazoles, II—The Influence of Substituents and Solvents on the H and C NMR Chemical Shifts of 2-Substituted 1,3-Dimethylbenzimidazolium Perchlorates," Organic Magnetic Resonance, 1981, 17(1):1-5.
Ogretir et al., "Benzimidazole Studies IV. Investigation of the Nitration Kinetics of Some Benzimidazole Derivatives and Hammett Relationships," Chimica Acta Turcica, 1986, 14(2):199-211.
Prakash et al., "Alkoxide- and Hydroxide-Induced Nucleophilic Trifluoromethylation Using Trifluoromethyl Sulfone or Sulfoxide," Organic Letters, 2003, 5(18):3253-3256.
Prakash et al., "Nucleophilic Perfluoroalkylation of Imines and Carbonyls: Perfluoroalkyl Sulfones as Efficient Perfluoroalkyl-Transfer Motifs," Organic Letters, 2010, 12(13):2932-2935.
Riofski et al., "Amidinate Salt of Hexafluoroacetone Hydrate for the Preparation of Fluorinated Compounds by the Release of Trifluoroacetate," Organic Letters, 2013, 15(1):208-211.
Ruppert et al., "The First $CF_3$-Substituted Organyl(chloro)silane," Tetrahedron Letters, 1984, 25(21):2195-2198.
Russell et al., "Effective Nucleophilic Trifluoromethylation with Fluoroform and Common Base," Tetrahedron, 1998, 54:13771-13782.
Sevenard et al., "Noncyclic [10-S-5] Sulfuranide Dioxide Salts with Three S—C Bonds: A New Class of Stable Hypervalent Compounds," J. Am. Chem. Soc., 2003, 125:12366-12367.

* cited by examiner

FLUOROALKYLATING AGENT

CROSS-REFERENCE TO RELATED APPLICATIONS

This application is a National Stage application of PCT/JP2015/068127, filed Jun. 24, 2015, which claims priority from Japanese application JP 2014-131688, filed Jun. 26, 2014.

TECHNICAL FIELD

The present invention relates to a novel fluoroalkylating agent.

This invention also relates to a novel compound, a method for the production thereof and use thereof as a fluoroalkylating agent.

BACKGROUND ART

The compounds having a fluoroalkyl group are useful as various chemical products (for example, pharmaceuticals, agricultural chemicals, electronic materials and so on) and production intermediates thereof.

In order to produce the compounds having a fluoroalkyl group, fluoroalkylation reactions and fluoroalkylating agents have been developed heretofore. The fluoroalkylation reaction is a reaction by which a fluoroalkyl group is introduced into a starting compound (a material compound) which is an organic compound. In other words, the fluoroalkylation reaction is a reaction which produces a target compound having a fluoroalkyl group by reacting a starting compound (a material compound) which is an organic compound, with a fluoroalkylating agent.

(Fluoroalkyl) trialkylsilanes typified by (trifluoromethyl) trimethylsilane (Ruppert-Prakash reagent) are known as fluoroalkylating agents which have been conventionally used for fluoroalkylation reactions (see Non-Patent Document 1). Fluoroalkylation reactions using these fluoroalkylating agents are deduced to be nucleophilic reactions. In addition, these fluoroalkylating agents exhibit good reactivity. However, these fluoroalkylating agents require trifluoromethane ($CHF_3$, HFC-23) of a greenhouse effect gas, or trifluoroiodomethane ($CF_3I$) or bromotrifluoromethane ($CBrF_3$) of Freon gas, as a material therefor. Therefore, these fluoroalkylating agents put a heavy load on the environment. Furthermore, these fluoroalkylating agents require an initiator such as fluorides in fluoroalkylation reactions. Furthermore, in a reaction with some starting compounds such as aldehydes, these fluoroalkylating agents have a problem that the temperature cannot be controlled because of exotherm.

With regard to the fluoroalkylation reactions, a reaction with trifluoromethane ($CHF_3$) at low temperature is also known (see Non-Patent Document 2). However, there is a problem that this method requires trifluoromethane which is a greenhouse effect gas as described above.

Meanwhile, development of new products utilizing the compounds having a fluoroalkyl group has been carried out in various fields of biologically active substances, functional materials and others. In recent years, in order to meet demand thereof, various fluoroalkylating agents have been developed.

For example, as a fluoroalkylating agent, a fluoroalkyl phenyl sulfone compound is known (see Non-Patent Documents 3 and 4). The fluoroalkyl phenyl sulfone compound has been reported as an excellent fluoroalkylating agent for aldehydes, imines and the like. However, the reaction condition using the fluoroalkyl phenyl sulfone compound involves a low temperature of −70° C. to −30° C. Therefore, this fluoroalkylating agent is not industrially preferable because a special manufacturing facility is required.

It is known that, as another fluoroalkylating agent, the anhydrous salt obtained from hexafluoroacetone hydrate and 1,8-diazabicyclo[5.4.0]-7-undec-7-ene (DBU) reacts similarly to the fluoroalkyl phenyl sulfone compound described above (see Patent Document 3 and Non-Patent Document 5). In the reaction of this anhydrous salt, only one of the two fluoroalkyl groups which are contained in the same molecule of the anhydrous salt can be utilized for the reaction. Therefore, this method is inefficient. Furthermore, the method using this anhydrous salt requires a largely excessive amount of a quaternary ammonium salt and a low temperature. Therefore, this method is complicated.

As other fluoroalkylating agents, compounds having a fluoroalkyl group on their heteroatom such as sulfur or phosphorus have been reported. It is known that these compounds, i.e., fluoroalkylating agents also react similarly (Non-Patent Documents 6, 7 and 8). These fluoroalkylating agents can introduce a fluoroalkyl group into aldehydes or ketones under mild reaction conditions. However, the methods for the productions of these fluoroalkylating agents require the above-mentioned (trifluoromethyl)trimethylsilane (Ruppert-Prakash reagent), trifluoromethane ($CHF_3$, HFC-23) of a greenhouse effect gas, or trifluoroiodomethane ($CF_3I$) or bromotrifluoromethane ($CBrF_3$) of Freon gas, as a material therefor. Therefore, these fluoroalkylating agents cannot substantially solve the problems.

As described above, the conventional fluoroalkylating agents depend heavily on a greenhouse effect gas (for example, $CHF_3$) or Freon gas (for example, $CF_3I$ or $CBrF_3$). In view of environmental aspects, development of the industrially usable fluoroalkylating agent has not yet been achieved satisfactorily.

CITATION LIST

Patent Document

Patent Document 1: WO96/33168
Patent Document 2: WO2013/157229 A1
Patent Document 3: WO2012/129384 A2

Non-Patent Document

Non-Patent Document 1: Tetrahedon Lett., 25 (21), 2195-2198 (1984)
Non-Patent Document 2: Tetrahedon, 54, 13771-13782 (1998)
Non-Patent Document 3: Org. Lett., 5 (18), 3253-3256 (2003)
Non-Patent Document 4: Org. Lett., 12 (13), 2932-2935 (2010)
Non-Patent Document 5: Org. Lett., 15 (1), 208-211 (2013)
Non-Patent Document 6: J. Am. Chem. Soc., 125, 12366-12367 (2003)
Non-Patent Document 7: J. Fluoro. Chem., 70, 271-276 (1995)
Non-Patent Document 8: Tetrahedon Lett., 51 (2), 252-255 (2010)

SUMMARY OF INVENTION

Technical Problem

An object of the present invention is to provide an industrially preferable fluoroalkylating agent and use thereof, which can solve the above-mentioned one or more drawbacks or problems in the prior art.

Another object of the present invention is to provide a fluoroalkylating agent which is suitable for industrialization, economically preferable, and environmentally superior.

Specifically, for example, one of the objects of the present invention is to reduce the environmental load by not requiring a greenhouse effect gas (for example, CHF$_3$) or Freon gas (for example, CF$_3$I or CBrF$_3$) as a material for a fluoroalkylating agent.

A further object of the present invention is to provide a fluoroalkylation reaction, which can be carried out with a simple reaction operation, under a mild reaction condition, and without requiring a special facility.

Solution to Problem

In view of the circumstances as described above, the present inventors have earnestly studied a method for the production of a compound having a fluoroalkyl group. As a result, the present inventors unexpectedly found that a compound having a fluoroalkyl group can be produced by using a compound represented by the general formula (1) described later. Based on these findings, the present inventors have completed the present invention.

The present invention has solved the above-mentioned problems by providing aspects described in the following. That is, in one embodiment, the present invention is as follows:

[I-1] A fluoroalkylating agent represented by the general formula (1):

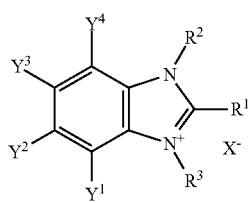

(1)

wherein R$^1$ is a C1 to C8 fluoroalkyl group;
R$^2$ and R$^3$ are each independently
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents, or
a C6 to C10 aryl group which may have one or more substituents;
Y$^1$, Y$^2$, Y$^3$ and Y$^4$ are each independently
a hydrogen atom, a halogen atom, a nitro group, a cyano group,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a hydroxy group,
a C1 to C6 alkoxy group,
a C1 to C6 alkylthio group, a C1 to C6 alkylsulfinyl group,
a C1 to C6 alkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom, or
two adjacent substituents of Y$^1$ and Y$^2$, Y$^2$ and Y$^3$, or Y$^3$ and Y$^4$, together with carbon atoms to which these substituents are attached, form a 4- to 8-membered carbocyclic ring or a 4- to 8-membered heterocyclic ring having 1 to 4 heteroatoms selected independently from an oxygen atom, a sulfur atom and a nitrogen atom, wherein the said formed ring may have one or more substituents; and
X$^-$ is a monovalent anion.

[I-2] The agent according to [I-1], wherein R$^1$ is a C1 to C8 perfluoroalkyl group.

[I-3] The agent according to [I-1], wherein R$^1$ is a C1 to C4 perfluoroalkyl group.

[I-4] The agent according to [I-1], wherein R$^1$ is a trifluoromethyl group or a pentafluoroethyl group.

[I-5] The agent according to [I-1], wherein R$^1$ is a trifluoromethyl group.

[I-6] The agent according to any one of [I-1] to [I-5], wherein R$^2$ and R$^3$ are each independently
a C1 to C6 alkyl group,
a phenyl group, wherein the said phenyl group may have 1 to 5 substituents selected independently from a halogen atom, a nitro group, a cyano group, a C1 to C6 alkyl group, a C1 to C6 haloalkyl group, a C2 to C6 acyl group and a C1 to C6 alkoxycarbonyl group, or
a phenyl C1 to C2 alkyl group, wherein the said phenyl group moiety may have 1 to 5 substituents selected independently from a halogen atom, a C1 to C6 alkyl group and a C1 to C6 haloalkyl group.

[I-7] The agent according to any one of [I-1] to [I-5], wherein R$^2$ and R$^3$ are each independently a C1 to C4 alkyl group or a phenyl group.

[I-8] The agent according to any one of [I-1] to [I-5], wherein R$^2$ and R$^3$ are each independently a methyl group, an ethyl group or a phenyl group.

[I-9] The agent according to any one of [I-1] to [I-5], wherein R$^2$ and R$^3$ are each a methyl group.

[I-10] The agent according to any one of [I-1] to [I-9], wherein Y$^1$, Y$^2$, Y$^3$ and Y$^4$ are each independently
a hydrogen atom, a halogen atom, a nitro group, a cyano group,
a C1 to C12 alkyl group, a C1 to C6 haloalkyl group,
a C1 to C6 alkylthio group, a C1 to C6 alkylsulfinyl group,
a C1 to C6 alkylsulfonyl group,
a C2 to C6 acyl group,
a C1 to C6 alkoxycarbonyl group,
a phenyl group, or
a pyridyl group.

[I-11] The agent according to any one of [I-1] to [I-9], wherein Y$^1$, Y$^2$, Y$^3$ and Y$^4$ are each independently
a hydrogen atom, a halogen atom, a nitro group, a cyano group,
a C1 to C4 alkyl group or a C1 to C4 haloalkyl group.

[I-12] The agent according to any one of [I-1] to [I-9], wherein $Y^1$, $Y^2$, $Y^3$ and $Y^4$ are each independently a hydrogen atom, a chlorine atom or a nitro group.

[I-13] The agent according to any one of [I-1] to [I-9], wherein $Y^1$, $Y^2$, $Y^3$ and $Y^4$ are each a hydrogen atom.

[I-14] The agent according to any one of [I-1] to [I-9], wherein $Y^1$, $Y^3$ and $Y^4$ are each a hydrogen atom; and $Y^2$ is a chlorine atom.

[I-15] The agent according to any one of [I-1] to [I-9], wherein $Y^1$, $Y^3$ and $Y^4$ are each a hydrogen atom; and $Y^2$ is a nitro group.

[I-16] The agent according to any one of [I-1] to [I-9], wherein $Y^1$, $Y^2$, $Y^3$ and $Y^4$ are each a chlorine atom.

[I-17] The agent according to any one of [I-1] to [I-16], wherein $X^-$ is any of halide ions, borate ions, phosphate ions, antimonate ions, carboxylate ions, sulfonate ions, sulfate ions, carbonate ions, nitrate ions and amide ions.

[I-18-1] The agent according to any one of [I-1] to [I-16], wherein $X^-$ is $F^-$, $Cl^-$,
$Br^-$, $I^-$,
$BF_4^-$, $C_6H_5BF_3^-$,
$PF_6^-$,
$SbF_6^-$,
$CH_3CO_2^-$, $CF_3CO_2^-$, $C_2F_5CO_2^-$,
$CH_3SO_3^-$, $C_2H_5SO_3^-$, $CF_3SO_3^-$, $C_6H_5SO_3^-$, 4-$CH_3$—$C_6H_4SO_3^-$, 4-Cl—$C_6H_4SO_3^-$, 4-$NO_2$—$C_6H_4SO_3^-$,
$HOSO_3^-$, $CH_3OSO_3^-$, $C_2H_5OSO_3^-$, $C_3H_7OSO_3^-$, iso-$C_3H_7OSO_3^-$, $C_4H_9OSO_3^-$,
$C_6H_5OSO_3^-$,
$HCO_3^-$, $CH_3OCO_2^-$
$NO_3^-$,
$(CN)_2N^-$ or $(CF_3SO_2)_2N^-$.

[I-18-2-1] The agent according to any one of [I-1] to [I-16], wherein $X^-$ is $F^-$,
$Cl^-$, $Br^-$, $I^-$,
$BF_4^-$,
$CH_3CO_2^-$, $CF_3CO_2^-$,
$CH_3SO_3^-$, $CF_3SO_3^-$,
$HOSO_3^-$, $CH_3OSO_3^-$ or $C_2H_5OSO_3^-$.

[I-18-2-2] The agent according to any one of [I-1] to [I-16], wherein $X^-$ is $I^-$,
$BF_4^-$,
$CF_3CO_2^-$,
$CF_3SO_3^-$,
$HOSO_3^-$, $CH_3OSO_3^-$ or $C_2H_5OSO_3^-$.

[I-18-2-3] The agent according to any one of [I-1] to [I-16], wherein $X^-$ is $I^-$,
$BF_4^-$,
$CF_3SO_3^-$,
$HOSO_3^-$, $CH_3OSO_3^-$ or $C_2H_5OSO_3^-$.

[I-18-2-4] The agent according to any one of [I-1] to [I-16], wherein $X^-$ is $I^-$,
$BF_4^-$,
$CF_3SO_3^-$,
$CH_3OSO_3^-$ or $C_2H_5OSO_3^-$.

[I-18-2-5] The agent according to any one of [I-1] to [I-16], wherein $X^-$ is $I^-$,
$BF_4^-$,
$CF_3SO_3^-$,
$CH_3OSO_3^-$.

[I-18-3] The agent according to any one of [I-1] to [I-16], wherein $X^-$ is $F^-$, $Cl^-$,
$Br^-$, $I^-$,
$BF_4^-$,
$CH_3CO_2^-$, $CF_3CO_2^-$,
$CH_3SO_3^-$, $CF_3SO_3^-$,
$CH_3OSO_3^-$ or $C_2H_5OSO_3^-$.

[I-19-1] The agent according to any one of [I-1] to [I-16], wherein $X^-$ is $Cl^-$,
$Br^-$, $I^-$,
$BF_4^-$,
$CF_3SO_3^-$,
$HOSO_3^-$, $CH_3OSO_3^-$ or $C_2H_5OSO_3^-$.

[I-19-2] The agent according to any one of [I-1] to [I-16], wherein $X^-$ is $Cl^-$,
$Br^-$, $I^-$,
$BF_4^-$,
$CF_3SO_3^-$,
$CH_3OSO_3^-$ or $C_2H_5OSO_3^-$.

[I-20] The agent according to any one of [I-1] to [I-16], wherein $X^-$ is $CH_3OSO_3^-$.

[I-21] A method for the production of a target compound having $R^1$, wherein $R^1$ is as defined below, which comprises reacting a starting compound with a fluoroalkylating agent represented by the general formula (1):

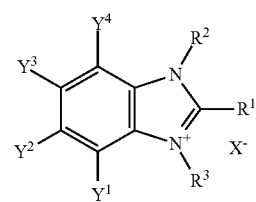

(1)

wherein $R^1$ is a C1 to C8 fluoroalkyl group;
$R^2$ and $R^3$ are each independently
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents, or
a C6 to C10 aryl group which may have one or more substituents;
$Y^1$, $Y^2$, $Y^3$ and $Y^4$ are each independently
a hydrogen atom, a halogen atom, a nitro group, a cyano group,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a hydroxy group,
a C1 to C6 alkoxy group,
a C1 to C6 alkylthio group, a C1 to C6 alkylsulfinyl group, a C1 to C6 alkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom, or two adjacent substituents of $Y^1$ and $Y^2$, $Y^2$ and $Y^3$, or $Y^3$ and $Y^4$, together with carbon atoms to which these substituents are attached, form a 4- to 8-membered carbocyclic ring or a 4- to 8-membered heterocyclic ring having 1 to 4 heteroatoms selected independently from an oxygen atom, a sulfur atom and a nitrogen atom, wherein the said formed ring may have one or more substituents; and $X^-$ is a monovalent anion.

[I-22] The method according to [I-21], wherein $R^1$ is a C1 to C8 perfluoroalkyl group.

[I-23] The method according to [I-21], wherein $R^1$ is a C1 to C4 perfluoroalkyl group.

[I-24] The method according to [I-21], wherein $R^1$ is a trifluoromethyl group or a pentafluoroethyl group.

[I-25] The method according to [I-21], wherein $R^1$ is a trifluoromethyl group.

[I-26] The method according to any one of [I-21] to [I-25], wherein $R^2$ and $R^3$ are each independently a C1 to C6 alkyl group, a phenyl group, wherein the said phenyl group may have 1 to 5 substituents selected independently from a halogen atom, a nitro group, a cyano group, a C1 to C6 alkyl group, a C1 to C6 haloalkyl group, a C2 to C6 acyl group and a C1 to C6 alkoxycarbonyl group, or a phenyl C1 to C2 alkyl group, wherein said the phenyl group moiety may have 1 to 5 substituents selected independently from a halogen atom, a C1 to C6 alkyl group and a C1 to C6 haloalkyl group.

[I-27] The method according to any one of [I-21] to [I-25], wherein $R^2$ and $R^3$ are each independently a C1 to C4 alkyl group or a phenyl group.

[I-28] The method according to any one of [I-21] to [I-25], wherein $R^2$ and $R^3$ are each independently a methyl group, an ethyl group or a phenyl group.

[I-29] The method according to any one of [I-21] to [I-25], wherein $R^2$ and $R^3$ are each a methyl group.

[I-30] The method according to any one of [I-21] to [I-29], wherein $Y^1$, $Y^2$, $Y^3$ and $Y^4$ are each independently a hydrogen atom, a halogen atom, a nitro group, a cyano group, a C1 to C12 alkyl group, a C1 to C6 haloalkyl group, a C1 to C6 alkylthio group, a C1 to C6 alkylsulfinyl group, a C1 to C6 alkylsulfonyl group, a C2 to C6 acyl group, a C1 to C6 alkoxycarbonyl group, a phenyl group, or a pyridyl group.

[I-31] The method according to any one of [I-21] to [I-29], wherein $Y^1$, $Y^2$, $Y^3$ and $Y^4$ are each independently a hydrogen atom, a halogen atom, a nitro group, a cyano group, a C1 to C4 alkyl group or a C1 to C4 haloalkyl group.

[I-32] The method according to any one of [I-21] to [I-29], wherein $Y^1$, $Y^2$, $Y^3$ and $Y^4$ are each independently a hydrogen atom, a chlorine atom or a nitro group.

[I-33] The method according to any one of [I-21] to [I-29], wherein $Y^1$, $Y^2$, $Y^3$ and $Y^4$ are each a hydrogen atom.

[I-34] The method according to any one of [I-21] to [I-29], wherein $Y^1$, $Y^3$ and $Y^4$ are each a hydrogen atom; and $Y^2$ is a chlorine atom.

[I-35] The method according to any one of [I-21] to [I-29], wherein $Y^1$, $Y^3$ and $Y^4$ are each a hydrogen atom; and $Y^2$ is a nitro group.

[I-36] The method according to any one of [I-21] to [I-29], wherein $Y^1$, $Y^2$, $Y^3$ and $Y^4$ are each a chlorine atom.

[I-37] The method according to any one of [I-21] to [I-36], wherein $X^-$ is any of halide ions, borate ions, phosphate ions, antimonate ions, carboxylate ions, sulfonate ions, sulfate ions, carbonate ions, nitrate ions and amide ions.

[I-38-1] The method according to any one of [I-21] to [I-36], wherein $X^-$ is $F^-$, $Cl^-$, $Br^-$, $I^-$, $BF_4^-$, $C_6H_5BF_3^-$, $PF_6^-$, $SbF_6^-$, $CH_3CO_2^-$, $CF_3CO_2^-$, $C_2F_5CO_2^-$, $CH_3SO_3^-$, $C_2H_5SO_3^-$, $CF_3SO_3^-$, $C_6H_5SO_3^-$, 4-$CH_3$—$C_6H_4SO_3^-$, 4-$Cl$—$C_6H_4SO_3^-$, 4-$NO_2$—$C_6H_4SO_3^-$, $HOSO_3^-$, $CH_3OSO_3^-$, $C_2H_5OSO_3^-$, $C_3H_7OSO_3^-$, iso-$C_3H_7OSO_3^-$, $C_4H_9OSO_3^-$, $C_6H_5OSO_3^-$, $HCO_3^-$, $CH_3OCO_2^-$ $NO_3^-$, $(CN)_2N^-$ or $(CF_3SO_2)_2N^-$.

[I-38-2-1] The method according to any one of [I-21] to [I-36], wherein $X^-$ is $F^-$, $Cl^-$, $Br^-$, $I^-$, $BF_4^-$, $CH_3CO_2^-$, $CF_3CO_2^-$, $CH_3SO_3^-$, $CF_3SO_3^-$, $HOSO_3^-$, $CH_3OSO_3^-$ or $C_2H_5OSO_3^-$.

[I-38-2-2] The method according to any one of [I-21] to [I-36], wherein $X^-$ is $I^-$, $BF_4^-$, $CF_3CO_2^-$, $CF_3SO_3^-$, $HOSO_3^-$, $CH_3OSO_3^-$ or $C_2H_5OSO_3^-$.

[I-38-2-3] The method according to any one of [I-21] to [I-36], wherein $X^-$ is $I^-$, $BF_4^-$, $CF_3SO_3^-$, $HOSO_3^-$, $CH_3OSO_3^-$ or $C_2H_5OSO_3^-$.

[I-38-2-4] The method according to any one of [I-21] to [I-36], wherein $X^-$ is $I^-$, $BF_4^-$, $CF_3SO_3^-$, $CH_3OSO_3^-$ or $C_2H_5OSO_3^-$.

[I-38-2-5] The method according to any one of [I-21] to [I-36], wherein $X^-$ is $I^-$, $BF_4^-$, $CF_3SO_3^-$, $CH_3OSO_3^-$.

[I-38-3] The method according to any one of [I-21] to [I-36], wherein $X^-$ is $F^-$, $Cl^-$, $Br^-$, $I^-$, $BF_4^-$, $CH_3CO_2^-$, $CF_3CO_2^-$, $CH_3SO_3^-$, $CF_3SO_3^-$, $CH_3OSO_3^-$ or $C_2H_5OSO_3^-$.

[I-39-1] The method according to any one of [I-21] to [I-36], wherein $X^-$ is $Cl^-$, $Br^-$, $I^-$, $BF_4^-$, $CF_3SO_3^-$, $HOSO_3^-$, $CH_3OSO_3^-$ or $C_2H_5OSO_3^-$.

[I-39-2] The method according to any one of [I-21] to [I-36], wherein X⁻ is Cl⁻,
Br⁻, I⁻,
BF₄⁻,
CF₃SO₃⁻,
CH₃OSO₃⁻ or C₂H₅OSO₃⁻.

[I-40] The method according to any one of [I-21] to [I-36], wherein X⁻ is CH₃OSO₃⁻.

[I-41-A] The method according to any one of [I-21] to [I-40], wherein the reaction of the starting compound with the fluoroalkylating agent represented by the general formula (1) is carried out in the presence of a base.

[I-42-A-1] The method according to [I-41-A], wherein the base is an alkali metal hydroxide, an alkali metal carbonate, an alkali metal hydride or a mixture thereof.

[I-42-A-2] The method according to [I-41-A], wherein the base is an alkali metal hydroxide, an alkali metal hydride or a mixture thereof.

[I-42-A-3] The method according to [I-41-A], wherein the base is an alkali metal hydroxide.

[I-42-A-4] The method according to [I-41-A], wherein the base is an alkali metal hydride.

[I-42-A-5] The method according to [I-41-A], wherein the base is a mixture of an alkali metal hydroxide and an alkali metal hydride.

[I-43-A-1] The method according to [I-41-A], wherein the base is
lithium hydroxide, sodium hydroxide, potassium hydroxide, sodium carbonate, potassium carbonate, cesium carbonate, sodium hydride, or
a mixture thereof.

[I-43-A-2] The method according to [I-41-A], wherein the base is sodium hydroxide, potassium hydroxide, sodium hydride or a mixture thereof.

[I-43-A-3] The method according to [I-41-A], wherein the base is potassium hydroxide, sodium hydride or a mixture thereof.

[I-43-A-4] The method according to [I-41-A], wherein the base is sodium hydroxide.

[I-43-A-5] The method according to [I-41-A], wherein the base is potassium hydroxide.

[I-43-A-6] The method according to [I-41-A], wherein the base is sodium hydride.

[I-43-A-7] The method according to [I-41-A], wherein the base is a mixture of potassium hydroxide and sodium hydride.

[I-41-B] The method according to any one of [I-21] to [I-40], wherein the reaction of the starting compound with the fluoroalkylating agent represented by the general formula (1) is carried out using a base.

[I-42-B-1] The method according to [I-41-B], wherein the base is an alkali metal hydroxide, an alkali metal carbonate, an alkali metal hydride or a combination thereof.

[I-42-B-2] The method according to [I-41-B], wherein the base is an alkali metal hydroxide, an alkali metal hydride or a combination thereof.

[I-42-B-3] The method according to [I-41-B], wherein the base is an alkali metal hydroxide.

[I-42-B-4] The method according to [I-41-B], wherein the base is an alkali metal hydride.

[I-42-B-5] The method according to [I-41-B], wherein the base is a combination of an alkali metal hydroxide and an alkali metal hydride.

[I-43-B-1] The method according to [I-41-B], wherein the base is
lithium hydroxide, sodium hydroxide, potassium hydroxide, sodium carbonate, potassium carbonate, cesium carbonate, sodium hydride, or
a combination thereof.

[I-43-B-2] The method according to [I-41-B], wherein the base is sodium hydroxide, potassium hydroxide, sodium hydride or a combination thereof.

[I-43-B-3] The method according to [I-41-B], wherein the base is potassium hydroxide, sodium hydride or a combination thereof.

[I-43-B-4] The method according to [I-41-B], wherein the base is sodium hydroxide.

[I-43-B-5] The method according to [I-41-B], wherein the base is potassium hydroxide.

[I-43-B-6] The method according to [I-41-B], wherein the base is sodium hydride.

[I-43-B-7] The method according to [I-41-B], wherein the base is a combination of potassium hydroxide and sodium hydride.

[I-44] The method according to any one of [I-21] to [I-43-B-7], wherein the reaction of the starting compound with the fluoroalkylating agent represented by the general formula (1) is carried out in the presence of a zeolite.

[I-45-1] The method according to [I-44], wherein the zeolite is a molecular sieve 3 A, a molecular sieve 4 A or a molecular sieve 5 A.

[I-45-2] The method according to [I-44], wherein the zeolite is a molecular sieve 4 A.

[I-46] The method according to any one of [I-21] to [I-43-B-7], wherein the reaction of the starting compound with the fluoroalkylating agent represented by the general formula (1) is carried out in the presence of a molecular sieve.

[I-47-1] The method according to [I-46], wherein the molecular sieve is a molecular sieve 3 A, a molecular sieve 4 A or a molecular sieve 5 A.

[I-47-2] The method according to [I-46], wherein the molecular sieve is a molecular sieve 4 A.

[I-48] The method according to any one of [I-21] to [I-47-2], wherein the reaction of the starting compound with the fluoroalkylating agent represented by the general formula (1) is carried out in the presence of a phase transfer catalyst.

[I-49] The method according to [I-48], wherein the phase transfer catalyst is a quaternary ammonium salt.

[I-50] The method according to [I-48], wherein the phase transfer catalyst is tetrabutylammonium bromide.

[I-51] The method according to any one of [I-21] to [I-50], wherein the starting compound is a compound represented by the general formula (2):

(2)

wherein $R^4$ is
a straight chain or branched chain hydrocarbon group which may have one or more substituents,
a cyclic hydrocarbon group which may have one or more substituents, or
a heterocyclic group which may have one or more substituents; and
Z is a leaving group; and
the target compound having $R^1$ is a compound represented by the general formula (3):

(3)

wherein $R^1$ is as defined in [I-21] to [I-50]; and $R^4$ is as defined above.

[I-52] The method according to [I-51], wherein $R^4$ is
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom.

[I-53-1] The method according to [I-51], wherein $R^4$ is
a C3 to C7 alkyl group,
a C3 to C7 alkyl group having a benzyloxy group,
a C3 to C7 alkyl group having a C2 to C4 acyloxy group,
a C3 to C7 alkyl group having a phenyloxy group which may have 1 to 4 substituents selected independently from a halogen atom, a C1 to C4 alkyl group, a C1 to C6 haloalkylthio group and a C1 to C6 haloalkylsulfinyl group,
a C6 to C10 aryl group which may have 1 to 4 substituents selected independently from a halogen atom, a C1 to C4 alkyl group, a C1 to C4 haloalkyl group, a C1 to C4 alkoxy group, a C1 to C4 haloalkoxy group and a C6 to C10 aryl group, or
a thienyl group, a pyrazolyl group, an imidazolyl group, a thiazolyl group, an isothiazolyl group, a pyridyl group or a pyrimidyl group, each of which may have 1 to 4 substituents selected independently from a halogen atom, a C1 to C4 alkyl group, a C1 to C4 haloalkyl group, a C1 to C4 alkoxy group, a C1 to C4 haloalkoxy group and a C6 to C10 aryl group.

[I-53-2] The method according to [I-51], wherein $R^4$ is
a C3 to C7 alkyl group,
a C3 to C7 alkyl group having a benzyloxy group,
a C3 to C7 alkyl group having a C2 to C4 acyloxy group,
a C3 to C7 alkyl group having a phenyloxy group which may have 1 to 4 substituents selected independently from a halogen atom, a C1 to C4 alkyl group and a C1 to C6 haloalkylthio group,
a C6 to C10 aryl group which may have 1 to 4 substituents selected independently from a halogen atom, a C1 to C4 alkyl group, a C1 to C4 haloalkyl group, a C1 to C4 alkoxy group, a C1 to C4 haloalkoxy group and a C6 to C10 aryl group, or
a pyrazolyl group or a pyridyl group, each of which may have 1 to 4 substituents selected independently from a halogen atom, a C1 to C4 alkyl group, a C1 to C4 haloalkyl group, a C1 to C4 alkoxy group, a C1 to C4 haloalkoxy group and a C6 to C10 aryl group.

[I-53-3] The method according to [I-51], wherein $R^4$ is
a C3 to C7 alkyl group,
a C3 to C7 alkyl group having a benzyloxy group,
a C3 to C7 alkyl group having a C2 to C4 acyloxy group,
a C3 to C7 alkyl group having a phenyloxy group which may have 1 to 4 substituents selected independently from a halogen atom and a C1 to C6 haloalkylthio group, or
a C6 to C10 aryl group which may have 1 to 4 substituents selected independently from a halogen atom, a C1 to C4 alkyl group, a C1 to C4 haloalkyl group, a C1 to C4 alkoxy group and a C1 to C4 haloalkoxy group.

[I-53-4] The method according to [I-51], wherein $R^4$ is
a C3 to C7 alkyl group,
a C3 to C7 alkyl group having a benzyloxy group,
a C3 to C7 alkyl group having a C2 to C4 acyloxy group,
a C3 to C7 alkyl group having a phenyloxy group which may have 1 to 4 substituents selected independently from a halogen atom and a C1 to C6 haloalkylthio group, or
a C6 to C10 aryl group which may have 1 to 4 substituents selected independently from a halogen atom, a C1 to C4 alkyl group and a C1 to C4 alkoxy group.

[I-53-5] The method according to [I-51], wherein $R^4$ is
a C3 to C7 alkyl group,
a C3 to C7 alkyl group having a benzyloxy group,
a C3 to C7 alkyl group having a C2 to C4 acyloxy group,
a C3 to C7 alkyl group having a phenyloxy group which may have 1 to 4 substituents selected independently from a halogen atom and a C1 to C6 haloalkylthio group, or
a phenyl group which may have 1 to 4 substituents selected independently from a halogen atom, a C1 to C4 alkyl group and a C1 to C4 alkoxy group.

[I-53-6] The method according to [I-51], wherein $R^4$ is
a C3 to C7 alkyl group,
a C3 to C7 alkyl group having a benzyloxy group,
a C3 to C7 alkyl group having a C2 to C4 acyloxy group, or
a C3 to C7 alkyl group having a phenyloxy group which may have 1 to 4 substituents selected independently from a halogen atom, a C1 to C4 alkyl group, a C1 to C6 haloalkylthio group and a C1 to C6 haloalkylsulfinyl group.

[I-53-7] The method according to [I-51], wherein $R^4$ is
a C3 to C7 alkyl group,
a C3 to C7 alkyl group having a benzyloxy group,
a C3 to C7 alkyl group having a C2 to C4 acyloxy group, or
a C3 to C7 alkyl group having a phenyloxy group which may have 1 to 4 substituents selected independently from a halogen atom and a C1 to C6 haloalkylthio group.

[I-53-8] The method according to [I-51], wherein $R^4$ is a C3 to C7 alkyl group having a benzyloxy group or a C3 to C7 alkyl group having a C2 to C4 acyloxy group.

[I-53-9] The method according to [I-51], wherein $R^4$ is a C3 to C7 alkyl group having a phenyloxy group which may have 1 to 4 substituents selected independently from a halogen atom, a C1 to C4 alkyl group, a C1 to C6 haloalkylthio group and a C1 to C6 haloalkylsulfinyl group.

[I-53-10] The method according to [I-51], wherein $R^4$ is a C3 to C7 alkyl group having a phenyloxy group which may have 1 to 4 substituents selected independently from a halogen atom and a C1 to C6 haloalkylthio group.

[I-54-1] The method according to [I-51], wherein $R^4$ is
a 5-benzyloxypentyl group, a 5-acetyloxypentyl group, a 6-benzyloxyhexyl group, a 6-acetyloxyhexyl group,
a 5-[4-chloro-2-fluoro-5-(2,2,2-trifluoroethylthio)phenoxy]pentyl group, or
a 6-[2,4-dimethyl-5-(2,2,2-trifluoroethylthio)phenoxy]hexyl group.

[I-54-2] The method according to [I-51], wherein $R^4$ is
a 5-benzyloxypentyl group, a 5-acetyloxypentyl group, a 6-benzyloxyhexyl group, a 6-acetyloxyhexyl group, or
a 5-[4-chloro-2-fluoro-5-(2,2,2-trifluoroethylthio)phenoxy]pentyl group.

[I-54-3] The method according to [I-51], wherein $R^4$ is a 5-benzyloxypentyl group, a 5-acetyloxypentyl group, a 6-benzyloxyhexyl group or a 6-acetyloxyhexyl group.

[I-54-4] The method according to [I-51], wherein $R^4$ is a 5-[4-chloro-2-fluoro-5-(2,2,2-trifluoroethylthio)phenoxy] pentyl group, or
a 6-[2,4-dimethyl-5-(2,2,2-trifluoroethylthio)phenoxy]hexyl group.

[I-54-5] The method according to [I-51], wherein $R^4$ is a 5-[4-chloro-2-fluoro-5-(2,2,2-trifluoroethylthio)phenoxy] pentyl group.

[I-55-1] The method according to any one of [I-51] to [I-54-5], wherein Z is a cyano group,
a C1 to C4 alkylsulfonyl group, or
a phenylsulfonyl group, wherein the phenyl group moiety may have 1 to 5 substituents selected independently from a halogen atom and a C1 to C4 alkyl group.

[I-55-2] The method according to any one of [I-51] to [I-54-5], wherein Z is a cyano group, or
a phenylsulfonyl group, wherein the phenyl group moiety may have 1 to 5 substituents selected independently from a halogen atom and a C1 to C4 alkyl group.

[I-55-3] The method according to any one of [I-51] to [I-54-5], wherein Z is a cyano group, or
a phenylsulfonyl group, wherein the phenyl group moiety may have 1 to 5 substituents selected independently from a C1 to C4 alkyl group.

[I-55-4] The method according to any one of [I-51] to [I-54-5], wherein Z is a C1 to C4 alkylsulfonyl group, or
a phenylsulfonyl group, wherein the phenyl group moiety may have 1 to 5 substituents selected independently from a halogen atom and a C1 to C4 alkyl group.

[I-55-5] The method according to any one of [I-51] to [I-54-5], wherein Z is a phenylsulfonyl group, wherein the phenyl group moiety may have 1 to 5 substituents selected independently from a halogen atom and a C1 to C4 alkyl group.

[I-55-6] The method according to any one of [I-51] to [I-54-5], wherein Z is a phenylsulfonyl group, wherein the said phenyl group moiety may have 1 to 5 substituents selected independently from a C1 to C4 alkyl group.

[I-56-1] The method according to any one of [I-51] to [I-54-5], wherein Z is a cyano group,
a methylsulfonyl group,
a phenylsulfonyl group, a 4-methylphenylsulfonyl group or a 4-chlorophenylsulfonyl group.

[I-56-2] The method according to any one of [I-51] to [I-54-5], wherein Z is a cyano group,
a phenylsulfonyl group, a 4-methylphenylsulfonyl group or a 4-chlorophenylsulfonyl group.

[I-56-3] The method according to any one of [I-51] to [I-54-5], wherein Z is a cyano group,
a phenylsulfonyl group or a 4-methylphenylsulfonyl group.

[I-56-4] The method according to any one of [I-51] to [I-54-5], wherein Z is a cyano group or a 4-methylphenylsulfonyl group.

[I-57-1] The method according to any one of [I-51] to [I-54-5], wherein Z is a cyano group.

[I-57-2] The method according to any one of [I-51] to [I-54-5], wherein Z is a phenylsulfonyl group, a 4-methylphenylsulfonyl group or a 4-chlorophenylsulfonyl group.

[I-57-3] The method according to any one of [I-51] to [I-54-5], wherein Z is a 4-methylphenylsulfonyl group.

[I-58] The method according to any one of [I-21] to [I-50], wherein the starting compound is a compound represented by the general formula (4):

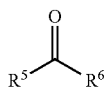

wherein $R^5$ is
a straight chain or branched chain hydrocarbon group which may have one or more substituents,
a cyclic hydrocarbon group which may have one or more substituents, or
a heterocyclic group which may have one or more substituents; and
$R^6$ is
a hydrogen atom,
a straight chain or branched chain hydrocarbon group which may have one or more substituents,
a cyclic hydrocarbon group which may have one or more substituents, or
a heterocyclic group which may have one or more substituents; and
the target compound having $R^1$ is a compound represented by the general formula (5):

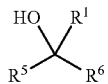

wherein $R^1$ is as defined in [I-21] to [I-50]; and $R^5$ and $R^6$ are as defined above.

[I-59] The method according to [I-58], wherein $R^5$ is
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a C6 to C10 aryl group which may have one or more substituents, or
a heterocyclic group which may have one or more substituents, wherein said the heterocyclic group is a 5- to 10-membered heterocyclic group having 1 to 9 carbon atoms and 1 to 4 heteroatoms selected independently from a nitrogen atom, an oxygen atom and a sulfur atom.

[I-60] The method according to [I-58] or [I-59], wherein $R^6$ is a hydrogen atom, a C1 to C4 alkyl group or a C1 to C4 haloalkyl group.

[I-61] The method according to [I-58] or [I-59], wherein $R^6$ is a hydrogen atom.

[I-62] A compound represented by the general formula (1):

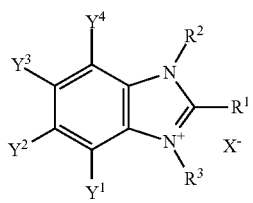

wherein $R^1$ is a C1 to C8 fluoroalkyl group;
$R^2$ and $R^3$ are each independently
a C1 to C12 alkyl group which may have one or more substituents, a C2 to C6 alkenyl group which may have one or more substituents,
a C2 to C6 alkynyl group which may have one or more substituents,
a C3 to C8 cycloalkyl group which may have one or more substituents, or
a C6 to C10 aryl group which may have one or more substituents;
$Y^1$, $Y^2$, $Y^3$ and $Y^4$ are each independently
a hydrogen atom, a halogen atom, a nitro group, a cyano group,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a hydroxy group,
a C1 to C6 alkoxy group,
a C1 to C6 alkylthio group, a C1 to C6 alkylsulfinyl group, a C1 to C6 alkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom, or
two adjacent substituents of $Y^1$ and $Y^2$, $Y^2$ and $Y^3$, or $Y^3$ and $Y^4$, together with carbon atoms to which these substituents are attached, form a 4- to 8-membered carbocyclic ring or a 4- to 8-membered heterocyclic ring having 1 to 4 heteroatoms selected independently from an oxygen atom, a sulfur atom and a nitrogen atom, wherein the said formed ring may have one or more substituents; and
$X^-$ is a monovalent anion.

[I-63] A compound represented by the general formula (1A):

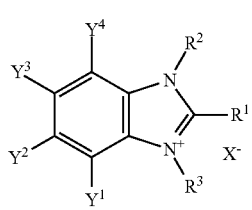

(1A)

wherein $R^1$ is a C1 to C8 fluoroalkyl group;
$R^2$ and $R^3$ are each independently
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents, or
a C6 to C10 aryl group which may have one or more substituents;
$Y^1$, $Y^2$, $Y^3$ and $Y^4$ are each independently
a hydrogen atom, a halogen atom, a nitro group, a cyano group,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a hydroxy group,
a C1 to C6 alkoxy group,
a C1 to C6 alkylthio group, a C1 to C6 alkylsulfinyl group, a C1 to C6 alkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom, or
two adjacent substituents of $Y^1$ and $Y^2$, $Y^2$ and $Y^3$, or $Y^3$ and $Y^4$, together with carbon atoms to which these substituents are attached, form a 4- to 8-membered carbocyclic ring or a 4- to 8-membered heterocyclic ring having 1 to 4 heteroatoms selected independently from an oxygen atom, a sulfur atom and a nitrogen atom, wherein the said formed ring may have one or more substituents; and
$X^-$ is a monovalent anion;
provided that the following cases of (i) to (v) are excluded:
(i) $R^1$ is a trifluoromethyl group,
  $R^2$ and $R^3$ are each a methyl group,
  $Y^1$, $Y^2$, $Y^3$ and $Y^4$ are each a hydrogen atom, and
  $X^-$ is $Br^-$;
(ii) $R^1$ is a trifluoromethyl group,
  $R^2$ and $R^3$ are each a methyl group,
  $Y^1$, $Y^2$, $Y^3$ and $Y^4$ are each a hydrogen atom, and
  $X^-$ is $I^-$;
(iii) $R^1$ is a trifluoromethyl group,
  $R^2$ and $R^3$ are each a methyl group,
  $Y^1$ is a hydrogen atom,
  $Y^2$ is a methyl group,
  $Y^3$ is a methyl group,
  $Y^4$ is a hydrogen atom, and
  $X^-$ is $I^-$;
(iv) $R^1$ is a trifluoromethyl group,
  $R^2$ and $R^3$ are each a methyl group,
  $Y^1$ is a hydrogen atom,
  $Y^2$ is a chlorine atom,
  $Y^3$ is a hydrogen atom,
  $Y^4$ is a hydrogen atom, and
  $X^-$ is $Br^-$; and (v) $R^1$ is a trifluoromethyl group,
$R^2$ and $R^3$ are each a methyl group,
$Y^1$, $Y^2$, $Y^3$ and $Y^4$ are each a bromine atom, and
$X^-$ is $Br^-$.

[I-64] The compound according to [I-62] or [I-63], wherein $R^1$ is a C1 to C8 perfluoroalkyl group.

[I-65] The compound according to [I-62] or [I-63], wherein $R^1$ is a C1 to C4 perfluoroalkyl group.

[I-66] The compound according to [I-62] or [I-63], wherein $R^1$ is a trifluoromethyl group or a pentafluoroethyl group.

[I-67] The compound according to [I-62] or [I-63], wherein $R^1$ is a trifluoromethyl group.

[I-68] The compound according to any one of [I-62] to [I-67], wherein $R^2$ and $R^3$ are each independently
a C1 to C6 alkyl group,
a phenyl group, wherein the said phenyl group may have 1 to 5 substituents selected independently from a halogen atom, a nitro group, a cyano group, a C1 to C6 alkyl group, a C1 to C6 haloalkyl group, a C2 to C6 acyl group and a C1 to C6 alkoxycarbonyl group, or
a phenyl C1 to C2 alkyl group, wherein the said phenyl group moiety may have 1 to 5 substituents selected independently from a halogen atom, a C1 to C6 alkyl group and a C1 to C6 haloalkyl group.

[I-69] The compound according to any one of [I-62] to [I-67], wherein $R^2$ and $R^3$ are each independently a C1 to C4 alkyl group or a phenyl group.

[I-70] The compound according to any one of [I-62] to [I-67], wherein $R^2$ and $R^3$ are each independently a methyl group, an ethyl group or a phenyl group.

[I-71] The compound according to any one of [I-62] to [I-67], wherein $R^2$ and $R^3$ are each a methyl group.

[I-72] The compound according to any one of [I-62] to [I-71], wherein $Y^1$, $Y^2$, $Y^3$ and $Y^4$ are each independently
a hydrogen atom, a halogen atom, a nitro group, a cyano group,
a C1 to C12 alkyl group, a C1 to C6 haloalkyl group,
a C1 to C6 alkylthio group, a C1 to C6 alkylsulfinyl group,
a C1 to C6 alkylsulfonyl group,
a C2 to C6 acyl group,
a C1 to C6 alkoxycarbonyl group,
a phenyl group, or
a pyridyl group.

[I-73] The compound according to any one of [I-62] to [I-71], wherein $Y^1$, $Y^2$, $Y^3$ and $Y^4$ are each independently
a hydrogen atom, a halogen atom, a nitro group, a cyano group,
a C1 to C4 alkyl group or a C1 to C4 haloalkyl group.

[I-74] The compound according to any one of [I-62] to [I-71], wherein $Y^1$, $Y^2$, $Y^3$ and $Y^4$ are each independently a hydrogen atom, a chlorine atom or a nitro group.

[I-75] The compound according to any one of [I-62] to [I-71], wherein $Y^1$, $Y^2$, $Y^3$ and $Y^4$ are each a hydrogen atom.

[I-76] The compound according to any one of [I-62] to [I-71], wherein $Y^1$, $Y^3$ and $Y^4$ are each a hydrogen atom; and $Y^2$ is a chlorine atom.

[I-77] The compound according to any one of [I-62] to [I-71], wherein $Y^1$, $Y^3$ and $Y^4$ are each a hydrogen atom; and $Y^2$ is a nitro group.

[I-78] The compound according to any one of [I-62] to [I-71], wherein $Y^1$, $Y^2$, $Y^3$ and $Y^4$ are each a chlorine atom.

[I-79] The compound according to any one of [I-62] to [I-78], wherein $X^-$ is any of halide ions, borate ions, phosphate ions, antimonate ions, carboxylate ions, sulfonate ions, sulfate ions, carbonate ions, nitrate ions and amide ions.

[I-80-1] The compound according to any one of [I-62] to [I-78], wherein $X^-$ is
$F^-$, $Cl^-$, $Br^-$, $I^-$,
$BF_4^-$, $C_6H_5BF_3^-$,
$PF_6^-$,
$SbF_6^-$,
$CH_3CO_2^-$, $CF_3CO_2^-$, $C_2F_5CO_2^-$,
$CH_3SO_3^-$, $C_2H_5SO_3^-$, $CF_3SO_3^-$, $C_6H_5SO_3^-$, 4-$CH_3$—$C_6H_4SO_3^-$, 4-Cl—$C_6H_4SO_3^-$, 4-$NO_2$—$C_6H_4SO_3^-$,
$HOSO_3^-$, $CH_3OSO_3^-$, $C_2H_5OSO_3^-$, $C_3H_7OSO_3^-$, iso-$C_3H_7OSO_3^-$, $C_4H_9OSO_3^-$,
$C_6H_5OSO_3^-$,
$HCO_3^-$, $CH_3OCO_2^-$
$NO_3^-$,
$(CN)_2N^-$ or $(CF_3SO_2)_2N^-$.

[I-80-2-1] The compound according to any one of [I-62] to [I-78], wherein $X^-$ is $F^-$, $Cl^-$, $Br^-$, $I^-$,
$BF_4^-$,
$CH_3CO_2^-$, $CF_3CO_2^-$,
$CH_3SO_3^-$, $CF_3SO_3^-$,
$HOSO_3^-$, $CH_3OSO_3^-$ or $C_2H_5OSO_3^-$.

[I-80-2-2] The compound according to any one of [I-62] to [I-78], wherein $X^-$
is $I^-$,
$BF_4^-$,
$CF_3CO_2^-$,
$CF_3SO_3^-$,
$HOSO_3^-$, $CH_3OSO_3^-$ or $C_2H_5OSO_3^-$.

[I-80-2-3] The compound according to any one of [I-62] to [I-78], wherein $X^-$
is $I^-$,
$BF_4^-$,
$CF_3SO_3^-$,
$HOSO_3^-$, $CH_3OSO_3^-$ or $C_2H_5OSO_3^-$.

[I-80-2-4] The compound according to any one of [I-62] to [I-78], wherein $X^-$
is $I^-$,
$BF_4^-$,
$CF_3SO_3^-$,
$CH_3OSO_3^-$ or $C_2H_5OSO_3^-$.

[I-80-2-5] The compound according to any one of [I-62] to [I-78], wherein $X^-$
is $I^-$,
$BF_4^-$,
$CF_3SO_3^-$,
$CH_3OSO_3^-$.

[I-80-3] The compound according to any one of [I-62] to [I-78], wherein $X^-$ is
$F^-$, $Cl^-$, $Br^-$, $I^-$,
$BF_4^-$,
$CH_3CO_2^-$, $CF_3CO_2^-$,
$CH_3SO_3^-$, $CF_3SO_3^-$,
$CH_3OSO_3^-$ or $C_2H_5OSO_3^-$.

[I-81-1] The compound according to any one of [I-62] to [I-78], wherein $X^-$ is
$Cl^-$, $Br^-$, $I^-$,
$BF_4^-$,
$CF_3SO_3^-$,
$HOSO_3^-$, $CH_3OSO_3^-$ or $C_2H_5OSO_3^-$.

[I-81-2] The compound according to any one of [I-62] to [I-78], wherein $X^-$ is
$Cl^-$, $Br^-$, $I^-$,
$BF_4^-$,
$CF_3SO_3^-$,
$CH_3OSO_3^-$ or $C_2H_5OSO_3^-$.

[I-82] The compound according to any one of [I-62] to [I-78], wherein $X^-$ is $CF_3SO_3^-$, $CH_3OSO_3^-$ or $C_2H_5OSO_3^-$.

[I-83] The compound according to any one of [I-62] to [I-78], wherein X⁻ is CH₃OSO₃⁻ or C₂H₅OSO₃⁻.

[I-84] The compound according to any one of [I-62] to [I-78], wherein X⁻ is CH₃OSO₃⁻.

[I-85] Use of a compound according to any one of [I-62] to [I-84] as a fluoroalkylating agent.

[I-86] A method for the production of a compound represented by the general formula (1):

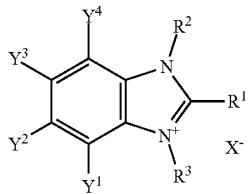
(1)

wherein $R^1$, $R^2$, $R^3$, $Y^1$, $Y^2$, $Y^3$, $Y^4$ and $X^-$ are as defined in [I-1], which comprises reacting a compound represented by the general formula (6):

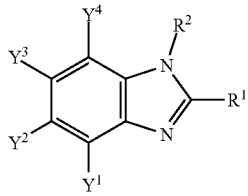
(6)

wherein $R^1$, $R^2$, $Y^1$, $Y^2$, $Y^3$ and $Y^4$ are as defined in [I-1], with a compound represented by the general formula (7):

$$R^3\text{—}X \quad (7)$$

wherein $R^3$ is as defined in [I-1];

X is a leaving group corresponding to $X^-$ defined in [I-1].

[I-87] A method for the production of a compound represented by the general formula (1):

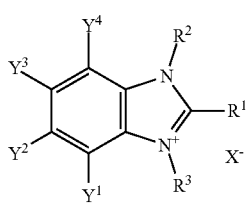
(1)

wherein $R^1$, $R^2$, $Y^1$, $Y^2$, $Y^3$ and $Y^4$ are as defined in [I-1]; $R^3$ is a C1 to C4 alkyl group; and $X^-$ is $BF_4^-$, which comprises reacting a compound represented by the general formula (6):

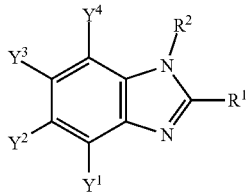
(6)

wherein $R^1$, $R^2$, $Y^1$, $Y^2$, $Y^3$ and $Y^4$ are as defined in [I-1] with tri (C1 to C4 alkyl) oxonium tetrafluoroborate.

[I-88] The method according to [I-87], wherein the tri (C1 to C4 alkyl) oxonium tetrafluoroborate is trimethyloxonium tetrafluoroborate;

$R^3$ is a methyl group; and $X^-$ is $BF_4^-$.

[I-89] The method according to any one of [I-86] to [I-88], wherein the compound represented by the general formula (6):

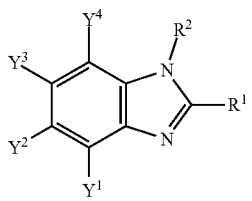
(6)

wherein $R^1$, $R^2$, $Y^1$, $Y^2$, $Y^3$ and $Y^4$ are as defined in [I-1], is produced by reacting a compound represented by the general formula (8):

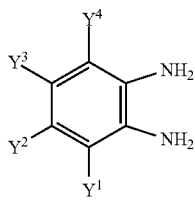
(8)

wherein $Y^1$, $Y^2$, $Y^3$ and $Y^4$ are as defined in [I-1], with a compound represented by the general formula (9):

(9)

wherein $R^1$ is as defined in [I-1]; and

Q is a hydroxy group, a halogen atom or a —O—C(=O)—$R^7$ group, wherein $R^7$ is the same as $R^1$, to produce a compound represented by the general formula (10):

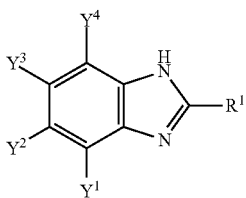

(10)

wherein $R^1$, $Y^1$, $Y^2$, $Y^3$ and $Y^4$ are as defined in [I-1],
and then reacting the obtained compound represented by the general formula (10)
with a compound represented by the general formula (11):

$$R^2\text{—W} \quad (11)$$

wherein $R^2$ is as defined in [I-1]; and
W is a leaving group.

[I-90] The method according to any one of [I-86] to [I-88], wherein the compound represented by the general formula (6):

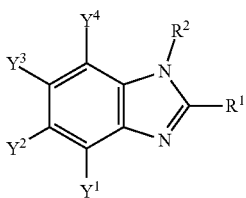

(6)

wherein $R^1$, $R^2$, $Y^1$, $Y^2$, $Y^3$ and $Y^4$ are as defined in [I-1], is produced by reacting a compound represented by the general formula (12):

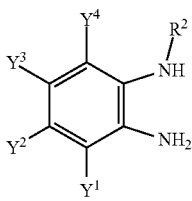

(12)

wherein $R^2$, $Y^1$, $Y^2$, $Y^3$ and $Y^4$ are as defined in [I-1], with a compound represented by the general formula (9):

(9)

wherein $R^1$ is as defined in [I-1]; and
Q is a hydroxy group, a halogen atom or a —O—C(=O)—$R^7$ group, wherein $R^7$ is the same as $R^1$.

Here, the branch numbers in the present specification will be described.

For example, the phrase "I-a to I-d-z" includes I-a, I-b, I-c and I-d, and, if applicable, includes all branch numbers such as I-b-x, I-b-y and I-b-z, and I-d-x, I-d-y and I-d-z.

Furthermore, for example, the phrase "I-a to I-d" also includes I-a, I-b, I-c and I-d, and, if applicable, includes all branch numbers such as I-b-x, I-b-y and I-b-z, and I-d-x, I-d-y and I-d-z.

Specifically, for example, the phrase "I-21 to I-43-B-7" includes I-21, I-22, I-23 . . . , and includes all branch numbers of I-42-A-1, I-42-A-2 . . . I-43-A-1, I-43-A-2 . . . I-42-B-1, I-42-B-2 . . . I-43-B-1, I-43-B-2 . . . I-43-B-7.

Furthermore, for example, also when described as "I-21 to I-43", the phrase "I-21 to I-43" includes I-21, I-22, I-23 . . . , and includes all branch numbers of I-42-A-1, I-42-A-2 . . . I-43-A-1, I-43-A-2 . . . I-42-B-1, I-42-B-2 . . . I-43-B-1, I-43-B-2 . . . I-43-B-7.

In another embodiment, the present invention is as follows:

[II-1] A fluoroalkylating agent represented by the general formula (1):

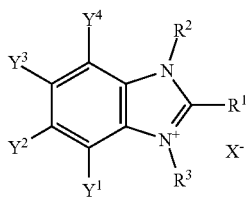

(1)

wherein $R^1$ is a C1 to C8 fluoroalkyl group;
$R^2$ and $R^3$ are each independently
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents, or
a C6 to C10 aryl group which may have one or more substituents;
$Y^1$, $Y^2$, $Y^3$ and $Y^4$ are each independently
a hydrogen atom, a halogen atom, a nitro group, a cyano group,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a hydroxy group,
a C1 to C6 alkoxy group,
a C1 to C6 alkylthio group, a C1 to C6 alkylsulfinyl group, a C1 to C6 alkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom, or two adjacent substituents of $Y^1$ and $Y^2$, $Y^2$ and $Y^3$, or $Y^3$ and $Y^4$, together with carbon atoms to which these substituents are attached, form a 4- to 8-membered carbocyclic ring or a 4- to 8-membered heterocyclic ring having 1 to 4 heteroatoms selected independently from an oxygen atom, a sulfur atom and a nitrogen atom, wherein the said formed ring may have one or more substituents; and $X^-$ is a monovalent anion.

[II-2] The agent according to [II-1], wherein
$R^1$ is a C1 to C4 perfluoroalkyl group;
$R^2$ and $R^3$ are each independently a C1 to C4 alkyl group or a phenyl group;
$Y^1$, $Y^2$, $Y^3$ and $Y^4$ are each independently
a hydrogen atom, a halogen atom, a nitro group, a cyano group,
a C1 to C4 alkyl group or a C1 to C4 haloalkyl group; and
$X^-$ is $Cl^-$, $Br^-$, $I^-$,
$BF_4^-$,
$CF_3SO_3^-$,
$HOSO_3^-$, $CH_3OSO_3^-$ or $C_2H_5OSO_3^-$.

[II-3] The agent according to [II-1], wherein
$R^1$ is a trifluoromethyl group or a pentafluoroethyl group;
$R^2$ and $R^3$ are each independently a methyl group, an ethyl group or a phenyl group;
$Y^1$, $Y^2$, $Y^3$ and $Y^4$ are each independently a hydrogen atom, a chlorine atom or a nitro group; and
$X^-$ is $Cl^-$, $Br^-$, $I^-$,
$BF_4^-$,
$CF_3SO_3^-$,
$HOSO_3^-$, $CH_3OSO_3^-$ or $C_2H_5OSO_3^-$.

[II-4] The agent according to [II-1], wherein
$R^1$ is a trifluoromethyl group;
$R^2$ and $R^3$ are each a methyl group;
$Y^1$, $Y^2$, $Y^3$ and $Y^4$ are each a hydrogen atom; and
$X^-$ is $CH_3OSO_3^-$.

[II-5] A method for the production of a target compound having $R^1$, wherein $R^1$ is as defined below, which comprises reacting a starting compound with a fluoroalkylating agent represented by the general formula (1):

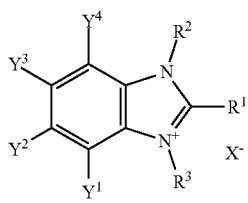

(1)

wherein $R^1$ is a C1 to C8 fluoroalkyl group;
$R^2$ and $R^3$ are each independently
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents, or
a C6 to C10 aryl group which may have one or more substituents;

$Y^1$, $Y^2$, $Y^3$ and $Y^4$ are each independently
a hydrogen atom, a halogen atom, a nitro group, a cyano group,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a hydroxy group,
a C1 to C6 alkoxy group,
a C1 to C6 alkylthio group, a C1 to C6 alkylsulfinyl group, a C1 to C6 alkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom, or two adjacent substituents of $Y^1$ and $Y^2$, $Y^2$ and $Y^3$, or $Y^3$ and $Y^4$, together with carbon atoms to which these substituents are attached, form a 4- to 8-membered carbocyclic ring or a 4- to 8-membered heterocyclic ring having 1 to 4 heteroatoms selected independently from an oxygen atom, a sulfur atom and a nitrogen atom, wherein the said formed ring may have one or more substituents; and $X^-$ is a monovalent anion.

[II-6] The method according to [II-5], wherein
$R^1$ is a C1 to C4 perfluoroalkyl group;
$R^2$ and $R^3$ are each independently a C1 to C4 alkyl group or a phenyl group;
$Y^1$, $Y^2$, $Y^3$ and $Y^4$ are each independently
a hydrogen atom, a halogen atom, a nitro group, a cyano group,
a C1 to C4 alkyl group or a C1 to C4 haloalkyl group; and
$X^-$ is $Cl^-$, $Br^-$, $I^-$,
$BF_4^-$,
$CF_3SO_3^-$,
$HOSO_3^-$, $CH_3OSO_3^-$ or $C_2H_5OSO_3^-$.

[II-7] The method according to [II-5], wherein
$R^1$ is a trifluoromethyl group or a pentafluoroethyl group;
$R^2$ and $R^3$ are each independently a methyl group, an ethyl group or a phenyl group;
$Y^1$, $Y^2$, $Y^3$ and $Y^4$ are each independently a hydrogen atom, a chlorine atom or a nitro group; and
$X^-$ is $Cl^-$, $Br^-$, $I^-$,
$BF_4^-$,
$CF_3SO_3^-$,
$HOSO_3^-$, $CH_3OSO_3^-$ or $C_2H_5OSO_3^-$.

[II-8] The method according to [II-5], wherein
$R^1$ is a trifluoromethyl group;
$R^2$ and $R^3$ are each a methyl group;
$Y^1$, $Y^2$, $Y^3$ and $Y^4$ are each a hydrogen atom; and
$X^-$ is $CH_3OSO_3^-$.

[II-9] The method according to any one of [II-5] to [II-8], wherein the reaction is carried out in the presence of a zeolite.

[II-10] The method according to [II-9], wherein the zeolite is a molecular sieve 3 A, a molecular sieve 4 A or a molecular sieve 5 A.

[II-11] The method according to [II-5], wherein the starting compound is a compound represented by the general formula (2):

(2)

wherein R$^4$ is
a straight chain or branched chain hydrocarbon group which may have one or more substituents,
a cyclic hydrocarbon group which may have one or more substituents, or
a heterocyclic group which may have one or more substituents; and
Z is a leaving group; and
the target compound having R$^1$ is a compound represented by the general formula (3):

(3)

wherein R$^1$ is as defined in [II-5]; and R$^4$ is as defined above.

[II-12] The method according to [II-11], wherein
R$^1$ is a C1 to C4 perfluoroalkyl group;
R$^2$ and R$^3$ are each independently a C1 to C4 alkyl group or a phenyl group;
Y$^1$, Y$^2$, Y$^3$ and Y$^4$ are each independently
a hydrogen atom, a halogen atom, a nitro group, a cyano group,
a C1 to C4 alkyl group or a C1 to C4 haloalkyl group; and
X$^-$ is Cl$^-$, Br$^-$, I$^-$,
BF$_4^-$,
CF$_3$SO$_3^-$,
HOSO$_3^-$, CH$_3$OSO$_3^-$ or C$_2$H$_5$OSO$_3^-$;
R$^4$ is
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom; and
Z is a cyano group,
a C1 to C4 alkylsulfonyl group, or
a phenylsulfonyl group, wherein the said phenyl group moiety may have 1 to 5 substituents selected independently from a halogen atom and a C1 to C4 alkyl group.

[II-13] The method according to [II-11], wherein
R$^1$ is a trifluoromethyl group or a pentafluoroethyl group;
R$^2$ and R$^3$ are each independently a methyl group, an ethyl group or a phenyl group;
Y$^1$, Y$^2$, Y$^3$ and Y$^4$ are each independently a hydrogen atom, a chlorine atom or a nitro group;
X$^-$ is Cl$^-$, Br$^-$, I$^-$,
BF$_4^-$,
CF$_3$SO$_3^-$,
HOSO$_3^-$, CH$_3$OSO$_3^-$ or C$_2$H$_5$OSO$_3^-$;
R$^4$ is a C3 to C7 alkyl group,
a C3 to C7 alkyl group having a benzyloxy group,
a C3 to C7 alkyl group having a C2 to C4 acyloxy group,
a C3 to C7 alkyl group having a phenyloxy group which may have 1 to 4 substituents selected independently from a halogen atom, a C1 to C4 alkyl group, a C1 to C6 haloalkylthio group and a C1 to C6 haloalkylsulfinyl group,
a C6 to C10 aryl group which may have 1 to 4 substituents selected independently from a halogen atom, a C1 to C4 alkyl group, a C1 to C4 haloalkyl group, a C1 to C4 alkoxy group, a C1 to C4 haloalkoxy group and a C6 to C10 aryl group, or
a thienyl group, a pyrazolyl group, an imidazolyl group, a thiazolyl group, an isothiazolyl group, a pyridyl group or a pyrimidyl group, each of which may have 1 to 4 substituents selected independently from a halogen atom, a C1 to C4 alkyl group,
a C1 to C4 haloalkyl group, a C1 to C4 alkoxy group, a C1 to C4 haloalkoxy group and a C6 to C10 aryl group; and
Z is a cyano group,
a C1 to C4 alkylsulfonyl group, or
a phenylsulfonyl group, wherein the said phenyl group moiety may have 1 to 5 substituents selected independently from a halogen atom and a C1 to C4 alkyl group.

[II-14] The method according to [II-11], wherein
R$^1$ is a trifluoromethyl group;
R$^2$ and R$^3$ are each a methyl group;
Y$^1$, Y$^2$, Y$^3$ and Y$^4$ are each a hydrogen atom;
X$^-$ is CH$_3$OSO$_3^-$;
R$^4$ is a 5-benzyloxypentyl group, a 5-acetyloxypentyl group, a 6-benzyloxyhexyl group, a 6-acetyloxyhexyl group,
a 5-[4-chloro-2-fluoro-5-(2,2,2-trifluoroethylthio)phenoxy]pentyl group, or
a 6-[2,4-dimethyl-5-(2,2,2-trifluoroethylthio)phenoxy]hexyl group; and
Z is a cyano group,
a methylsulfonyl group,
a phenylsulfonyl group, a 4-methylphenylsulfonyl group or a 4-chlorophenylsulfonyl group.

[II-15] The method according to any one of [II-11] to [II-14], wherein the reaction is carried out in the presence of a zeolite.

[II-16] The method according to [II-15], wherein the zeolite is a molecular sieve 3 A, a molecular sieve 4 A or a molecular sieve 5 A.

[II-17] The method according to [II-5], wherein the starting compound is a compound represented by the general formula (4):

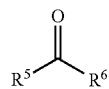
(4)

wherein R$^5$ is
a straight chain or branched chain hydrocarbon group which may have one or more substituents,
a cyclic hydrocarbon group which may have one or more substituents, or
a heterocyclic group which may have one or more substituents; and R⁶ is
a hydrogen atom,
a straight chain or branched chain hydrocarbon group which may have one or more substituents,
a cyclic hydrocarbon group which may have one or more substituents, or
a heterocyclic group which may have one or more substituents; and
the target compound having R¹ is a compound represented by the general formula (5):

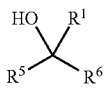

wherein R¹ is as defined in [II-5]; and R⁵ and R⁶ are as defined above.

[II-18] The method according to [II-17], wherein
R¹ is a C1 to C4 perfluoroalkyl group;
R² and R³ are each independently a C1 to C4 alkyl group or a phenyl group;
Y¹, Y², Y³ and Y⁴ are each independently
a hydrogen atom, a halogen atom, a nitro group, a cyano group,
a C1 to C4 alkyl group or a C1 to C4 haloalkyl group; and
X⁻ is Cl⁻, Br⁻, I⁻,
BF₄⁻,
CF₃SO₃⁻,
HOSO₃⁻, CH₃OSO₃⁻ or C₂H₅OSO₃⁻.

[II-19] The method according to [II-17], wherein
R¹ is a trifluoromethyl group or a pentafluoroethyl group;
R² and R³ are each independently a methyl group, an ethyl group or a phenyl group;
Y¹, Y², Y³ and Y⁴ are each independently a hydrogen atom, a chlorine atom or a nitro group;
X⁻ is Cl⁻, Br⁻, I⁻,
BF₄⁻,
CF₃SO₃⁻,
HOSO₃⁻, CH₃OSO₃⁻ or C₂H₅OSO₃⁻;
R⁵ is
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom; and
R⁶ is a hydrogen atom, a C1 to C4 alkyl group or a C1 to C4 haloalkyl group.

[II-20] The method according to [II-17], wherein
R¹ is a trifluoromethyl group;
R² and R³ are each a methyl group;
Y¹, Y², Y³ and Y⁴ are each a hydrogen atom;
X⁻ is CH₃OSO₃⁻;
R⁵ is
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom; and
R⁶ is a hydrogen atom.

[II-21] The method according to any one of [II-17] to [II-20], wherein the reaction is carried out in the presence of a zeolite.

[II-22] The method according to [II-21], wherein the zeolite is a molecular sieve 3 A, a molecular sieve 4 A or a molecular sieve 5 A.

[II-23] A compound represented by the general formula (1A):

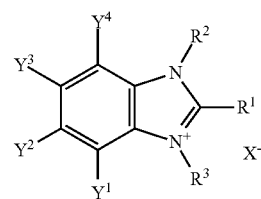

wherein R¹ is a C1 to C8 fluoroalkyl group;
R² and R³ are each independently
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents, or
a C6 to C10 aryl group which may have one or more substituents;
Y¹, Y², Y³ and Y⁴ are each independently
a hydrogen atom, a halogen atom, a nitro group, a cyano group,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a hydroxy group,
a C1 to C6 alkoxy group,
a C1 to C6 alkylthio group, a C1 to C6 alkylsulfinyl group, a C1 to C6 alkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group, a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom, or
two adjacent substituents of $Y^1$ and $Y^2$, $Y^2$ and $Y^3$, or $Y^3$ and $Y^4$, together with carbon atoms to which these substituents are attached, form a 4- to 8-membered carbocyclic ring or a 4- to 8-membered heterocyclic ring having 1 to 4 heteroatoms selected independently from an oxygen atom, a sulfur atom and a nitrogen atom, wherein the said formed ring may have one or more substituents; and
$X^-$ is a monovalent anion;
provided that the following cases of (i) to (v) are excluded:
(i) $R^1$ is a trifluoromethyl group,
  $R^2$ and $R^3$ are each a methyl group,
  $Y^1$, $Y^2$, $Y^3$ and $Y^4$ are each a hydrogen atom, and
  $X^-$ is $Br^-$;
(ii) $R^1$ is a trifluoromethyl group,
  $R^2$ and $R^3$ are each a methyl group,
  $Y^1$, $Y^2$, $Y^3$ and $Y^4$ are each a hydrogen atom, and
  $X^-$ is $I^-$;
(iii) $R^1$ is a trifluoromethyl group,
  $R^2$ and $R^3$ are each a methyl group,
  $Y^1$ is a hydrogen atom,
  $Y^2$ is a methyl group,
  $Y^3$ is a methyl group,
  $Y^4$ is a hydrogen atom, and
  $X^-$ is $I^-$;
(iv) $R^1$ is a trifluoromethyl group,
  $R^2$ and $R^3$ are each a methyl group,
  $Y^1$ is a hydrogen atom,
  $Y^2$ is a chlorine atom,
  $Y^3$ is a hydrogen atom,
  $Y^4$ is a hydrogen atom, and
  $X^-$ is $Br^-$; and
(v) $R^1$ is a trifluoromethyl group,
  $R^2$ and $R^3$ are each a methyl group,
  $Y^1$, $Y^2$, $Y^3$ and $Y^4$ are each a bromine atom, and
  $X^-$ is $Br^-$.
[II-24] The compound according to [II-23], wherein
$R^1$ is a C1 to C4 perfluoroalkyl group;
$R^2$ and $R^3$ are each independently a C1 to C4 alkyl group or a phenyl group;
$Y^1$, $Y^2$, $Y^3$ and $Y^4$ are each independently
a hydrogen atom, a halogen atom, a nitro group, a cyano group,
a C1 to C4 alkyl group or a C1 to C4 haloalkyl group; and
$X^-$ is $Cl^-$, $Br^-$, $I^-$,
$BF_4^-$,
$CF_3SO_3^-$,
$HOSO_3^-$, $CH_3OSO_3^-$ or $C_2H_5OSO_3^-$.
[II-25] The compound according to [II-23], wherein
$R^1$ is a trifluoromethyl group or a pentafluoroethyl group;
$R^2$ and $R^3$ are each independently a methyl group, an ethyl group or a phenyl group;
$Y^1$, $Y^2$, $Y^3$ and $Y^4$ are each independently a hydrogen atom, a chlorine atom or a nitro group; and
$X^-$ is $Cl^-$, $Br^-$, $I^-$,
$BF_4^-$,
$CF_3SO_3^-$,
$HOSO_3^-$, $CH_3OSO_3^-$ or $C_2H_5OSO_3^-$.
[II-26] The compound according to [II-23], wherein
$R^1$ is a trifluoromethyl group;
$R^2$ and $R^3$ are each a methyl group;
$Y^1$, $Y^2$, $Y^3$ and $Y^4$ are each a hydrogen atom; and
$X^-$ is $CH_3OSO_3^-$.
[II-27] Use of a compound represented by the general formula (1):

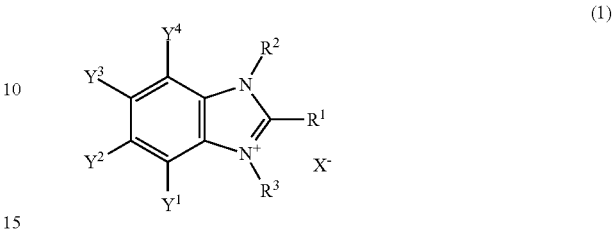

wherein $R^1$ is a C1 to C8 fluoroalkyl group;
$R^2$ and $R^3$ are each independently
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents, or
a C6 to C10 aryl group which may have one or more substituents;
$Y^1$, $Y^2$, $Y^3$ and $Y^4$ are each independently
a hydrogen atom, a halogen atom, a nitro group, a cyano group,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a hydroxy group,
a C1 to C6 alkoxy group,
a C1 to C6 alkylthio group, a C1 to C6 alkylsulfinyl group, a C1 to C6 alkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom, or
two adjacent substituents of $Y^1$ and $Y^2$, $Y^2$ and $Y^3$, or $Y^3$ and $Y^4$, together with carbon atoms to which these substituents are attached, form a 4- to 8-membered carbocyclic ring or a 4- to 8-membered heterocyclic ring having 1 to 4 heteroatoms selected independently from an oxygen atom, a sulfur atom and a nitrogen atom, wherein the said formed ring may have one or more substituents; and
$X^-$ is a monovalent anion, as a fluoroalkylating agent.
[II-28] The use according to [II-27], wherein
$R^1$ is a C1 to C4 perfluoroalkyl group;
$R^2$ and $R^3$ are each independently a C1 to C4 alkyl group or a phenyl group;

Y¹, Y², Y³ and Y⁴ are each independently
a hydrogen atom, a halogen atom, a nitro group, a cyano group,
a C1 to C4 alkyl group or a C1 to C4 haloalkyl group; and
X⁻ is Cl⁻, Br⁻, I⁻,
BF₄⁻,
CF₃SO₃⁻,
HOSO₃⁻, CH₃OSO₃⁻ or C₂H₅OSO₃⁻.

[II-29] The use according to [II-27], wherein
R¹ is a trifluoromethyl group or a pentafluoroethyl group;
R² and R³ are each independently a methyl group, an ethyl group or a phenyl group;
Y¹, Y², Y³ and Y⁴ are each independently a hydrogen atom, a chlorine atom or a nitro group; and
X⁻ is Cl⁻, Br⁻, I⁻,
BF₄⁻,
CF₃SO₃⁻,
HOSO₃⁻, CH₃OSO₃⁻ or C₂H₅OSO₃⁻.

[II-30] The use according to [II-27], wherein
R¹ is a trifluoromethyl group;
R² and R³ are each a methyl group;
Y¹, Y², Y³ and Y⁴ are each a hydrogen atom; and
X⁻ is CH₃OSO₃⁻.

Advantageous Effects of Invention

The present invention provides an industrially preferable and novel fluoroalkylating agent and use thereof (i.e., a method for the production of a compound having a fluoroalkyl group), which can solve the above-mentioned one or more drawbacks or problems in the prior art. Furthermore, the present invention also provides a novel compound which is useful as a fluoroalkylating agent.

Furthermore, the fluoroalkylating agent of the present invention can be efficiently produced from an easily available acetic acid derivative such as trifluoroacetic acid as a material. In other words, the fluoroalkylating agent of the present invention can be produced without using a greenhouse effect gas (for example, CHF₃) or Freon gas (for example, CF₃I or CBrF₃) as a source of fluorine. Therefore, the present invention can reduce the environmental load.

Furthermore, according to the present invention, a fluoroalkylation reaction can be carried out with a simple reaction operation, under a mild reaction condition, and without requiring a special facility. Specifically, for example, the present invention provides a novel fluoroalkylating agent. It is easy to control the reaction temperature and the extreme low temperature is not required in the fluoroalkylation reaction using the fluoroalkylating agent.

In addition, in the present invention, the safety of a fluoroalkylation reaction can be increased, since the control of the reaction temperature is easy.

Furthermore, according to the present invention, the fluoroalkyl group moiety in the molecule of the fluoroalkylating agent can be efficiently utilized. Therefore, the generation of waste containing fluorine can be suppressed. In addition, the novel fluoroalkylating agent of the present invention does not require an initiator such as fluorides and a largely excessive amount of a quaternary ammonium salt. From these points as well, the present invention is economical, simple, and environmentally superior.

As described above, from technical and economic viewpoints, a method for the production of a compound having a fluoroalkyl group is dramatically improved. Therefore, the present invention is economical and also environmentally friendly, and has a high industrial utility value.

DESCRIPTION OF EMBODIMENTS

The present invention will be described in detail below.
The terms and symbols used in the present specification will be described below.

The term "fluoroalkylation reaction" means a reaction by which a fluoroalkyl group is introduced into a starting compound (a material compound) which is an organic compound. In other words, the term "fluoroalkylation reaction" means a reaction which produces a target compound having a fluoroalkyl group by reacting a starting compound (a material compound) which is an organic compound, with a fluoroalkylating agent.

The term "fluoroalkylating agent" means an agent which is used as a source of a fluoroalkyl group in the fluoroalkylation reaction defined above.

The "fluoroalkylation reaction" includes a "perfluoroalkylation reaction".

The "fluoroalkylating agent" includes a "perfluoroalkylating agent".

The term "perfluoroalkylation reaction" means a reaction by which a perfluoroalkyl group is introduced into a starting compound (a material compound) which is an organic compound. In other words, the term "perfluoroalkylation reaction" means a reaction which produces a target compound having a perfluoroalkyl group by reacting a starting compound (a material compound) which is an organic compound, with a perfluoroalkylating agent.

The term "perfluoroalkylating agent" means an agent which is used as a source of a perfluoroalkyl group in the perfluoroalkylation reaction defined above.

The halogen atom is a fluorine atom, a chlorine atom, a bromine atom or an iodine atom.

The phrase "Ca to Cb" means that the number of carbon is a to b. For example, the phrase "C1 to C4" in a "C1 to C4 alkyl group" means that the number of carbon in an alkyl group is 1 to 4. The phrase "Ca to Cb" in the present specification excludes the number of carbon in "substituent(s)" in the phrases "may have substituent(s)" and "may be substituted". For example, the phrase "C1 to C12" in a "C1 to C12 alkyl group which may have substituent(s)" excludes the number of carbon in the "substituent(s)" in the phrase "may have substituent(s)". For example, the phrase "C1 to C12" in a "C1 to C12 alkyl group which may be substituted" excludes the number of carbon in the "substituent(s)" in the phrase "may be substituted".

In the present specification, when a definition of a substituent having a specific number of carbon is not described, the definition is generally to be understood by appropriately replacing the number of carbon, etc., in the definition of a related substituent having the number of carbon different from the specific number of carbon.

In the present specification, when specific examples of a substituent having a specific number of carbon are not described, the appropriate examples among the specific examples of a related substituent having the number of carbon larger than the specific number of carbon can generally be referred to.

Herein, it is to be understood that generic terms such as "alkyl" include both the straight chain and branched chain groups such as a butyl group and a tert-butyl group. However, when a specific term such as a "butyl group" is used, it is specific for a "normal butyl group", i.e., a "n-butyl group". In other words, the specific term "butyl group"

refers to a "normal butyl group" of the straight chain group, and branched chain isomers such as a "tert-butyl group" are referred to specifically when intended. For another example, the specific term "pentyl group" refers to a "normal pentyl group" of the straight chain group. For still another example, the specific term "hexyl group" refers to a "normal hexyl group" of the straight chain group.

The prefixes "n-", "s-" and "sec-", "i-", "t-" and "tert-", "neo-", "c-" and "cyc-", "o-", "m-" and "p-" have their usual meanings as follows: normal, secondary ("s-" and "sec-"), iso, tertiary ("t-" and "tert-"), neo, cyclo, ortho, meta and para.

Herein, the following abbreviations may be used:
"Me" means a methyl group;
"Et" means an ethyl group;
"Pr", "n-Pr" and "Pr-n" mean a propyl group (i.e., a normal propyl group);
"i-Pr" and "Pr-i" mean an isopropyl group;
"Bu", "n-Bu" and "Bu-n" mean a butyl group (i.e., a normal butyl group);
"s-Bu" and "Bu-s" mean a sec-butyl group;
"i-Bu" and "Bu-i" mean an isobutyl group;
"t-Bu" and "Bu-t" mean a tert-butyl group;
"Pen", "n-Pen" and "Pen-n" mean a pentyl group (i.e., a normal pentyl group);
"Hex", "n-Hex" and "Hex-n" mean a hexyl group (i.e., a normal hexyl group);
"Dec", "n-Dec" and "Dec-n" mean a decyl group (i.e., a normal decyl group);
"c-Pr" and "Pr-c" mean a cyclopropyl group;
"c-Bu" and "Bu-c" mean a cyclobutyl group;
"c-Pen" and "Pen-c" mean a cyclopentyl group;
"c-Hex" and "Hex-c" mean a cyclohexyl group;
"Ph" means a phenyl group; and
"Bn" means a benzyl group.

Examples of the hydrocarbon group include a straight chain or branched chain hydrocarbon group, and a cyclic hydrocarbon group, each of which may be interrupted by one or more —O— groups, —S— groups, —SO— groups, —SO$_2$— groups, and/or —NR$^a$— groups. Examples of R$^a$ include a hydrogen atom, an alkyl group, an alkenyl group, an alkynyl group, a cycloalkyl group, an aryl group and the like.

The "hydrocarbon group" is also referred to herein as a "hydrocarbyl group".

Examples of the straight chain or branched chain hydrocarbon group include an alkyl group, an alkenyl group, an alkynyl group and the like.

In the present specification, the cyclic hydrocarbon group means a cyclic group which is aromatic or non-aromatic, and is monocyclic or multicyclic, wherein all of the ring-constituting atoms are carbon atoms.

In one embodiment, examples of the cyclic hydrocarbon group include, but are not limited to, a 3- to 14-membered (preferably 4- to 14-membered, more preferably 5- to 14-membered, further preferably 5- to 10-membered, particularly preferably 6- to 10-membered) cyclic hydrocarbon group, which is aromatic or non-aromatic, and is monocyclic, bicyclic or tricyclic.

In another embodiment, examples of the cyclic hydrocarbon group include, but are not limited to, a 4- to 8-membered (preferably 5- to 6-membered) cyclic hydrocarbon group, which is aromatic or non-aromatic, and is monocyclic or bicyclic (preferably monocyclic).

Examples of the cyclic hydrocarbon group include a cycloalkyl group, an aryl group and the like.

The aryl group is an aromatic cyclic group among the cyclic hydrocarbon groups as defined above.

The "aryl group" is also referred to herein as an "aromatic carbocyclic group".

The cyclic hydrocarbon group as defined or exemplified above may include a non-fused cyclic group (for example, a monocyclic group or a spirocyclic group) and a fused cyclic group, when possible.

The cyclic hydrocarbon group as defined or exemplified above may be unsaturated, partially saturated or saturated, when possible.

The cyclic hydrocarbon group as defined or exemplified above is also referred to herein as a carbocyclic group. In addition, the cyclic hydrocarbon group is also referred to herein as a carbocyclyl group.

In the present specification, the carbocyclic ring is a ring which corresponds to the cyclic hydrocarbon group as defined or exemplified above.

Examples of the alkyl group include, but are not limited to, a C1 to C12 alkyl group, a C1 to C6 alkyl group, a C1 to C4 alkyl group, a C1 to C2 alkyl group and the like.

The C1 to C12 alkyl group means a straight chain or branched chain alkyl group having 1 to 12 carbon atoms.

Specific examples of the C1 to C12 alkyl group include, but are not limited to,
a methyl group, an ethyl group, a propyl group, an isopropyl group,
a butyl group, a sec-butyl group, an isobutyl group, a tert-butyl group,
a pentyl group, a 1-methylbutyl group, a 2-methylbutyl group, an isopentyl group, a 1-ethylpropyl group, a 1,1-dimethylpropyl group, a 1,2-dimethylpropyl group, a neopentyl group,
a hexyl group, a 1-methylpentyl group, a 2-methylpentyl group, a 3-methylpentyl group, an isohexyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1,2,2-trimethylpropyl group, a 1-ethyl-1-methylpropyl group, a 1-ethyl-2-methylpropyl group,
a heptyl group, a 1-methylhexyl group, a 2-methylhexyl group, a 3-methylhexyl group, a 4-methylhexyl group, an isoheptyl group, a 1,1-dimethylpentyl group, a 2,2-dimethylpentyl group, a 4,4-dimethylpentyl group, a 1-ethylpentyl group, a 2-ethylpentyl group, a 1,1,3-trimethylbutyl group, a 1,2,2-trimethylbutyl group, a 1,3,3-trimethylbutyl group, a 2,2,3-trimethylbutyl group, a 2,3,3-trimethylbutyl group, a 1-propylbutyl group, a 1,1,2,2-tetramethylpropyl group,
an octyl group, a 1-methylheptyl group, a 3-methylheptyl group, an isooctyl group, a 2-ethylhexyl group, a 5,5-dimethylhexyl group, a 2,4,4-trimethylpentyl group, a 1-ethyl-1-methylpentyl group, a 1-propylpentyl group,
a nonyl group, a 1-methyloctyl group, a 2-methyloctyl group, a 3-methyloctyl group,
an isononyl group, a 1-ethylheptyl group, a 1,1-dimethylheptyl group, a 6,6-dimethylheptyl group,
a decyl group, a 1-methylnonyl group, a 2-methylnonyl group, a 6-methylnonyl group, an isodecyl group, a 1-ethyloctyl group, a 1-propylheptyl group,
a undecyl group, a 1-methyldecyl group, an isoundecyl group,
a dodecyl group, a 1-methylundecyl group, an isododecyl group and the like.

The C3 to C7 alkyl group means a straight chain or branched chain alkyl group having 3 to 7 carbon atoms.

Specific examples of the C3 to C7 alkyl group include the appropriate examples among the above specific examples of the C1 to C12 alkyl group.

The C1 to C6 alkyl group means a straight chain or branched chain alkyl group having 1 to 6 carbon atoms.

Specific examples of the C1 to C6 alkyl group include the appropriate examples among the above specific examples of the C1 to C12 alkyl group.

The C1 to C4 alkyl group means a straight chain or branched chain alkyl group having 1 to 4 carbon atoms.

Specific examples of the C1 to C4 alkyl group are the appropriate examples among the above specific examples of the C1 to C12 alkyl group.

The C1 to C2 alkyl group means a straight chain alkyl group having 1 to 2 carbon atoms.

Specific examples of the C1 to C2 alkyl group are the appropriate examples among the above specific examples of the C1 to C12 alkyl group.

Examples of the alkenyl group include, but are not limited to, a C2 to C6 alkenyl group and the like.

The C2 to C6 alkenyl group means a straight chain or branched chain alkenyl group having 2 to 6 carbon atoms.

Specific examples of the C2 to C6 alkenyl group include, but are not limited to, a vinyl group, a 1-propenyl group, an isopropenyl group, a 2-propenyl group, a 1-butenyl group, a 1-methyl-1-propenyl group, a 2-methyl-1-propenyl group, a 2-butenyl group, a 1-methyl-2-propenyl group, a 2-methyl-2-propenyl group, a 3-butenyl group, a 1,3-butadienyl group, a 1-pentenyl group, a 2-pentenyl group, a 3-pentenyl group, a 4-pentenyl group, a 1,3-pentadienyl group, a 1-vinyl-2-propenyl group, a 1-hexenyl group and the like.

Examples of the alkynyl group include, but are not limited to, a C2 to C6 alkynyl group and the like.

The C2 to C6 alkynyl group means a straight chain or branched chain alkynyl group having 2 to 6 carbon atoms.

Specific examples of the C2 to C6 alkynyl group include, but are not limited to, an ethynyl group, a 1-propynyl group, a 2-propynyl group, a 1-butynyl group, a 1-methyl-2-propynyl group, a 2-butynyl group, a 3-butynyl group, a 1-pentynyl group, a 3-methyl-1-butynyl group, a 2-pentynyl group, a 1-methyl-2-butynyl group, a 1-ethyl-2-propynyl group, a 3-pentynyl group, a 1-methyl-3-butynyl group, a 2-methyl-3-butynyl group, a 4-pentynyl group, a 1-hexynyl group and the like.

Examples of the cycloalkyl group include, but are not limited to, a C3 to C8 cycloalkyl group, preferably a C5 to C6 cycloalkyl group.

The C3 to C8 cycloalkyl group means a cycloalkyl group having 3 to 8 carbon atoms.

Specific examples of the C3 to C8 cycloalkyl group are a cyclopropyl group, a cyclobutyl group, a cyclopentyl group, a cyclohexyl group, a cycloheptyl group and a cyclooctyl group.

Specific examples of the C5 to C6 cycloalkyl group are a cyclopentyl group and a cyclohexyl group.

Examples of the haloalkyl group include, but are not limited to, a C1 to C6 haloalkyl group, preferably a C1 to C4 haloalkyl group.

The C1 to C6 haloalkyl group means a straight chain or branched chain alkyl group having 1 to 6 carbon atoms which is substituted with 1 to 13 same or different halogen atoms, wherein the halogen atoms have the same meaning as defined above.

Specific examples of the C1 to C6 haloalkyl group include, but are not limited to, a fluoromethyl group, a chloromethyl group, a bromomethyl group, a difluoromethyl group, a dichloromethyl group, a trifluoromethyl group, a trichloromethyl group, a chlorodifluoromethyl group, a bromodifluoromethyl group, a 2-fluoroethyl group, a 1-chloroethyl group, a 2-chloroethyl group, a 2,2,2-trifluoroethyl group, a pentafluoroethyl group, a 3-fluoropropyl group, a 3-chloropropyl group, a 2-chloro-1-methylethyl group, a 2,2,3,3,3-pentafluoropropyl group, a 2,2,2-trifluoro-1-trifluoromethylethyl group, a heptafluoropropyl group, a 1,2,2,2-tetrafluoro-1-trifluoromethylethyl group, a 4-fluorobutyl group, a 4-chlorobutyl group, a 2,2,3,3,4,4,4-heptafluorobutyl group, a nonafluorobutyl group, a 1,1,2,3,3,3-hexafluoro-2-trifluoromethylpropyl group, a 2,2,2-trifluoro-1,1-di(trifluoromethyl)ethyl group, an undecafluoropentyl group, a tridecafluorohexyl group and the like.

The C1 to C4 haloalkyl group means a straight chain or branched chain alkyl group having 1 to 4 carbon atoms which is substituted with 1 to 9 same or different halogen atoms.

Specific examples of the C1 to C4 haloalkyl group include, but are not limited to, the appropriate examples among the above specific examples of the C1 to C6 haloalkyl group.

The fluoroalkyl group means a straight chain or branched chain alkyl group, wherein one or more hydrogen atoms are substituted with fluorine atoms.

Examples of the fluoroalkyl group include, but are not limited to, a C1 to C8 fluoroalkyl group, a C1 to C4 fluoroalkyl group, a C1 to C8 perfluoroalkyl group, a C1 to C4 perfluoroalkyl group and the like.

The C1 to C8 fluoroalkyl group means a straight chain or branched chain alkyl group having 1 to 8 carbon atoms which is substituted with 1 to 17 fluorine atoms.

Specific examples of the C1 to C8 fluoroalkyl group include, but are not limited to, a fluoromethyl group (i.e., —$CH_2F$), a difluoromethyl group (i.e., —$CHF_2$), a trifluoromethyl group (i.e., —$CF_3$), a 2-fluoroethyl group (i.e., —$CH_2CH_2F$), a 1-fluoroethyl group (i.e., —$CHFCH_3$), a 2,2,2-trifluoroethyl group (i.e., —$CH_2CF_3$), a pentafluoroethyl group (i.e., —$CF_2CF_3$), a 3-fluoropropyl group (i.e., —$CH_2CH_2CH_2F$), a 2,2,3,3,3-pentafluoropropyl group (i.e., —$CH_2CF_2CF_3$), a 2,2,2-trifluoro-1-trifluoromethylethyl group (i.e., —$CH(CF_3)_2$), a heptafluoropropyl group (i.e., —$CF_2CF_2CF_3$), a 1,2,2,2-tetrafluoro-1-trifluoromethylethyl group (i.e., —$CF(CF_3)_2$), a 2,2,3,3,4,4,4-heptafluorobutyl group (i.e., —$CH_2CF_2CF_2CF_3$), a nonafluorobutyl group (i.e., —$CF_2CF_2CF_2CF_3$), a 1,2,2,3,3,3-hexafluoro-1-trifluoromethylpropyl group (i.e., —$CF(CF_3)CF_2CF_3$), a 1,1,2,3,3,3-hexafluoro-2-trifluoromethylpropyl group (i.e., —$CF_2CF(CF_3)_2$), a 2,2,2-trifluoro-1,1-di(trifluoromethyl)ethyl group (i.e., —$C(CF_3)_3$), a undecafluoropentyl group and isomers thereof, a tridecafluorohexyl group and isomers thereof, a pentadecafluoropentyl group and isomers thereof, a heptadecafluorohexyl group and isomers thereof and the like.

In one embodiment, preferable specific examples of the C1 to C8 fluoroalkyl group include a difluoromethyl group (i.e., —$CHF_2$), a trifluoromethyl group (i.e., —$CF_3$), a pentafluoroethyl group (i.e., —$CF_2CF_3$), a 2,2,2-trifluoro-1-trifluoromethylethyl group (i.e., —CH(CF$_3$)$_2$), a heptafluoropropyl group (i.e., —CF$_2$CF$_2$CF$_3$), a 1,2,2,2-tetrafluoro-1-trifluoromethylethyl group (i.e., —CF(CF$_3$)$_2$), a nonafluorobutyl group (i.e., —CF$_2$CF$_2$CF$_2$CF$_3$), a 1,2,2,3,3,3-hexafluoro-1-trifluoromethylpropyl group (i.e., —CF(CF$_3$)CF$_2$CF$_3$), a 1,1,2,3,3,3-hexafluoro-2-trifluoromethylpropyl group (i.e., —CF$_2$CF(CF$_3$)$_2$), a 2,2,2-trifluoro-1,1-di(trifluoromethyl)ethyl group (i.e., —C(CF$_3$)$_3$), a undecafluoropentyl group and isomers thereof,
a tridecafluorohexyl group and isomers thereof,
a pentadecafluoropentyl group and isomers thereof,
a heptadecafluorohexyl group and isomers thereof.

The C1 to C4 fluoroalkyl group means a straight chain or branched chain alkyl group having 1 to 4 carbon atoms which is substituted with 1 to 9 fluorine atoms.

Specific examples of the C1 to C4 fluoroalkyl group include, but are not limited to, the appropriate examples among the above specific examples of the C1 to C8 fluoroalkyl group.

In one embodiment, preferable specific examples of the C1 to C4 fluoroalkyl group include the appropriate examples among the above preferable specific examples of the C1 to C8 fluoroalkyl group.

The perfluoroalkyl group means a straight chain or branched chain alkyl group, wherein all hydrogen atoms are substituted with fluorine atoms.

Examples of the perfluoroalkyl group include, but are not limited to, a C1 to C8 perfluoroalkyl group, a C1 to C4 perfluoroalkyl group and the like.

The C1 to C8 perfluoroalkyl group means a straight chain or branched chain alkyl group having 1 to 8 carbon atoms, wherein all hydrogen atoms are substituted with fluorine atoms.

Specific examples of the C1 to C8 perfluoroalkyl group include
a trifluoromethyl group (i.e., —CF$_3$),
a pentafluoroethyl group (i.e., —CF$_2$CF$_3$),
a heptafluoropropyl group (i.e., —CF$_2$CF$_2$CF$_3$), a 1,2,2,2-tetrafluoro-1-trifluoromethylethyl group (i.e., —CF(CF$_3$)$_2$),
a nonafluorobutyl group (i.e., —CF$_2$CF$_2$CF$_2$CF$_3$), a 1,2,2,3,3,3-hexafluoro-1-trifluoromethylpropyl group (i.e., —CF(CF$_3$)CF$_2$CF$_3$), a 1,1,2,3,3,3-hexafluoro-2-trifluoromethylpropyl group (i.e., —CF$_2$CF(CF$_3$)$_2$), a 2,2,2-trifluoro-1,1-di(trifluoromethyl)ethyl group (i.e., —C(CF$_3$)$_3$),
a undecafluoropentyl group and isomers thereof,
a tridecafluorohexyl group and isomers thereof,
a pentadecafluoropentyl group and isomers thereof,
a heptadecafluorohexyl group and isomers thereof.

The C1 to C4 perfluoroalkyl group means a straight chain or branched chain alkyl group having 1 to 4 carbon atoms which is substituted with 1 to 9 fluorine atoms.

Specific examples of the C1 to C4 perfluoroalkyl group include, but are not limited to, the appropriate examples among the above specific examples of the C1 to C8 perfluoroalkyl group.

Examples of the alkoxy group include, but are not limited to, a C1 to C6 alkoxy group, a C1 to C4 alkoxy group and the like.

The C1 to C6 alkoxy group means a (C1 to C6 alkyl)-O— group, wherein the C1 to C6 alkyl group moiety has the same meaning as defined above.

Specific examples of the C1 to C6 alkoxy group include, but are not limited to, a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group, an isohexyloxy group and the like.

The C1 to C4 alkoxy group means a (C1 to C4 alkyl)-O— group, wherein the C1 to C4 alkyl group moiety has the same meaning as defined above.

Specific examples of the C1 to C4 alkoxy group are the appropriate examples among the above specific examples of the C1 to C6 alkoxy group.

The C1 to C6 haloalkoxy group means a (C1 to C6 haloalkyl)-O— group, wherein the C1 to C6 haloalkyl group moiety has the same meaning as above.

Examples of the C1 to C6 haloalkoxy group include, but are not limited to, a fluoromethoxy group, a difluoromethoxy group, a trifluoromethoxy group, a chlorodifluoromethoxy group,
a 2-fluoroethoxy group, a 2-chloroethoxy group, a 2,2,2-trifluoroethoxy group, a pentafluoroethoxy group,
a 3-fluoropropoxy group, a 3-chloropropoxy group, a 2,2,3,3,3-pentafluoropropoxy group, a heptafluoropropoxy group, a 2,2,2-trifluoro-1-trifluoromethylethoxy group,
a 4-fluorobutoxy group, a 2,2,3,3,4,4,4-heptafluorobutoxy group,
a 2,2,3,3,4,4,5,5,5-nonafluoropentyloxy group,
a 2,2,3,3,4,4,5,5,6,6,6-undecafluorohexyloxy group and the like.

Examples of the alkylthio group include, but are not limited to, a C1 to C6 alkylthio group and the like.

The C1 to C6 alkylthio group means a (C1 to C6 alkyl)-S— group, wherein the C1 to C6 alkyl group moiety has the same meaning as defined above.

Specific examples of the C1 to C6 alkylthio group include, but are not limited to, a methylthio group, an ethylthio group, a propylthio group, an isopropylthio group, a butylthio group, a pentylthio group, a hexylthio group and the like.

Examples of the alkylsulfinyl group include, but are not limited to, a C1 to C6 alkylsulfinyl group and the like.

The C1 to C6 alkylsulfinyl group means a (C1 to C6 alkyl)-SO— group, wherein the C1 to C6 alkyl group moiety has the same meaning as defined above.

Specific examples of the C1 to C6 alkylsulfinyl group include, but are not limited to, a methylsulfinyl group, an ethylsulfinyl group, a propylsulfinyl group, an isopropylsulfinyl group, a butylsulfinyl group, a pentylsulfinyl group, a hexyl group and the like.

Examples of the alkylsulfonyl group include, but are not limited to, a C1 to C6 alkylsulfonyl group and the like.

The C1 to C6 alkylsulfonyl group means a (C1 to C6 alkyl)-SO$_2$— group, wherein the C1 to C6 alkyl group moiety has the same meaning as defined above.

Specific examples of the C1 to C6 alkylsulfonyl group include, but are not limited to, a methylsulfonyl group, an ethylsulfonyl group, a propylsulfonyl group, an isopropylsulfonyl group, a butylsulfonyl group, a pentylsulfonyl group, a hexylsulfonyl group and the like.

The C1 to C6 haloalkylthio group means a (C1 to C6 haloalkyl)-S— group, wherein the C1 to C6 haloalkyl group moiety has the same meaning as above.

Examples of the C1 to C6 haloalkylthio group include, but are not limited to, a fluoromethylthio group, a difluoromethylthio group, a trifluoromethylthio group, a chlorodifluoromethylthio group,
a 2-fluoroethylthio group, a 2-chloroethylthio group, a 2,2,2-trifluoroethylthio group, a pentafluoroethylthio group, a 3-fluoropropylthio group, a 3-chloropropylthio group, a 2,2,3,3,3-pentafluoropropylthio group, a heptafluoropropylthio group, a 2,2,2-trifluoro-1-trifluoromethylethylthio group,
a 4-fluorobutylthio group, a 2,2,3,3,4,4,4-heptafluorobutylthio group,
a 2,2,3,3,4,4,5,5,5-nonafluoropentylthio group,
a 2,2,3,3,4,4,5,5,6,6,6-undecafluorohexylthio group and the like.

The C1 to C6 haloalkylsulfinyl group means a (C1 to C6 haloalkyl)-SO— group, wherein the C1 to C6 haloalkyl group moiety has the same meaning as above.

Examples of the C1 to C6 haloalkylsulfinyl group include, but are not limited to,
a fluoromethylsulfinyl group, a difluoromethylsulfinyl group, a trifluoromethylsulfinyl group, a chlorodifluoromethylsulfinyl group,
a 2-fluoroethylsulfinyl group, a 2-chloroethylsulfinyl group, a 2,2,2-trifluoroethylsulfinyl group, a pentafluoroethylsulfinyl group,
a 3-fluoropropylsulfinyl group, a 3-chloropropylsulfinyl group, a 2,2,3,3,3-pentafluoropropylsulfinyl group, a heptafluoropropylsulfinyl group, a 2,2,2-trifluoro-1-trifluoromethylethylsulfinyl group,
a 4-fluorobutylsulfinyl group, a 2,2,3,3,4,4,4-heptafluorobutylsulfinyl group,
a 2,2,3,3,4,4,5,5,5-nonafluoropentylsulfinyl group,
a 2,2,3,3,4,4,5,5,6,6,6-undecafluorohexylsulfinyl group and the like.

The C1 to C6 haloalkylsulfonyl group means a (C1 to C6 haloalkyl)-SO$_2$— group, wherein the C1 to C6 haloalkyl group moiety has the same meaning as above.

Examples of the C1 to C6 haloalkylsulfonyl group include, but are not limited to,
a fluoromethylsulfonyl group, a difluoromethylsulfonyl group, a trifluoromethylsulfonyl group, a chlorodifluoromethylsulfonyl group,
a 2-fluoroethylsulfonyl group, a 2-chloroethylsulfonyl group, a 2,2,2-trifluoroethylsulfonyl group, a pentafluoroethylsulfonyl group,
a 3-fluoropropylsulfonyl group, a 3-chloropropylsulfonyl group, a 2,2,3,3,3-pentafluoropropylsulfonyl group, a heptafluoropropylsulfonyl group, a 2,2,2-trifluoro-1-trifluoromethylethylsulfonyl group,
a 4-fluorobutylsulfonyl group, a 2,2,3,3,4,4,4-heptafluorobutylsulfonyl group,
a 2,2,3,3,4,4,5,5,5-nonafluoropentylsulfonyl group,
a 2,2,3,3,4,4,5,5,6,6,6-undecafluorohexylsulfonyl group and the like.

Examples of the monoalkylamino group include, but are not limited to, a mono (C1 to C6 alkyl) amino group and the like.

The mono (C1 to C6 alkyl) amino group means a (C1 to C6 alkyl)-NH— group, wherein the C1 to C6 alkyl group moiety has the same meaning as defined above.

Specific examples of the mono (C1 to C6 alkyl) amino group include, but are not limited to, a methylamino group, an ethylamino group, a propylamino group, an isopropylamino group, a butylamino group, a pentylamino group, a hexylamino group and the like.

Examples of the dialkylamino group include, but are not limited to, a di (C1 to C6 alkyl) amino group and the like.

The di (C1 to C6 alkyl) amino group means a (C1 to C6 alkyl)$_2$N— group, wherein the C1 to C6 alkyl group moieties may be the same or different and have the same meaning as defined above.

Specific examples of the di (C1 to C6 alkyl) amino group include, but are not limited to, a dimethylamino group, a diethylamino group, a dipropylamino group, a dibutylamino group, a dipentylamino group, a dihexylamino group, a methylethylamino group, a methylhexylamino group and the like.

Examples of the acyl group include, but are not limited to,
a formyl group,
a C1 to C6 acyl group, a C2 to C6 acyl group,
a C1 to C4 acyl group, a C2 to C4 acyl group and the like.

The C1 to C6 acyl group is
a formyl group,
a straight chain or branched chain alkanoyl group having 2 to 6 carbon atoms (i.e., a C2 to C6 alkanoyl group), or
a straight chain or branched chain alkenoyl group having 2 to 6 carbon atoms (i.e., a C2 to C6 alkenoyl group).

The C1 to C6 acyl group is preferably
a formyl group or
a straight chain or branched chain alkanoyl group having 2 to 6 carbon atoms.

The C2 to C6 acyl group is
a straight chain or branched chain alkanoyl group having 2 to 6 carbon atoms (i.e., a C2 to C6 alkanoyl group) or
a straight chain or branched chain alkenoyl group having 2 to 6 carbon atoms (i.e., a C2 to C6 alkenoyl group).

The C2 to C6 acyl group is preferably
a straight chain or branched chain alkanoyl group having 2 to 6 carbon atoms.

The C1 to C4 acyl group is
a formyl group,
a straight chain or branched chain alkanoyl group having 2 to 4 carbon atoms (i.e., a C2 to C4 alkanoyl group), or
a straight chain or branched chain alkenoyl group having 2 to 4 carbon atoms (i.e., a C2 to C4 alkenoyl group).

The C1 to C4 acyl group is preferably
a formyl group or
a straight chain or branched chain alkanoyl group having 2 to 4 carbon atoms.

The C2 to C4 acyl group is
a straight chain or branched chain alkanoyl group having 2 to 4 carbon atoms (i.e., a C2 to C4 alkanoyl group) or
a straight chain or branched chain alkenoyl group having 2 to 4 carbon atoms (i.e., a C2 to C4 alkenoyl group).

The C2 to C4 acyl group is preferably
a straight chain or branched chain alkanoyl group having 2 to 4 carbon atoms.

Specific examples of the C2 to C6 alkanoyl group include, but are not limited to,
an acetyl group, a propionyl group, a butyryl group, an isobutyryl group,
a valeryl group, a 2-methylbutanoyl group, an isovaleryl group, a pivaloyl group,
a hexanoyl group and the like.

Specific examples of the C2 to C4 alkanoyl group include, but are not limited to, the appropriate examples among the above specific examples of the C2 to C6 alkanoyl group.

Specific examples of the C2 to C6 alkenoyl group include, but are not limited to,
an acryloyl group, a crotonoyl group, an isocrotonoyl group, a methacryloyl group and the like.

Specific examples of the C2 to C4 alkenoyl group include, but are not limited to, the appropriate examples among the above specific examples of the C2 to C6 alkenoyl group.

Examples of the acyloxy group include, but are not limited to,
a C1 to C6 acyloxy group, a C2 to C6 acyloxy group,
a C1 to C4 acyloxy group, a C2 to C4 acyloxy group and the like.

The C1 to C6 acyloxy group means a (C1 to C6 acyl)-O— group, wherein the C1 to C6 acyl group moiety has the same meaning as defined above.

Specific examples of the C1 to C6 acyloxy group include, but are not limited to,
a formyloxy group, an acetyloxy group, a propionyloxy group, a butyryloxy group,
an isobutyryloxy group,
a valeryloxy group, a 2-methylbutanoyloxy group, an isovaleryloxy group, a pivaloyloxy group, a hexanoyloxy group, an acryloyloxy group, a crotonoyloxy group, an isocrotonoyloxy group, a methacryloyloxy group and the like.

Preferable specific examples of the C1 to C6 acyloxy group include
a formyloxy group, an acetyloxy group, a propionyloxy group, a butyryloxy group,
an isobutyryloxy group,
a valeryloxy group, a 2-methylbutanoyloxy group, an isovaleryloxy group, a pivaloyloxy group,
a hexanoyloxy group and the like.

More preferable specific examples of the C1 to C6 acyloxy group include an acetyloxy group, a propionyloxy group, a butyryloxy group and an isobutyryloxy group.

Further preferable specific examples of the C1 to C6 acyloxy group include an acetyloxy group.

The C2 to C6 acyloxy group means a (C2 to C6 acyl)-O— group, wherein the C2 to C6 acyl group moiety has the same meaning as defined above.

Specific examples of the C2 to C6 acyloxy group include, but are not limited to, the appropriate examples among the above specific examples of the C1 to C6 acyloxy group.

Preferable specific examples of the C2 to C6 acyloxy group include the appropriate examples among the above preferable specific examples of the C1 to C6 acyloxy group.

More preferable specific examples of the C2 to C6 acyloxy group include the appropriate examples among the above more preferable specific examples of the C1 to C6 acyloxy group.

Further preferable specific examples of the C2 to C6 acyloxy group include the appropriate examples among the above further preferable specific examples of the C1 to C6 acyloxy group.

The C1 to C4 acyloxy group means a (C1 to C4 acyl)-O— group, wherein the C1 to C4 acyl group moiety has the same meaning as defined above.

Specific examples of the C1 to C4 acyloxy group include
a formyloxy group, an acetyloxy group, a propionyloxy group, a butyryloxy group,
an isobutyryloxy group,
an acryloyloxy group, a crotonoyloxy group, an isocrotonoyloxy group and a methacryloyloxy group.

Preferable specific examples of the C1 to C4 acyloxy group include a formyloxy group, an acetyloxy group, a propionyloxy group, a butyryloxy group and an isobutyryloxy group.

More preferable specific examples of the C1 to C4 acyloxy group include an acetyloxy group.

The C2 to C4 acyloxy group means a (C2 to C4 acyl)-O— group, wherein the C1 to C4 acyl group moiety has the same meaning as defined above.

Specific examples of the C1 to C4 acyloxy group include
an acetyloxy group, a propionyloxy group, a butyryloxy group, an isobutyryloxy group,
an acryloyloxy group, a crotonoyloxy group, an isocrotonoyloxy group and a methacryloyloxy group.

Preferable specific examples of the C1 to C4 acyloxy group include an acetyloxy group, a propionyloxy group, a butyryloxy group and an isobutyryloxy group.

More preferable specific examples of the C1 to C4 acyloxy group include an acetyloxy group.

Examples of the acylamino group include, but are not limited to, a C1 to C6 acylamino group and the like.

The C1 to C6 acylamino group means an amino group which is substituted with a C1 to C6 acyl group, wherein the C1 to C6 acyl group moiety has the same meaning as defined above.

Specific examples of the C1 to C6 acylamino group include, but are not limited to,
a formylamino group, an acetylamino group, a propionylamino group, an isopropionylamino group,
a butyrylamino group, an isobutyrylamino group, a valerylamino group, an isovalerylamino group, a pivaloylamino group,
a hexanoylamino group,
an acryloylamino group, a crotonoylamino group, a methacryloylamino group and the like.

Examples of the alkoxycarbonyl group include, but are not limited to, a C1 to C6 alkoxycarbonyl group and the like.

The C1 to C6 alkoxycarbonyl group means a (C1 to C6 alkyl)-O—C(=O)— group, wherein the C1 to C6 alkyl group moiety has the same meaning as defined above.

Specific examples of the C1 to C6 alkoxycarbonyl group include, but are not limited to,
a methoxycarbonyl group, an ethoxycarbonyl group, a propoxycarbonyl group, an isopropoxycarbonyl group,
a butoxycarbonyl group, a pentyloxycarbonyl group, a hexyloxycarbonyl group and the like.

Examples of the alkoxyimino group include, but are not limited to, a C1 to C6 alkoxyimino group and the like.

The C1 to C6 alkoxyimino group means a (C1 to C6 alkyl)-O—N= group, wherein the C1 to C6 alkyl group moiety has the same meaning as defined above.

Specific examples of the C1 to C6 alkoxyimino group include, but are not limited to,
a methoxyimino group, an ethoxyimino group, a propoxyimino group, an isopropoxyimino group,
a butoxyimino group, a pentyloxyimino group and a hexyloxyimino group.

Examples of the monoalkylaminocarbonyl group include, but are not limited to, a mono (C1 to C6 alkyl) aminocarbonyl group, a mono (C1 to C4 alkyl) aminocarbonyl group and the like.

The mono (C1 to C6 alkyl) aminocarbonyl group means a (C1 to C6 alkyl)-NH—C(=O)— group, wherein the C1 to C6 alkyl group moiety has the same meaning as defined above.

Specific examples of the mono (C1 to C6 alkyl) aminocarbonyl group include, but are not limited to, a N-methylaminocarbonyl group, a N-ethylaminocarbonyl group, a N-propylaminocarbonyl group, a N-isopropylaminocarbonyl group, a N-butylaminocarbonyl group, a N-pentylaminocarbonyl group, a N-hexylaminocarbonyl group and the like.

The mono (C1 to C4 alkyl) aminocarbonyl group means a (C1 to C4 alkyl)-NH—C(=O)— group, wherein the C1 to C4 alkyl group moiety has the same meaning as defined above.

Specific examples of the mono (C1 to C4 alkyl) aminocarbonyl group include, but are not limited to, the appropriate examples among the above specific examples of the mono (C1 to C6 alkyl) aminocarbonyl group.

Examples of the dialkylaminocarbonyl group include, but are not limited to, a di (C1 to C6 alkyl) aminocarbonyl group, a di (C1 to C4 alkyl) aminocarbonyl group and the like.

The di (C1 to C6 alkyl) aminocarbonyl group means a (C1 to C6 alkyl)$_2$N—C(=O)— group, wherein the C1 to C6 alkyl group moieties may be the same or different and have the same meaning as defined above.

Specific examples of the (C1 to C6 alkyl) aminocarbonyl group include, but are not limited to, a N,N-dimethylaminocarbonyl group, a N,N-diethylaminocarbonyl group, a N,N-dipropylaminocarbonyl group, a N,N-dibutylaminocarbonyl group, a N,N-dipentylaminocarbonyl group, a N,N-dihexylaminocarbonyl group, a N,N-methylethylaminocarbonyl group, a N,N-methylhexylaminocarbonyl group and the like.

The di (C1 to C4 alkyl) aminocarbonyl group means a (C1 to C4 alkyl)$_2$N—C(=O)— group, wherein the C1 to C4 alkyl group moieties may be the same or different and have the same meaning as defined above.

Specific examples of the di (C1 to C4 alkyl) aminocarbonyl group include, but are not limited to, the appropriate examples among the above specific examples of the di (C1 to C6 alkyl) aminocarbonyl group.

Examples of the aryl group include, but are not limited to, a C6 to C10 aryl group and the like.

The C6 to C10 aryl group means an aryl group having 6 to 10 carbon atoms.

Specific examples of the C6 to C10 aryl group are a phenyl group, a 1-naphthyl group and a 2-naphthyl group. The 1-naphthyl group is also referred to as a naphthalen-1-yl group. The 2-naphthyl group is also referred to as a naphthalen-2-yl group.

The C6 to C10 aryloxy group means a (C6 to C10 aryl)-O— group, wherein the C6 to C10 aryl group moiety has the same meaning as defined above.

Specific examples of the C6 to C10 aryloxy group are a phenoxy group, a naphthalen-1-yloxy group and a naphthalen-2-yloxy group.

Examples of the arylalkyl group include, but are not limited to, a C6 to C10 aryl C1 to C4 alkyl group, a C6 to C10 aryl C1 to C2 alkyl group, a phenyl C1 to C2 alkyl group and the like.

The arylalkyl group is also referred to as an aralkyl group.

The C6 to C10 aryl C1 to C4 alkyl group means a C1 to C4 alkyl group which is substituted with a C6 to C10 aryl group, wherein the C6 to 10 aryl group moiety and the C1 to C4 alkyl group moiety have the same meaning as defined above.

Specific examples of the C6 to C10 aryl C1 to C4 alkyl group include, but are not limited to, a benzyl group, a 1-phenylethyl group, a 2-phenylethyl group, a 3-phenylpropyl group, a 4-phenylbutyl group, a naphthalen-1-ylmethyl group, a naphthalen-2-ylmethyl group and the like.

The C6 to C10 aryl C1 to C2 alkyl group means a C1 to C2 alkyl group which is substituted with a C6 to 10 aryl group, wherein the C6 to 10 aryl group moiety and the C1 to C2 alkyl group moiety have the same meaning as defined above.

Specific examples of the C6 to C10 aryl C1 to C2 alkyl group include, but are not limited to, the appropriate examples among the above specific examples of the C6 to C10 aryl C1 to C4 alkyl group.

The phenyl C1 to C2 alkyl group means a C1 to C2 alkyl group which is substituted with a phenyl group, wherein the C1 to C2 alkyl group moiety has the same meaning as defined above.

Specific examples of the phenyl C1 to C2 alkyl group are the appropriate examples among the above specific examples of the C6 to C10 aryl C1 to C4 alkyl group.

In the present specification, the heterocyclic group means a cyclic group having one or more same or different heteroatoms (for example, a nitrogen atom, an oxygen atom and/or a sulfur atom) instead of one or more carbon atoms, which is aromatic or non-aromatic, and is monocyclic or multicyclic.

In one embodiment, examples of the heterocyclic group include, but are not limited to, a 3- to 14-membered (preferably 4- to 14-membered, more preferably 5- to 14-membered) heterocyclic group having 1 to 13 carbon atoms and 1 to 4 heteroatoms selected independently from a nitrogen atom, an oxygen atom and a sulfur atom, which is aromatic or non-aromatic, and is monocyclic, bicyclic or tricyclic.

In another embodiment, examples of the heterocyclic group include, but are not limited to, a 3- to 10-membered (preferably 4- to 10-membered, more preferably 5- to 10-membered, further preferably 5- to 7-membered) heterocyclic group having 1 to 9 carbon atoms and 1 to 4 heteroatoms selected independently from a nitrogen atom, an oxygen atom and a sulfur atom, which is aromatic or non-aromatic, and is monocyclic or bicyclic.

In yet another embodiment, examples of the heterocyclic group include, but are not limited to, a 4- to 8-membered (preferably 5- to 6-membered) heterocyclic group having 1 to 5 carbon atoms and 1 to 4 heteroatoms selected independently from a nitrogen atom, an oxygen atom and a sulfur atom, which is aromatic or non-aromatic, and is monocyclic.

Specific examples of the monocyclic heterocyclic group include, but are not limited to,
a pyrrolyl group, a furyl group, a thienyl group,
a pyrazolyl group, an imidazolyl group, an oxazolyl group, an isoxazolyl group, a thiazolyl group, an isothiazolyl group, a triazolyl group, an oxadiazolyl group (for example, a 1,2,4-oxadiazolyl group, a 1,2,5-oxadiazolyl group and the like), a thiadiazolyl group (for example, a 1,2,3-thiadiazolyl group, a 1,3,4-thiadiazolyl group and the like),
a tetrazolyl group,
a pyridyl group, a pyridazinyl group, a pyrimidyl group, a pyrazinyl group, a triazinyl group (for example, a 1,3,5-triazinyl group and the like),
a piperidinyl group, a piperazinyl group, a morpholinyl group and the like.

Specific examples of the bicyclic heterocyclic group include, but are not limited to,
an indolyl group, an isoindolyl group, an indolizinyl group, a benzofuryl group, a benzothienyl group, a benzimidazolyl group, an indazolyl group, a benzoxazolyl group, a benzisoxazolyl group, a benzothiazolyl group, a benzisothiazolyl group,
a quinolyl group, an isoquinolyl group, a quinolizinyl group, a cinnolinyl group, a quinoxalinyl group, a quinazolinyl group, a phthalazinyl group,
a naphthyridinyl group (for example, a 1,5-naphthyridinyl group, a 1,6-naphthyridinyl group, a 1,7-naphthyridinyl group, a 1,8-naphthyridinyl group, a 2,6-naphthyridinyl group and a 2,7-naphthyridinyl group),
an indolinyl group, an isoindolinyl group,
a chromanyl group, an isochromanyl group, a cumarinyl group, an isocumarinyl group, a benzotriazinyl group, a tetrahydroisoquinolinyl group, a pyridopyridyl group, a pyridopyrazyl group, an isobenzothienyl group, a benzotetrahydrofuryl group, a benzotetrahydrothienyl group, an isobenzotetrahydrofuryl group, an isobenzotetrahydrothienyl group, a purinyl group, a benzodioxolyl group, a phenoxazinyl group, a phenothiazinyl group, a pteridinyl group, an oxazolopyridyl group, an imidazopyridyl group, an imidazothiazolyl group, a dihydrobenzisoxazinyl group, a benzoxazinyl group, a benzisoxazinyl group, a dihydrobenzisothiazinyl group, a benzopyranyl group, a benzothiopyranyl group, a chromonyl group, a chromanonyl group, a pyridyl-N-oxide tetrahydroquinolinyl group, a dihydroquinolinyl group, a dihydroquinolinoyl group, a dihydroisoquinolinoyl group, a dihydrocumarinyl group, a dihydroisocumarinyl group, an isoindolinonyl group, a benzodioxanyl group, a benzoxazolinonyl group and the like.

Specific examples of the tricyclic heterocyclic group include, but are not limited to, a carbazolyl group, a β-carbolinyl group, an acridinyl group, a phenanthridinyl group, a phenanthrolinyl group (for example, a 4,7-phenanthrolinyl group, a 1,10-phenanthrolinyl group and the like) and a phenazinyl group.

Preferable specific examples of the heterocyclic group include
a pyrrolyl group, a furyl group, a thienyl group,
a pyrazolyl group, an imidazolyl group, an oxazolyl group, an isoxazolyl group, a thiazolyl group, an isothiazolyl group, a triazolyl group, an oxadiazolyl group, a thiadiazolyl group, a tetrazolyl group,
a pyridyl group, a pyridazinyl group, a pyrimidyl group, a pyrazinyl group, a triazinyl group,
an indolyl group, a benzofuryl group, a benzothienyl group, a benzimidazolyl group,
an indazolyl group, a benzoxazolyl group, a benzisoxazolyl group, a benzothiazolyl group, a benzisothiazolyl group,
a quinolyl group and an isoquinolyl group.

More preferable specific examples of the heterocyclic group include
a pyrrolyl group, a thienyl group,
a pyrazolyl group, an imidazolyl group, an oxazolyl group, an isoxazolyl group, a thiazolyl group, an isothiazolyl group, a triazolyl group,
a pyridyl group, a pyridazinyl group, a pyrimidyl group, a pyrazinyl group and a triazinyl group.

Further preferable specific examples of the heterocyclic group include a thienyl group, a pyrazolyl group, an imidazolyl group, a thiazolyl group, an isothiazolyl group, a pyridyl group and a pyrimidyl group.

Further preferable specific examples of the heterocyclic group include a thienyl group, a pyrazolyl group and a pyridyl group.

Particularly preferable specific examples of the heterocyclic group include a pyrazolyl group and a pyridyl group.

In this context, there are no particular limitations on the substitution position. That is, the heterocyclic group includes all positional isomers thereof. For example, when the heterocyclic group is a pyridyl group, the pyridyl group includes a 2-pyridyl group, a 3-pyridyl group and a 4-pyridyl group.

The heterocyclic group as defined or exemplified above may include a non-fused cyclic group (for example, a monocyclic group or a spirocyclic group) and a fused cyclic group, when possible.

The heterocyclic group as defined or exemplified above may be unsaturated, partially saturated or saturated, when possible.

The heterocyclic group as defined or exemplified above is also referred to herein as a heterocyclyl group.

When the heteroatom in the heterocyclic group as defined or exemplified above is a nitrogen atom, the nitrogen atom may be a N-oxide group.

When the heteroatom in the heterocyclic group as defined or exemplified above is a sulfur atom, the sulfur atom may be a sulfinyl group (—SO— group) or a sulfonyl group (—SO$_2$— group).

In the present specification, the heterocyclic ring is a ring which corresponds to the heterocyclic group as defined or exemplified above.

Herein, there are no particular limitations on the "substituents" in the phrase "may have one or more substituents", as long as they are chemically acceptable and allow the effects of the present invention to be demonstrated.

Herein, examples of "one or more substituents" in the phrase "may have one or more substituents" include, but are not limited to, one or more substituents (preferably 1 to 4 substituents) selected independently from Substituent Group (a).

Substituent Group (a) is a group comprising
a halogen atom, a nitro group, a cyano group,
a C1 to C6 alkyl group (preferably a C1 to C4 alkyl group),
a C2 to C6 alkenyl group (preferably a C2 to C4 alkenyl group),
a C2 to C6 alkynyl group (preferably a C2 to C4 alkynyl group),
a C3 to C8 cycloalkyl group (preferably a C3 to C6 cycloalkyl group),
a C1 to C6 haloalkyl group (preferably a C1 to C4 haloalkyl group),
a hydroxy group,
a C1 to C6 alkoxy group (preferably a C1 to C4 alkoxy group),
a C1 to C6 haloalkoxy group (preferably a C1 to C4 haloalkoxy group),
a C1 to C6 alkylthio group (preferably a C1 to C4 alkylthio group), a C1 to C6 alkylsulfinyl group (preferably a C1 to C4 alkylsulfinyl group), a C1 to C6 alkylsulfonyl group (preferably a C1 to C4 alkylsulfonyl group),
a C1 to C6 haloalkylthio group (preferably a C1 to C4 haloalkylthio group), a C1 to C6 haloalkylsulfinyl group (preferably a C1 to C4 haloalkylsulfinyl group), a C1 to C6 haloalkylsulfonyl group (preferably a C1 to C4 haloalkylsulfonyl group),
an amino group, a mono (C1 to C6 alkyl) amino group (preferably a mono (C1 to C4 alkyl) amino group), a di (C1 to C6 alkyl) amino group (preferably a di (C1 to C4 alkyl) amino group),
a C1 to C6 acylamino group (preferably a C1 to C4 acylamino group),
a formyl group, a C2 to C6 acyl group (preferably a C2 to C4 acyl group),
a C1 to C6 alkoxycarbonyl group (preferably a C1 to C4 alkoxycarbonyl group),
a mono (C1 to C6 alkyl) aminocarbonyl group (preferably a mono (C1 to C4 alkyl) aminocarbonyl group), a di (C1 to C6 alkyl) aminocarbonyl group (preferably a di (C1 to C4 alkyl) aminocarbonyl group),
a C6 to C10 aryl group (preferably a phenyl group),
a C6 to C10 aryloxy group (preferably a phenoxy group),
a C6 to C10 aryl C1 to C4 alkyl group (preferably a phenyl C1 to C2 alkyl group), and
a heterocyclic group, wherein the heterocyclic group is a 5- to 10-membered heterocyclic group having 1 to 9 carbon atoms and 1 to 4 heteroatoms selected independently from a nitrogen atom, an oxygen atom and a sulfur atom and the like.

In addition, one or more substituents (preferably one to four substituents) selected independently from Substituent Group (a) may each independently have one or more substituents (preferably one to four substituents) selected independently from Substituent Group (b).

In this context, Substituent Group (b) is the same as Substituent Group (a).

Examples of the monovalent anion include, but are not limited to, halide ions, borate ions, phosphate ions, antimonate ions, carboxylate ions, sulfonate ions, sulfate ions, carbonate ions, nitrate ions, amide ions and the like.

Examples of the halide ions include, but are not limited to, $F^-$ (fluoride ion), $Cl^-$ (chloride ion), $Br^-$ (bromide ion), $I^-$ (iodide ion) and the like.

Examples of the borate ions include, but are not limited to, $BF_4^-$ (tetrafluoroborate ion), $C_6H_5BF_3^-$ (phenyl trifluoroborate ion) and the like.

Examples of the phosphate ions include, but are not limited to, $PF_6^-$ (hexafluorophosphate ion) and the like.

Examples of the antimonate ions include, but are not limited to, $SbF_6^-$ (hexafluoroantimonate ion) and the like.

Examples of the carboxylate ions include, but are not limited to, $CH_3CO_2^-$ (acetate ion), $CF_3CO_2^-$ (trifluoroacetate ion), $C_2F_5CO_2^-$ (pentafluoropropionate ion) and the like.

Examples of the sulfonate ions include, but are not limited to, $CH_3SO_3^-$ (methanesulfonate ion), $C_2H_5SO_3^-$ (ethanesulfonate ion), $CF_3SO_3^-$ (trifluoromethanesulfonate ion), $C_6H_5SO_3^-$ (benzenesulfonate ion), 4-$CH_3$—$C_6H_4SO_3^-$ (p-toluenesulfonate ion), 4-Cl—$C_6H_4SO_3^-$ (p-chlorobenzenesulfonate ion), 4-$NO_2$—$C_6H_4SO_3^-$ (p-nitrobenzenesulfonate ion) and the like.

Examples of the sulfate ions include, but are not limited to, $HOSO_3^-$ (bisulfate ion), $CH_3OSO_3^-$ (methyl sulfate ion), $C_2H_5OSO_3^-$ (ethyl sulfate ion), $C_3H_7OSO_3^-$ (propyl sulfate ion), iso-$C_3H_7OSO_3^-$ (isopropyl sulfate ion), $C_4H_9OSO_3^-$ (butyl sulfate ion), $C_6H_5OSO_3^-$ (phenyl sulfate ion) and the like.

Examples of the carbonate ions include, but are not limited to, $HCO_3^-$ (bicarbonate ion), $CH_3OCO_2^-$ (methyl carbonate ion) and the like.

Examples of the nitrate ions include, but are not limited to, $NO_3^-$ (nitrate ion) and the like.

Examples of the amide ions include, but are not limited to, $(CN)_2N^-$ (dicyanamide ion or dicyanoamine ion), $(CF_3SO_2)_2N^-$ (bis(trifluoromethylsulfonyl)amide anion) and the like.

Examples of the inorganic bases include, but are not limited to,
alkali metal hydroxides, alkaline earth metal hydroxides,
alkali metal carbonates, alkaline earth metal carbonates,
alkali metal bicarbonates, alkaline earth metal bicarbonates,
alkali metal phosphates, alkaline earth metal phosphates,
alkali metal biphosphates, alkaline earth metal biphosphates,
alkali metal hydrides, alkaline earth metal hydrides and the like.

Examples of the alkali metal hydroxides include lithium hydroxide, sodium hydroxide, potassium hydroxide and the like.

Examples of the alkaline earth metal hydroxides include magnesium hydroxide, calcium hydroxide, barium hydroxide and the like.

Examples of the alkali metal carbonates include lithium carbonate, sodium carbonate, potassium carbonate, cesium carbonate and the like.

Examples of the alkaline earth metal carbonates include magnesium carbonate, calcium carbonate, barium carbonate and the like.

Examples of the alkali metal bicarbonates include lithium bicarbonate, sodium bicarbonate, potassium bicarbonate, cesium bicarbonate and the like.

Examples of the alkaline earth metal bicarbonates include magnesium bicarbonate, calcium bicarbonate, barium bicarbonate and the like.

Examples of the phosphate include alkali metal phosphates, alkaline earth metal phosphates and the like.

Examples of the alkali metal phosphates include sodium phosphate, potassium phosphate and the like.

Examples of the alkaline earth metal phosphates include calcium phosphate and the like.

Examples of the alkali metal biphosphates include sodium biphosphate, potassium biphosphate and the like.

Examples of the alkaline earth metal biphosphates include calcium biphosphate and the like.

Examples of the metal hydrides include alkali metal hydrides, alkaline earth metal hydrides and the like.

Examples of the alkali metal hydrides include lithium hydride, sodium hydride, potassium hydride and the like.

Examples of the alkaline earth metal hydrides include calcium hydride and the like.

Examples of the organic bases include, but are not limited to, pyridines, quinolines, isoquinolines, tertiary amines, secondary amines, primary amines, aromatic amines, cyclic amines and the like.

Examples of the pyridines include pyridine, 4-(dimethylamino)-pyridine, 4-pyrrolidinopyridine, 2,6-lutidine and the like.

Examples of the quinolines include quinoline, 2-methylquinoline, 3-methylquinoline, 4-methylquinoline and the like.

Examples of the isoquinolines include isoquinoline, 1-methylisoquinoline and the like.

Examples of the tertiary amines include trimethylamine, triethylamine, tributylamine, diisopropylethylamine, triisopropylamine and the like.

Examples of the secondary amines include diethylamine, dipropylamine, diisopropylamine and the like.

Examples of the primary amines include propylamine, butylamine and the like.

Examples of the aromatic amines include aniline, N,N-diethylaniline, N,N-dimethylaniline and the like.

Examples of the cyclic amines include pyrrolidine, piperidine, morpholine, N-methylmorpholine, piperazine, 1,8-diazabicyclo[5.4.0]-7-undec-7-ene (DBU), 1,5-diazabicyclo[4.3.0]non-5-ene (DBN), 1,4-diazabicyclo[2.2.2]octane (DABCO) and the like.

Examples of the metal alkoxide include alkali metal alkoxides, alkaline earth metal alkoxides and the like.

Examples of the alkali metal alkoxides include sodium methoxide, sodium ethoxide, sodium tert-butoxide, potassium tert-butoxide and the like.

Examples of the alkaline earth metal alkoxides include magnesium ethoxide and the like.

Examples of the carboxylate include carboxylic acid alkali metal salts, carboxylic acid alkaline earth metal salts and the like.

Examples of the carboxylic acid alkali metal salts include formic acid alkali metal salts (for example, sodium formate, potassium formate and the like), acetic acid alkali metal salts (for example, lithium acetate, sodium acetate, potassium acetate and the like), propionic acid alkali metal salts (for example, sodium propionate, potassium propionate and the like) and the like.

Examples of the carboxylic acid alkaline earth metal salts include acetic acid alkaline earth metal salts (for example, magnesium acetate, calcium acetate and the like), propionic acid alkaline earth metal salts (for example, magnesium propionate, calcium propionate and the like) and the like.

Examples of the cyanide include alkali metal cyanides and the like.

Examples of the alkali metal cyanides include potassium cyanide, sodium cyanide and the like.

Examples of the fluoride include alkali metal fluorides, quaternary ammonium fluorides and the like.

Examples of the alkali metal fluorides include sodium fluoride, potassium fluoride and the like.

Examples of the quaternary ammonium fluorides include tetrabutylammonium fluoride and the like.

Examples of the silanol salt include alkali metal silanolates and the like.

Examples of the alkali metal silanolates include sodium trimethyl silanolate, potassium trimethyl silanolate and the like.

Examples of the amides include N,N-dimethylformamide (DMF), N,N-diethylformamide, N,N-dimethylacetamide (DMAC), N,N-diethylacetamide, N-methylpyrrolidone (NMP) and the like.

Examples of the alkyl ureas include tetramethyl urea, N,N'-dimethylimidazolidinone (DMI) and the like.

Examples of the sulfoxides include dimethyl sulfoxide (DMSO) and the like.

Examples of the sulfones include sulfolane, dimethyl sulfone and the like.

Examples of the ethers include tetrahydrofuran (THF), 2-methyltetrahydrofuran, 1,4-dioxane, diethyl ether, dipropyl ether, diisopropyl ether, dibutyl ether, di-tert-butyl ether, cyclopentyl methyl ether (CPME), methyl tert-butyl ether, 1,2-dimethoxyethane (DME), diglyme, triglyme, diphenyl ether and the like.

Examples of the ketones include acetone, ethyl methyl ketone, isopropyl methyl ketone, isobutyl methyl ketone (MIBK) cyclohexanone and the like.

Examples of the carboxylic acid esters include methyl acetate, ethyl acetate, propyl acetate, butyl acetate and the like.

Examples of the nitriles include acetonitrile and the like.

Examples of the alcohols include methanol, ethanol, propanol, 2-propanol, butanol, ethylene glycol and the like.

Examples of the carboxylic acids include formic acid, acetic acid, propionic acid and the like.

Examples of the aromatic hydrocarbon derivatives include
benzene, toluene, xylene, trimethylbenzene, methylnaphthalene, dimethylnaphthalene, chlorobenzene, dichlorobenzene, trichlorobenzene, nitrobenzene and the like
preferably toluene, xylene, chlorobenzene and dichlorobenzene,
more preferably toluene, xylene and chlorobenzene,
further preferably toluene.

In this context, a compound having isomers includes all of the isomers and any mixture thereof in any ratio.

For example, xylene includes o-xylene, m-xylene, p-xylene and any mixture thereof in any ratio.

For example, dichlorobenzene includes o-dichlorobenzene, m-dichlorobenzene, p-dichlorobenzene and any mixture thereof in any ratio.

Examples of the aromatic heterocyclic rings as solvents include pyridine and the like.

Examples of the aliphatic hydrocarbons include
hexane, octane, decane, hexadecane, isohexadecane, cyclohexane, ethylcyclohexane, decalin, methyldecalin and the like.

Examples of the halogenated aliphatic hydrocarbons include dichloromethane, chloroform, carbon tetrachloride, 1,2-dichloroethane and the like,
preferably dichloromethane.

(Fluoroalkylating Agent Represented by General Formula (1))

The fluoroalkylating agent represented by the general formula (1) of the present invention will be described below. The compound represented by the general formula (1A) is a novel compound. The description about the compound represented by the general formula (1A) conforms to the description about the fluoroalkylating agent represented by the general formula (1) except for the provisos as to $R^1$, $R^2$, $R^3$, $Y^1$, $Y^2$, $Y^3$, $Y^4$ and $X^-$.

The fluoroalkylating agent of the present invention is a compound represented by the general formula (1):

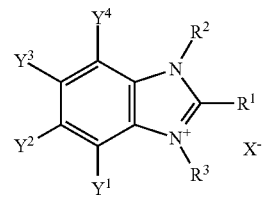

(1)

wherein $R^1$, $R^2$, $R^3$, $Y^1$, $Y^2$, $Y^3$, $Y^4$ and $X^-$ are as described below.

The compound represented by the general formula (1) can have tautomers shown below. Both of these and a mixture thereof are encompassed in the scope of the present invention. That is, the compound represented by the following general formula (1) is equivalent to the compound represented by the following general formula (1').

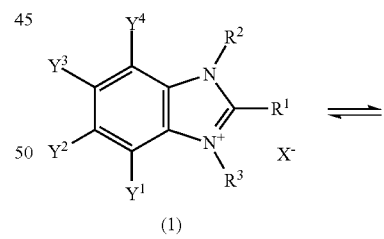

(1)

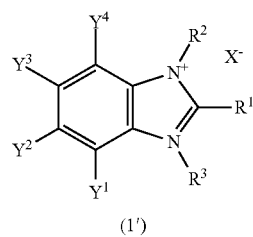

(1')

wherein $R^1$, $R^2$, $R^3$, $Y^1$, $Y^2$, $Y^3$, $Y^4$ and $X^-$ are as described below.

In the present specification, the numbers indicating the positions of substituents are as follows.

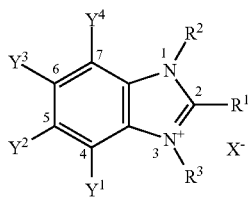

The present invention also includes a compound of the present invention in any isomeric form and in any isomeric mixture.

Examples of $R^1$ in the general formula (1) of the present invention include, but are not limited to, a C1 to C8 fluoroalkyl group.

From the viewpoints of usefulness of the fluoroalkylating agent represented by the general formula (1), economic efficiency and the like, preferable examples of $R^1$ include a C1 to C8 perfluoroalkyl group,
more preferably a C1 to C4 perfluoroalkyl group,
further preferably a trifluoromethyl group and a pentafluoroethyl group, particularly preferably a trifluoromethyl group.

Examples of $R^2$ and $R^3$ in the general formula (1) of the present invention include, but are not limited to,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents, and
a C6 to C10 aryl group which may have one or more substituents. In this context, $R^2$ and $R^3$ may be the same or different.

From the viewpoints of usefulness of the fluoroalkylating agent represented by the general formula (1), economic efficiency and the like, preferable examples of $R^2$ and $R^3$ include
a C1 to C6 alkyl group,
a phenyl group, wherein the phenyl group may have 1 to 5 substituents selected independently from a halogen atom, a nitro group, a cyano group, a C1 to C6 alkyl group, a C1 to C6 haloalkyl group, a C2 to C6 acyl group and a C1 to C6 alkoxycarbonyl group, and
a phenyl C1 to C2 alkyl group, wherein the phenyl group moiety may have 1 to 5 substituents selected independently from a halogen atom, a C1 to C6 alkyl group and
a C1 to C6 haloalkyl group. In this context, $R^2$ and $R^3$ may be the same or different.

More preferable examples of $R^2$ and $R^3$ include a C1 to C4 alkyl group and a phenyl group. In this context, $R^2$ and $R^3$ may be the same or different.

Further preferable examples of $R^2$ and $R^3$ include a methyl group, an ethyl group and a phenyl group. In this context, $R^2$ and $R^3$ may be the same or different.

Particularly preferable examples of $R^2$ and $R^3$ include a methyl group. In this context, $R^2$ and $R^3$ may be the same or different.

Examples of $Y^1$, $Y^2$, $Y^3$ and $Y^4$ in the general formula (1) of the present invention include, but are not limited to,
a hydrogen atom, a halogen atom, a nitro group, a cyano group,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a hydroxy group,
a C1 to C6 alkoxy group,
a C1 to C6 alkylthio group, a C1 to C6 alkylsulfinyl group, a C1 to C6 alkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group,
a C6 to C10 aryl group which may have one or more substituents, and
a heterocyclic group which may have one or more substituents, wherein the heterocyclic group is a 5- to 10-membered heterocyclic group having 1 to 9 carbon atoms and 1 to 4 heteroatoms selected independently from a nitrogen atom, an oxygen atom and a sulfur atom, and
a 4- to 8-membered carbocyclic ring or a 4- to 8-membered heterocyclic ring having 1 to 4 heteroatoms selected independently from an oxygen atom, a sulfur atom and a nitrogen atom, which is formed by two adjacent substituents of $Y^1$ and $Y^2$, $Y^2$ and $Y^3$, or $Y^3$ and $Y^4$, together with carbon atoms to which these substituents are attached, wherein the formed ring may have one or more substituents.

From the viewpoints of usefulness of the fluoroalkylating agent represented by the general formula (1), economic efficiency and the like, preferable examples of $Y^1$, $Y^2$, $Y^3$ and $Y^4$ include
a hydrogen atom, a halogen atom, a nitro group, a cyano group,
a C1 to C12 alkyl group, a C1 to C6 haloalkyl group,
a C1 to C6 alkylthio group, a C1 to C6 alkylsulfinyl group, a C1 to C6 alkylsulfonyl group,
a C2 to C6 acyl group,
a C1 to C6 alkoxycarbonyl group,
a phenyl group, and
a pyridyl group. In this context, $Y^1$, $Y^2$, $Y^3$ and $Y^4$ may be the same or different.

More preferable examples of $Y$, $Y^2$, $Y^3$ and $Y^4$ include a hydrogen atom, a halogen atom, a nitro group, a cyano group, a C1 to C4 alkyl group and a C1 to C4 haloalkyl group. In this context, $Y^1$, $Y^2$, $Y^3$ and $Y^4$ may be the same or different.

Further preferable examples of $Y^1$, $Y^2$, $Y^3$ and $Y^4$ include a hydrogen atom, a chlorine atom and a nitro group. In this context, $Y^1$, $Y^2$, $Y^3$ and $Y^4$ may be the same or different.

Particularly preferable examples of $Y^1$, $Y^2$, $Y^3$ and $Y^4$ include
a combination in which $Y^1$, $Y^2$, $Y^3$ and $Y^4$ are each a hydrogen atom;
a combination in which $Y^1$, $Y^3$ and $Y^4$ are each a hydrogen atom, and $Y^2$ is a chlorine atom;
a combination in which $Y^1$, $Y^3$ and $Y^4$ are each a hydrogen atom, and $Y^2$ is a nitro group; and
a combination in which $Y^1$, $Y^2$, $Y^3$ and $Y^4$ are each a chlorine atom.

Examples of $X^-$ in the general formula (1) of the present invention include, but are not limited to, a monovalent anion.

From the viewpoints of usefulness of the fluoroalkylating agent represented by the general formula (1), economic efficiency and the like, preferable examples of $X^-$ include halide ions, borate ions, phosphate ions, antimonate ions, carboxylate ions, sulfonate ions, sulfate ions, carbonate ions, nitrate ions and amide ions.

More preferable examples of $X^-$ include
$F^-$, $Cl^-$, $Br^-$, $I^-$,
$BF_4^-$, $C_6H_5BF_3^-$,
$PF_6^-$,
$SbF_6^-$,
$CH_3CO_2^-$, $CF_3CO_2^-$, $C_2F_5CO_2^-$,
$CH_3SO_3^-$, $C_2H_5SO_3^-$, $CF_3SO_3^-$, $C_6H_5SO_3^-$, 4-$CH_3$—$C_6H_4SO_3^-$, 4-Cl—$C_6H_4SO_3^-$, 4-$NO_2$—$C_6H_4SO_3^-$,
$HOSO_3^-$, $CH_3OSO_3^-$, $C_2H_5OSO_3^-$, $C_3H_7OSO_3^-$, iso—$C_3H_7OSO_3^-$, $C_4H_9OSO_3^-$,
$C_6H_5OSO_3^-$,
$HCO_3^-$, $CH_3OCO_2^-$
$NO_3^-$,
$(CN)_2N^-$ and $(CF_3SO_2)_2N^-$.

Further preferable examples of $X^-$ include
$F^-$, $Cl^-$, $Br^-$, $I^-$,
$BF_4^-$,
$CH_3CO_2^-$, $CF_3CO_2^-$,
$CH_3SO_3^-$, $CF_3SO_3^-$,
$HOSO_3^-$, $CH_3OSO_3^-$ and $C_2H_5OSO_3^-$.

Further preferable examples of $X^-$ include
$Cl^-$, $Br^-$, $I^-$,
$BF_4^-$,
$CF_3SO_3^-$,
$CH_3OSO_3^-$ and $C_2H_5OSO_3^-$.

Further preferable examples of $X^-$ include
$I^-$,
$BF_4^-$,
$CF_3SO_3^-$,
$CH_3OSO_3^-$ and $C_2H_5OSO_3^-$.

Particularly preferable examples of $X^-$ include $CH_3OSO_3^-$.

In one embodiment, specific examples of the compound represented by the general formula (1) as a fluoroalkylating agent include, but are not limited to, compounds shown in Tables 1 to 18 below. The compound numbers in the following Tables 1 to 18 are referred to herein.

TABLE 1

(1)

| Compound No. | $Y^1$ | $Y^2$ | $Y^3$ | $Y^4$ | $R^1$ | $R^2$ | $R^3$ | $X^-$ |
|---|---|---|---|---|---|---|---|---|
| 1-1 | H | H | H | H | $CF_3$ | Me | Me | $F^-$ |
| 1-2 | H | H | H | H | $CF_3$ | Me | Me | $Cl^-$ |
| 1-3 | H | H | H | H | $CF_3$ | Me | Me | $Br^-$ |
| 1-4 | H | H | H | H | $CF_3$ | Me | Me | $I^-$ |
| 1-5 | H | H | H | H | $CF_3$ | Me | Me | $BF_4^-$ |
| 1-6 | H | H | H | H | $CF_3$ | Me | Me | $PhBF_3^-$ |
| 1-7 | H | H | H | H | $CF_3$ | Me | Me | $PF_6^-$ |
| 1-8 | H | H | H | H | $CF_3$ | Me | Me | $SbF_6^-$ |
| 1-9 | H | H | H | H | $CF_3$ | Me | Me | $CH_3CO_2^-$ |
| 1-10 | H | H | H | H | $CF_3$ | Me | Me | $CF_3CO_2^-$ |
| 1-11 | H | H | H | H | $CF_3$ | Me | Me | $C_2F_5CO_2^-$ |
| 1-12 | H | H | H | H | $CF_3$ | Me | Me | $CH_3SO_3^-$ |
| 1-13 | H | H | H | H | $CF_3$ | Me | Me | $C_2H_5SO_3^-$ |
| 1-14 | H | H | H | H | $CF_3$ | Me | Me | $CF_3SO_3^-$ |

TABLE 1-continued (1)

| Compound No. | $Y^1$ | $Y^2$ | $Y^3$ | $Y^4$ | $R^1$ | $R^2$ | $R^3$ | $X^-$ |
|---|---|---|---|---|---|---|---|---|
| 1-15 | H | H | H | H | $CF_3$ | Me | Me | $PhSO_3^-$ |
| 1-16 | H | H | H | H | $CF_3$ | Me | Me | 4-MePHSO$_3^-$ |
| 1-17 | H | H | H | H | $CF_3$ | Me | Me | 4-NO$_2$PHSO$_3^-$ |
| 1-18 | H | H | H | H | $CF_3$ | Me | Me | $HOSO_3^-$ |
| 1-19 | H | H | H | H | $CF_3$ | Me | Me | $MeOSO_3^-$ |
| 1-20 | H | H | H | H | $CF_3$ | Me | Me | $EtOSO_3^-$ |
| 1-21 | H | H | H | H | $CF_3$ | Me | Me | $PhOSO_3^-$ |
| 1-22 | H | H | H | H | $CF_3$ | Me | Me | $HCO_3^-$ |
| 1-23 | H | H | H | H | $CF_3$ | Me | Me | $CH_3OCO_2^-$ |
| 1-24 | H | H | H | H | $CF_3$ | Me | Me | $NO_3^-$ |
| 1-25 | H | H | H | H | $CF_3$ | Me | Me | $(CN)_2N^-$ |
| 1-26 | H | H | H | H | $CF_3$ | Me | Me | $(CF_3SO_2)_2N^-$ |
| 1-27 | H | H | H | H | $CF_3$ | Me | Et | $I^-$ |
| 1-28 | H | H | H | H | $CF_3$ | Me | Et | $BF_4^-$ |
| 1-29 | H | H | H | H | $CF_3$ | Me | Et | $CF_3CO_2^-$ |
| 1-30 | H | H | H | H | $CF_3$ | Me | Et | $CF_3SO_3^-$ |
| 1-31 | H | H | H | H | $CF_3$ | Me | Et | $MeOSO_3^-$ |
| 1-32 | H | H | H | H | $CF_3$ | Me | Et | $EtOSO_3^-$ |
| 1-33 | H | H | H | H | $CF_3$ | Me | Et | $HOSO_3^-$ |

TABLE 2

| Compound No. | $Y^1$ | $Y^2$ | $Y^3$ | $Y^4$ | $R^1$ | $R^2$ | $R^3$ | $X^-$ |
|---|---|---|---|---|---|---|---|---|
| 1-34 | H | H | H | H | $CF_3$ | Me | i-Pr | $I^-$ |
| 1-35 | H | H | H | H | $CF_3$ | Me | i-Pr | $BF_4^-$ |
| 1-36 | H | H | H | H | $CF_3$ | Me | i-Pr | $CF_3CO_2^-$ |
| 1-37 | H | H | H | H | $CF_3$ | Me | i-Pr | $CF_3SO_3^-$ |
| 1-38 | H | H | H | H | $CF_3$ | Me | i-Pr | $MeOSO_3^-$ |
| 1-39 | H | H | H | H | $CF_3$ | Me | i-Pr | i-PrOSO$_3^-$ |
| 1-40 | H | H | H | H | $CF_3$ | Me | i-Pr | $HOSO_3^-$ |
| 1-41 | H | H | H | H | $CF_3$ | Me |  | $CH_2CH_2CH_2SO_3^-$ |
| 1-42 | H | H | H | H | $CF_3$ | Et | Et | $I^-$ |
| 1-43 | H | H | H | H | $CF_3$ | Et | Et | $BF_4^-$ |
| 1-44 | H | H | H | H | $CF_3$ | Et | Et | $CF_3CO_2^-$ |
| 1-45 | H | H | H | H | $CF_3$ | Et | Et | $CF_3SO_3^-$ |
| 1-46 | H | H | H | H | $CF_3$ | Et | Et | $MeOSO_3^-$ |
| 1-47 | H | H | H | H | $CF_3$ | Et | Et | $EtOSO_4^-$ |
| 1-48 | H | H | H | H | $CF_3$ | Et | Et | $HOSO_3^-$ |
| 1-49 | H | H | H | H | $CF_3$ | i-Pr | i-Pr | $I^-$ |
| 1-50 | H | H | H | H | $CF_3$ | i-Pr | i-Pr | $BF_4^-$ |
| 1-51 | H | H | H | H | $CF_3$ | i-Pr | i-Pr | $CF_3CO_2^-$ |
| 1-52 | H | H | H | H | $CF_3$ | i-Pr | i-Pr | $CF_3SO_3^-$ |
| 1-53 | H | H | H | H | $CF_3$ | i-Pr | i-Pr | $MeOSO_3^-$ |
| 1-54 | H | H | H | H | $CF_3$ | i-Pr | i-Pr | i-PrSO$_4^-$ |
| 1-55 | H | H | H | H | $CF_3$ | i-Pr | i-Pr | $HOSO_3^-$ |
| 1-56 | H | H | H | H | $CF_3$ | Bu | Bu | $I^-$ |
| 1-57 | H | H | H | H | $CF_3$ | Bu | Bu | $BF_4^-$ |
| 1-58 | H | H | H | H | $CF_3$ | Bu | Bu | $CF_3CO_2^-$ |
| 1-59 | H | H | H | H | $CF_3$ | Bu | Bu | $CF_3SO_3^-$ |
| 1-60 | H | H | H | H | $CF_3$ | Bu | Bu | $MeOSO_3^-$ |
| 1-61 | H | H | H | H | $CF_3$ | Bu | Bu | $BuOSO_3^-$ |
| 1-62 | H | H | H | H | $CF_3$ | Bu | Bu | $HOSO_3^-$ |
| 1-63 | H | H | H | H | $CF_3$ | Pen | Me | $MeOSO_3^-$ |
| 1-64 | H | H | H | H | $CF_3$ | Hex | Me | $MeOSO_3^-$ |
| 1-65 | H | H | H | H | $CF_3$ | $CH_2CONMe_2$ | Me | $I^-$ |
| 1-66 | H | H | H | H | $CF_3$ | $CH_2CONMe_2$ | Me | $BF_4^-$ |
| 1-67 | H | H | H | H | $CF_3$ | $CH_2CONMe_2$ | Me | $CF_3CO_2^-$ |
| 1-68 | H | H | H | H | $CF_3$ | $CH_2CONMe_2$ | Me | $CF_3SO_3^-$ |
| 1-69 | H | H | H | H | $CF_3$ | $CH_2CONMe_2$ | Me | $MeOSO_3^-$ |

TABLE 2-continued

| Compound No. | Y¹ | Y² | Y³ | Y⁴ | R¹ | R² | R³ | X⁻ |
|---|---|---|---|---|---|---|---|---|
| 1-70 | H | H | H | H | $CF_3$ | $CH_2CONMe_2$ | Et | $EtOSO_3^-$ |
| 1-71 | H | H | H | H | $CF_3$ | $CH_2CONMe_2$ | Et | $HOSO_3^-$ |

TABLE 3

| Compound No. | Y¹ | Y² | Y³ | Y⁴ | R¹ | R² | R³ | X⁻ |
|---|---|---|---|---|---|---|---|---|
| 1-72 | H | H | H | H | $CF_3$ | Bn | Me | $I^-$ |
| 1-73 | H | H | H | H | $CF_3$ | Bn | Me | $BF_4^-$ |
| 1-74 | H | H | H | H | $CF_3$ | Bn | Me | $CF_3CO_2^-$ |
| 1-75 | H | H | H | H | $CF_3$ | Bn | Me | $CF_3SO_3^-$ |
| 1-76 | H | H | H | H | $CF_3$ | Bn | Me | $MeOSO_3^-$ |
| 1-77 | H | H | H | H | $CF_3$ | Bn | Et | $EtOSO_3^-$ |
| 1-78 | H | H | H | H | $CF_3$ | Bn | Et | $HOSO_3^-$ |
| 1-79 | H | H | H | H | $CF_3$ | $CH=CH_2$ | Me | $MeOSO_3^-$ |
| 1-80 | H | H | H | H | $CF_3$ | $CH_2CH=CH_2$ | Me | $MeOSO_3^-$ |
| 1-81 | H | H | H | H | $CF_3$ | $C\equiv CH$ | Me | $MeOSO_3^-$ |
| 1-82 | H | H | H | H | $CF_3$ | $CH_2C\equiv CH$ | Me | $MeOSO_3^-$ |
| 1-83 | H | H | H | H | $CF_3$ | c-Pr | Me | $MeOSO_3^-$ |
| 1-84 | H | H | H | H | $CF_3$ | c-Bu | Me | $MeOSO_3^-$ |
| 1-85 | H | H | H | H | $CF_3$ | c-Pen | Me | $MeOSO_3^-$ |
| 1-86 | H | H | H | H | $CF_3$ | c-Hex | Me | $MeOSO_3^-$ |
| 1-87 | H | H | H | H | $CF_3$ | Ph | Me | $I^-$ |
| 1-88 | H | H | H | H | $CF_3$ | Ph | Me | $BF_4^-$ |
| 1-89 | H | H | H | H | $CF_3$ | Ph | Me | $CF_3CO_2^-$ |
| 1-90 | H | H | H | H | $CF_3$ | Ph | Me | $CF_3SO_3^-$ |
| 1-91 | H | H | H | H | $CF_3$ | Ph | Me | $MeOSO_3^-$ |
| 1-92 | H | H | H | H | $CF_3$ | Ph | Et | $EtOSO_3^-$ |
| 1-93 | H | H | H | H | $CF_3$ | Ph | Et | $HOSO_3^-$ |
| 1-94 | H | H | H | H | $C_2F_5$ | Me | Me | $I^-$ |
| 1-95 | H | H | H | H | $C_2F_5$ | Me | Me | $BF_4^-$ |
| 1-96 | H | H | H | H | $C_2F_5$ | Me | Me | $CF_3CO_2^-$ |
| 1-97 | H | H | H | H | $C_2F_5$ | Me | Me | $CF_3SO_3^-$ |
| 1-98 | H | H | H | H | $C_2F_5$ | Me | Me | $MeOSO_3^-$ |
| 1-99 | H | H | H | H | $C_2F_5$ | Me | Me | $EtOSO_3^-$ |
| 1-100 | H | H | H | H | $C_2F_5$ | Me | Me | $HOSO_3^-$ |
| 1-101 | H | H | H | H | $C_2F_5$ | Et | Me | $MeOSO_3^-$ |
| 1-102 | H | H | H | H | $C_2F_5$ | Et | Et | $EtOSO_3^-$ |
| 1-103 | H | H | H | H | $C_2F_5$ | Et | Et | $HOSO_3^-$ |
| 1-104 | H | H | H | H | $C_2F_5$ | i-Pr | Me | $MeOSO_3^-$ |

TABLE 4

| Compound No. | Y¹ | Y² | Y³ | Y⁴ | R¹ | R² | R³ | X⁻ |
|---|---|---|---|---|---|---|---|---|
| 1-105 | H | H | H | H | $C_3F_7$ | Me | Me | $I^-$ |
| 1-106 | H | H | H | H | $C_3F_7$ | Me | Me | $BF_4^-$ |
| 1-107 | H | H | H | H | $C_3F_7$ | Me | Me | $CF_3CO_2^-$ |
| 1-108 | H | H | H | H | $C_3F_7$ | Me | Me | $CF_3SO_3^-$ |
| 1-109 | H | H | H | H | $C_3F_7$ | Me | Me | $MeOSO_3^-$ |
| 1-110 | H | H | H | H | $C_3F_7$ | Me | Me | $EtOSO_3^-$ |
| 1-111 | H | H | H | H | $C_3F_7$ | Me | Me | $HOSO_3^-$ |
| 1-112 | H | H | H | H | $C_3F_7$ | Et | Me | $MeOSO_3^-$ |
| 1-113 | H | H | H | H | $C_3F_7$ | Et | Et | $EtOSO_3^-$ |
| 1-114 | H | H | H | H | $C_3F_7$ | Et | Et | $HOSO_3^-$ |
| 1-115 | H | H | H | H | $C_3F_7$ | i-Pr | Me | $MeOSO_3^-$ |
| 1-116 | H | H | H | H | $C_5F_{11}$ | Me | Me | $I^-$ |
| 1-117 | H | H | H | H | $C_5F_{11}$ | Me | Me | $BF_4^-$ |
| 1-118 | H | H | H | H | $C_5F_{11}$ | Me | Me | $CF_3CO_2^-$ |
| 1-119 | H | H | H | H | $C_5F_{11}$ | Me | Me | $CF_3SO_3^-$ |
| 1-120 | H | H | H | H | $C_5F_{11}$ | Me | Me | $MeOSO_3^-$ |
| 1-121 | H | H | H | H | $C_5F_{11}$ | Me | Me | $EtOSO_3^-$ |
| 1-122 | H | H | H | H | $C_5F_{11}$ | Me | Me | $HOSO_3^-$ |
| 1-123 | H | H | H | H | $C_5F_{11}$ | Et | Me | $MeOSO_3^-$ |
| 1-124 | H | H | H | H | $C_5F_{11}$ | Et | Et | $EtOSO_3^-$ |
| 1-125 | H | H | H | H | $C_5F_{11}$ | Et | Et | $HOSO_3^-$ |
| 1-126 | H | H | H | H | $C_5F_{11}$ | i-Pr | Me | $MeOSO_3^-$ |
| 1-127 | F | H | H | H | $CF_3$ | Me | Me | $I^-$ |
| 1-128 | F | H | H | H | $CF_3$ | Me | Me | $BF_4^-$ |
| 1-129 | F | H | H | H | $CF_3$ | Me | Me | $CF_3CO_2^-$ |
| 1-130 | F | H | H | H | $CF_3$ | Me | Me | $CF_3SO_3^-$ |
| 1-131 | F | H | H | H | $CF_3$ | Me | Me | $MeOSO_3^-$ |
| 1-132 | F | H | H | H | $CF_3$ | Me | Me | $EtOSO_3^-$ |
| 1-133 | F | H | H | H | $CF_3$ | Me | Me | $HOSO_3^-$ |
| 1-134 | F | H | H | H | $CF_3$ | Et | Me | $MeOSO_3^-$ |
| 1-135 | F | H | H | H | $CF_3$ | Et | Et | $EtOSO_3^-$ |
| 1-136 | F | H | H | H | $CF_3$ | Et | Et | $HOSO_3^-$ |
| 1-137 | F | H | H | H | $CF_3$ | i-Pr | Me | $MeOSO_3^-$ |
| 1-138 | F | H | H | H | $C_2F_5$ | Me | Me | $MeOSO_3^-$ |
| 1-139 | F | H | H | H | $C_3F_7$ | Me | Me | $MeOSO_3^-$ |

TABLE 5

| Compound No. | Y¹ | Y² | Y³ | Y⁴ | R¹ | R² | R³ | X⁻ |
|---|---|---|---|---|---|---|---|---|
| 1-140 | Cl | H | H | H | $CF_3$ | Me | Me | $I^-$ |
| 1-141 | Cl | H | H | H | $CF_3$ | Me | Me | $BF_4^-$ |
| 1-142 | Cl | H | H | H | $CF_3$ | Me | Me | $CF_3CO_2^-$ |
| 1-143 | Cl | H | H | H | $CF_3$ | Me | Me | $CF_3SO_3^-$ |
| 1-144 | Cl | H | H | H | $CF_3$ | Me | Me | $MeOSO_3^-$ |
| 1-145 | Cl | H | H | H | $CF_3$ | Me | Me | $EtOSO_3^-$ |
| 1-146 | Cl | H | H | H | $CF_3$ | Me | Me | $HOSO_3^-$ |
| 1-147 | Cl | H | H | H | $CF_3$ | Et | Me | $MeOSO_3^-$ |
| 1-148 | Cl | H | H | H | $CF_3$ | Et | Et | $EtOSO_3^-$ |
| 1-149 | Cl | H | H | H | $CF_3$ | Et | Et | $HOSO_3^-$ |
| 1-150 | Cl | H | H | H | $CF_3$ | i-Pr | Me | $MeOSO_3^-$ |
| 1-151 | Cl | H | H | H | $C_2F_5$ | Me | Me | $MeOSO_3^-$ |
| 1-152 | Cl | H | H | H | $C_3F_7$ | Me | Me | $MeOSO_3^-$ |
| 1-153 | Br | H | H | H | $CF_3$ | Me | Me | $I^-$ |
| 1-154 | Br | H | H | H | $CF_3$ | Me | Me | $BF_4^-$ |
| 1-155 | Br | H | H | H | $CF_3$ | Me | Me | $CF_3CO_2^-$ |
| 1-156 | Br | H | H | H | $CF_3$ | Me | Me | $CF_3SO_3^-$ |
| 1-157 | Br | H | H | H | $CF_3$ | Me | Me | $MeOSO_3^-$ |
| 1-158 | Br | H | H | H | $CF_3$ | Me | Me | $EtOSO_3^-$ |
| 1-159 | Br | H | H | H | $CF_3$ | Me | Me | $HOSO_3^-$ |
| 1-160 | Br | H | H | H | $CF_3$ | Et | Me | $MeOSO_3^-$ |
| 1-161 | Br | H | H | H | $CF_3$ | Et | Et | $EtOSO_3^-$ |
| 1-162 | Br | H | H | H | $CF_3$ | Et | Et | $HOSO_3^-$ |
| 1-163 | Br | H | H | H | $CF_3$ | i-Pr | Me | $MeOSO_3^-$ |
| 1-164 | Br | H | H | H | $C_2F_5$ | Me | Me | $MeOSO_3^-$ |
| 1-165 | Br | H | H | H | $C_3F_7$ | Me | Me | $MeOSO_3^-$ |
| 1-166 | I | H | H | H | $CF_3$ | Me | Me | $I^-$ |
| 1-167 | I | H | H | H | $CF_3$ | Me | Me | $BF_4^-$ |
| 1-168 | I | H | H | H | $CF_3$ | Me | Me | $CF_3CO_2^-$ |
| 1-169 | I | H | H | H | $CF_3$ | Me | Me | $CF_3SO_3^-$ |
| 1-170 | I | H | H | H | $CF_3$ | Me | Me | $MeOSO_3^-$ |
| 1-171 | I | H | H | H | $CF_3$ | Me | Me | $EtOSO_3^-$ |
| 1-172 | I | H | H | H | $CF_3$ | Me | Me | $HOSO_3^-$ |
| 1-173 | I | H | H | H | $CF_3$ | Et | Me | $MeOSO_3^-$ |
| 1-174 | I | H | H | H | $CF_3$ | Et | Et | $EtOSO_3^-$ |
| 1-175 | I | H | H | H | $CF_3$ | Et | Et | $HOSO_3^-$ |
| 1-176 | I | H | H | H | $CF_3$ | i-Pr | Me | $MeOSO_3^-$ |
| 1-177 | I | H | H | H | $C_2F_5$ | Me | Me | $MeOSO_3^-$ |
| 1-178 | I | H | H | H | $C_3F_7$ | Me | Me | $MeOSO_3^-$ |

TABLE 6

| Compound No. | Y¹ | Y² | Y³ | Y⁴ | R¹ | R² | R³ | X⁻ |
|---|---|---|---|---|---|---|---|---|
| 1-179 | H | F | H | H | $CF_3$ | Me | Me | $I^-$ |
| 1-180 | H | F | H | H | $CF_3$ | Me | Me | $BF_4^-$ |
| 1-181 | H | F | H | H | $CF_3$ | Me | Me | $CF_3CO_2^-$ |
| 1-182 | H | F | H | H | $CF_3$ | Me | Me | $CF_3SO_3^-$ |
| 1-183 | H | F | H | H | $CF_3$ | Me | Me | $MeOSO_3^-$ |
| 1-184 | H | F | H | H | $CF_3$ | Me | Me | $EtOSO_3^-$ |
| 1-185 | H | F | H | H | $CF_3$ | Me | Me | $HOSO_3^-$ |
| 1-186 | H | F | H | H | $CF_3$ | Et | Me | $MeOSO_3^-$ |
| 1-187 | H | F | H | H | $CF_3$ | Et | Et | $EtOSO_3^-$ |
| 1-188 | H | F | H | H | $CF_3$ | Et | Et | $HOSO_3^-$ |
| 1-189 | H | F | H | H | $CF_3$ | i-Pr | Me | $MeOSO_3^-$ |

TABLE 6-continued

| Compound No. | Y¹ | Y² | Y³ | Y⁴ | R¹ | R² | R³ | X⁻ |
|---|---|---|---|---|---|---|---|---|
| 1-190 | H | F | H | H | $C_2F_5$ | Me | Me | $MeOSO_3^-$ |
| 1-191 | H | F | H | H | $C_3F_7$ | Me | Me | $MeOSO_3^-$ |
| 1-192 | H | Cl | H | H | $CF_3$ | Me | Me | $I^-$ |
| 1-193 | H | Cl | H | H | $CF_3$ | Me | Me | $BF_4^-$ |
| 1-194 | H | Cl | H | H | $CF_3$ | Me | Me | $CF_3CO_2^-$ |
| 1-195 | H | Cl | H | H | $CF_3$ | Me | Me | $CF_3SO_3^-$ |
| 1-196 | H | Cl | H | H | $CF_3$ | Me | Me | $MeOSO_3^-$ |
| 1-197 | H | Cl | H | H | $CF_3$ | Me | Me | $EtOSO_3^-$ |
| 1-198 | H | Cl | H | H | $CF_3$ | Me | Me | $HOSO_3^-$ |
| 1-199 | H | Cl | H | H | $CF_3$ | Et | Me | $MeOSO_3^-$ |
| 1-200 | H | Cl | H | H | $CF_3$ | Et | Et | $EtOSO_3^-$ |
| 1-201 | H | Cl | H | H | $CF_3$ | Et | Et | $HOSO_3^-$ |
| 1-202 | H | Cl | H | H | $CF_3$ | i-Pr | Me | $MeOSO_3^-$ |
| 1-203 | H | Cl | H | H | $C_2F_5$ | Me | Me | $MeOSO_3^-$ |
| 1-204 | H | Cl | H | H | $C_3F_7$ | Me | Me | $MeOSO_3^-$ |
| 1-205 | H | Br | H | H | $CF_3$ | Me | Me | $I^-$ |
| 1-206 | H | Br | H | H | $CF_3$ | Me | Me | $BF_4^-$ |
| 1-207 | H | Br | H | H | $CF_3$ | Me | Me | $CF_3CO_2^-$ |
| 1-208 | H | Br | H | H | $CF_3$ | Me | Me | $CF_3SO_3^-$ |
| 1-209 | H | Br | H | H | $CF_3$ | Me | Me | $MeOSO_3^-$ |
| 1-210 | H | Br | H | H | $CF_3$ | Me | Me | $EtOSO_3^-$ |
| 1-211 | H | Br | H | H | $CF_3$ | Me | Me | $HOSO_3^-$ |
| 1-212 | H | Br | H | H | $CF_3$ | Et | Me | $MeOSO_3^-$ |
| 1-213 | H | Br | H | H | $CF_3$ | Et | Et | $EtOSO_3^-$ |
| 1-214 | H | Br | H | H | $CF_3$ | Et | Et | $HOSO_3^-$ |
| 1-215 | H | Br | H | H | $CF_3$ | i-Pr | Me | $MeOSO_3^-$ |
| 1-216 | H | Br | H | H | $C_2F_5$ | Me | Me | $MeOSO_3^-$ |
| 1-217 | H | Br | H | H | $C_3F_7$ | Me | Me | $MeOSO_3^-$ |

TABLE 7

| Compound No. | Y¹ | Y² | Y³ | Y⁴ | R¹ | R² | R³ | X⁻ |
|---|---|---|---|---|---|---|---|---|
| 1-218 | H | I | H | H | $CF_3$ | Me | Me | $I^-$ |
| 1-219 | H | I | H | H | $CF_3$ | Me | Me | $BF_4^-$ |
| 1-220 | H | I | H | H | $CF_3$ | Me | Me | $CF_3CO_2^-$ |
| 1-221 | H | I | H | H | $CF_3$ | Me | Me | $CF_3SO_3^-$ |
| 1-222 | H | I | H | H | $CF_3$ | Me | Me | $MeOSO_3^-$ |
| 1-223 | H | I | H | H | $CF_3$ | Me | Me | $EtOSO_3^-$ |
| 1-224 | H | I | H | H | $CF_3$ | Me | Me | $HOSO_3^-$ |
| 1-225 | H | I | H | H | $CF_3$ | Et | Me | $MeOSO_3^-$ |
| 1-226 | H | I | H | H | $CF_3$ | Et | Et | $EtOSO_3^-$ |
| 1-227 | H | I | H | H | $CF_3$ | Et | Et | $HOSO_3^-$ |
| 1-228 | H | I | H | H | $CF_3$ | i-Pr | Me | $MeOSO_3^-$ |
| 1-229 | H | I | H | H | $C_2F_5$ | Me | Me | $MeOSO_3^-$ |
| 1-230 | H | I | H | H | $C_3F_7$ | Me | Me | $MeOSO_3^-$ |
| 1-231 | H | F | F | H | $CF_3$ | Me | Me | $I^-$ |
| 1-232 | H | F | F | H | $CF_3$ | Me | Me | $BF_4^-$ |
| 1-233 | H | F | F | H | $CF_3$ | Me | Me | $CF_3CO_2^-$ |
| 1-234 | H | F | F | H | $CF_3$ | Me | Me | $CF_3SO_3^-$ |
| 1-235 | H | F | F | H | $CF_3$ | Me | Me | $MeOSO_3^-$ |
| 1-236 | H | F | F | H | $CF_3$ | Me | Me | $EtOSO_3^-$ |
| 1-237 | H | F | F | H | $CF_3$ | Me | Me | $HOSO_3^-$ |
| 1-238 | H | F | F | H | $CF_3$ | Et | Me | $MeOSO_3^-$ |
| 1-239 | H | F | F | H | $CF_3$ | Et | Et | $EtOSO_3^-$ |
| 1-240 | H | F | F | H | $CF_3$ | Et | Et | $HOSO_3^-$ |
| 1-241 | H | F | F | H | $CF_3$ | i-Pr | Me | $MeOSO_3^-$ |
| 1-242 | H | F | F | H | $C_2F_5$ | Me | Me | $MeOSO_3^-$ |
| 1-243 | H | F | F | H | $C_3F_7$ | Me | Me | $MeOSO_3^-$ |
| 1-244 | H | Cl | Cl | H | $CF_3$ | Me | Me | $I^-$ |
| 1-245 | H | Cl | Cl | H | $CF_3$ | Me | Me | $BF_4^-$ |
| 1-246 | H | Cl | Cl | H | $CF_3$ | Me | Me | $CF_3CO_2^-$ |
| 1-247 | H | Cl | Cl | H | $CF_3$ | Me | Me | $CF_3SO_3^-$ |
| 1-248 | H | Cl | Cl | H | $CF_3$ | Me | Me | $MeOSO_3^-$ |
| 1-249 | H | Cl | Cl | H | $CF_3$ | Me | Me | $EtOSO_3^-$ |
| 1-250 | H | Cl | Cl | H | $CF_3$ | Me | Me | $HOSO_3^-$ |
| 1-251 | H | Cl | Cl | H | $CF_3$ | Et | Me | $MeOSO_3^-$ |
| 1-252 | H | Cl | Cl | H | $CF_3$ | Et | Et | $EtOSO_3^-$ |
| 1-253 | H | Cl | Cl | H | $CF_3$ | Et | Et | $HOSO_3^-$ |
| 1-254 | H | Cl | Cl | H | $CF_3$ | i-Pr | Me | $MeOSO_3^-$ |
| 1-255 | H | Cl | Cl | H | $C_2F_5$ | Me | Me | $MeOSO_3^-$ |
| 1-256 | H | Cl | Cl | H | $C_3F_7$ | Me | Me | $MeOSO_3^-$ |

TABLE 8

| Compound No. | Y¹ | Y² | Y³ | Y⁴ | R¹ | R² | R³ | X⁻ |
|---|---|---|---|---|---|---|---|---|
| 1-257 | H | Br | Br | H | $CF_3$ | Me | Me | $I^-$ |
| 1-258 | H | Br | Br | H | $CF_3$ | Me | Me | $BF_4^-$ |
| 1-259 | H | Br | Br | H | $CF_3$ | Me | Me | $CF_3CO_2^-$ |
| 1-260 | H | Br | Br | H | $CF_3$ | Me | Me | $CF_3SO_3^-$ |
| 1-261 | H | Br | Br | H | $CF_3$ | Me | Me | $MeOSO_3^-$ |
| 1-262 | H | Br | Br | H | $CF_3$ | Me | Me | $EtOSO_3^-$ |
| 1-263 | H | Br | Br | H | $CF_3$ | Me | Me | $HOSO_3^-$ |
| 1-264 | H | Br | Br | H | $CF_3$ | Et | Me | $MeOSO_3^-$ |
| 1-265 | H | Br | Br | H | $CF_3$ | Et | Et | $EtOSO_3^-$ |
| 1-266 | H | Br | Br | H | $CF_3$ | Et | Et | $HOSO_3^-$ |
| 1-267 | H | Br | Br | H | $CF_3$ | i-Pr | Me | $MeOSO_3^-$ |
| 1-268 | H | Br | Br | H | $C_2F_5$ | Me | Me | $MeOSO_3^-$ |
| 1-269 | H | Br | Br | H | $C_3F_7$ | Me | Me | $MeOSO_3^-$ |
| 1-270 | H | F | Cl | H | $CF_3$ | Me | Me | $I^-$ |
| 1-271 | H | F | Cl | H | $CF_3$ | Me | Me | $BF_4^-$ |
| 1-272 | H | F | Cl | H | $CF_3$ | Me | Me | $CF_3CO_2^-$ |
| 1-273 | H | F | Cl | H | $CF_3$ | Me | Me | $CF_3SO_3^-$ |
| 1-274 | H | F | Cl | H | $CF_3$ | Me | Me | $MeOSO_3^-$ |
| 1-275 | H | F | Cl | H | $CF_3$ | Me | Me | $EtOSO_3^-$ |
| 1-276 | H | F | Cl | H | $CF_3$ | Me | Me | $HOSO_3^-$ |
| 1-277 | H | F | Cl | H | $CF_3$ | Et | Me | $MeOSO_3^-$ |
| 1-278 | H | F | Cl | H | $CF_3$ | Et | Et | $EtOSO_3^-$ |
| 1-279 | H | F | Cl | H | $CF_3$ | Et | Et | $HOSO_3^-$ |
| 1-280 | H | F | Cl | H | $CF_3$ | i-Pr | Me | $MeOSO_3^-$ |
| 1-281 | H | F | Cl | H | $C_2F_5$ | Me | Me | $MeOSO_3^-$ |
| 1-282 | H | F | Cl | H | $C_3F_7$ | Me | Me | $MeOSO_3^-$ |
| 1-283 | F | F | F | F | $CF_3$ | Me | Me | $I^-$ |
| 1-284 | F | F | F | F | $CF_3$ | Me | Me | $BF_4^-$ |
| 1-285 | F | F | F | F | $CF_3$ | Me | Me | $CF_3CO_2^-$ |
| 1-286 | F | F | F | F | $CF_3$ | Me | Me | $CF_3SO_3^-$ |
| 1-287 | F | F | F | F | $CF_3$ | Me | Me | $MeOSO_3^-$ |
| 1-288 | F | F | F | F | $CF_3$ | Me | Me | $EtOSO_3^-$ |
| 1-289 | F | F | F | F | $CF_3$ | Me | Me | $HOSO_3^-$ |
| 1-290 | F | F | F | F | $CF_3$ | Et | Me | $MeOSO_3^-$ |
| 1-291 | F | F | F | F | $CF_3$ | Et | Et | $EtOSO_3^-$ |
| 1-292 | F | F | F | F | $CF_3$ | Et | Et | $HOSO_3^-$ |
| 1-293 | F | F | F | F | $CF_3$ | i-Pr | Me | $MeOSO_3^-$ |
| 1-294 | F | F | F | F | $C_2F_5$ | Me | Me | $MeOSO_3^-$ |
| 1-295 | F | F | F | F | $C_3F_7$ | Me | Me | $MeOSO_3^-$ |

TABLE 9

| Compound No. | Y¹ | Y² | Y³ | Y⁴ | R¹ | R² | R³ | X⁻ |
|---|---|---|---|---|---|---|---|---|
| 1-296 | Cl | Cl | Cl | Cl | $CF_3$ | Me | Me | $I^-$ |
| 1-297 | Cl | Cl | Cl | Cl | $CF_3$ | Me | Me | $BF_4^-$ |
| 1-298 | Cl | Cl | Cl | Cl | $CF_3$ | Me | Me | $CF_3CO_2^-$ |
| 1-299 | Cl | Cl | Cl | Cl | $CF_3$ | Me | Me | $CF_3SO_3^-$ |
| 1-300 | Cl | Cl | Cl | Cl | $CF_3$ | Me | Me | $MeOSO_3^-$ |
| 1-301 | Cl | Cl | Cl | Cl | $CF_3$ | Me | Me | $EtOSO_3^-$ |
| 1-302 | Cl | Cl | Cl | Cl | $CF_3$ | Me | Me | $HOSO_3^-$ |
| 1-303 | Cl | Cl | Cl | Cl | $CF_3$ | Et | Me | $MeOSO_3^-$ |
| 1-304 | Cl | Cl | Cl | Cl | $CF_3$ | Et | Et | $EtOSO_3^-$ |
| 1-305 | Cl | Cl | Cl | Cl | $CF_3$ | Et | Et | $HOSO_3^-$ |
| 1-306 | Cl | Cl | Cl | Cl | $CF_3$ | i-Pr | Me | $MeOSO_3^-$ |
| 1-307 | Cl | Cl | Cl | Cl | $C_2F_5$ | Me | Me | $MeOSO_3^-$ |
| 1-308 | Cl | Cl | Cl | Cl | $C_3F_7$ | Me | Me | $MeOSO_3^-$ |
| 1-309 | Br | Br | Br | Br | $CF_3$ | Me | Me | $I^-$ |
| 1-310 | Br | Br | Br | Br | $CF_3$ | Me | Me | $BF_4^-$ |
| 1-311 | Br | Br | Br | Br | $CF_3$ | Me | Me | $CF_3CO_2^-$ |
| 1-312 | Br | Br | Br | Br | $CF_3$ | Me | Me | $CF_3SO_3^-$ |
| 1-313 | Br | Br | Br | Br | $CF_3$ | Me | Me | $MeOSO_3^-$ |
| 1-314 | Br | Br | Br | Br | $CF_3$ | Me | Me | $EtOSO_3^-$ |
| 1-315 | Br | Br | Br | Br | $CF_3$ | Me | Me | $HOSO_3^-$ |
| 1-316 | Br | Br | Br | Br | $CF_3$ | Et | Me | $MeOSO_3^-$ |
| 1-317 | Br | Br | Br | Br | $CF_3$ | Et | Et | $EtOSO_3^-$ |
| 1-318 | Br | Br | Br | Br | $CF_3$ | Et | Et | $HOSO_3^-$ |
| 1-319 | Br | Br | Br | Br | $CF_3$ | i-Pr | Me | $MeOSO_3^-$ |
| 1-320 | Br | Br | Br | Br | $C_3F_7$ | Me | Me | $MeOSO_3^-$ |
| 1-321 | Br | Br | Br | Br | $C_3F_7$ | Me | Me | $MeOSO_3^-$ |
| 1-322 | $NO_2$ | H | H | H | $CF_3$ | Me | Me | $I^-$ |
| 1-323 | $NO_2$ | H | H | H | $CF_3$ | Me | Me | $BF_4^-$ |
| 1-324 | $NO_2$ | H | H | H | $CF_3$ | Me | Me | $CF_3CO_2^-$ |

TABLE 9-continued

| Compound No. | Y$^1$ | Y$^2$ | Y$^3$ | Y$^4$ | R$^1$ | R$^2$ | R$^3$ | X$^-$ |
|---|---|---|---|---|---|---|---|---|
| 1-325 | NO$_2$ | H | H | H | CF$_3$ | Me | Me | CF$_3$SO$_3^-$ |
| 1-326 | NO$_2$ | H | H | H | CF$_3$ | Me | Me | MeOSO$_3^-$ |
| 1-327 | NO$_2$ | H | H | H | CF$_3$ | Me | Me | EtOSO$_3^-$ |
| 1-328 | NO$_2$ | H | H | H | CF$_3$ | Me | Me | HOSO$_3^-$ |
| 1-329 | NO$_2$ | H | H | H | CF$_3$ | Et | Me | MeOSO$_3^-$ |
| 1-330 | NO$_2$ | H | H | H | CF$_3$ | Et | Et | EtOSO$_3^-$ |
| 1-331 | NO$_2$ | H | H | H | CF$_3$ | Et | Et | HOSO$_3^-$ |
| 1-332 | NO$_2$ | H | H | H | CF$_3$ | i-Pr | Me | MeOSO$_3^-$ |
| 1-333 | NO$_2$ | H | H | H | C$_2$F$_5$ | Me | Me | MeOSO$_3^-$ |
| 1-334 | NO$_2$ | H | H | H | C$_3$F$_7$ | Me | Me | MeOSO$_3^-$ |

TABLE 10

| Compound No. | Y$^1$ | Y$^2$ | Y$^3$ | Y$^4$ | R$^1$ | R$^2$ | R$^3$ | X$^-$ |
|---|---|---|---|---|---|---|---|---|
| 1-335 | H | NO$_2$ | H | H | CF$_3$ | Me | Me | I$^-$ |
| 1-336 | H | NO$_2$ | H | H | CF$_3$ | Me | Me | BF$_4^-$ |
| 1-337 | H | NO$_2$ | H | H | CF$_3$ | Me | Me | CF$_3$CO$_2^-$ |
| 1-338 | H | NO$_2$ | H | H | CF$_3$ | Me | Me | CF$_3$SO$_3^-$ |
| 1-339 | H | NO$_2$ | H | H | CF$_3$ | Me | Me | MeOSO$_3^-$ |
| 1-340 | H | NO$_2$ | H | H | CF$_3$ | Me | Me | EtOSO$_3^-$ |
| 1-341 | H | NO$_2$ | H | H | CF$_3$ | Me | Me | HOSO$_3^-$ |
| 1-342 | H | NO$_2$ | H | H | CF$_3$ | Et | Me | MeOSO$_3^-$ |
| 1-343 | H | NO$_2$ | H | H | CF$_3$ | Et | Et | EtOSO$_3^-$ |
| 1-344 | H | NO$_2$ | H | H | CF$_3$ | Et | Et | HOSO$_3^-$ |
| 1-345 | H | NO$_2$ | H | H | CF$_3$ | i-Pr | Me | MeOSO$_3^-$ |
| 1-346 | H | NO$_2$ | H | H | C$_2$F$_5$ | Me | Me | MeOSO$_3^-$ |
| 1-347 | H | NO$_2$ | H | H | C$_3$F$_7$ | Me | Me | MeOSO$_3^-$ |
| 1-348 | CN | H | H | H | CF$_3$ | Me | Me | I$^-$ |
| 1-349 | CN | H | H | H | CF$_3$ | Me | Me | BF$_4^-$ |
| 1-350 | CN | H | H | H | CF$_3$ | Me | Me | CF$_3$CO$_2^-$ |
| 1-351 | CN | H | H | H | CF$_3$ | Me | Me | CF$_3$SO$_3^-$ |
| 1-352 | CN | H | H | H | CF$_3$ | Me | Me | MeOSO$_3^-$ |
| 1-353 | CN | H | H | H | CF$_3$ | Me | Me | EtOSO$_3^-$ |
| 1-354 | CN | H | H | H | CF$_3$ | Me | Me | HOSO$_3^-$ |
| 1-355 | CN | H | H | H | CF$_3$ | Et | Me | MeOSO$_3^-$ |
| 1-356 | CN | H | H | H | CF$_3$ | Et | Et | EtOSO$_3^-$ |
| 1-357 | CN | H | H | H | CF$_3$ | Et | Et | HOSO$_3^-$ |
| 1-358 | CN | H | H | H | CF$_3$ | i-Pr | Me | MeOSO$_3^-$ |
| 1-359 | CN | H | H | H | C$_2$F$_5$ | Me | Me | MeOSO$_3^-$ |
| 1-360 | CN | H | H | H | C$_3$F$_7$ | Me | Me | MeOSO$_3^-$ |
| 1-361 | H | CN | H | H | CF$_3$ | Me | Me | I$^-$ |
| 1-362 | H | CN | H | H | CF$_3$ | Me | Me | BF$_4^-$ |
| 1-363 | H | CN | H | H | CF$_3$ | Me | Me | CF$_3$CO$_2^-$ |
| 1-364 | H | CN | H | H | CF$_3$ | Me | Me | CF$_3$SO$_3^-$ |
| 1-365 | H | CN | H | H | CF$_3$ | Me | Me | MeOSO$_3^-$ |
| 1-366 | H | CN | H | H | CF$_3$ | Me | Me | EtOSO$_3^-$ |
| 1-367 | H | CN | H | H | CF$_3$ | Me | Me | HOSO$_3^-$ |
| 1-368 | H | CN | H | H | CF$_3$ | Et | Me | MeOSO$_3^-$ |
| 1-369 | H | CN | H | H | CF$_3$ | Et | Et | EtOSO$_3^-$ |
| 1-370 | H | CN | H | H | CF$_3$ | Et | Et | HOSO$_3^-$ |
| 1-371 | H | CN | H | H | CF$_3$ | i-Pr | Me | MeOSO$_3^-$ |
| 1-372 | H | CN | H | H | C$_2$F$_5$ | Me | Me | MeOSO$_3^-$ |
| 1-373 | H | CN | H | H | C$_3$F$_7$ | Me | Me | MeOSO$_3^-$ |

TABLE 11

| Compound No. | Y$^1$ | Y$^2$ | Y$^3$ | Y$^4$ | R$^1$ | R$^2$ | R$^3$ | X$^-$ |
|---|---|---|---|---|---|---|---|---|
| 1-374 | Me | H | H | H | CF$_3$ | Me | Me | I$^-$ |
| 1-375 | Me | H | H | H | CF$_3$ | Me | Me | BF$_4^-$ |
| 1-376 | Me | H | H | H | CF$_3$ | Me | Me | CF$_3$CO$_2^-$ |
| 1-377 | Me | H | H | H | CF$_3$ | Me | Me | CF$_3$SO$_3^-$ |
| 1-378 | Me | H | H | H | CF$_3$ | Me | Me | MeOSO$_3^-$ |
| 1-379 | Me | H | H | H | CF$_3$ | Me | Me | EtOSO$_3^-$ |
| 1-380 | Me | H | H | H | CF$_3$ | Me | Me | HOSO$_3^-$ |
| 1-381 | Me | H | H | H | CF$_3$ | Et | Me | MeOSO$_3^-$ |
| 1-382 | Me | H | H | H | CF$_3$ | Et | Et | EtOSO$_3^-$ |
| 1-383 | Me | H | H | H | CF$_3$ | Et | Et | HOSO$_3^-$ |
| 1-384 | Me | H | H | H | CF$_3$ | i-Pr | Me | MeOSO$_3^-$ |
| 1-385 | Me | H | H | H | C$_2$F$_5$ | Me | Me | MeOSO$_3^-$ |
| 1-386 | Me | H | H | H | C$_3$F$_7$ | Me | Me | MeOSO$_3^-$ |
| 1-387 | H | Me | H | H | CF$_3$ | Me | Me | I$^-$ |
| 1-388 | H | Me | H | H | CF$_3$ | Me | Me | BF$_4^-$ |
| 1-389 | H | Me | H | H | CF$_3$ | Me | Me | CF$_3$CO$_2^-$ |
| 1-390 | H | Me | H | H | CF$_3$ | Me | Me | CF$_3$SO$_3^-$ |
| 1-391 | H | Me | H | H | CF$_3$ | Me | Me | MeOSO$_3^-$ |
| 1-392 | H | Me | H | H | CF$_3$ | Me | Me | EtOSO$_3^-$ |
| 1-393 | H | Me | H | H | CF$_3$ | Me | Me | HOSO$_3^-$ |
| 1-394 | H | Me | H | H | CF$_3$ | Et | Me | MeOSO$_3^-$ |
| 1-395 | H | Me | H | H | CF$_3$ | Et | Et | EtOSO$_3^-$ |
| 1-396 | H | Me | H | H | CF$_3$ | Et | Et | HOSO$_3^-$ |
| 1-397 | H | Me | H | H | CF$_3$ | i-Pr | Me | MeOSO$_3^-$ |
| 1-398 | H | Me | H | H | C$_2$F$_5$ | Me | Me | MeOSO$_3^-$ |
| 1-399 | H | Me | H | H | C$_3$F$_7$ | Me | Me | MeOSO$_3^-$ |
| 1-400 | H | Me | Me | H | CF$_3$ | Me | Me | I$^-$ |
| 1-401 | H | Me | Me | H | CF$_3$ | Me | Me | BF$_4^-$ |
| 1-402 | H | Me | Me | H | CF$_3$ | Me | Me | CF$_3$CO$_2^-$ |
| 1-403 | H | Me | Me | H | CF$_3$ | Me | Me | CF$_3$SO$_3^-$ |
| 1-404 | H | Me | Me | H | CF$_3$ | Me | Me | MeOSO$_3^-$ |
| 1-405 | H | Me | Me | H | CF$_3$ | Me | Me | EtOSO$_3^-$ |
| 1-406 | H | Me | Me | H | CF$_3$ | Me | Me | HOSO$_3^-$ |
| 1-407 | H | Me | Me | H | CF$_3$ | Et | Me | MeOSO$_3^-$ |
| 1-408 | H | Me | Me | H | CF$_3$ | Et | Et | EtOSO$_3^-$ |
| 1-409 | H | Me | Me | H | CF$_3$ | Et | Et | HOSO$_3^-$ |
| 1-410 | H | Me | Me | H | CF$_3$ | i-Pr | Me | MeOSO$_3^-$ |
| 1-411 | H | Me | Me | H | C$_2$F$_5$ | Me | Me | MeOSO$_3^-$ |
| 1-412 | H | Me | Me | H | C$_3$F$_7$ | Me | Me | MeOSO$_3^-$ |

TABLE 12

| Compound No. | Y$^1$ | Y$^2$ | Y$^3$ | Y$^4$ | R$^1$ | R$^2$ | R$^3$ | X$^-$ |
|---|---|---|---|---|---|---|---|---|
| 1-413 | H | Et | H | H | CF$_3$ | Me | Me | MeOSO$_3^-$ |
| 1-414 | H | Pr | H | H | CF$_3$ | Me | Me | MeOSO$_3^-$ |
| 1-415 | H | i-Pr | H | H | CF$_3$ | Me | Me | MeOSO$_3^-$ |
| 1-416 | H | Bu | H | H | CF$_3$ | Me | Me | MeOSO$_3^-$ |
| 1-417 | H | Pen | H | H | CF$_3$ | Me | Me | MeOSO$_3^-$ |
| 1-418 | H | Hex | H | H | CF$_3$ | Me | Me | MeOSO$_3^-$ |
| 1-419 | H | Dec | H | H | CF$_3$ | Me | Me | MeOSO$_3^-$ |
| 1-420 | H | CH$_2$NO$_2$ | H | H | CF$_3$ | Me | Me | MeOSO$_3^-$ |
| 1-421 | H | CH$_2$CN | H | H | CF$_3$ | Me | Me | MeOSO$_3^-$ |
| 1-422 | H | CH$_2$-c-Pr | H | H | CF$_3$ | Me | Me | MeOSO$_3^-$ |
| 1-423 | H | CH$_2$OH | H | H | CF$_3$ | Me | Me | MeOSO$_3^-$ |
| 1-424 | H | CH$_2$OMe | H | H | CF$_3$ | Me | Me | MeOSO$_3^-$ |
| 1-425 | H | CH$_2$SMe | H | H | CF$_3$ | Me | Me | MeOSO$_3^-$ |
| 1-426 | H | CH$_2$SOMe | H | H | CF$_3$ | Me | Me | MeOSO$_3^-$ |
| 1-427 | H | CH$_2$SO$_2$Me | H | H | CF$_3$ | Me | Me | MeOSO$_3^-$ |
| 1-428 | H | CH$_2$NH$_2$ | H | H | CF$_3$ | Me | Me | MeOSO$_3^-$ |
| 1-429 | H | CH$_2$NHMe | H | H | CF$_3$ | Me | Me | MeOSO$_3^-$ |
| 1-430 | H | CH$_2$NMe$_2$ | H | H | CF$_3$ | Me | Me | MeOSO$_3^-$ |
| 1-431 | H | CH$_2$NHAc | H | H | CF$_3$ | Me | Me | MeOSO$_3^-$ |
| 1-432 | H | CH$_2$CHO | H | H | CF$_3$ | Me | Me | MeOSO$_3^-$ |
| 1-433 | H | CH$_2$COMe | H | H | CF$_3$ | Me | Me | MeOSO$_3^-$ |
| 1-434 | H | CH$_2$CO$_2$Me | H | H | CF$_3$ | Me | Me | MeOSO$_3^-$ |
| 1-435 | H | CH$_2$Ph | H | H | CF$_3$ | Me | Me | MeOSO$_3^-$ |
| 1-436 | H | C$_2$H$_4$Ph | H | H | CF$_3$ | Me | Me | MeOSO$_3^-$ |
| 1-437 | H | CH$_2$-2-thienyl | H | H | CF$_3$ | Me | Me | MeOSO$_3^-$ |
| 1-438 | H | CH=CH$_2$ | H | H | CF$_3$ | Me | Me | MeOSO$_3^-$ |
| 1-439 | H | CH$_2$CH=CH$_2$ | H | H | CF$_3$ | Me | Me | MeOSO$_3^-$ |
| 1-440 | H | C≡CH | H | H | CF$_3$ | Me | Me | MeOSO$_3^-$ |
| 1-441 | H | CH$_2$C≡CH | H | H | CF$_3$ | Me | Me | MeOSO$_3^-$ |
| 1-442 | H | c-Pr | H | H | CF$_3$ | Me | Me | MeOSO$_3^-$ |
| 1-443 | H | c-Bu | H | H | CF$_3$ | Me | Me | MeOSO$_3^-$ |
| 1-444 | H | c-Pen | H | H | CF$_3$ | Me | Me | MeOSO$_3^-$ |
| 1-445 | H | c-Hex | H | H | CF$_3$ | Me | Me | MeOSO$_3^-$ |
| 1-446 | H | OH | H | H | CF$_3$ | Me | Me | MeOSO$_3^-$ |

TABLE 13

| Compound No. | $Y^1$ | $Y^2$ | $Y^3$ | $Y^4$ | $R^1$ | $R^2$ | $R^3$ | $X^-$ |
|---|---|---|---|---|---|---|---|---|
| 1-447 | H | $CH_2F$ | H | H | $CF_3$ | Me | Me | $MeOSO_3^-$ |
| 1-448 | H | $CH_2Cl$ | H | H | $CF_3$ | Me | Me | $MeOSO_3^-$ |
| 1-449 | H | $CH_2Br$ | H | H | $CF_3$ | Me | Me | $MeOSO_3^-$ |
| 1-450 | H | $CHF_2$ | H | H | $CF_3$ | Me | Me | $MeOSO_3^-$ |
| 1-451 | H | $CHCl_2$ | H | H | $CF_3$ | Me | Me | $MeOSO_3^-$ |
| 1-452 | H | $CF_3$ | H | H | $CF_3$ | Me | Me | $MeOSO_3^-$ |
| 1-453 | H | $CCl_3$ | H | H | $CF_3$ | Me | Me | $MeOSO_3^-$ |
| 1-454 | H | $CClF_2$ | H | H | $CF_3$ | Me | Me | $MeOSO_3^-$ |
| 1-455 | H | $CBrF_2$ | H | H | $CF_3$ | Me | Me | $MeOSO_3^-$ |
| 1-456 | H | $CH_2CH_2F$ | H | H | $CF_3$ | Me | Me | $MeOSO_3^-$ |
| 1-457 | H | $CHClCH_3$ | H | H | $CF_3$ | Me | Me | $MeOSO_3^-$ |
| 1-458 | H | $CH_2CH_2Cl$ | H | H | $CF_3$ | Me | Me | $MeOSO_3^-$ |
| 1-459 | H | $CH_2CF_3$ | H | H | $CF_3$ | Me | Me | $MeOSO_3^-$ |
| 1-460 | H | $C_2F_5$ | H | H | $CF_3$ | Me | Me | $MeOSO_3^-$ |
| 1-461 | H | $(CH_2)_3F$ | H | H | $CF_3$ | Me | Me | $MeOSO_3^-$ |
| 1-462 | H | $(CH_2)_3Cl$ | H | H | $CF_3$ | Me | Me | $MeOSO_3^-$ |
| 1-463 | H | $CHMeCH_2Cl$ | H | H | $CF_3$ | Me | Me | $MeOSO_3^-$ |
| 1-464 | H | $CH_2C_2F_5$ | H | H | $CF_3$ | Me | Me | $MeOSO_3^-$ |
| 1-465 | H | $CH(CF_3)_2$ | H | H | $CF_3$ | Me | Me | $MeOSO_3^-$ |
| 1-466 | H | $C_3F_7$ | H | H | $CF_3$ | Me | Me | $MeOSO_3^-$ |
| 1-467 | H | $i\text{-}C_3F_7$ | H | H | $CF_3$ | Me | Me | $MeOSO_3^-$ |
| 1-468 | H | $(CH_2)_4F$ | H | H | $CF_3$ | Me | Me | $MeOSO_3^-$ |
| 1-469 | H | $(CH_2)_4Cl$ | H | H | $CF_3$ | Me | Me | $MeOSO_3^-$ |
| 1-470 | H | $CH_2C_3F_7$ | H | H | $CF_3$ | Me | Me | $MeOSO_3^-$ |
| 1-471 | H | $C_4F_9$ | H | H | $CF_3$ | Me | Me | $MeOSO_3^-$ |
| 1-472 | H | $i\text{-}C_4F_9$ | H | H | $CF_3$ | Me | Me | $MeOSO_3^-$ |
| 1-473 | H | $t\text{-}C_4F_9$ | H | H | $CF_3$ | Me | Me | $MeOSO_3^-$ |
| 1-474 | H | $C_5F_{11}$ | H | H | $CF_3$ | Me | Me | $MeOSO_3^-$ |
| 1-475 | H | $C_6F_{13}$ | H | H | $CF_3$ | Me | Me | $MeOSO_3^-$ |

TABLE 14

| Compound No. | $Y^1$ | $Y^2$ | $Y^3$ | $Y^4$ | $R^1$ | $R^2$ | $R^3$ | $X^-$ |
|---|---|---|---|---|---|---|---|---|
| 1-476 | OMe | H | H | H | $CF_3$ | Me | Me | $I^-$ |
| 1-477 | OMe | H | H | H | $CF_3$ | Me | Me | $BF_4^-$ |
| 1-478 | OMe | H | H | H | $CF_3$ | Me | Me | $CF_3CO_2^-$ |
| 1-479 | OMe | H | H | H | $CF_3$ | Me | Me | $CF_3SO_3^-$ |
| 1-480 | OMe | H | H | H | $CF_3$ | Me | Me | $MeOSO_3^-$ |
| 1-481 | OMe | H | H | H | $CF_3$ | Me | Me | $EtOSO_3^-$ |
| 1-482 | OMe | H | H | H | $CF_3$ | Me | Me | $HOSO_3^-$ |
| 1-483 | OMe | H | H | H | $CF_3$ | Et | Me | $MeOSO_3^-$ |
| 1-484 | OMe | H | H | H | $CF_3$ | Et | Et | $EtOSO_3^-$ |
| 1-485 | OMe | H | H | H | $CF_3$ | Et | Et | $HOSO_3^-$ |
| 1-486 | OMe | H | H | H | $CF_3$ | i-Pr | Me | $MeOSO_3^-$ |
| 1-487 | OMe | H | H | H | $C_2F_5$ | Me | Me | $MeOSO_3^-$ |
| 1-488 | OMe | H | H | H | $C_3F_7$ | Me | Me | $MeOSO_3^-$ |
| 1-489 | H | OMe | H | H | $CF_3$ | Me | Me | $I^-$ |
| 1-490 | H | OMe | H | H | $CF_3$ | Me | Me | $BF_4^-$ |
| 1-491 | H | OMe | H | H | $CF_3$ | Me | Me | $CF_3CO_2^-$ |
| 1-492 | H | OMe | H | H | $CF_3$ | Me | Me | $CF_3SO_3^-$ |
| 1-493 | H | OMe | H | H | $CF_3$ | Me | Me | $MeOSO_3^-$ |
| 1-494 | H | OMe | H | H | $CF_3$ | Me | Me | $EtOSO_3^-$ |
| 1-495 | H | OMe | H | H | $CF_3$ | Me | Me | $HOSO_3^-$ |
| 1-496 | H | OMe | H | H | $CF_3$ | Et | Me | $MeOSO_3^-$ |
| 1-497 | H | OMe | H | H | $CF_3$ | Et | Et | $EtOSO_3^-$ |
| 1-498 | H | OMe | H | H | $CF_3$ | Et | Et | $HOSO_3^-$ |
| 1-499 | H | OMe | H | H | $CF_3$ | i-Pr | Me | $MeOSO_3^-$ |
| 1-500 | H | OMe | H | H | $C_2F_5$ | Me | Me | $MeOSO_3^-$ |
| 1-501 | H | OMe | H | H | $C_3F_7$ | Me | Me | $MeOSO_3^-$ |
| 1-502 | H | OEt | H | H | $CF_3$ | Me | Me | $MeOSO_3^-$ |
| 1-503 | H | OPr | H | H | $CF_3$ | Me | Me | $MeOSO_3^-$ |
| 1-504 | H | OPr-i | H | H | $CF_3$ | Me | Me | $MeOSO_3^-$ |
| 1-505 | H | OBu | H | H | $CF_3$ | Me | Me | $MeOSO_3^-$ |
| 1-506 | H | OPen | H | H | $CF_3$ | Me | Me | $MeOSO_3^-$ |
| 1-507 | H | OHex | H | H | $CF_3$ | Me | Me | $MeOSO_3^-$ |

TABLE 15

| Compound No. | $Y^1$ | $Y^2$ | $Y^3$ | $Y^4$ | $R^1$ | $R^2$ | $R^3$ | $X^-$ |
|---|---|---|---|---|---|---|---|---|
| 1-508 | SMe | H | H | H | $CF_3$ | Me | Me | $I^-$ |
| 1-509 | SMe | H | H | H | $CF_3$ | Me | Me | $BF_4^-$ |
| 1-510 | SMe | H | H | H | $CF_3$ | Me | Me | $CF_3CO_2^-$ |
| 1-511 | SMe | H | H | H | $CF_3$ | Me | Me | $CF_3SO_3^-$ |
| 1-512 | SMe | H | H | H | $CF_3$ | Me | Me | $MeOSO_3^-$ |
| 1-513 | SMe | H | H | H | $CF_3$ | Me | Me | $EtOSO_3^-$ |
| 1-514 | SMe | H | H | H | $CF_3$ | Me | Me | $HOSO_3^-$ |
| 1-515 | SMe | H | H | H | $CF_3$ | Et | Me | $MeOSO_3^-$ |
| 1-516 | SMe | H | H | H | $CF_3$ | Et | Et | $EtOSO_3^-$ |
| 1-517 | SMe | H | H | H | $CF_3$ | Et | Et | $HOSO_3^-$ |
| 1-518 | SMe | H | H | H | $CF_3$ | i-Pr | Me | $MeOSO_3^-$ |
| 1-519 | SMe | H | H | H | $C_2F_5$ | Me | Me | $MeOSO_3^-$ |
| 1-520 | SMe | H | H | H | $C_3F_7$ | Me | Me | $MeOSO_3^-$ |
| 1-521 | H | SMe | H | H | $CF_3$ | Me | Me | $I^-$ |
| 1-522 | H | SMe | H | H | $CF_3$ | Me | Me | $BF_4^-$ |
| 1-523 | H | SMe | H | H | $CF_3$ | Me | Me | $CF_3CO_2^-$ |
| 1-524 | H | SMe | H | H | $CF_3$ | Me | Me | $CF_3SO_3^-$ |
| 1-525 | H | SMe | H | H | $CF_3$ | Me | Me | $MeOSO_3^-$ |
| 1-526 | H | SMe | H | H | $CF_3$ | Me | Me | $EtOSO_3^-$ |
| 1-527 | H | SMe | H | H | $CF_3$ | Me | Me | $HOSO_3^-$ |
| 1-528 | H | SMe | H | H | $CF_3$ | Et | Me | $MeOSO_3^-$ |
| 1-529 | H | SMe | H | H | $CF_3$ | Et | Et | $EtOSO_3^-$ |
| 1-530 | H | SMe | H | H | $CF_3$ | Et | Et | $HOSO_3^-$ |
| 1-531 | H | SMe | H | H | $CF_3$ | i-Pr | Me | $MeOSO_3^-$ |
| 1-532 | H | SMe | H | H | $C_2F_5$ | Me | Me | $MeOSO_3^-$ |
| 1-533 | H | SMe | H | H | $C_3F_7$ | Me | Me | $MeOSO_3^-$ |
| 1-534 | H | SEt | H | H | $CF_3$ | Me | Me | $MeOSO_3^-$ |
| 1-535 | H | SPr | H | H | $CF_3$ | Me | Me | $MeOSO_3^-$ |
| 1-536 | H | SPr-i | H | H | $CF_3$ | Me | Me | $MeOSO_3^-$ |
| 1-537 | H | SBu | H | H | $CF_3$ | Me | Me | $MeOSO_3^-$ |
| 1-538 | H | SPen | H | H | $CF_3$ | Me | Me | $MeOSO_3^-$ |
| 1-539 | H | SHex | H | H | $CF_3$ | Me | Me | $MeOSO_3^-$ |

TABLE 16

| Compound No. | $Y^1$ | $Y^2$ | $Y^3$ | $Y^4$ | $R^1$ | $R^2$ | $R^3$ | $X^-$ |
|---|---|---|---|---|---|---|---|---|
| 1-540 | SOMe | H | H | H | $CF_3$ | Me | Me | $I^-$ |
| 1-541 | SOMe | H | H | H | $CF_3$ | Me | Me | $BF_4^-$ |
| 1-542 | SOMe | H | H | H | $CF_3$ | Me | Me | $CF_3CO_2^-$ |
| 1-543 | SOMe | H | H | H | $CF_3$ | Me | Me | $CF_3SO_3^-$ |
| 1-544 | SOMe | H | H | H | $CF_3$ | Me | Me | $MeOSO_3^-$ |
| 1-545 | SOMe | H | H | H | $CF_3$ | Me | Me | $EtOSO_3^-$ |
| 1-546 | SOMe | H | H | H | $CF_3$ | Me | Me | $HOSO_3^-$ |
| 1-547 | SOMe | H | H | H | $CF_3$ | Et | Me | $MeOSO_3^-$ |
| 1-548 | SOMe | H | H | H | $CF_3$ | Et | Et | $EtOSO_3^-$ |
| 1-549 | SOMe | H | H | H | $CF_3$ | Et | Et | $HOSO_3^-$ |
| 1-550 | SOMe | H | H | H | $CF_3$ | i-Pr | Me | $MeOSO_3^-$ |
| 1-551 | SOMe | H | H | H | $C_2F_5$ | Me | Me | $MeOSO_3^-$ |
| 1-552 | SOMe | H | H | H | $C_3F_7$ | Me | Me | $MeOSO_3^-$ |
| 1-553 | H | SOMe | H | H | $CF_3$ | Me | Me | $I^-$ |
| 1-554 | H | SOMe | H | H | $CF_3$ | Me | Me | $BF_4^-$ |
| 1-555 | H | SOMe | H | H | $CF_3$ | Me | Me | $CF_3CO_2^-$ |
| 1-556 | H | SOMe | H | H | $CF_3$ | Me | Me | $CF_3SO_3^-$ |
| 1-557 | H | SOMe | H | H | $CF_3$ | Me | Me | $MeOSO_3^-$ |
| 1-558 | H | SOMe | H | H | $CF_3$ | Me | Me | $EtOSO_3^-$ |
| 1-559 | H | SOMe | H | H | $CF_3$ | Me | Me | $HOSO_3^-$ |
| 1-560 | H | SOMe | H | H | $CF_3$ | Et | Me | $MeOSO_3^-$ |
| 1-561 | H | SOMe | H | H | $CF_3$ | Et | Et | $EtOSO_3^-$ |
| 1-562 | H | SOMe | H | H | $CF_3$ | Et | Et | $HOSO_3^-$ |
| 1-563 | H | SOMe | H | H | $CF_3$ | i-Pr | Me | $MeOSO_3^-$ |
| 1-564 | H | SOMe | H | H | $C_2F_5$ | Me | Me | $MeOSO_3^-$ |
| 1-565 | H | SOMe | H | H | $C_3F_7$ | Me | Me | $MeOSO_3^-$ |
| 1-566 | H | SOEt | H | H | $CF_3$ | Me | Me | $MeOSO_3^-$ |
| 1-567 | H | SOPr | H | H | $CF_3$ | Me | Me | $MeOSO_3^-$ |
| 1-568 | H | SOPr-i | H | H | $CF_3$ | Me | Me | $MeOSO_3^-$ |
| 1-569 | H | SOBu | H | H | $CF_3$ | Me | Me | $MeOSO_3^-$ |
| 1-570 | H | SOPen | H | H | $CF_3$ | Me | Me | $MeOSO_3^-$ |
| 1-571 | H | SOHex | H | H | $CF_3$ | Me | Me | $MeOSO_3^-$ |

TABLE 17

| Compound No. | Y¹ | Y² | Y³ | Y⁴ | R¹ | R² | R³ | X⁻ |
|---|---|---|---|---|---|---|---|---|
| 1-572 | SO₂Me | H | H | H | CF₃ | Me | Me | I⁻ |
| 1-573 | SO₂Me | H | H | H | CF₃ | Me | Me | BF₄⁻ |
| 1-574 | SO₂Me | H | H | H | CF₃ | Me | Me | CF₃CO₂⁻ |
| 1-575 | SO₂Me | H | H | H | CF₃ | Me | Me | CF₃SO₃⁻ |
| 1-576 | SO₂Me | H | H | H | CF₃ | Me | Me | MeOSO₃⁻ |
| 1-577 | SO₂Me | H | H | H | CF₃ | Me | Me | EtOSO₃⁻ |
| 1-578 | SO₂Me | H | H | H | CF₃ | Me | Me | HOSO₃⁻ |
| 1-579 | SO₂Me | H | H | H | CF₃ | Et | Me | MeOSO₃⁻ |
| 1-580 | SO₂Me | H | H | H | CF₃ | Et | Et | EtOSO₃⁻ |
| 1-581 | SO₂Me | H | H | H | CF₃ | Et | Et | HOSO₃⁻ |
| 1-582 | SO₂Me | H | H | H | CF₃ | i-Pr | Me | MeOSO₃⁻ |
| 1-583 | SO₂Me | H | H | H | C₂F₅ | Me | Me | MeOSO₃⁻ |
| 1-584 | SO₂Me | H | H | H | C₃F₇ | Me | Me | MeOSO₃⁻ |
| 1-585 | H | SO₂Me | H | H | CF₃ | Me | Me | I⁻ |
| 1-586 | H | SO₂Me | H | H | CF₃ | Me | Me | BF₄⁻ |
| 1-587 | H | SO₂Me | H | H | CF₃ | Me | Me | CF₃CO₂⁻ |
| 1-588 | H | SO₂Me | H | H | CF₃ | Me | Me | CF₃SO₃⁻ |
| 1-589 | H | SO₂Me | H | H | CF₃ | Me | Me | MeOSO₃⁻ |
| 1-590 | H | SO₂Me | H | H | CF₃ | Me | Me | EtOSO₃⁻ |
| 1-591 | H | SO₂Me | H | H | CF₃ | Me | Me | HOSO₃⁻ |
| 1-592 | H | SO₂Me | H | H | CF₃ | Et | Me | MeOSO₃⁻ |
| 1-593 | H | SO₂Me | H | H | CF₃ | Et | Et | EtOSO₃⁻ |
| 1-594 | H | SO₂Me | H | H | CF₃ | Et | Et | HOSO₃⁻ |
| 1-595 | H | SO₂Me | H | H | CF₃ | i-Pr | Me | MeOSO₃⁻ |
| 1-596 | H | SO₂Me | H | H | C₂F₅ | Me | Me | MeOSO₃⁻ |
| 1-597 | H | SO₂Me | H | H | C₃F₇ | Me | Me | MeOSO₃⁻ |
| 1-598 | H | SO₂Et | H | H | CF₃ | Me | Me | MeOSO₃⁻ |
| 1-599 | H | SO₂Pr | H | H | CF₃ | Me | Me | MeOSO₃⁻ |
| 1-600 | H | SO₂Pr-i | H | H | CF₃ | Me | Me | MeOSO₃⁻ |
| 1-601 | H | SO₂Bu | H | H | CF₃ | Me | Me | MeOSO₃⁻ |
| 1-602 | H | SO₂Pen | H | H | CF₃ | Me | Me | MeOSO₃⁻ |

TABLE 18

| Compound No. | Y¹ | Y² | Y³ | Y⁴ | R¹ | R² | R³ | X⁻ |
|---|---|---|---|---|---|---|---|---|
| 1-603 | H | SO₂Hex | H | H | CF₃ | Me | Me | MeOSO₃⁻ |
| 1-604 | H | NH₂ | H | H | CF₃ | Me | Me | MeOSO₃⁻ |
| 1-605 | H | NHMe | H | H | CF₃ | Me | Me | MeOSO₃⁻ |
| 1-606 | H | NMe₂ | H | H | CF₃ | Me | Me | MeOSO₃⁻ |
| 1-607 | H | NHAc | H | H | CF₃ | Me | Me | MeOSO₃⁻ |
| 1-608 | H | CHO | H | H | CF₃ | Me | Me | MeOSO₃⁻ |
| 1-609 | H | COMe | H | H | CF₃ | Me | Me | MeOSO₃⁻ |
| 1-610 | CO₂Me | H | H | H | CF₃ | Me | Me | MeOSO₃⁻ |
| 1-611 | H | CO₂Me | H | H | CF₃ | Me | Me | MeOSO₃⁻ |
| 1-612 | H | Ph | H | H | CF₃ | Me | Me | MeOSO₃⁻ |
| 1-613 | H | 2-thienyl | H | H | CF₃ | Me | Me | MeOSO₃⁻ |
| 1-614 | H | CH=CH—CH=CH | H | H | CF₃ | Me | Me | MeOSO₃⁻ |
| 1-615 | H | (see structure below) | | H | CF₃ | Me | Me | MeOSO₃⁻ |

Structure for 1-615: Me–N=C(CF₃)–N⁺(Me)– with MeOSO₃⁻ counterion

In another embodiment, specific examples of the compound represented by the general formula (1) as a fluoroalkylating agent include, but are not limited to, the following compounds:

1,3-dimethyl-2-trifluoromethylbenzimidazolium fluoride,
1,3-dimethyl-2-trifluoromethylbenzimidazolium chloride,
1,3-dimethyl-2-trifluoromethylbenzimidazolium bromide,
1,3-dimethyl-2-trifluoromethylbenzimidazolium iodide,
1,3-dimethyl-2-trifluoromethylbenzimidazolium tetrafluoroborate,
1,3-dimethyl-2-trifluoromethylbenzimidazolium hexafluorophosphate,
1,3-dimethyl-2-trifluoromethylbenzimidazolium methanesulfonate,
1,3-dimethyl-2-trifluoromethylbenzimidazolium triflate,
1,3-dimethyl-2-trifluoromethylbenzimidazolium methyl sulfate,
3-ethyl-1-methyl-2-trifluoromethylbenzimidazolium fluoride,
3-ethyl-1-methyl-2-trifluoromethylbenzimidazolium chloride,
3-ethyl-1-methyl-2-trifluoromethylbenzimidazolium bromide,
3-ethyl-1-methyl-2-trifluoromethylbenzimidazolium iodide,
3-ethyl-1-methyl-2-trifluoromethylbenzimidazolium tetrafluoroborate,
3-ethyl-1-methyl-2-trifluoromethylbenzimidazolium hexafluorophosphate,
3-ethyl-1-methyl-2-trifluoromethylbenzimidazolium methanesulfonate,
3-ethyl-1-methyl-2-trifluoromethylbenzimidazolium triflate,
3-ethyl-1-methyl-2-trifluoromethylbenzimidazolium methyl sulfate,
3-ethyl-1-methyl-2-trifluoromethylbenzimidazolium ethyl sulfate,
1-methyl-3-phenyl-2-trifluoromethylbenzimidazolium fluoride,
1-methyl-3-phenyl-2-trifluoromethylbenzimidazolium chloride,
1-methyl-3-phenyl-2-trifluoromethylbenzimidazolium bromide,
1-methyl-3-phenyl-2-trifluoromethylbenzimidazolium iodide,
1-methyl-3-phenyl-2-trifluoromethylbenzimidazolium tetrafluoroborate,
1-methyl-3-phenyl-2-trifluoromethylbenzimidazolium hexafluorophosphate,
1-methyl-3-phenyl-2-trifluoromethylbenzimidazolium methanesulfonate,
1-methyl-3-phenyl-2-trifluoromethylbenzimidazolium triflate,
1-methyl-3-phenyl-2-trifluoromethylbenzimidazolium methyl sulfate,
3-benzyl-1-methyl-2-trifluoromethylbenzimidazolium fluoride,
3-benzyl-1-methyl-2-trifluoromethylbenzimidazolium chloride,
3-benzyl-1-methyl-2-trifluoromethylbenzimidazolium bromide, 3-benzyl-1-methyl-2-trifluoromethylbenzimidazolium iodide,
3-benzyl-1-methyl-2-trifluoromethylbenzimidazolium tetrafluoroborate,
3-benzyl-1-methyl-2-trifluoromethylbenzimidazolium hexafluorophosphate,
3-benzyl-1-methyl-2-trifluoromethylbenzimidazolium methanesulfonate,
3-benzyl-1-methyl-2-trifluoromethylbenzimidazolium triflate,
3-benzyl-1-methyl-2-trifluoromethylbenzimidazolium methyl sulfate,
5-chloro-1,3-dimethyl-2-trifluoromethylbenzimidazolium fluoride,
5-chloro-1,3-dimethyl-2-trifluoromethylbenzimidazolium chloride,
5-chloro-1,3-dimethyl-2-trifluoromethylbenzimidazolium bromide,
5-chloro-1,3-dimethyl-2-trifluoromethylbenzimidazolium iodide,
5-chloro-1,3-dimethyl-2-trifluoromethylbenzimidazolium tetrafluoroborate,
5-chloro-1,3-dimethyl-2-trifluoromethylbenzimidazolium hexafluorophosphate,
5-chloro-1,3-dimethyl-2-trifluoromethylbenzimidazolium methanesulfonate,
5-chloro-1,3-dimethyl-2-trifluoromethylbenzimidazolium triflate,
5-chloro-1,3-dimethyl-2-trifluoromethylbenzimidazolium methyl sulfate,
5,6-dichloro-1,3-dimethyl-2-trifluoromethylbenzimidazolium fluoride,
5,6-dichloro-1,3-dimethyl-2-trifluoromethylbenzimidazolium chloride,
5,6-dichloro-1,3-dimethyl-2-trifluoromethylbenzimidazolium bromide,
5,6-dichloro-1,3-dimethyl-2-trifluoromethylbenzimidazolium iodide,
5,6-dichloro-1,3-dimethyl-2-trifluoromethylbenzimidazolium tetrafluoroborate,
5,6-dichloro-1,3-dimethyl-2-trifluoromethylbenzimidazolium hexafluorophosphate,
5,6-dichloro-1,3-dimethyl-2-trifluoromethylbenzimidazolium methanesulfonate,
5,6-dichloro-1,3-dimethyl-2-trifluoromethylbenzimidazolium triflate,
5,6-dichloro-1,3-dimethyl-2-trifluoromethylbenzimidazolium methyl sulfate,
1,3-dimethyl-4,5,6,7-tetrachloro-2-trifluoromethylbenzimidazolium fluoride,
1,3-dimethyl-4,5,6,7-tetrachloro-2-trifluoromethylbenzimidazolium chloride,
1,3-dimethyl-4,5,6,7-tetrachloro-2-trifluoromethylbenzimidazolium bromide,
1,3-dimethyl-4,5,6,7-tetrachloro-2-trifluoromethylbenzimidazolium iodide,
1,3-dimethyl-4,5,6,7-tetrachloro-2-trifluoromethylbenzimidazolium tetrafluoroborate,
1,3-dimethyl-4,5,6,7-tetrachloro-2-trifluoromethylbenzimidazolium hexafluorophosphate,
1,3-dimethyl-4,5,6,7-tetrachloro-2-trifluoromethylbenzimidazolium methanesulfonate,
1,3-dimethyl-4,5,6,7-tetrachloro-2-trifluoromethylbenzimidazolium triflate,
1,3-dimethyl-4,5,6,7-tetrachloro-2-trifluoromethylbenzimidazolium methyl sulfate,
1,3,5-trimethyl-2-trifluoromethylbenzimidazolium fluoride,
1,3,5-trimethyl-2-trifluoromethylbenzimidazolium chloride,
1,3,5-trimethyl-2-trifluoromethylbenzimidazolium bromide,
1,3,5-trimethyl-2-trifluoromethylbenzimidazolium iodide,
1,3,5-trimethyl-2-trifluoromethylbenzimidazolium tetrafluoroborate,
1,3,5-trimethyl-2-trifluoromethylbenzimidazolium hexafluorophosphate,
1,3,5-trimethyl-2-trifluoromethylbenzimidazolium methanesulfonate,
1,3,5-trimethyl-2-trifluoromethylbenzimidazolium triflate,
1,3,5-trimethyl-2-trifluoromethylbenzimidazolium methyl sulfate,
1,3,5,6-tetramethyl-2-trifluoromethylbenzimidazolium fluoride,
1,3,5,6-tetramethyl-2-trifluoromethylbenzimidazolium chloride,
1,3,5,6-tetramethyl-2-trifluoromethylbenzimidazolium bromide,
1,3,5,6-tetramethyl-2-trifluoromethylbenzimidazolium iodide,
1,3,5,6-tetramethyl-2-trifluoromethylbenzimidazolium tetrafluoroborate,
1,3,5,6-tetramethyl-2-trifluoromethylbenzimidazolium hexafluorophosphate,
1,3,5,6-tetramethyl-2-trifluoromethylbenzimidazolium methanesulfonate,
1,3,5,6-tetramethyl-2-trifluoromethylbenzimidazolium triflate,
1,3,5,6-tetramethyl-2-trifluoromethylbenzimidazolium methyl sulfate,
1,3-dimethyl-5-nitro-2-trifluoromethylbenzimidazolium fluoride,
1,3-dimethyl-5-nitro-2-trifluoromethylbenzimidazolium chloride,
1,3-dimethyl-5-nitro-2-trifluoromethylbenzimidazolium bromide,
1,3-dimethyl-5-nitro-2-trifluoromethylbenzimidazolium iodide,
1,3-dimethyl-5-nitro-2-trifluoromethylbenzimidazolium tetrafluoroborate,
1,3-dimethyl-5-nitro-2-trifluoromethylbenzimidazolium hexafluorophosphate,
1,3-dimethyl-5-nitro-2-trifluoromethylbenzimidazolium methanesulfonate,
1,3-dimethyl-5-nitro-2-trifluoromethylbenzimidazolium triflate,
1,3-dimethyl-5-nitro-2-trifluoromethylbenzimidazolium methyl sulfate,
1,3-dimethyl-2-pentafluoroethylbenzimidazolium fluoride,
1,3-dimethyl-2-pentafluoroethylbenzimidazolium chloride,
1,3-dimethyl-2-pentafluoroethylbenzimidazolium bromide,
1,3-dimethyl-2-pentafluoroethylbenzimidazolium iodide,
1,3-dimethyl-2-pentafluoroethylbenzimidazolium tetrafluoroborate,
1,3-dimethyl-2-pentafluoroethylbenzimidazolium hexafluorophosphate,
1,3-dimethyl-2-pentafluoroethylbenzimidazolium methanesulfonate,
1,3-dimethyl-2-pentafluoroethylbenzimidazolium triflate,
1,3-dimethyl-2-pentafluoroethylbenzimidazolium methyl sulfate,
1,3-dimethyl-2-heptafluoropropylbenzimidazolium fluoride,
1,3-dimethyl-2-heptafluoropropylbenzimidazolium chloride,
1,3-dimethyl-2-heptafluoropropylbenzimidazolium bromide, 1,3-dimethyl-2-heptafluoropropylbenzimidazolium iodide,
1,3-dimethyl-2-heptafluoropropylbenzimidazolium tetrafluoroborate,
1,3-dimethyl-2-heptafluoropropylbenzimidazolium hexafluorophosphate,
1,3-dimethyl-2-heptafluoropropylbenzimidazolium methanesulfonate,
1,3-dimethyl-2-heptafluoropropylbenzimidazolium triflate,
1,3-dimethyl-2-heptafluoropropylbenzimidazolium methyl sulfate,
1,3-dimethyl-2-nonafluorobutylbenzimidazolium fluoride,
1,3-dimethyl-2-nonafluorobutylbenzimidazolium chloride,
1,3-dimethyl-2-nonafluorobutylbenzimidazolium bromide,
1,3-dimethyl-2-nonafluorobutylbenzimidazolium iodide,
1,3-dimethyl-2-nonafluorobutylbenzimidazolium tetrafluoroborate,
1,3-dimethyl-2-nonafluorobutylbenzimidazolium hexafluorophosphate,
1,3-dimethyl-2-nonafluorobutylbenzimidazolium methanesulfonate,
1,3-dimethyl-2-nonafluorobutylbenzimidazolium triflate,
1,3-dimethyl-2-nonafluorobutylbenzimidazolium methyl sulfate,
1,3-dimethyl-2-undecafluoropentylbenzimidazolium fluoride,
1,3-dimethyl-2-undecafluoropentylbenzimidazolium chloride,
1,3-dimethyl-2-undecafluoropentylbenzimidazolium bromide,
1,3-dimethyl-2-undecafluoropentylbenzimidazolium iodide,
1,3-dimethyl-2-undecafluoropentylbenzimidazolium tetrafluoroborate,
1,3-dimethyl-2-undecafluoropentylbenzimidazolium hexafluorophosphate,
1,3-dimethyl-2-undecafluoropentylbenzimidazolium methanesulfonate,
1,3-dimethyl-2-undecafluoropentylbenzimidazolium triflate,
1,3-dimethyl-2-undecafluoropentylbenzimidazolium methyl sulfate,
1,3,5,7-tetramethyl-2,6-bis(trifluoromethyl)-3,5-dihydrobenzodiimidazolium bisfluoride,
1,3,5,7-tetramethyl-2,6-bis(trifluoromethyl)-3,5-dihydrobenzodiimidazolium bischloride,
1,3,5,7-tetramethyl-2,6-bis(trifluoromethyl)-3,5-dihydrobenzodiimidazolium bisbromide,
1,3,5,7-tetramethyl-2,6-bis(trifluoromethyl)-3,5-dihydrobenzodiimidazolium bisiodide,
1,3,5,7-tetramethyl-2,6-bis(trifluoromethyl)-3,5-dihydrobenzodiimidazolium bistetrafluoroborate,
1,3,5,7-tetramethyl-2,6-bis(trifluoromethyl)-3,5-dihydrobenzodiimidazolium bishexafluorophosphate,
1,3,5,7-tetramethyl-2,6-bis(trifluoromethyl)-3,5-dihydrobenzodiimidazolium bismethanesulfonate,
1,3,5,7-tetramethyl-2,6-bis(trifluoromethyl)-3,5-dihydrobenzodiimidazolium bistriflate,
1,3,5,7-tetramethyl-2,6-bis(trifluoromethyl)-3,5-dihydrobenzodiimidazolium bismethyl sulfate and the like.

Preferable specific examples of the compound represented by the general formula (1) as a fluoroalkylating agent include the following compounds:
1,3-dimethyl-2-trifluoromethylbenzimidazolium triflate,
1,3-dimethyl-2-trifluoromethylbenzimidazolium methyl sulfate,
5-chloro-1,3-dimethyl-2-trifluoromethylbenzimidazolium triflate,
5-chloro-1,3-dimethyl-2-trifluoromethylbenzimidazolium methyl sulfate,
1,3-dimethyl-4,5,6,7-tetrachloro-2-trifluoromethylbenzimidazolium triflate,
1,3-dimethyl-4,5,6,7-tetrachloro-2-trifluoromethylbenzimidazolium methyl sulfate,
1,3-dimethyl-5-nitro-2-trifluoromethylbenzimidazolium triflate,
1,3-dimethyl-5-nitro-2-trifluoromethylbenzimidazolium methyl sulfate,
1,3-dimethyl-2-pentafluoroethylbenzimidazolium methyl sulfate, and
1,3-dimethyl-2-pentafluoroethylbenzimidazolium triflate.

More preferable specific examples of the compound represented by the general formula (1) as a fluoroalkylating agent include the following compounds:
1,3-dimethyl-2-trifluoromethylbenzimidazolium triflate,
1,3-dimethyl-2-trifluoromethylbenzimidazolium methyl sulfate,
5-chloro-1,3-dimethyl-2-trifluoromethylbenzimidazolium triflate,
5-chloro-1,3-dimethyl-2-trifluoromethylbenzimidazolium methyl sulfate,
1,3-dimethyl-5-nitro-2-trifluoromethylbenzimidazolium triflate,
1,3-dimethyl-5-nitro-2-trifluoromethylbenzimidazolium methyl sulfate,
1,3-dimethyl-2-pentafluoroethylbenzimidazolium methyl sulfate, and
1,3-dimethyl-2-pentafluoroethylbenzimidazolium triflate.

(Method for Production of Compound Represented by General Formula (1))

Methods for the production of the compound represented by the general formula (1) (i.e., the fluoroalkylating agent of the present invention) will be described below. However, the methods for the production of the compound represented by the general formula (1) are not limited to these methods.

According to the method shown in the following reaction scheme, the compound represented by the general formula (1) (i.e., the fluoroalkylating agent of the present invention) can be produced.

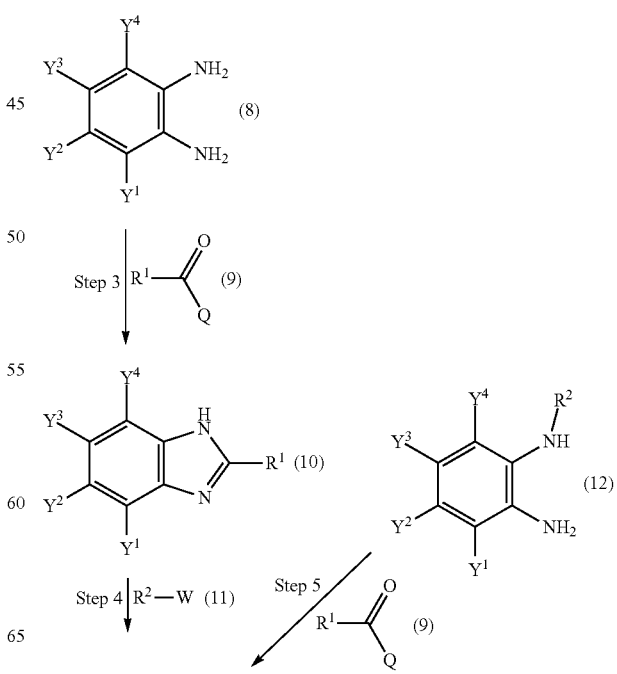

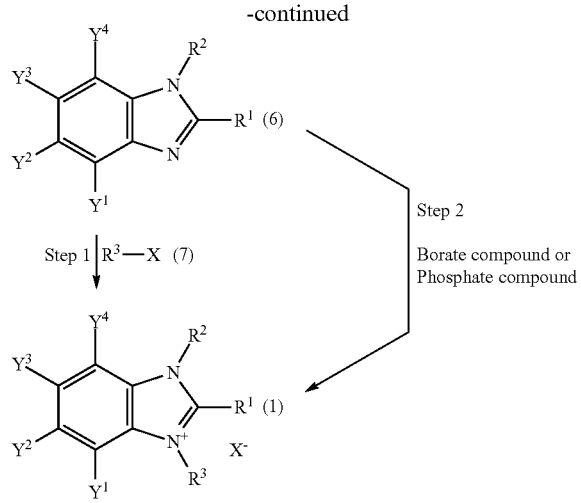

(Step 1)
(Method for Production of Compound Represented by General Formula (1) by Reaction of Compound Represented by General Formula (6) with Compound Represented by General Formula (7))

One method for the production of the compound represented by the general formula (1) (fluoroalkylating agent) will be described. As shown in the following reaction scheme, the compound represented by the general formula (1) can be produced by reacting the compound represented by the general formula (6) with the compound represented by the general formula (7).

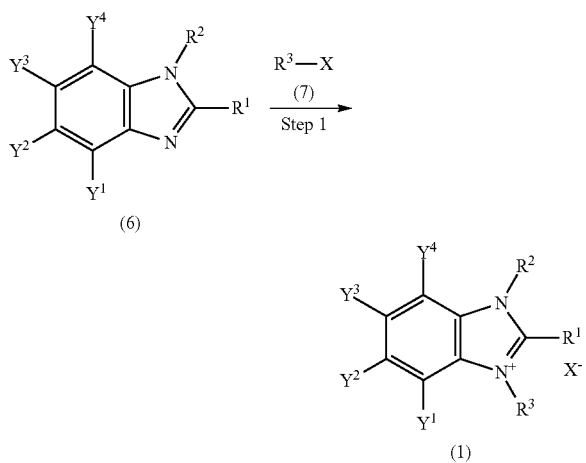

In the above reaction scheme, $R^1$, $R^2$, $R^3$, $Y^1$, $Y^2$, $Y^3$, $Y^4$ and $X^-$ are as described above; and $X^-$ is as described below.

(Material Compound-1 of Step 1)
(Compound Represented by General Formula (6))

The compound represented by the general formula (6) can be produced by the method described below. In addition, the compound represented by the general formula (6) can also be produced from a known compound in accordance with a known method.

(Material Compound-2 of Step 1)
(Compound Represented by General Formula (7))

X in the general formula (7) is a leaving group corresponding to $X^-$ in the general formula (1).

As the compound represented by the general formula (7), a known alkylating agent can be used with no particular restriction.

Examples of the compound represented by the general formula (7) include, but are not limited to, methyl chloride, methyl bromide, methyl iodide, methyl methanesulfonate, methyl triflate, methyl p-toluenesulfonate, dimethyl sulfate, ethyl chloride, ethyl bromide, ethyl iodide, ethyl methanesulfonate, ethyl triflate, ethyl p-toluenesulfonate, diethyl sulfate, propyl bromide, propyl iodide, propyl methanesulfonate, propyl triflate, dipropyl sulfate, isopropyl bromide, isopropyl iodide, isopropyl methanesulfonate, isopropyl triflate, diisopropyl sulfate, butyl bromide, butyl iodide, butyl methanesulfonate, butyl triflate, dibutyl sulfate, benzyl chloride, benzyl bromide and the like. "Alkyl p-toluenesulfonate" is also referred to as "alkyl 4-methylbenzenesulfonate" or "alkyl 4-methylphenylsulfonate". For example, "methyl p-toluenesulfonate" is also referred to as "methyl 4-methylbenzenesulfonate" or "methyl 4-methylphenylsulfonate". The same applies to analogues thereof and derivatives thereof. In addition, herein, "benzenesulfonic acid" in all the terms is also referred to as "phenylsulfonic acid". That is, herein, "benzenesulfonic acid" in all the terms can be replaced by "phenylsulfonic acid".

From the viewpoints of reactivity, yield, usefulness of the fluoroalkylating agent represented by the general formula (1), economic efficiency and the like, preferable examples of the compound represented by the general formula (7) include methyl iodide, methyl methanesulfonate, methyl triflate, methyl p-toluenesulfonate, dimethyl sulfate, ethyl iodide, ethyl methanesulfonate, ethyl triflate, ethyl p-toluenesulfonate, diethyl sulfate, benzyl chloride and benzyl bromide.

More preferable examples of the compound represented by the general formula (7) include methyl iodide, methyl methanesulfonate, methyl triflate, dimethyl sulfate, ethyl iodide, ethyl methanesulfonate, ethyl triflate and diethyl sulfate.

Further preferable examples of the compound represented by the general formula (7) include dimethyl sulfate.

(Amount of Compound Represented by the General Formula (7) Used in Step 1)

The amount of the used compound represented by the general formula (7) may be any amount as long as the reaction proceeds. From the viewpoints of yield, suppression of by-products, economic efficiency and the like, the range of generally 1 equivalent or more, preferably 1 to 50 equivalents, more preferably 1 to 10 equivalents, further preferably 1 to 3 equivalents, based on the compound represented by the general formula (6), can be mentioned as examples. The amount less than 1 equivalent leaves the unreacted compound represented by the general formula (6). The amount more than 50 equivalents brings no remarkable improvement on the reaction yield.

(Solvent in Step 1)

The reaction of the step 1 may be carried out without a solvent. However, from the viewpoints of smooth progress of the reaction, economic efficiency and the like, a solvent may be used in the reaction of the step 1. The solvent used in the reaction of the step 1 may be any solvent as long as the reaction proceeds.

Examples of the solvent used in the reaction of the step 1 include, but are not limited to, amides, alkyl ureas, sulfoxides, sulfones, ethers, ketones, carboxylic acid esters, nitriles, aromatic hydrocarbon derivatives, aliphatic hydrocarbons, halogenated aliphatic hydrocarbons, and any combination thereof in any ratio.

Preferable examples of the solvent used in the reaction of the step 1 include amides, alkyl ureas, sulfoxides, sulfones, ethers, ketones, nitriles, aromatic hydrocarbon derivatives, halogenated aliphatic hydrocarbons, and any combination thereof in any ratio,
more preferably amides, alkyl ureas, ketones, nitriles, aromatic hydrocarbon derivatives, halogenated aliphatic hydrocarbons, and any combination thereof in any ratio.

Preferable specific examples of the solvent used in the reaction of the step 1 include, but are not limited to, N,N-dimethylformamide (DMF), N,N-diethylformamide, N,N-dimethylacetamide (DMAC), N,N-diethylacetamide, N-methylpyrrolidone (NMP), N,N'-dimethylimidazolidinone (DMI),
dimethyl sulfoxide (DMSO),
sulfolane, dimethyl sulfone,
tetrahydrofuran (THF), 2-methyltetrahydrofuran, 1,4-dioxane, diisopropyl ether, dibutyl ether, di-tert-butyl ether, cyclopentyl methyl ether (CPME), methyl tert-butyl ether, 1,2-dimethoxyethane (DME), diglyme
acetone, ethyl methyl ketone, isopropyl methyl ketone, isobutyl methyl ketone (MIBK),
acetonitrile,
toluene, xylene, chlorobenzene, dichlorobenzene, trichlorobenzene,
dichloromethane, and
any combination thereof in any ratio.

More preferable specific examples of the solvent used in the reaction of the step 1 include
N,N-dimethylformamide (DMF), N,N-dimethylacetamide (DMAC), N-methylpyrrolidone (NMP),
N,N'-dimethylimidazolidinone (DMI),
acetone, ethyl methyl ketone, isopropyl methyl ketone, isobutyl methyl ketone (MIBK),
acetonitrile,
toluene, xylene, chlorobenzene, dichlorobenzene, and any combination thereof in any ratio.

(Amount of Solvent Used in Step 1)
The amount of the solvent used in the reaction of the step 1 may be any amount as long as the reaction proceeds. From the viewpoints of reaction efficiency and ease of operation and the like, the range of generally 0 (zero) to 10.0 L (liters), preferably 0.01 to 10 L,
further preferably 0.1 to 5 L, based on 1 mol of the compound represented by the general formula (6), can be mentioned as examples. However, the amount used can be adjusted appropriately by a person skilled in the art. When a combination of two or more solvents is used, the ratio of the two or more solvents may be any ratio as long as the reaction proceeds.

(Reaction Temperature of Step 1)
The reaction temperature is not particularly limited. From the viewpoints of yield, suppression of by-products, economic efficiency and the like, more specifically, for example, from the viewpoints of reaction rate, stability of the product and the like, the range of generally −20 (minus 20) to 200° C.,
preferably −20 to 150° C.,
more preferably 0 to 150° C.,
further preferably 20 to 130° C. can be mentioned as examples.

(Reaction Time of Step 1)
The reaction time is not particularly limited. From the viewpoints of yield, suppression of by-products, economic efficiency and the like, the range of 0.5 to 72 hours or 0.5 hours to 48 hours,
preferably 1 to 36 hours or 1 to 24 hours can be mentioned as examples. However, the reaction time can be adjusted appropriately by a person skilled in the art.

(Step 2)
(Method for Production of Compound Represented by General Formula (1) by Reaction of Compound Represented by General Formula (6) with Borate Compound or Phosphate Compound)

Another method for the production of the compound represented by the general formula (1) (fluoroalkylating agent) will be described. As shown in the following reaction scheme, the compound represented by the general formula (1) can be produced by reacting the compound represented by the general formula (6) with the borate compound or the phosphate compound.

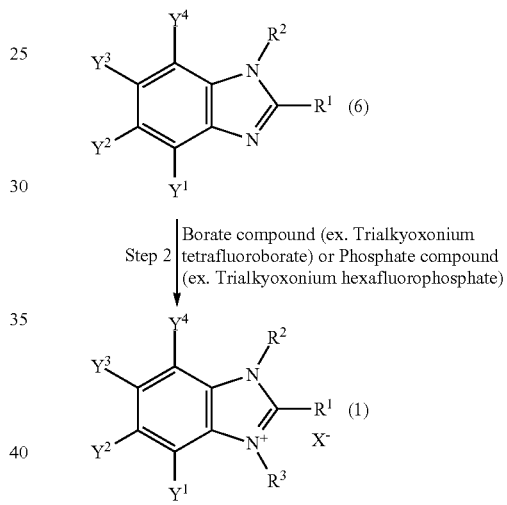

In the above reaction scheme, $R^1$, $R^2$, $R^3$, $Y^1$, $Y^2$, $Y^3$ and $Y^4$ are as described above; and $X^-$ is as described below.

(Material Compound-1 of Step 2)
(Compound Represented by General Formula (6))
The compound represented by the general formula (6) can be produced by the method described below. In addition, the compound represented by the general formula (6) can also be produced from a known compound in accordance with a known method.

(Material Compound-2-1 of Step 2)
(Borate Compound)
Examples of the borate compound include, but are not limited to, trialkyloxonium tetrafluoroborate and the like.

From the viewpoints of reactivity, yield, usefulness of the fluoroalkylating agent represented by the general formula (1), economic efficiency and the like, preferable examples of the borate compound include tri (C1 to C4 alkyl) oxonium tetrafluoroborate and the like.

Specific examples of the tri (C1 to C4 alkyl) oxonium tetrafluoroborate include trimethyloxonium tetrafluoroborate, triethyloxonium tetrafluoroborate and the like,
preferably trimethyloxonium tetrafluoroborate.

A known compound can be used as such a borate compound.

(Material Compound-2-2 of Step 2)
(Phosphate Compound)
Examples of the phosphate compound include, but are not limited to, trialkyloxonium hexafluorophosphate and the like.

From the viewpoints of reactivity, yield, usefulness of the fluoroalkylating agent represented by the general formula (1), economic efficiency and the like, preferable examples of the phosphate compound include tri (C1 to C4 alkyl) oxonium hexafluorophosphate and the like.

Specific examples of the tri (C1 to C4 alkyl) hexafluorophosphate include trimethyloxonium hexafluorophosphate, triethyloxonium hexafluorophosphate and the like,
preferably trimethyloxonium hexafluorophosphate.

A known compound can be used as such a phosphate compound.

(Amounts of Borate Compound and Phosphate Compound Used in Step 2)

The amount of the used borate compound or phosphate compound may be any amount as long as the reaction proceeds. From the viewpoints of yield, suppression of by-products, economic efficiency and the like, the range of generally 1 equivalent or more,
preferably 1 to 10 equivalents,
more preferably 1 to 3 equivalents,
further preferably 1 to 2 equivalents, based on the compound represented by the general formula (6), can be mentioned as examples.

(Solvent in Step 2)

The reaction of the step 2 may be carried out without a solvent. However, from the viewpoints of smooth progress of the reaction, economic efficiency and the like, a solvent may be used in the reaction of the step 2. The solvent used in the reaction of the step 2 may be any solvent as long as the reaction proceeds.

Examples of the solvent used in the reaction of the step 2 include, but are not limited to, nitriles, aromatic hydrocarbon derivatives, aliphatic hydrocarbons, halogenated aliphatic hydrocarbons, and any combination thereof in any ratio.

Preferable examples of the solvent used in the reaction of the step 2 include halogenated aliphatic hydrocarbons.

Specific examples of the solvent used in the reaction of the step 2 include, but are not limited to,
acetonitrile,
toluene, xylene, chlorobenzene, dichlorobenzene, trichlorobenzene,
hexane, cyclohexane, ethylcyclohexane,
dichloromethane, and
any combination thereof in any ratio.

Preferable specific examples of the solvent used in the reaction of the step 2 include dichloromethane.

(Amount of Solvent Used in Step 2)

The amount of the solvent used in the reaction of the step 2 may be any amount as long as the reaction proceeds. The range of generally 0 (zero) to 10.0 L (liters),
preferably 0.01 to 10 L,
further preferably 0.1 to 5 L, based on 1 mol of the compound represented by the general formula (6), can be mentioned as examples. However, the amount used can be adjusted appropriately by a person skilled in the art. When a combination of two or more solvents is used, the ratio of the two or more solvents may be any ratio as long as the reaction proceeds.

(Reaction Temperature of Step 2)

The reaction temperature is not particularly limited. From the viewpoints of yield, suppression of by-products, economic efficiency and the like, more specifically, for example, from the viewpoints of reaction rate, stability of the product and the like, the range of generally −20 (minus 20) to 200° C.,
preferably −20 to 150° C.,
more preferably 0 to 150° C.,
further preferably 0 to 70° C. can be mentioned as examples.

(Reaction Time of Step 2)

The reaction time is not particularly limited. From the viewpoints of yield, suppression of by-products, economic efficiency and the like, the range of 0.5 to 48 hours,
preferably 1 to 24 hours can be mentioned as examples. However, the reaction time can be adjusted appropriately by a person skilled in the art.

(Product of Step 2)

In the step 2, $X^-$ in the general formula (1) is a monovalent anion derived from the borate compound or the phosphate compound. Examples of $X^-$ include, but are not limited to, borate ions (for example, $BF_4^-$ (tetrafluoroborate ion)), phosphate ions (for example, $PF_6^-$ (hexafluorophosphate ion)) and the like.

(Steps 3 and 4)

One method for the production of the compound represented by the general formula (6), which is an intermediate for the compound represented by the general formula (1) (fluoroalkylating agent), will be described. As shown in the following reaction scheme, the compound represented by the general formula (6) can be produced by reacting the compound represented by the general formula (8) with the compound represented by the general formula (9) to produce the compound represented by the general formula (10), and then reacting the obtained compound represented by the general formula (10) with the compound represented by the general formula (11).

In the above reaction scheme, $R^1$, $R^2$, $Y^1$, $Y^2$, $Y^3$ and $Y^4$ are as described above; and Q and W are as described below.

(Step 3)

(Method for Production of Compound Represented by General Formula (10) by Reaction of Compound Represented by General Formula (8) with Compound Represented by General Formula (9))

The step of producing the compound represented by the general formula (10) by reacting the compound represented by the general formula (8) with the compound represented by the general formula (9), as shown in the following reaction scheme, will be described.

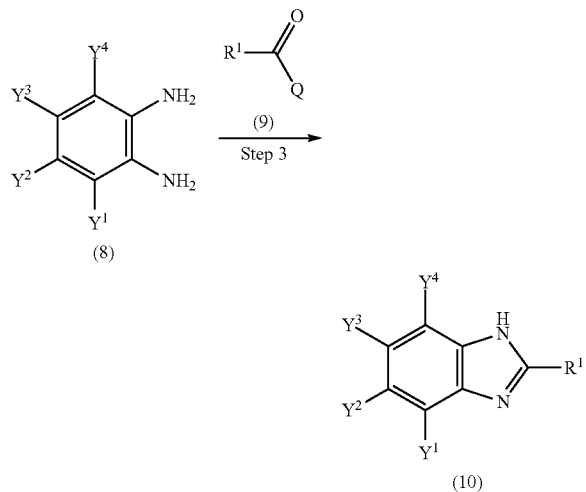

In the above reaction scheme, $R^1$, $Y^1$, $Y^2$, $Y^3$ and $Y^4$ are as described above; and Q is as described below.

(Material Compound-1 of Step 3)

(Compound Represented by General Formula (8))

The compound represented by the general formula (8) is a known compound or is a compound which can be produced from a known compound in accordance with a known method.

Examples of the compound represented by the general formula (8) include, but are not limited to,
1,2-phenylenediamine,
4-chloro-1,2-phenylenediamine,
4,5-dichloro-1,2-phenylenediamine,
3,4,5,6-tetrachloro-1,2-phenylenediamine,
4-methyl-1,2-phenylenediamine,
4,5-dimethyl-1,2-phenylenediamine,
4-nitro-1,2-phenylenediamine and the like.

Preferable examples of the compound represented by the general formula (8) include
1,2-phenylenediamine,
4-chloro-1,2-phenylenediamine,
3,4,5,6-tetrachloro-1,2-phenylenediamine, and
4-nitro-1,2-phenylenediamine.

More preferable examples of the compound represented by the general formula (8) include
1,2-phenylenediamine,
4-chloro-1,2-phenylenediamine, and
4-nitro-1,2-phenylenediamine.

(Material Compound-2 of Step 3)

(Compound Represented by General Formula (9))

Q in the general formula (9) is a hydroxy group, a halogen atom (preferably a chlorine atom) or a —O—C(=O)—$R^7$ group.

$R^7$ in the general formula (9) is the same as $R^1$ in the general formula (9).

The compound represented by the general formula (9) is a known compound or is a compound which can be produced from a known compound in accordance with a known method.

Examples of the compound represented by the general formula (9) include, but are not limited to,
trifluoroacetic acid, trifluoroacetic acid chloride, trifluoroacetic anhydride, pentafluoropropionic acid, pentafluoropropionic acid chloride, pentafluoropropionic anhydride,
heptafluorobutanoic acid, heptafluorobutanoic acid chloride, heptafluorobutanoic anhydride,
nonafluoropentanoic acid, nonafluoropentanoic acid chloride, nonafluoropentanoic anhydride,
undecafluorohexanoic acid, undecafluorohexanoic acid chloride, undecafluorohexanoic anhydride,
difluoroacetic acid, difluoroacetic acid chloride, trifluoroacetic anhydride and the like.

From the viewpoints of usefulness of the fluoroalkylating agent represented by the general formula (1), economic efficiency and the like, preferable examples of the compound represented by the general formula (9) include trifluoroacetic acid, trifluoroacetic acid chloride, trifluoroacetic anhydride, pentafluoropropionic acid, pentafluoropropionic acid chloride and pentafluoropropionic acid chloride anhydride.

The compound represented by the general formula (9) is a carboxylic acid or a derivative thereof. One carboxylic acid has derivatives such as acid halides (preferably acid chloride) and acid anhydrides. When Q in the general formula (9) is a hydroxy group, the compound represented by the general formula (9) is a carboxylic acid. A specific example of the carboxylic acid is trifluoroacetic acid. When Q in the general formula (9) is a halogen atom, the compound represented by the general formula (9) is an acid halide. A specific example of the carboxylic acid halide is trifluoroacetic acid chloride. When Q in the general formula (9) is a —O—C(=O)—$R^7$ group, the compound represented by the general formula (9) is an acid anhydride. A specific example of the acid anhydride is trifluoroacetic anhydride. As to one carboxylic acid derivative, one of the carboxylic acid, the acid halides and the acid anhydrides may be used alone, or a combination of two or more thereof in any ratio may be used.

(Amount of Compound Represented by General Formula (9) Used in Step 3)

The amount of the used compound represented by the general formula (9) may be any amount as long as the reaction proceeds. From the viewpoints of yield, suppression of by-products, economic efficiency and the like, the range of generally 1 equivalent or more,
preferably 1 to 10 equivalents,
more preferably 1 to 5 equivalents, based on the compound represented by the general formula (8), can be mentioned as examples. However, the amount used can be adjusted appropriately by a person skilled in the art. The amount less than 1 equivalent leaves the unreacted compound represented by the general formula (8). The amount more than 10 equivalents brings no remarkable improvement on the reaction yield.

(Base in Step 3)

If necessary, a base may be used in the reaction of the step 3. For example, when the compound represented by the general formula (9) is acid chloride, a base may be used. A base may or may not be used as long as the reaction proceeds. In the case of using a base in the reaction of the step 3, the base may be any base as long as the reaction proceeds. Examples of the base which can be used in the reaction of the step 3 include, but are not limited to, inorganic bases and organic bases.

Examples of the inorganic base which can be used in the reaction of the step 3 include, but are not limited to,
alkali metal hydroxides (for example, lithium hydroxide, sodium hydroxide, potassium hydroxide and the like),
alkaline earth metal hydroxides (for example, magnesium hydroxide, calcium hydroxide, barium hydroxide and the like),
alkali metal carbonates (for example, lithium carbonate, sodium carbonate, potassium carbonate and the like),
alkaline earth metal carbonates (for example, magnesium carbonate, calcium carbonate, barium carbonate and the like),
alkali metal bicarbonates (for example, lithium bicarbonate, sodium bicarbonate, potassium bicarbonate and the like),
alkaline earth metal bicarbonates (for example, magnesium bicarbonate, calcium bicarbonate, barium bicarbonate and the like) and the like.

Examples of the organic base which can be used in the reaction of the step 3 include
pyridines (for example, pyridine, 4-(dimethylamino)-pyridine, 4-pyrrolidinopyridine, 2,6-lutidine and the like),
quinolines and isomers thereof (for example, quinoline, isoquinoline and the like), tertiary amines (for example, triethylamine, tributylamine, diisopropylethylamine and the like),
secondary amines (for example, diethylamine, dipropylamine, diisopropylamine and the like),
primary amines (for example, butylamine and the like),
aromatic amines (for example, N,N-diethylaniline, N,N-dimethylaniline and the like), cyclic amines (for example, piperidine, morpholine, 1,8-diazabicyclo[5.4.0]-7-undec-7-ene (DBU), 1,5-diazabicyclo[4.3.0]non-5-ene (DBN), 1,4-diazabicyclo[2.2.2]octane (DABCO) and the like) and the like.

(Amount of Base Used in Step 3)

The amount of the base used in the reaction of the step 3 may be any amount as long as the reaction proceeds. In the case of using the base in the reaction of the step 3, from the viewpoints of yield, suppression of by-products, economic efficiency and the like, the range of generally 1 to 10 equivalents
preferably 1 to 5 equivalents,
more preferably 1 to 2 equivalents, based on the compound represented by the general formula (8), can be mentioned as examples.

(Solvent in Step 3)

The reaction of the step 3 is carried out in the presence or absence of a solvent. As shown in Examples, the reaction of the step 3 can be carried out without a solvent. On the other hand, a solvent can also be used in the reaction of the step 3. In the case of using a solvent in the reaction of the step 3, the solvent may be any solvent as long as the reaction proceeds.

Examples of the solvent which can be used in the reaction of the step 3 include, but are not limited to,
amides (for example, N,N-dimethylformamide (DMF), N,N-dimethylacetamide (DMAC), N-methylpyrrolidone (NMP) and the like),
alkyl ureas (for example, N,N'-dimethylimidazolidinone (DMI) and the like),
sulfoxides (for example, dimethyl sulfoxide (DMSO) and the like),
sulfones (for example, sulfolane and the like),
ethers (for example, tetrahydrofuran (THF), 1,4-dioxane, diisopropyl ether, dibutyl ether, di-tert-butyl ether, cyclopentyl methyl ether (CPME), methyl tert-butyl ether, 1,2-dimethoxyethane (DME), diglyme and the like),
nitriles (for example, acetonitrile and the like),
aromatic hydrocarbon derivatives (for example, benzene, toluene, xylene, chlorobenzene, dichlorobenzene, trichlorobenzene, nitrobenzene and the like), halogenated aliphatic hydrocarbons (for example, dichloromethane and the like), and any combination thereof in any ratio.

Preferable examples of the solvent which can be used in the reaction of the step 3 include, but are not limited to, N,N-dimethylformamide (DMF), N,N'-dimethylimidazolidinone, acetonitrile, dichloromethane, toluene, xylene, chlorobenzene, dichlorobenzene, and any combination thereof in any ratio.

(Amount of Solvent Used in Step 3)

The amount of the solvent used in the reaction of the step 3 may be any amount as long as the reaction proceeds.

In one embodiment, from the viewpoints of reaction efficiency and the like, the amount of the solvent used in the reaction of the step 3 is 0 L (zero liter) based on 1 mol of the compound represented by the general formula (8).

In another embodiment, from the viewpoints of reaction efficiency and ease of operation and the like, the range of generally 0 (zero) to 10.0 L (liters), preferably 0 to 5 L, based on 1 mol of the compound represented by the general formula (8), can be mentioned as examples of the amount of the solvent used in the reaction of the step 3. However, the amount used can be adjusted appropriately by a person skilled in the art. When a combination of two or more solvents is used, the ratio of the two or more solvents may be any ratio as long as the reaction proceeds.

(Reaction Temperature of Step 3)

The reaction temperature is not particularly limited. From the viewpoints of yield, suppression of by-products, economic efficiency and the like, more specifically, for example, from the viewpoints of reaction rate, stability of the product and the like, the range of generally −20 (minus 20) to 200° C.,
preferably −20 to 150° C.,
more preferably 0 to 130° C. can be mentioned as examples. The reaction temperature can be adjusted appropriately by a person skilled in the art.

(Reaction Time of Step 3)

The reaction time is not particularly limited. From the viewpoints of yield, suppression of by-products, economic efficiency and the like, the range of 0.5 to 48 hours,
preferably 1 to 24 hours can be mentioned as examples. However, the reaction time can be adjusted appropriately by a person skilled in the art.

(Step 4)

(Method for Production of Compound Represented by General Formula (6) by Reaction of Compound Represented by General Formula (10) with Compound Represented by General Formula (11))

The step of producing the compound represented by the general formula (6) by reacting the compound represented by the general formula (10) with the compound represented by the general formula (11), as shown in the following reaction scheme, will be described.

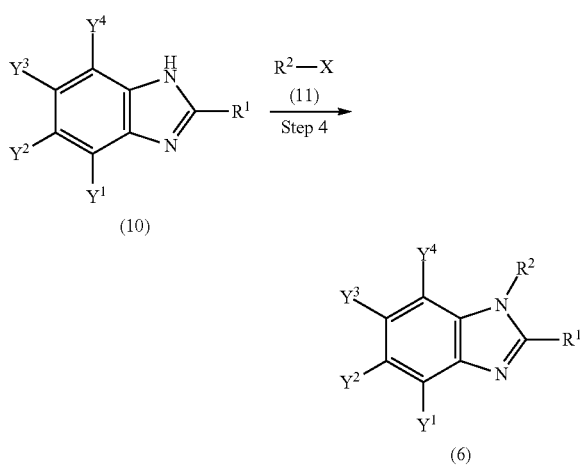

In the above reaction scheme, $R^1$, $R^2$, $Y^1$, $Y^2$, $Y^3$ and $Y^4$ are as described above; and W is as described below.

(Material Compound-1 of Step 4)
(Compound Represented by General Formula (10))

The compound represented by the general formula (10) can be produced by the method described above. In addition, the compound represented by the general formula (10) can also be produced from a known compound in accordance with a known method.

(Material Compound-2 of Step 4)
(Compound Represented by General Formula (11))

As the compound represented by the general formula (11), a known alkylating agent can be used with no particular restriction.

Examples of the compound represented by the general formula (11) include, but are not limited to,
methyl chloride, methyl bromide, methyl iodide, methyl methanesulfonate, methyl triflate, methyl p-toluenesulfonate, dimethyl sulfate,
ethyl chloride, ethyl bromide, ethyl iodide, ethyl methanesulfonate, ethyl triflate, ethyl p-toluenesulfonate, diethyl sulfate,
propyl bromide, propyl iodide, propyl methanesulfonate, propyl triflate, dipropyl sulfate,
isopropyl bromide, isopropyl iodide, isopropyl methanesulfonate, isopropyl triflate, diisopropyl sulfate,
butyl bromide, butyl iodide, butyl methanesulfonate, butyl triflate, dibutyl sulfate, benzyl chloride, benzyl bromide and the like.

From the viewpoints of reactivity, yield, usefulness of the fluoroalkylating agent represented by the general formula (1), economic efficiency and the like, preferable examples of the compound represented by the general formula (11) include
methyl iodide, methyl methanesulfonate, methyl triflate, methyl p-toluenesulfonate, dimethyl sulfate,
ethyl iodide, ethyl methanesulfonate, ethyl triflate, ethyl p-toluenesulfonate, diethyl sulfate,
benzyl chloride and benzyl bromide.

More preferable examples of the compound represented by the general formula (11) include
methyl iodide, methyl methanesulfonate, methyl triflate, dimethyl sulfate, ethyl iodide, ethyl methanesulfonate, ethyl triflate and diethyl sulfate.

Further preferable examples of the compound represented by the general formula (11) include methyl iodide, methyl methanesulfonate, methyl triflate and dimethyl sulfate.

W in the general formula (11) is a leaving group. W in the general formula (11) may be any atom or atomic group as long as it functions as a leaving group in the reaction of the step 4. Examples of the leaving group as W in the general formula (11) include, but are not limited to,
a halogen atom (for example, a chlorine atom, a bromine atom, an iodine atom and the like),
a C1 to C4 alkylsulfonyloxy group (for example, a methanesulfonyloxy group, an ethanesulfonyloxy group and the like),
a C1 to C4 haloalkylsulfonyloxy group (for example, a difluoromethanesulfonyloxy group, a trifluoromethanesulfonyloxy group and the like),
a benzenesulfonyloxy group which may have a C1 to C4 alkyl group or a halogen atom (for example, a benzenesulfonyloxy group, a 4-methylbenzenesulfonyloxy group, a 4-chlorobenzenesulfonyloxy group and the like) and the like.

The "methanesulfonyloxy group" is also referred to as a "methylsulfonyloxy group". The same applies to analogues thereof and derivatives thereof. Therefore, for example, a "trifluoromethanesulfonyloxy group" is also referred to as a "trifluoromethylsulfonyloxy group".

Furthermore, the "benzenesulfonyloxy group" is also referred to as a "phenylsulfonyloxy group". The same applies to analogues thereof and derivatives thereof. Therefore, for example, a "4-methylbenzenesulfonyloxy group" is also referred to as a "4-methylphenylsulfonyloxy group". Furthermore, a "4-methylbenzenesulfonyloxy group" is also referred to as a "p-toluenesulfonyloxy group". In addition, herein, "benzenesulfonyloxy" in all the terms is also referred to as "phenylsulfonyloxy". That is, herein, "benzenesulfonyloxy" in all the terms can be replaced by "phenylsulfonyloxy".

(Amount of Compound Represented by General Formula (11) Used in Step 4)

The amount of the used compound represented by the general formula (11) may be any amount as long as the reaction proceeds. From the viewpoints of yield, suppression of by-products, economic efficiency and the like, the range of generally 1 equivalent or more,
preferably 1 to 10 equivalents,
more preferably 1 to 5 equivalents,
further preferably 1 to 3 equivalents, based on the compound represented by the general formula (11), can be mentioned as examples. However, the amount used can be adjusted appropriately by a person skilled in the art. The amount less than 1 equivalent leaves the unreacted compound represented by the general formula (10). The amount more than 10 equivalents brings no remarkable improvement on the reaction yield.

(Base in Step 4)

The reaction of the step 4 is carried out in the presence of a base. The base may be any base as long as the reaction proceeds. Examples of the base which can be used in the reaction of the step 4 include, but are not limited to, inorganic bases and organic bases.

Examples of the inorganic base which can be used in the reaction of the step 4 include, but are not limited to,
alkali metal hydroxides (for example, lithium hydroxide, sodium hydroxide, potassium hydroxide and the like),
alkaline earth metal hydroxides (for example, magnesium hydroxide, calcium hydroxide, barium hydroxide and the like),
alkali metal carbonates (for example, lithium carbonate, sodium carbonate, potassium carbonate and the like), alkaline earth metal carbonates (for example, magnesium carbonate, calcium carbonate, barium carbonate and the like),
alkali metal bicarbonates (for example, lithium bicarbonate, sodium bicarbonate, potassium bicarbonate and the like),
alkaline earth metal bicarbonates (for example, magnesium bicarbonate, calcium bicarbonate, barium bicarbonate and the like),
alkali metal hydrides (for example, lithium hydride, sodium hydride, potassium hydride and the like) and the like.

Examples of the organic base which can be used in the reaction of the step 4 include
pyridines (for example, pyridine, 4-(dimethylamino)-pyridine, 4-pyrrolidinopyridine, 2,6-lutidine and the like),
quinolines and isomers thereof (for example, quinoline, isoquinoline and the like),
tertiary amines (for example, triethylamine, tributylamine, diisopropylethylamine and the like),
secondary amines (for example, diethylamine, dipropylamine, diisopropylamine and the like),
primary amines (for example, butylamine and the like),
aromatic amines (for example, N,N-diethylaniline, N,N-dimethylaniline and the like),
cyclic amines (for example, piperidine, morpholine, 1,8-diazabicyclo[5.4.0]-7-undec-7-ene (DBU), 1,5-diazabicyclo[4.3.0]non-5-ene (DBN), 1,4-diazabicyclo[2.2.2]octane (DABCO) and the like) and the like. These bases may be used alone or in a combination of two or more thereof in any ratio. The form of the base may be any form as long as the reaction proceeds. The form of the base can be selected appropriately by a person skilled in the art.

From the viewpoints of yield, suppression of by-products, economic efficiency and the like, preferable examples of the base which can be used in the reaction of the step 4 include alkali metal hydroxides, alkali metal carbonates, alkali metal bicarbonates and alkali metal hydrides, more preferably alkali metal hydroxides, alkali metal carbonates and alkali metal bicarbonates.

Preferable specific examples of the base which can be used in the reaction of the step 4 include sodium hydroxide, potassium hydroxide, sodium carbonate, potassium carbonate, sodium bicarbonate, potassium bicarbonate, sodium hydride and potassium hydride,
more preferably sodium hydroxide, potassium hydroxide, sodium carbonate, potassium carbonate sodium bicarbonate.

(Amount of Base Used in Step 4)

The amount of the base used in the reaction of the step 4 may be any amount as long as the reaction proceeds. From the viewpoints of yield, suppression of by-products, economic efficiency and the like, the range of generally 1 to 10 equivalents preferably 1 to 5 equivalents,
more preferably 1 to 2 equivalents, based on the compound represented by the general formula (10), can be mentioned as examples.

(Solvent in Step 4)

The reaction of the step 4 may be carried out without a solvent. However, from the viewpoints of smooth progress of the reaction, economic efficiency and the like, a solvent may be used in the reaction of the step 4. The solvent used in the reaction of the step 4 may be any solvent as long as the reaction proceeds.

Examples of the solvent used in the reaction of the step 4 include, but are not limited to, amides, alkyl ureas, sulfoxides, sulfones, ethers, ketones, carboxylic acid esters, nitriles, aromatic hydrocarbon derivatives, aliphatic hydrocarbons, halogenated aliphatic hydrocarbons, water, and any combination thereof in any ratio.

Preferable examples of the solvent used in the reaction of the step 4 include amides, alkyl ureas, sulfoxides, sulfones, ethers, ketones, nitriles, aromatic hydrocarbon derivatives, halogenated aliphatic hydrocarbons, and any combination thereof in any ratio,
more preferably amides, alkyl ureas, ketones, nitriles, aromatic hydrocarbon derivatives, halogenated aliphatic hydrocarbons, and any combination thereof in any ratio.

Preferable specific examples of the solvent used in the reaction of the step 4 include, but are not limited to,
N,N-dimethylformamide (DMF), N,N-diethylformamide, N,N-dimethylacetamide (DMAC), N,N-diethylacetamide, N-methylpyrrolidone (NMP), N,N'-dimethylimidazolidinone (DMI),
dimethyl sulfoxide (DMSO),
sulfolane, dimethyl sulfone,
tetrahydrofuran (THF), 2-methyltetrahydrofuran, 1,4-dioxane, diisopropyl ether, dibutyl ether, di-tert-butyl ether, cyclopentyl methyl ether (CPME), methyl tert-butyl ether, 1,2-dimethoxyethane (DME), diglyme,
acetone, ethyl methyl ketone, isopropyl methyl ketone, isobutyl methyl ketone (MIBK),
acetonitrile,
toluene, xylene, chlorobenzene, dichlorobenzene, trichlorobenzene, dichloromethane, and
any combination thereof in any ratio.

More preferable specific examples of the solvent used in the reaction of the step 4 include
N,N-dimethylformamide (DMF), N,N-dimethylacetamide (DMAC), N-methylpyrrolidone (NMP), N,N'-dimethylimidazolidinone (DMI),
acetone, ethyl methyl ketone, isopropyl methyl ketone, isobutyl methyl ketone (MIBK),
acetonitrile,
toluene, xylene, chlorobenzene, dichlorobenzene, and
any combination thereof in any ratio. However, the solvent can be selected appropriately by a person skilled in the art.

(Amount of Solvent Used in Step 4)

The amount of the solvent used in the reaction of the step 4 may be any amount as long as the reaction proceeds. From the viewpoints of reaction efficiency and ease of operation and the like, the range of generally 0 (zero) to 10.0 L (liters), preferably 0.01 to 10 L,
further preferably 0.1 to 5 L, based on 1 mol of the compound represented by the general formula (6), can be mentioned as examples. However, the amount used can be adjusted appropriately by a person skilled in the art. When a combination of two or more solvents is used, the ratio of the two or more solvents may be any ratio as long as the reaction proceeds.

(Reaction Temperature of Step 4)

The reaction temperature is not particularly limited. From the viewpoints of yield, suppression of by-products, economic efficiency and the like, more specifically, for example, from the viewpoints of reaction rate, stability of the product and the like, the range of generally −20 (minus 20) to 200° C.,
preferably −20 to 150° C.,
more preferably 0 to 150° C.,
further preferably 50 to 120° C. can be mentioned as examples. The reaction temperature can be adjusted appropriately by a person skilled in the art.

(Reaction Time of Step 4)

The reaction time is not particularly limited. From the viewpoints of yield, suppression of by-products, economic efficiency and the like, the range of 0.5 to 48 hours, preferably 1 to 24 hours can be mentioned as examples. However, the reaction time can be adjusted appropriately by a person skilled in the art.

(Step 5)

(Method for Production of Compound Represented by General Formula (6) by Reaction of Compound Represented by General Formula (12) with Compound Represented by General Formula (9))

Another method for the production of the compound represented by the general formula (6), which is an intermediate for the compound represented by the general formula (1) (fluoroalkylating agent), will be described. As shown in the following reaction scheme, the compound represented by the general formula (6) can be produced by reacting the compound represented by the general formula (12) with the compound represented by the general formula (9).

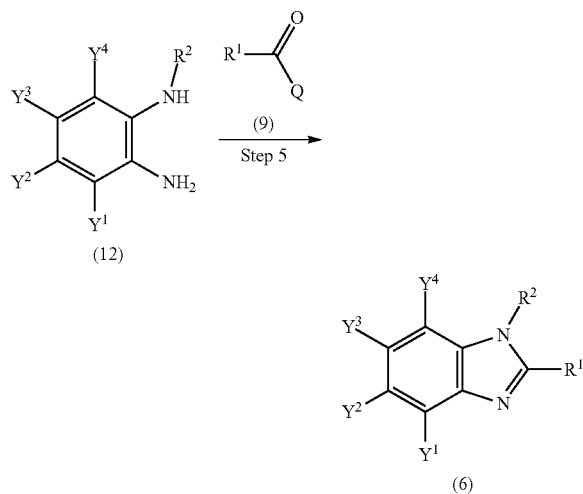

In the above reaction scheme, $R^1$, $R^2$, $Y^1$, $Y^2$, $Y^3$, $Y^4$ and Q are as described above.

(Material Compound of Step 5)

(Compound Represented by General Formula (12))

The compound represented by the general formula (12) is a known compound or is a compound which can be produced from a known compound in accordance with a known method.

Examples of the compound represented by the general formula (12) include, but are not limited to, $N^1$-methyl-1,2-phenylenediamine, 4,5-dichloro-$N^1$-methyl-1,2-phenylenediamine, $N^1$-methyl-3,4,5,6-tetrachloro-1,2-phenylenediamine, 4-$N^1$-dimethyl-1,2-phenylenediamine, and 4-nitro-$N^1$-methyl-1,2-phenylenediamine.

Preferable examples of the compound represented by the general formula (12) include $N^1$-methyl-1,2-phenylenediamine, 4-chloro-$N^1$-methyl-1,2-phenylenediamine, $N^1$-methyl-3,4,5,6-tetrachloro-1,2-phenylenediamine, and 4-nitro-$N^1$-methyl-1,2-phenylenediamine.

More preferable examples of the compound represented by the general formula (12) include 1,2-phenylenediamine, 4-chloro-1,2-phenylenediamine, and 4-nitro-1,2-phenylenediamine.

The compound represented by the general formula (9), the amount used thereof and the method for use thereof, etc., in the step 5 are the same as those in the step 3.

The base, the amount used thereof and the form thereof, etc., in the step 5 are the same as those in the step 3.

The solvent and the amount used thereof, etc., in the step 5 are the same as those in the step 3.

The reaction temperature in the step 5 is the same as that in the step 3.

The reaction time in the step 5 is the same as that in the step 3.

(Method for Production of Compound Having Fluoroalkyl Group)

(Fluoroalkylation Reaction)

Methods for the production of the compound having a fluoroalkyl group (i.e., fluoroalkylation reactions) according to the present invention will be described below.

The method for the production of the compound having a fluoroalkyl group according to the present invention is as follows:

a method for the production of a target compound having a fluoroalkyl group represented by $R^1$, wherein $R^1$ is as described above, which comprises reacting a starting compound which is an organic compound, with a fluoroalkylating agent represented by the general formula (1):

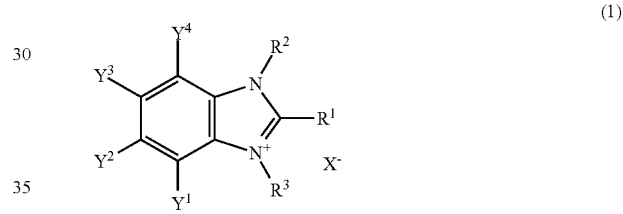

wherein $R^1$, $R^2$, $R^3$, $Y^1$, $Y^2$, $Y^3$, $Y^4$ and $X^-$ are as described above.

Therefore, in the fluoroalkylation reaction of the present invention, the fluoroalkyl group represented by $R^1$ is introduced into the starting compound (material compound) which is an organic compound, by using the fluoroalkylating agent represented by the general formula (1).

(Amount of Fluoroalkylating Agent Used)

The amount of the fluoroalkylating agent represented by the general formula (1) used in the fluoroalkylation reaction of the present invention is as described in detail in the paragraphs "Method for Production of Compound Having Fluoroalkyl Group (A)" and "Fluoroalkylation Reaction (A)" described below.

(Base in Method for Production of Compound Having Fluoroalkyl Group)

In the method for the production of the compound having a fluoroalkyl group of the present invention, a base is used. In other words, the fluoroalkylation reaction of the present invention is carried out in the presence of a base.

In the method disclosed in Non-Patent Document 2 using trifluoromethane ($CHF_3$), the reaction is carried out in the presence of a strong base. In addition, the method disclosed in Non-Patent Documents 3 and 4 using the fluoroalkyl phenyl sulfone compound, requires an excessive amount of potassium tert-butoxide as a strong base. Even in the method using the anhydrous salt obtained from hexafluoroacetone hydrate and 1,8-diazabicyclo[5.4.0]-7-undec-7-ene (DBU), which is disclosed in Patent Document 3 and Non-Patent Document 5, potassium tert-butoxide as a strong base is used. In addition, DBU is also used in this method. In short, in all of these methods, a strong base is used.

On the other hand, the fluoroalkylating agent of the present invention has excellent reactivity. Therefore, the present invention can provide an option of using no strong base, as required. In other words, there is a possibility that the fluoroalkylating agent of the present invention can be applicable to a starting compound which is unstable against a strong base. Therefore, it is considered that the present invention has a broad range of application, i.e., wide versatility.

The base, the amount used thereof and the form thereof, etc., in the fluoroalkylation reaction of the present invention are as described in detail in the paragraphs "Method for Production of Compound Having Fluoroalkyl Group (A)" and "Fluoroalkylation Reaction (A)" described below.

(Zeolite (For Example, Molecular Sieve) in Method for Production of Compound Having Fluoroalkyl Group)

In the method for the production of the compound having a fluoroalkyl group of the present invention, a zeolite (for example, a molecular sieve) may or may not be used as long as the reaction proceeds. For example, as shown in Examples 37 to 39, the reaction proceeds sufficiently even when a zeolite (for example, a molecular sieve) is not used. However, from the viewpoints of yield, versatility, generality, economic efficiency and the like, preferably, a zeolite (for example, a molecular sieve) is used in the fluoroalkylation reaction of the present invention. In other words, the fluoroalkylation reaction of the present invention is preferably carried out in the presence of a zeolite (for example, a molecular sieve). The zeolite (for example, a molecular sieve), the amount used thereof, the form thereof and the method for use thereof, etc., in the fluoroalkylation reaction of the present invention are as described in detail in the paragraphs "Method for Production of Compound Having Fluoroalkyl Group (A)" and "Fluoroalkylation Reaction (A)" described below.

(Phase Transfer Catalyst in Method for Production of Compound Having Fluoroalkyl Group)

In the method for the production of the compound having a fluoroalkyl group of the present invention, a phase transfer catalyst may be used. In other words, the fluoroalkylation reaction of the present invention may be carried out in the presence of a phase transfer catalyst. However, as shown in Examples, the reaction proceeds sufficiently even when a phase transfer catalyst is not used. The phase transfer catalyst, the amount used thereof and the form thereof, etc., in the fluoroalkylation reaction of the present invention are as described in detail in the paragraphs "Method for Production of Compound Having Fluoroalkyl Group (A)" and "Fluoroalkylation Reaction (A)" described below.

(Solvent in Method for Production of Compound Having Fluoroalkyl Group)

The solvent and the amount used thereof, etc., in the method for the production of the compound having a fluoroalkyl group of the present invention are as described in detail in the paragraphs "Method for Production of Compound Having Fluoroalkyl Group (A)" and "Fluoroalkylation Reaction (A)" described below.

(Reaction Temperature in Method for Production of Compound Having Fluoroalkyl Group)

The reaction temperature in the method for the production of the compound having a fluoroalkyl group of the present invention is as described in detail in the paragraphs "Method for Production of Compound Having Fluoroalkyl Group (A)" and "Fluoroalkylation Reaction (A)" described below.

(Reaction Time in Method for Production of Compound Having Fluoroalkyl Group)

The reaction time in the method for the production of the compound having a fluoroalkyl group of the present invention is as described in detail in the paragraphs "Method for Production of Compound Having Fluoroalkyl Group (A)" and "Fluoroalkylation Reaction (A)" described below.

(Product in Method for Production of Compound Having Fluoroalkyl Group)

The target compound obtained in the method for the production of the compound having a fluoroalkyl group of the present invention is an organic compound having the fluoroalkyl group represented by $R^1$.

$R^1$ in the obtained target compound is the same as that in the fluoroalkylating agent represented by the general formula (1).

The compound having a fluoroalkyl group $R^1$, which is formed by the fluoroalkylation reaction of the present invention, can be separated from the reaction mixture by the usual manner known to a person skilled in the art (for example, distillation, extraction, recrystallization, column chromatography and/or other procedures, preferably distillation and the like).

The fluoroalkylation reaction of the present invention forms a 2,3-dihydro-1,3-dimethylbenzimidazole-2-one compound represented by the general formula (13):

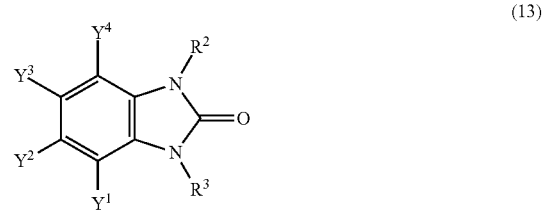

as a product derived from the fluoroalkylating agent. This compound can be removed from the reaction mixture by the usual manner known to a person skilled in the art (for example, distillation, extraction, recrystallization, column chromatography and/or other procedures, preferably distillation and the like).

More specifically, the methods for the production of the compound having a fluoroalkyl group (i.e., fluoroalkylation reactions) according to the present invention are shown in the following reaction schemes.

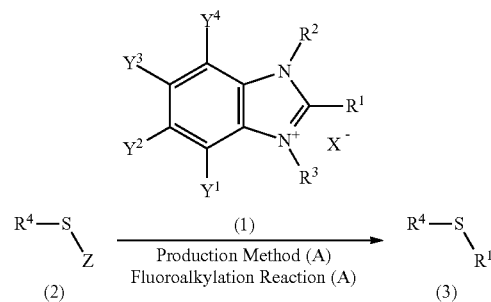

-continued

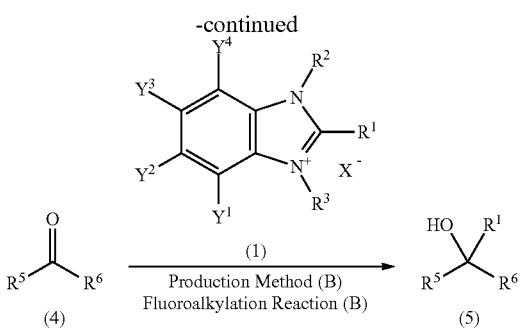

However, the methods for the production of the compound having a fluoroalkyl group (i.e., fluoroalkylation reaction) according to the present invention are not limited to those described above.

(Method for Production of Compound Having Fluoroalkyl Group (A))
(Fluoroalkylation Reaction (A))

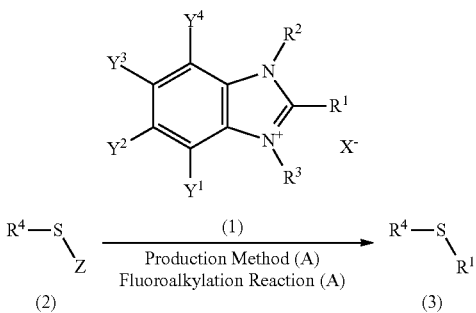

In the above reaction scheme, $R^1$, $R^2$, $R^3$, $Y^1$, $Y^2$, $Y^3$, $Y^4$ and $X^-$ are as described above; and $R^4$ and Z are as described below.

As shown in the above reaction scheme, the compound represented by the general formula (3) can be produced by reacting the compound represented by the general formula (2) with the fluoroalkylating agent represented by the general formula (1). Herein, as shown in the above reaction scheme, the "method for the production of the compound having a fluoroalkyl group (A)" is the method for the production of the compound represented by the general formula (3) by the reaction of the compound represented by the general formula (2) with the fluoroalkylating agent represented by the general formula (1). Herein, the phrase "method for the production of the compound having a fluoroalkyl group (A)" may be briefly referred to as the "production method (A)". Herein, as shown in the above reaction scheme, the "fluoroalkylation reaction (A)" is the reaction of the compound represented by the general formula (2) with the fluoroalkylating agent represented by the general formula (1) to produce the compound represented by the general formula (3).

(Starting Compound of Production Method (A))
(Compound Represented by General Formula (2))

The compound represented by the general formula (2) is used as the starting compound (material compound) of the production method (A).

The compound represented by the general formula (2) is a known compound or is a compound which can be produced from a known compound in accordance with a known method.

Examples of $R^4$ in the general formula (2) include, but are not limited to, a straight chain or branched chain hydrocarbon group which may have one or more substituents,
a cyclic hydrocarbon group which may have one or more substituents, and
a heterocyclic group which may have one or more substituents.

From the viewpoints of usefulness of the product and the like, preferable examples of $R^4$ include
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a C6 to C10 aryl group which may have one or more substituents, and
a heterocyclic group which may have one or more substituents, wherein the heterocyclic group is a 5- to 10-membered heterocyclic group having 1 to 9 carbon atoms and 1 to 4 heteroatoms selected independently from a nitrogen atom, an oxygen atom and a sulfur atom,
more preferably a C3 to C7 alkyl group which may have a benzyloxy group or a C2 to C4 acyloxy group,
further preferably a 5-benzyloxypentyl group, a 5-acetyloxypentyl group, a 6-benzyloxyhexyl group and a 6-acetyloxyhexyl group.

Z in the general formula (2) is a leaving group. Z in the general formula (2) may be any atom or atomic group as long as it functions as a leaving group in the fluoroalkylation reaction (A).

From the viewpoints of reactivity, yield, usefulness of the product, economic efficiency and the like, preferable examples of Z include
a cyano group,
a C1 to C4 alkylsulfonyl group, and
a phenylsulfonyl group, wherein the phenyl group moiety may have 1 to 5 substituents selected independently from a halogen atom and a C1 to C4 alkyl group, more preferably
a cyano group,
a methylsulfonyl group,
a phenylsulfonyl group, a 4-methylphenylsulfonyl group and a 4-chlorophenylsulfonyl group,
further preferably a cyano group, a phenylsulfonyl group, a 4-methylphenylsulfonyl group and a 4-chlorophenylsulfonyl group.

In one embodiment, further preferable examples of Z include a phenylsulfonyl group, a 4-methylphenylsulfonyl group and a 4-chlorophenylsulfonyl group. Particularly preferable examples of Z include a 4-methylphenylsulfonyl group.

In another embodiment, particularly preferable examples of Z include a cyano group.

Examples of the compound represented by the general formula (2) include, but are not limited to,
methyl thiocyanate, ethyl thiocyanate, propyl thiocyanate, isopropyl thiocyanate, butyl thiocyanate, isobutyl thiocyanate, butyl thiocyanate, sec-butyl thiocyanate, isobutyl thiocyanate, tert-butyl thiocyanate, pentyl thiocyanate, hexyl thiocyanate, heptyl thiocyanate, octyl thiocyanate, nonyl thiocyanate, decyl thiocyanate, undecyl thiocyanate, dodecyl thiocyanate,
benzyloxythiocyanatomethane,
1-benzyloxy-2-thiocyanatoethane,
1-benzyloxy-3-thiocyanatopropane, 1-benzyloxy-4-thiocyanatobutane,
1-benzyloxy-5-thiocyanatopentane,
1-benzyloxy-6-thiocyanatohexane,
1-benzyloxy-7-thiocyanatoheptane,
1-benzyloxy-8-thiocyanatooctane,
1-benzyloxy-9-thiocyanatononane,
1-benzyloxy-10-thiocyanatodecane,
1-benzyloxy-11-thiocyanatoundecane,
1-benzyloxy-12-thiocyanatododecane,
1-acetyloxythiocyanatomethane,
1-acetyloxy-2-thiocyanatoethane,
1-acetyloxy-3-thiocyanatopropane,
1-acetyloxy-4-thiocyanatobutane,
1-acetyloxy-5-thiocyanatopentane,
1-acetyloxy-6-thiocyanatohexane,
1-acetyloxy-7-thiocyanatoheptane,
1-acetyloxy-8-thiocyanatooctane,
1-acetyloxy-9-thiocyanatononane,
1-acetyloxy-10-thiocyanatodecane,
1-acetyloxy-11-thiocyanatoundecane,
1-acetyloxy-12-thiocyanatododecane,
1-propionyloxy-5-thiocyanatopentane,
1-propionyloxy-6-thiocyanatohexane,
1-butyryloxy-5-thiocyanatopentane,
1-butyryloxy-6-thiocyanatohexane,
1-isobutyryloxy-5-thiocyanatopentane,
1-isobutyryl oxy-6-thiocyanatohexane,
S-methyl methanesulfonothioate, S-ethyl methanesulfonothioate, S-propyl methanesulfonothioate, S-isopropyl methanesulfonothioate, S-butyl methanesulfonothioate,
methanethiosulfonic acid-5-(1-benzyloxy)pentane,
methanethiosulfonic acid-6-(1-benzyloxy)hexane,
S-methyl p-toluenesulfonothioate,
S-ethyl p-toluenesulfonothioate,
S-propyl p-toluenesulfonothioate,
S-isopropyl p-toluenesulfonothioate,
S-butyl p-toluenesulfonothioate,
benzenethiosulfonic acid-5-(1-benzyloxy)pentyl,
benzenethiosulfonic acid-6-(1-benzyloxy)hexyl,
p-toluenethiosulfonic acid-5-(1-benzyloxy)pentyl,
p-toluenethiosulfonic acid-6-(1-benzyloxy)hexyl,
4-chlorobenzenethiosulfonic acid-5-(1-benzyloxy)pentyl,
4-chlorobenzenethiosulfonic acid-6-(1-benzyloxy)hexyl,
benzenethiosulfonic acid-5-(1-acetyloxy)pentyl,
benzenethiosulfonic acid-6-(1-acetyloxy)hexyl,
p-toluenethiosulfonic acid-5-(1-acetyloxy)pentyl,
p-toluenethiosulfonic acid-6-(1-acetyloxy)hexyl,
4-chlorobenzenethiosulfonic acid-5-(1-acetyloxy)pentyl,
4-chlorobenzenethiosulfonic acid-6-(1-acetyloxy)hexyl and the like.

From the viewpoints of reactivity, yield, usefulness of the product, economic efficiency and the like, preferable examples of the compound represented by the general formula (2) include
1-benzyloxy-3-thiocyanatopropane,
1-benzyloxy-4-thiocyanatobutane,
1-benzyloxy-5-thiocyanatopentane,
1-benzyloxy-6-thiocyanatohexane,
1-benzyloxy-7-thiocyanatoheptane,
1-acetyloxy-3-thiocyanatopropane,
1-acetyloxy-4-thiocyanatobutane,
1-acetyloxy-5-thiocyanatopentane,
1-acetyloxy-6-thiocyanatohexane,
1-acetyloxy-7-thiocyanatoheptane,
methanethiosulfonic acid-5-(1-benzyloxy)pentane,
methanethiosulfonic acid-6-(1-benzyloxy)hexane,
benzenethiosulfonic acid-5-(1-benzyloxy)pentyl,
benzenethiosulfonic acid-6-(1-benzyloxy)hexyl,
p-toluenethiosulfonic acid-5-(1-benzyloxy)pentyl,
p-toluenethiosulfonic acid-6-(1-benzyloxy)hexyl,
4-chlorobenzenethiosulfonic acid-5-(1-benzyloxy)pentyl,
4-chlorobenzenethiosulfonic acid-6-(1-benzyloxy)hexyl,
benzenethiosulfonic acid-5-(1-acetyloxy)pentyl,
benzenethiosulfonic acid-6-(1-acetyloxy)hexyl,
p-toluenethiosulfonic acid-5-(1-acetyloxy)pentyl,
p-toluenethiosulfonic acid-6-(1-acetyloxy)hexyl,
4-chlorobenzenethiosulfonic acid-5-(1-acetyloxy)pentyl, and
4-chlorobenzenethiosulfonic acid-6-(1-acetyloxy)hexyl.

More preferable examples of the compound represented by the general formula (2) include
1-benzyloxy-5-thiocyanatopentane,
1-benzyloxy-6-thiocyanatohexane,
1-acetyloxy-5-thiocyanatopentane,
1-acetyloxy-6-thiocyanatohexane,
methanethiosulfonic acid-5-(1-benzyloxy)pentane,
methanethiosulfonic acid-6-(1-benzyloxy)hexane,
benzenethiosulfonic acid-5-(1-benzyloxy)pentyl,
benzenethiosulfonic acid-6-(1-benzyloxy)hexyl,
p-toluenethiosulfonic acid-5-(1-benzyloxy)pentyl,
p-toluenethiosulfonic acid-6-(1-benzyloxy)hexyl,
4-chlorobenzenethiosulfonic acid-5-(1-benzyloxy)pentyl,
4-chlorobenzenethiosulfonic acid-6-(1-benzyloxy)hexyl,
benzenethiosulfonic acid-5-(1-acetyloxy)pentyl,
benzenethiosulfonic acid-6-(1-acetyloxy)hexyl,
p-toluenethiosulfonic acid-5-(1-acetyloxy)pentyl,
p-toluenethiosulfonic acid-6-(1-acetyloxy)hexyl,
4-chlorobenzenethiosulfonic acid-5-(1-acetyloxy)pentyl, and
4-chlorobenzenethiosulfonic acid-6-(1-acetyloxy)hexyl.

Further preferable examples of the compound represented by the general formula (2) include
1-benzyloxy-5-thiocyanatopentane,
1-benzyloxy-6-thiocyanatohexane,
1-acetyloxy-5-thiocyanatopentane,
1-acetyloxy-6-thiocyanatohexane,
benzenethiosulfonic acid-5-(1-benzyloxy)pentyl,
benzenethiosulfonic acid-6-(1-benzyloxy)hexyl,
p-toluenethiosulfonic acid-5-(1-benzyloxy)pentyl,
p-toluenethiosulfonic acid-6-(1-benzyloxy)hexyl,
4-chlorobenzenethiosulfonic acid-5-(1-benzyloxy)pentyl,
4-chlorobenzenethiosulfonic acid-6-(1-benzyloxy)hexyl,
benzenethiosulfonic acid-5-(1-acetyloxy)pentyl,
benzenethiosulfonic acid-6-(1-acetyloxy)hexyl,
p-toluenethiosulfonic acid-5-(1-acetyloxy)pentyl,
p-toluenethiosulfonic acid-6-(1-acetyloxy)hexyl,
4-chlorobenzenethiosulfonic acid-5-(1-acetyloxy)pentyl, and
4-chlorobenzenethiosulfonic acid-6-(1-acetyloxy)hexyl.

Further preferable examples of the compound represented by the general formula (2) include
1-acetyloxy-5-thiocyanatopentane,
1-acetyloxy-6-thiocyanatohexane,
benzenethiosulfonic acid-5-(1-acetyloxy)pentyl,
benzenethiosulfonic acid-6-(1-acetyloxy)hexyl,
p-toluenethiosulfonic acid-5-(1-acetyloxy)pentyl,
p-toluenethiosulfonic acid-6-(1-acetyloxy)hexyl,
4-chlorobenzenethiosulfonic acid-5-(1-acetyloxy)pentyl, and
4-chlorobenzenethiosulfonic acid-6-(1-acetyloxy)hexyl.

Particularly preferable examples of the compound represented by the general formula (2) include
1-acetyloxy-5-thiocyanatopentane,
1-acetyloxy-6-thiocyanatohexane, p-toluenethiosulfonic acid-5-(1-acetyloxy)pentyl, and p-toluenethiosulfonic acid-6-(1-acetyloxy)hexyl.

The p-toluenethiosulfonic acid-5-(1-benzyloxy)pentyl is also referred to as 1-benzyloxy-5-thiotosylate pentane.

The p-toluenethiosulfonic acid-6-(1-benzyloxy)hexyl is also referred to as 1-benzyloxy-6-thiotosylate hexane.

The p-toluenethiosulfonic acid-5-(1-acetyloxy)pentyl is also referred to as 1-acetyloxy-5-thiotosylate pentane.

The p-toluenethiosulfonic acid-6-(1-acetyloxy)hexyl is also referred to as 1-acetyloxy-6-thiotosylate hexane.

(Fluoroalkylating Agent in Production Method (A))

(Compound Represented by General Formula (1) in Production Method (A))

The fluoroalkylating agent used in the production method (A) is the fluoroalkylating agent represented by the general formula (1). $R^1$, $R^2$, $R^3$, $Y^1$, $Y^2$, $Y^3$, $Y^4$ and $X^-$ in the fluoroalkylating agent represented by the general formula (1) used in the production method (A) are as described above.

(Amount of Fluoroalkylating Agent Used in Production Method (A))

The amount of the used fluoroalkylating agent represented by the general formula (1) may be any amount as long as the fluoroalkylation reaction (A) proceeds. From the viewpoints of yield, suppression of by-products, economic efficiency and the like, the amount of the used fluoroalkylating agent represented by the general formula (1) can be generally 1 equivalent or more,
preferably 1 to 10 equivalents,
more preferably 1 to 5 equivalents,
further preferably 1 to 2 equivalents, based on 1 mol of the compound represented by the general formula (2) (starting compound).

(Base in Production Method (A))

In the reaction of the production method (A), a base is used. In other words, the fluoroalkylation reaction (A) is carried out in the presence of a base. The base used in the fluoroalkylation reaction (A) may be any known base as long as the reaction proceeds.

Examples of the base used in the fluoroalkylation reaction (A) include, but are not limited to,
alkali metal hydroxides, alkaline earth metal hydroxides,
alkali metal carbonates, alkaline earth metal carbonates,
alkali metal bicarbonates, alkaline earth metal bicarbonates,
alkali metal phosphates, alkaline earth metal phosphates,
alkali metal biphosphates, alkaline earth metal biphosphates,
alkali metal hydrides, alkaline earth metal hydrides,
alkali metal alkoxides, alkaline earth metal alkoxides,
carboxylic acid alkali metal salts, carboxylic acid alkaline earth metal salts,
alkali metal cyanides,
alkali metal fluorides, quaternary ammonium fluorides,
alkali metal silanolates,
pyridines, quinolines, isoquinolines,
tertiary amines, secondary amines, primary amines,
aromatic amines,
cyclic amines, and
combinations thereof.

From the viewpoints of reactivity, yield, economic efficiency and the like, preferable examples of the base used in the fluoroalkylation reaction (A) include alkali metal hydroxides, alkaline earth metal hydroxides,
alkali metal carbonates, alkaline earth metal carbonates,
alkali metal bicarbonates, alkaline earth metal bicarbonates,
alkali metal hydrides, alkaline earth metal hydrides,
alkali metal alkoxides, alkaline earth metal alkoxides,
carboxylic acid alkali metal salts, carboxylic acid alkaline earth metal salts,
alkali metal cyanides,
alkali metal fluorides, quaternary ammonium fluorides,
alkali metal silanolates,
cyclic amines, and
combinations thereof.

More preferable examples of the base used in the fluoroalkylation reaction (A) include alkali metal hydroxides, alkali metal carbonates, alkali metal bicarbonates, alkali metal hydrides, alkali metal alkoxides, carboxylic acid alkali metal salts, alkali metal cyanides, alkali metal fluorides, quaternary ammonium fluorides, cyclic amines, and combinations thereof.

Further preferable examples of the base used in the fluoroalkylation reaction (A) include alkali metal hydroxides, alkali metal carbonates, alkali metal hydrides, and combinations thereof.

Particularly preferable examples of the base used in the fluoroalkylation reaction (A) include alkali metal hydroxides, alkali metal hydrides, and combinations thereof.

From the viewpoints of reactivity, yield, economic efficiency and the like, preferable specific examples of the base used in the fluoroalkylation reaction (A) include
lithium hydroxide, sodium hydroxide, potassium hydroxide, magnesium hydroxide, calcium hydroxide, barium hydroxide,
lithium carbonate, sodium carbonate, potassium carbonate, cesium carbonate, magnesium carbonate, calcium carbonate, barium carbonate, lithium bicarbonate, sodium bicarbonate, potassium bicarbonate, cesium bicarbonate, magnesium bicarbonate, calcium bicarbonate, barium bicarbonate,
lithium hydride, sodium hydride, potassium hydride, calcium hydride,
sodium methoxide, sodium ethoxide, sodium tert-butoxide, potassium tert-butoxide, magnesium ethoxide,
sodium formate, potassium formate, lithium acetate, sodium acetate, potassium acetate, sodium propionate, potassium propionate, magnesium acetate, calcium acetate,
potassium cyanide, sodium cyanide,
sodium fluoride, potassium fluoride, tetrabutylammonium fluoride,
sodium trimethyl silanolate, potassium trimethyl silanolate,
1,8-diazabicyclo[5.4.0]-7-undec-7-ene (DBU), 1,5-diazabicyclo[4.3.0]non-5-ene (DBN), 1,4-diazabicyclo[2.2.2]octane (DABCO), and
combinations thereof.

More preferable specific examples of the base used in the fluoroalkylation reaction (A) include
lithium hydroxide, sodium hydroxide, potassium hydroxide,
lithium carbonate, sodium carbonate, potassium carbonate, cesium carbonate, lithium bicarbonate, sodium bicarbonate, potassium bicarbonate, cesium bicarbonate,
lithium hydride, sodium hydride, potassium hydride,
sodium methoxide, sodium ethoxide, sodium tert-butoxide, potassium tert-butoxide, sodium formate, potassium formate, sodium acetate, potassium acetate,
potassium cyanide, sodium cyanide,
sodium fluoride, potassium fluoride, tetrabutylammonium fluoride,
1,8-diazabicyclo[5.4.0]-7-undec-7-ene (DBU), 1,5-diazabicyclo[4.3.0]non-5-ene (DBN), 1,4-diazabicyclo[2.2.2]octane (DABCO), and
combinations thereof.

Further preferable specific examples of the base used in the fluoroalkylation reaction (A) include
lithium hydroxide, sodium hydroxide, potassium hydroxide, sodium carbonate, potassium carbonate, cesium carbonate, sodium hydride, and
combinations thereof.

Further preferable specific examples of the base used in the fluoroalkylation reaction (A) include lithium hydroxide, sodium hydroxide, potassium hydroxide, sodium hydride, and combinations thereof.

Further preferable specific examples of the base used in the fluoroalkylation reaction (A) include sodium hydroxide, potassium hydroxide, sodium hydride, and combinations thereof.

Particularly preferable specific examples of the base used in the fluoroalkylation reaction (A) include potassium hydroxide, sodium hydride, and combinations thereof.

These bases may be used alone or in a combination of two or more thereof in any ratio in the fluoroalkylation reaction (A). When a combination of the bases is used, the two or more bases may be added separately into the reaction system. In this case, the order in which the two or more bases are added is not particularly limited. When a combination of the bases is used, the two or more bases may be added at the same time into the reaction system. The combination of the bases may be a mixture of the bases.

The form of the base used in the fluoroalkylation reaction (A) may be any form as long as the reaction proceeds. The form of the base used in the fluoroalkylation reaction (A) can be selected appropriately by a person skilled in the art.

(Amount of Base Used in Production Method (A))

The amount of the base used in the fluoroalkylation reaction (A) may be any amount as long as the reaction proceeds. From the viewpoints of yield, suppression of by-products, economic efficiency and the like, the range of generally 1 equivalent or more,
preferably 1 to 10 equivalents, 1 to 5 equivalents or 1 to 3 equivalents,
more preferably 2 to 10 equivalents, 2 to 5 equivalents or 2 to 3 equivalents, further preferably 2 to 5 equivalents,
particularly preferably 2 to 3 equivalents, based on 1 mol of the fluoroalkylating agent represented by the general formula (1), can be mentioned as examples.

When a combination of the bases is used, the amount of the used base exemplified above means the total amount of all bases used.

(Zeolite (For Example, Molecular Sieve) in Production Method (A))

In the reaction of the production method (A), a zeolite (for example, a molecular sieve) may or may not be used as long as the reaction proceeds.

For example, as shown in Examples 37 to 39, the reaction proceeds sufficiently even when a zeolite (for example, a molecular sieve) is not used. However, from the viewpoints of yield, versatility, generality, economic efficiency and the like, preferably, a zeolite (for example, a molecular sieve) is used in the reaction of the production method (A). In other words, the fluoroalkylation reaction (A) is preferably carried out in the presence of a zeolite (for example, a molecular sieve).

The zeolite is an aluminosilicate represented by the following general formula, but is not limited thereto:

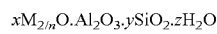

$$x\mathrm{M}_{2/n}\mathrm{O}\cdot\mathrm{Al}_2\mathrm{O}_3\cdot y\mathrm{SiO}_2\cdot z\mathrm{H}_2\mathrm{O}$$

wherein
M is a cation (for example, an alkali metal ion such as $Li^+$, $Na^+$ or $K^+$, and/or an alkaline earth metal ion such as $Mg^{2+}$, $Ca^{2+}$ or $Ba^{2+}$, and the like),
n is the valence of the cation M,
x is a number of 1 or smaller (for example, 0.01 to 1),
y is a number of 2 or larger (for example, 2 to 100), and
z is a number larger than 0 (for example, 0 to 10).

The zeolite (for example, a molecular sieve) may retain a cation of an alkali metal and/or an alkaline earth metal and the like, and/or a water molecule, and the like in the pores. However, the zeolite is used, if necessary, in the reaction after removal of the cation of an alkali metal and/or an alkaline earth metal and the like, and/or the water molecule, and the like in the pores. In general, it is well known to a person skilled in the art that the zeolite after removal of a water molecule in the pores of the zeolite by heating and the like is used as an activated zeolite. The degree of and the method for the removal of the cation of an alkali metal and/or an alkaline earth metal and the like, and/or the water molecule, and the like in the pores (i.e., purification and activation of the zeolite) can be selected and adjusted appropriately by a person skilled in the art. For example, the degree of and the method for the removal of the water molecule by heating or by heating and reduction in pressure can be selected and adjusted appropriately by a person skilled in the art. A commercially available activated zeolite (for example, an activated molecular sieve) can also be used.

The zeolite (for example, a molecular sieve) used in the fluoroalkylation reaction (A) may be any zeolite (for example, any molecular sieve) as long as the reaction proceeds.

The zeolite (for example, a molecular sieve) used in the fluoroalkylation reaction (A) may be a natural zeolite or may be a synthetic zeolite.

Examples of the zeolite (for example, a molecular sieve) used in the fluoroalkylation reaction (A) include, but are not limited to, zeolite A, ZK-5, Cabazite, ZSM-5, zeolite L, zeolite Y, zeolite X and the like, and mixtures thereof.

The pore size of the zeolite (for example, a molecular sieve) used in the fluoroalkylation reaction (A) may be any pore size as long as the reaction proceeds. From the viewpoints of yield, economic efficiency and the like, the range of generally 10 angstroms or smaller,
preferably 1 to 10 angstroms,
more preferably 2 to 7 angstroms, 2 to 6 angstroms, 2 to 5 angstroms or 2 to 4 angstroms,
further preferably 3 to 7 angstroms,
further preferably 3 to 5 angstroms,
further preferably 3 to 4 angstroms can be mentioned as examples.
4 angstroms are particularly preferable.

Preferable examples of the zeolite (for example, a molecular sieve) used in the fluoroalkylation reaction (A) include, but are not limited to, zeolite A and mixtures thereof.

Preferable specific examples of the zeolite (for example, a molecular sieve) used in the fluoroalkylation reaction (A) include, but are not limited to,
a molecular sieve 3 A, a molecular sieve 4 A, a molecular sieve 5 A, a molecular sieve 13X and mixtures thereof,
more preferably a molecular sieve 3 A, a molecular sieve 4 A, a molecular sieve 5 A and mixtures thereof,
further preferably a molecular sieve 3 A, a molecular sieve 4 A and mixtures thereof, particularly preferably a molecular sieve 4 A.

These zeolites (for example, molecular sieves) may be used alone or in a combination of two or more thereof in any ratio in the fluoroalkylation reaction (A). The form of the zeolite (for example, a molecular sieve) used in the fluoroalkylation reaction (A) may be any form as long as the reaction proceeds. Examples of the form of the zeolite (for example, a molecular sieve) used in the fluoroalkylation reaction (A) include, but are not limited to, powders, beads, pellets (for example, cylinders) and the like, preferably powders. The form of the zeolite (for example, a molecular sieve) used in the fluoroalkylation reaction (A) can be selected appropriately by a person skilled in the art.

(Amount of Zeolite (For Example, Molecular Sieve) Used in Production Method (A))

The amount of the zeolite (for example, a molecular sieve) used in the fluoroalkylation reaction (A) may be any amount as long as the reaction proceeds. From the viewpoints of yield, economic efficiency and the like, the range of
generally 0 (zero) to 10 kg,
preferably 0 to 2 kg or 0 to 1 kg,
more preferably 0.1 to 2 kg or 0.1 to 1 kg,
further preferably 0.15 to 2 kg or 0.15 to 1 kg,
particularly preferably 0.17 to 1 kg, based on 1 mol of the compound represented by the general formula (2) (starting compound), can be mentioned as examples.

Therefore, in general, the range of generally 0 (zero) to 10 kg,
preferably 0 to 2 kg or 0 to 1 kg,
more preferably 0.1 to 2 kg or 0.1 to 1 kg,
further preferably 0.15 to 2 kg or 0.15 to 1 kg,
particularly preferably 0.17 to 1 kg, based on 1 mol of the starting compound, can be mentioned as examples of the amount of the zeolite (for example, a molecular sieve) used in the fluoroalkylation reaction of the present invention.

(Phase Transfer Catalyst in Production Method (A))

In the reaction of the production method (A), a phase transfer catalyst may be used. In other words, the fluoroalkylation reaction (A) may be carried out in the presence of a phase transfer catalyst. However, as shown in Examples, the reaction proceeds sufficiently even when a phase transfer catalyst is not used. The phase transfer catalyst which may be used in the fluoroalkylation reaction (A) may be any known phase transfer catalyst as long as the reaction proceeds.

Examples of the phase transfer catalyst which may be used in the fluoroalkylation reaction (A) include, but are not limited to, quaternary ammonium salts, quaternary phosphonium salts, crown ethers and the like.

Examples of the quaternary ammonium salts include, but are not limited to, tetrabutylammonium chloride, tetrabutylammonium bromide, tetrabutylammonium iodide, tetrabutylammonium bisulfate,
benzyltrimethylammonium chloride, benzyltrimethylammonium bromide, octyltrimethylammonium chloride, octyltrimethylammonium bromide, trioctylmethylammonium chloride, trioctylmethylammonium bromide, benzyllauryldimethylammonium chloride (benzyldodecyldimethylammonium chloride), benzyllauryldimethylammonium bromide
(benzyldodecyldimethylammonium bromide),
myristyltrimethylammonium chloride (tetradecyltrimethylammonium chloride), myristyltrimethylammonium bromide (tetradecyltrimethylammonium bromide), benzyldimethylstearylammonium chloride (benzyloctadecyldimethylammonium chloride), benzyldimethylstearylammonium bromide
(benzyloctadecyldimethylammonium bromide) and the like.

Examples of the quaternary phosphonium salts include, but are not limited to, tetrabutylphosphonium bromide, tetraoctylphosphonium bromide, tetraphenylphosphonium bromide and the like.

Examples of the crown ethers include, but are not limited to, 12-crown-4, 15-crown-5, 18-crown-6 and the like.

From the viewpoints of reactivity, yield, economic efficiency and the like, the phase transfer catalyst is
preferably a quaternary ammonium salt,
more preferably tetrabutylammonium bromide.

These phase transfer catalysts may be used alone or in a combination of two or more thereof in any ratio. The form of the phase transfer catalyst may be any form as long as the reaction proceeds. The form of the phase transfer catalyst can be selected appropriately by a person skilled in the art.

(Amount of Phase Transfer Catalyst Used in Production Method (A))

The amount of the phase transfer catalyst used in the fluoroalkylation reaction (A) may be any amount as long as the reaction proceeds. From the viewpoints of yield, suppression of by-products, economic efficiency and the like, the range of
generally 0 (zero) to 1.5 mol or 0 to 1 mol,
preferably 0 to 0.3 mol or 0 to 0.2 mol,
more preferably 0 to 0.1 mol, based on 1 mol of the compound represented by the general formula (2) (starting compound), can be mentioned as examples.

(Solvent in Production Method (A))

The reaction of the production method (A) may be carried out without a solvent. However, from the viewpoints of smooth progress of the reaction, economic efficiency and the like, a solvent may be used in this reaction. The solvent used in the fluoroalkylation reaction (A) may be any solvent as long as the reaction proceeds.

Examples of the solvent used in the fluoroalkylation reaction (A) include, but are not limited to, amides, alkyl ureas, sulfoxides, sulfones, ethers, ketones, carboxylic acid esters, nitriles, aromatic hydrocarbon derivatives, aliphatic hydrocarbons, halogenated aliphatic hydrocarbons, and any combination thereof in any ratio.

From the viewpoints of reactivity, yield, economic efficiency and the like, preferable examples of the solvent used in the fluoroalkylation reaction (A) include amides, alkyl ureas, sulfoxides, sulfones, ethers, nitriles, aromatic hydrocarbon derivatives, halogenated aliphatic hydrocarbons, and any combination thereof in any ratio,
more preferably amides, alkyl ureas, sulfoxides, sulfones, nitriles, aromatic hydrocarbon derivatives, and any combination thereof in any ratio,
further preferably amides, sulfoxides, nitriles, aromatic hydrocarbon derivatives, and any combination thereof in any ratio,
particularly preferably amides, aromatic hydrocarbon derivatives, and any combination thereof in any ratio.

Specific examples of the solvent used in the fluoroalkylation reaction (A) include, but are not limited to,
N,N-dimethylformamide (DMF), N,N-diethylformamide, N,N-dimethylacetamide (DMAC), N,N-diethylacetamide, N-methylpyrrolidone (NMP),
N,N'-dimethylimidazolidinone (DMI),
dimethyl sulfoxide (DMSO),
sulfolane, dimethyl sulfone,
tetrahydrofuran (THF), 2-methyltetrahydrofuran, 1,4-dioxane, diisopropyl ether, dibutyl ether, di-tert-butyl ether, cyclopentyl methyl ether (CPME), methyl tert-butyl ether, 1,2-dimethoxyethane (DME), diglyme, acetone, ethyl methyl ketone, isopropyl methyl ketone, isobutyl methyl ketone (MIBK),
ethyl acetate, butyl acetate,
acetonitrile,
toluene, xylene, chlorobenzene, dichlorobenzene, trichlorobenzene, nitrobenzene, dichloromethane, and
any combination thereof in any ratio.

From the viewpoints of reactivity, yield, economic efficiency and the like preferable specific examples of the solvent used in the fluoroalkylation reaction (A) include
N,N-dimethylformamide (DMF), N,N-diethylformamide, N,N-dimethylacetamide (DMAC), N,N-diethylacetamide, N-methylpyrrolidone (NMP),
N,N'-dimethylimidazolidinone (DMI),
dimethyl sulfoxide (DMSO),
sulfolane, dimethyl sulfone,
tetrahydrofuran (THF), 2-methyltetrahydrofuran, 1,4-dioxane, diisopropyl ether, dibutyl ether, di-tert-butyl ether, cyclopentyl methyl ether (CPME), methyl tert-butyl ether, 1,2-dimethoxyethane (DME), diglyme, acetonitrile,
toluene, xylene, chlorobenzene, dichlorobenzene, trichlorobenzene, dichloromethane, and
any combination thereof in any ratio.

From the same viewpoints as above, more preferable specific examples of the solvent used in the fluoroalkylation reaction (A) include
N,N-dimethylformamide (DMF), N,N-dimethylacetamide (DMAC), N-methylpyrrolidone (NMP),
N,N'-dimethylimidazolidinone (DMI),
dimethyl sulfoxide (DMSO),
sulfolane, dimethyl sulfone,
acetonitrile,
toluene, xylene, chlorobenzene, dichlorobenzene, and
any combination thereof in any ratio.

From the same viewpoints as above, further preferable specific examples of the solvent used in the fluoroalkylation reaction (A) include
N,N-dimethylformamide (DMF), N,N-dimethylacetamide (DMAC), N-methylpyrrolidone (NMP),
dimethyl sulfoxide (DMSO),
acetonitrile,
toluene, xylene, chlorobenzene, dichlorobenzene, and
any combination thereof in any ratio.

From the same viewpoints as above, further preferable specific examples of the solvent used in the fluoroalkylation reaction (A) include
N,N-dimethylformamide (DMF), N,N-dimethylacetamide (DMAC), N-methylpyrrolidone (NMP),
toluene, xylene, chlorobenzene, dichlorobenzene, and
any combination thereof in any ratio.

From the same viewpoints as above, particularly preferable specific examples of the solvent used in the fluoroalkylation reaction (A) include
N,N-dimethylformamide (DMF), N,N-dimethylacetamide (DMAC), toluene, xylene, and
any combination thereof in any ratio.

(Amount of Solvent Used in Production Method (A))

The amount of the solvent used in the reaction of the production method (A) may be any amount as long as the reaction proceeds. From the viewpoints of reaction efficiency and ease of operation and the like, the range of generally 0 (zero) to 10.0 L (liters),
preferably 0.01 to 10 L,
further preferably 0.1 to 5 L, based on 1 mol of the compound represented by the general formula (2) (starting compound), can be mentioned as examples. However, the amount used can be adjusted appropriately by a person skilled in the art. When a combination of two or more solvents is used, the ratio of the two or more solvents may be any ratio as long as the reaction proceeds. The ratio can be adjusted appropriately by a person skilled in the art.

(Reaction Temperature of Production Method (A))

The reaction temperature is not particularly limited. From the viewpoints of yield, suppression of by-products, economic efficiency and the like, more specifically, for example, from the viewpoints of reaction rate, stability of the product and the like, the reaction temperature is in the range of generally −80° C. (minus 80° C.) to 200° C. (plus 200° C.), −80° C. to 150° C. or −80° C. to 100° C.,
preferably −80° C. (minus 80° C.) to 60° C. (plus 60° C.), −60° C. to 60° C. or −50° C. to 60° C.,
more preferably −80° C. (minus 80° C.) to 40° C. (plus 40° C.), −60° C. to 40° C. or −50° C. to 40° C.,
further preferably −80° C. (minus 80° C.) to 0° C. (zero ° C.), −60° C. to 0° C. or −50° C. to 0° C.,
further preferably −50° C. to 0° C. (minus 50° C. to zero ° C.),
particularly preferably −50° C. to −5° C. (minus 50° C. to minus 5° C.).

(Reaction Time of Production Method (A))

The reaction time is not particularly limited. From the viewpoints of yield, suppression of by-products, economic efficiency and the like, the range of generally 0.5 to 120 hours or 0.5 hours to 48 hours,
preferably 1 hour to 48 hours or 1 hour to 24 hours can be mentioned as examples. However, the reaction time can be adjusted appropriately by a person skilled in the art.

(Product of Production Method (A))
(Compound Represented by General Formula (3))

The target compound obtained in the production method (A) is the compound represented by the general formula (3).

$R^1$ in the general formula (3) is the same as that in the fluoroalkylating agent represented by the general formula (1).

The compound represented by the general formula (3) having a fluoroalkyl group $R^1$, which is formed by the fluoroalkylation reaction (A), can be isolated from the reaction mixture by the usual manner known to a person skilled in the art (for example, distillation, extraction, recrystallization, column chromatography and/or other procedures, preferably distillation and the like).

(Method for Production of Compound Having Fluoroalkyl Group (B))
(Fluoroalkylation Reaction (B))

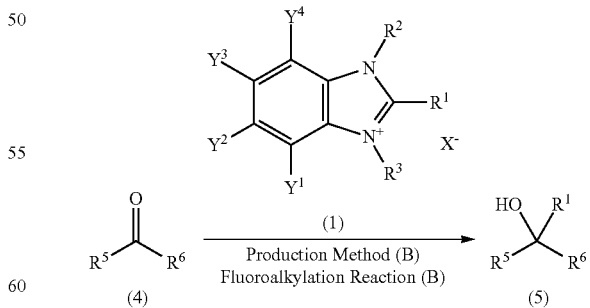

In the above reaction scheme, $R^1$, $R^2$, $R^3$, $Y^1$, $Y^2$, $Y^3$, $Y^4$ and $X^−$ are as described above; and $R^5$ and $R^6$ are as described below.

As shown in the above reaction scheme, the compound represented by the general formula (5) can be produced by reacting the compound represented by the general formula (4) with the fluoroalkylating agent represented by the general formula (1). Herein, as shown in the above reaction scheme, the "method for the production of the compound having a fluoroalkyl group (B)" is the method for the production of the compound represented by the general formula (5) by the reaction of the compound represented by the general formula (4) with the fluoroalkylating agent represented by the general formula (1). Herein, the phrase "method for the production of the compound having a fluoroalkyl group (B)" may be briefly referred to as the "production method (B)". Herein, as shown in the above reaction scheme, the "fluoroalkylation reaction (B)" is the reaction of the compound represented by the general formula (4) with the fluoroalkylating agent represented by the general formula (1) to produce the compound represented by the general formula (5).

(Starting Compound of Production Method (B))
(Compound Represented by General Formula (4))

The compound represented by the general formula (4) is used as the starting compound (material compound) of the production method (B).

The compound represented by the general formula (4) is a known compound or is a compound which can be produced from a known compound in accordance with a known method.

Examples of $R^5$ in the general formula (4) include, but are not limited to,
a straight chain or branched chain hydrocarbon group which may have one or more substituents,
a cyclic hydrocarbon group which may have one or more substituents, and
a heterocyclic group which may have one or more substituents.

From the viewpoints of usefulness of the product and the like, preferable examples of $R^5$ include
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a C6 to C10 aryl group which may have one or more substituents, and
a heterocyclic group which may have one or more substituents, wherein the heterocyclic group is a 5- to 10-membered heterocyclic group having 1 to 9 carbon atoms and 1 to 4 heteroatoms selected independently from a nitrogen atom, an oxygen atom and a sulfur atom.

Examples of $R^6$ in the general formula (4) include, but are not limited to,
a hydrogen atom,
a straight chain or branched chain hydrocarbon group which may have one or more substituents,
a cyclic hydrocarbon group which may have one or more substituents, and
a heterocyclic group which may have one or more substituents.

From the viewpoints of usefulness of the product and the like, preferable examples of $R^6$ include
a hydrogen atom, a C1 to C4 alkyl group and a C1 to C4 haloalkyl group,
more preferably a hydrogen atom.

Examples of the compound represented by the general formula (4) include, but are not limited to,
acetaldehyde, propionaldehyde, butanal, pentanal, hexanal, heptanal, octanal, phenylacetaldehyde, 3-phenylpropionaldehyde, 4-phenylbutanal, 5-phenylpentanal, benzaldehyde, 2-fluorobenzaldehyde, 3-fluorobenzaldehyde, 4-fluorobenzaldehyde,
2,4-difluorobenzaldehyde, 3,4-difluorobenzaldehyde,
2-chlorobenzaldehyde, 3-chlorobenzaldehyde, 4-chlorobenzaldehyde,
2,4-dichlorobenzaldehyde, 3,4-dichlorobenzaldehyde,
2-nitrobenzaldehyde, 3-nitrobenzaldehyde, 4-nitrobenzaldehyde,
2-cyanobenzaldehyde, 3-cyanobenzaldehyde, 4-cyanobenzaldehyde,
2-methylbenzaldehyde, 3-methylbenzaldehyde, 4-methylbenzaldehyde,
2-methoxybenzaldehyde, 3-methoxybenzaldehyde, 4-methoxybenzaldehyde,
2-pyridinecarboxaldehyde, 3-pyridinecarboxaldehyde, 4-pyridinecarboxaldehyde,
2-thiophenecarboxaldehyde, 3-thiophenecarboxaldehyde, 4-thiophenecarboxaldehyde
acetone, ethyl methyl ketone, diethyl ketone,
benzylacetone, 5-phenyl-2-propanone,
acetophenone,
2'-chloroacetophenone, 3'-chloroacetophenone, 4'-chloroacetophenone,
2'-nitroacetophenone, 3'-nitroacetophenone, 4'-nitroacetophenone,
2'-cyanoacetophenone, 3'-cyanoacetophenone, 4'-cyanoacetophenone,
2'-methylacetophenone, 3'-methylacetophenone, 4'-methylacetophenone,
2'-methoxyacetophenone, 3'-methoxyacetophenone, 4'-methoxyacetophenone,
2-acetylpyridine, 3-acetylpyridine, 4-acetylpyridine,
2-acetylthiophene, 3-acetylthiophene, 4-acetylthiophene,
benzophenone,
2-chlorobenzophenone, 3-chlorobenzophenone, 4-chlorobenzophenone,
2-nitrobenzophenone, 3-nitrobenzophenone, 4-nitrobenzophenone,
2-cyanobenzophenone, 3-cyanobenzophenone, 4-cyanobenzophenone,
2-methylbenzophenone, 3-methylbenzophenone, 4-methylbenzophenone,
2-methoxybenzophenone, 3-methoxybenzophenone, 4-methoxybenzophenone,
2-benzoylpyridine, 3-benzoylpyridine, 4-benzoylpyridine,
2-benzoylthiophene, 3-benzoylthiophene, 4-benzoylthiophene and the like.

(Fluoroalkylating Agent in Production Method (B))
(Compound Represented by General Formula (1) in Production Method (B))

The fluoroalkylating agent represented by the general formula (1) and the amount used thereof, etc., in the method for the production of the compound having a fluoroalkyl group (B) are the same as those in the paragraphs "Method for Production of Compound Having Fluoroalkyl Group (A)" and "Fluoroalkylation Reaction (A)" described above.

(Base in Production Method (B))

The base, the amount used thereof and the form thereof, etc., in the method for the production of the compound having a fluoroalkyl group (B) are the same as those in the paragraphs "Method for Production of Compound Having Fluoroalkyl Group (A)" and "Fluoroalkylation Reaction (A)" described above.

(Zeolite (For Example, Molecular Sieve) in Production Method (B))

The zeolite (for example, a molecular sieve), the amount used thereof, the form thereof and the method for use thereof, etc., in the method for the production of the compound having a fluoroalkyl group (B) are the same as those in the paragraphs "Method for Production of Compound Having Fluoroalkyl Group (A)" and "Fluoroalkylation Reaction (A)" described above.

(Phase Transfer Catalyst in Production Method (B))

The phase transfer catalyst, the amount used thereof and the form thereof, etc., in the method for the production of the compound having a fluoroalkyl group (B) are the same as those in the paragraphs "Method for Production of Compound Having Fluoroalkyl Group (A)" and "Fluoroalkylation Reaction (A)" described above.

(Solvent in Production Method (B))

The solvent and the amount used thereof, etc., in the method for the production of the compound having a fluoroalkyl group (B) are the same as those in the paragraphs "Method for Production of Compound Having Fluoroalkyl Group (A)" and "Fluoroalkylation Reaction (A)" described above.

(Reaction Temperature of Production Method (B))

The reaction temperature in the method for the production of the compound having a fluoroalkyl group (B) is the same as that in the paragraphs "Method for Production of Compound Having Fluoroalkyl Group (A)" and "Fluoroalkylation Reaction (A)" described above.

(Reaction Time of Production Method (B))

The reaction time in the method for the production of the compound having a fluoroalkyl group (B) is the same as that in the paragraphs "Method for Production of Compound Having Fluoroalkyl Group (A)" and "Fluoroalkylation Reaction (A)" described above.

(Product of Production Method (B))

(Compound Represented by General Formula (5))

The target compound obtained in the production method (B) is the compound represented by the general formula (5).

$R^1$ in the general formula (5) is the same as that in the fluoroalkylating agent represented by the general formula (1).

The compound represented by the general formula (5) having a fluoroalkyl group $R^1$, which is formed by the fluoroalkylation reaction (B), can be isolated from the reaction mixture by the usual manner known to a person skilled in the art (for example, distillation, extraction, recrystallization, column chromatography and/or other procedures, preferably distillation and the like).

Hereinafter, the present invention will be described in more detail by Examples. However, the present invention is not limited in any way by these Examples.

Herein, room temperature is 10° C. to 35° C.

Herein, for the determination of each physical property in Examples and Reference Examples, following instruments were used.

$^1$H nuclear magnetic resonance spectrum ($^1$H-NMR); JEOL JMN-Lambda 300, or JEOL JMN-Lambda-400 (manufactured by JEOL Ltd.), Internal standard substance: tetramethylsilane (TMS)

Melting point; Yanaco MP-500V (manufactured by ANATEC YANACO CORPORATION).

Gas chromatography analysis (GC analysis); GC-2025 (manufactured by SHIMADZU CORPORATION), Detection method: FID Gas chromatography (GC) analysis method; Regarding the GC analysis method, the following documents can be referred to, if necessary.

Document (a): The Chemical Society of Japan ed., "Shin Jikken Kagaku Koza (New Experimental Chemistry Course) 9 Bunseki Kagaku (Analytical Chemistry) II", pages 60 to 86 (1977), published by Shingo Iizumi, Maruzen Co., Ltd. (For example, regarding liquids for a stationary phase that can be used in a column, page 66 can be referred to.)

Document (b): The Chemical Society of Japan ed., "Jikken Kagaku Koza (Experimental Chemistry Course) 20-1 Bunseki Kagaku (Analytical Chemistry)", 5th ed., pages 121 to 129 (2007), published by Seishiro Murata, Maruzen Co., Ltd. (For example, regarding the specific usage of a hollow capillary separation column, pages 124 to 125 can be referred to.)

Gas chromatography mass spectrometric analysis (GC-MS analysis); Analysis instrument: 6890N Network GC System (manufactured by Agilent Technologies), Mass detector: 5973N MSD (manufactured by Agilent Technologies)

High-performance liquid chromatography (HPLC) analysis method; Regarding the HPLC analysis method, the following documents can be referred to, if necessary.

Document (c): The Chemical Society of Japan ed., "Shin Jikken Kagaku Koza (New Experimental Chemistry Course) 9 Bunseki Kagaku (Analytical Chemistry) II", pages 86 to 112 (1977), published by Shingo Iizumi, Maruzen Co., Ltd. (For example, regarding combinations of packing materials and mobile phases that can be used in a column, pages 93 to 96 can be referred to.)

Document (b): The Chemical Society of Japan ed., "Jikken Kagaku Koza (Experimental Chemistry Course) 20-1 Bunseki Kagaku (Analytical Chemistry)", 5th ed., pages 130 to 151 (2007), published by Seishiro Murata, Maruzen Co., Ltd. (For example, regarding the specific usage and conditions of reversed phase chromatography analysis, pages 135 to 137 can be referred to.)

(Method for Measuring pH)

The pH was measured by a glass electrode type hydrogen ion concentration indicator. As the glass electrode type hydrogen ion concentration indicator, for example, Type: HM-20P manufactured by DKK-TOA CORPORATION can be used.

Herein, the potassium hydroxide used in Examples had a purity of 95.5%.

Example 1

Production of 2-trifluoromethylbenzimidazole

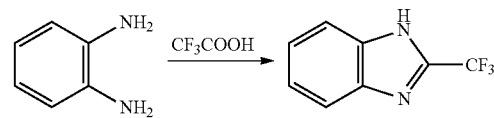 [SMILES: Nc1ccccc1N ; "CF3COOH" ; FC(F)(F)c1nc2ccccc2[nH]1]

To a 100 mL eggplant-shaped flask equipped with a magnetic stirrer, 10.8 g (100 mmol) of 1,2-phenylenediamine and 17.1 g (150 mmol) of trifluoroacetic acid were added. The mixture was heated to reflux for 4 hours. After cooling, the reaction mixture was poured into an aqueous sodium hydrogen carbonate solution, and extracted with ethyl acetate. The ethyl acetate layer was washed with a saturated aqueous sodium chloride solution and dried over anhydrous magnesium sulfate, and then the solvent was distilled off under reduced pressure to obtain 18.7 g of gray crystals. Yield: 100%.

$^1$H-NMR (400 MHz, CDCl$_3$, relative to TMS) δ (ppm): 7.37-7.47 (m, 2H), 7.56 (d, J=7.2 Hz, 1H), 7.90 (d, J=7.8 Hz, 1H), 9.96 (br, 1H).

Example 2

Production of 1-methyl-2-trifluoromethylbenzimidazole

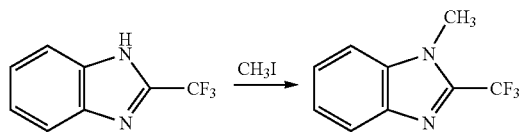

To a 200 mL eggplant-shaped flask equipped with a magnetic stirrer, 18.7 g (100 mmol) of 2-trifluoromethylbenzimidazole, 16.6 g (120 mmol) of potassium carbonate, 17.0 g (120 mmol) of methyl iodide and 100 mL of acetone were added. The mixture was heated to reflux for 3 hours. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure to obtain 19.7 g of gray crystals. Yield: 98%.

$^1$H-NMR (400 MHz, CDCl$_3$, relative to TMS) δ (ppm): 3.96 (s, 3H), 7.37-7.46 (m, 3H), 7.88 (d, J=6.0 Hz, 1H).

Example 3

Production of 1,3-dimethyl-2-trifluoromethylbenzimidazolium methyl sulfate

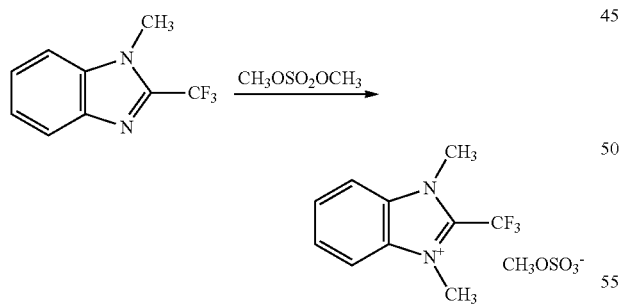

To a 200 mL eggplant-shaped flask equipped with a magnetic stirrer, 15.3 g (76 mmol) of 1-methyl-2-trifluoromethylbenzimidazole, 14.7 g (117 mmol) of dimethyl sulfate and 100 mL of toluene were added. The mixture was heated to reflux for 4 hours. After the reaction mixture was cooled, the solvent was distilled off under reduced pressure. The resultant residue was dissolved in dichloromethane, and then diethyl ether was added thereto. The precipitated crystals were collected by filtration and dried to obtain 21.8 g of gray crystals. Yield: 88%.

$^1$H-NMR (300 MHz, CDCl$_3$, relative to TMS) δ (ppm): 3.38 (s, 3H), 4.321 (s, 3H), 4.326 (s, 3H), 7.78-7.82, m, 2H), 7.91-7.94 (m, 2H).

Example 4

Production of 1,3-dimethyl-2-trifluoromethylbenzimidazolium triflate

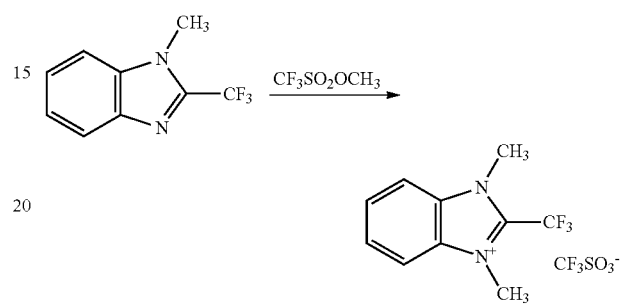

In a 200 mL eggplant-shaped flask equipped with a magnetic stirrer, 7.0 g (35 mmol) of 1-methyl-2-trifluoromethylbenzimidazole was dissolved in 100 mL of acetonitrile. 10.3 g (62.5 mmol) of methyl triflate (CF$_3$SO$_2$OCH$_3$) was added dropwise thereto. The mixture was stirred at room temperature for 3 hours. The solvent was distilled off under reduced pressure. The resultant residue was dissolved in acetonitrile, and then diethyl ether was added thereto. The precipitated crystals were collected by filtration and dried to obtain 1.3 g of white crystals. The resultant filtrate was concentrated under reduced pressure, and the resultant residue was dissolved in dichloromethane, and then diethyl ether was added thereto. The precipitated crystals were collected by filtration and dried to obtain 8.1 g of white crystals. Yield: 74%.

$^1$H-NMR (400 MHz, CDCl$_3$, relative to TMS) δ (ppm): 4.34 (s, 6H), 7.88-7.91, m, 2H), 8.01-8.04 (m, 2H).

Example 5

Production of 1,3-dimethyl-2-trifluoromethylbenzimidazolium iodide

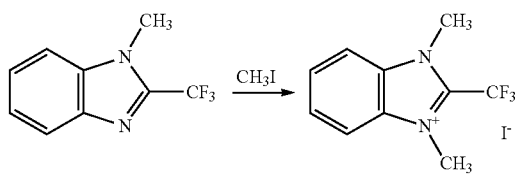

To a 50 mL eggplant-shaped flask equipped with a magnetic stirrer, 4.0 g (20 mmol) of 1-methyl-2-trifluoromethylbenzimidazole, 2.8 g (20 mmol) of methyl iodide and 20 mL of acetonitrile were added. The mixture was heated to reflux for 6 hours. After the reaction mixture was cooled, the solvent was distilled off under reduced pressure. The resultant residue was dissolved in dichloromethane, and then diethyl ether was added thereto. The precipitated crystals were collected by filtration and dried to obtain 0.8 g of gray crystals. Yield: 12%.

$^1$H-NMR (300 MHz, CDCl$_3$, relative to TMS) δ (ppm): 4.315 (s, 3H), 4.320 (s, 3H), 7.81-7.85 (m, 2H), 7.93-7.96 (m, 2H).

Example 6

Production of 1,3-dimethyl-2-trifluoromethylbenzimidazolium tetrafluoroborate

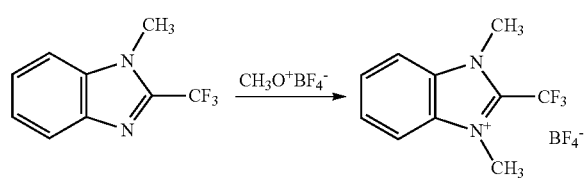

To a 50 mL eggplant-shaped flask equipped with a magnetic stirrer, 4.0 g (20 mmol) of 1-methyl-2-trifluoromethylbenzimidazole, 3.6 g (24 mmol) of trimethyloxonium tetrafluoroborate (CH$_3$O$^+$BF$_4^-$) and 20 mL of dichloromethane were added, and the mixture was stirred at room temperature for 8 hours. To the reaction mixture, acetonitrile and diethyl ether were added. The precipitated crystals were collected by filtration and dried to obtain 4.9 g of gray crystals. To the resultant filtrate, diethyl ether was added. The precipitated crystals were collected by filtration and dried to obtain 0.7 g of gray crystals. Yield: 93%.

$^1$H-NMR (400 MHz, CDCl$_3$, relative to TMS) δ (ppm): 4.26 (s, 6H), 7.86 (m, 2H), 8.25 (m, 2H).

Example 7

Production of 2-pentafluoroethylbenzimidazole

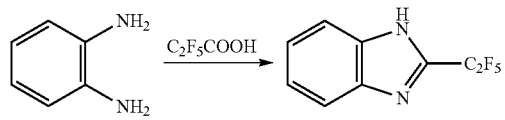

To a 50 mL eggplant-shaped flask equipped with a magnetic stirrer, 3.2 g (30 mmol) of 1,2-phenylenediamine and 9.8 g (60 mmol) of pentafluoropropionic acid were added. The mixture was heated to reflux for 4 hours. After cooling, the reaction mixture was poured into an aqueous sodium hydrogen carbonate solution, and extracted with ethyl acetate. The ethyl acetate layer was washed with a saturated aqueous sodium chloride solution and dried over anhydrous magnesium sulfate, and then the solvent was distilled off under reduced pressure to obtain 7.3 g of crystals. Yield: 100%.

$^1$H-NMR (400 MHz, CDCl$_3$, relative to TMS) δ (ppm): 7.43 (m, 2H), 7.58 (m, 1H), 7.92 (m, 1H), 9.87 (br, 1H).

Example 8

Production of 1-methyl-2-pentafluoroethylbenzimidazole

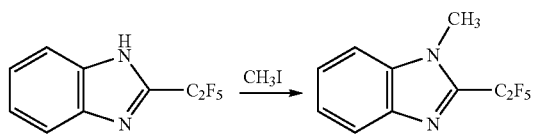

To a 100 mL eggplant-shaped flask equipped with a magnetic stirrer, 7.3 g (30 mmol) of 2-pentafluoroethylbenzimidazole, 4.6 g (33 mmol) of potassium carbonate, 4.7 g (33 mmol) of methyl iodide and 60 mL of acetone were added. The mixture was heated to reflux for 3 hours. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure. The resultant residue was purified by silica gel column chromatography to obtain 7.5 g of white crystals. Yield: 99%.

$^1$H-NMR (400 MHz, CDCl$_3$, relative to TMS) δ (ppm): 3.98 (s, 3H), 7.37-7.47 (m, 3H), 7.91 (d, J=6.0 Hz, 1H).

Example 9

Production of 1,3-dimethyl-2-pentafluoroethylbenzimidazolium methyl sulfate

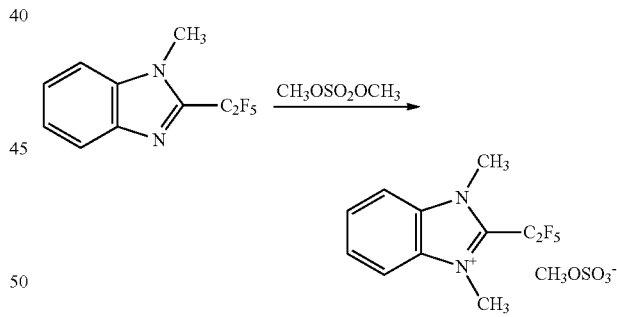

To a 50 mL eggplant-shaped flask equipped with a magnetic stirrer, 7.5 g (30 mmol) of 1-methyl-2-pentafluoroethylbenzimidazole, 5.7 g (45 mmol) of dimethyl sulfate and 30 mL of chloroform were added. The mixture was heated to reflux for 4 hours. The reaction mixture was cooled. The solvent was distilled off under reduced pressure, and the resultant residue was dissolved in dichloromethane, and then diethyl ether was added thereto, and the precipitated crystals were collected by filtration. This operation was repeated on the filtrate. A total of 5.5 g of gray crystals were obtained. Yield: 49%.

$^1$H-NMR (400 MHz, CDCl$_3$, relative to TMS) δ (ppm): 3.40 (s, 3H), 4.314 (s, 3H), 4.318 (s, 3H), 7.80-7.82, m, 2H), 7.95-7.98 (m, 2H).

Example 10

Production of 1,3-dimethyl-5-nitro-2-trifluoromethylbenzimidazolium triflate

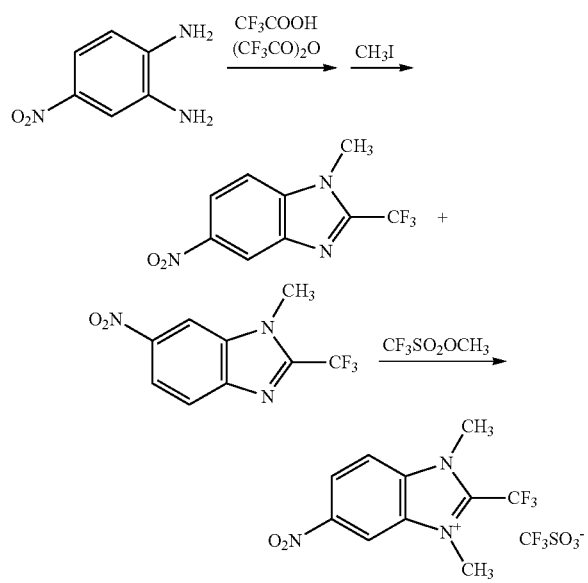

(1)

To a reaction vessel, 6.1 g (40 mmol) of 4-nitro-1,2-phenylenediamine and 10 mL (135 mmol) of trifluoroacetic acid were added, and then 10 mL (71 mmol) of trifluoroacetic anhydride was added. The mixture was heated to reflux for 48 hours. After cooling, the reaction mixture was poured into an aqueous sodium hydrogen carbonate solution, and extracted with ethyl acetate. The ethyl acetate layer was washed with a saturated aqueous sodium chloride solution and dried over anhydrous magnesium sulfate, and then the solvent was distilled off under reduced pressure. The resultant residue was purified by silica gel column chromatography to obtain 12.6 g of white crystals.

(2)

To another reaction vessel, the crystals obtained in (1) above, 5.6 g (40 mmol) of potassium carbonate, 5.6 g (40 mmol) of methyl iodide and 50 mL of acetone were added. The mixture was heated to reflux for 4 hours. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure, and the residual crystals were washed with a mixed solvent of diisopropyl ether-ethyl acetate (7:1). To the washed residual crystals, chloroform was added, and the precipitated N,N'-ditrifluoroacetyl-4-nitro-1,2-phenylenediamine was collected by filtration. The resultant filtrate was concentrated under reduced pressure to obtain 3.9 g of white crystals as a mixture of 1-methyl-5-nitro-2-trifluoromethylbenzimidazole and 1-methyl-6-nitro-2-trifluoromethylbenzimidazole.

(3)

In still another reaction vessel, the crystals obtained in (2) above were dissolved in 100 mL of acetonitrile, and then 3.9 g (23.6 mmol) of methyl triflate ($CF_3SO_2OCH_3$) was added dropwise thereto. The mixture was stirred at room temperature for 3 hours, and was stirred at 50° C. for 1 hour. The solvent was distilled off under reduced pressure. The resultant residue was dissolved in dichloromethane and acetonitrile, and then diethyl ether was added thereto. The precipitated crystals were collected by filtration and dried to obtain 1.3 g of 1,3-dimethyl-5-nitro-2-trifluoromethylbenzimidazolium triflate as white crystals. The resultant filtrate was concentrated under reduced pressure, and the resultant residue was dissolved in dichloromethane, and then diethyl ether was added thereto. The precipitated crystals were collected by filtration and dried to obtain 4.1 g of 1,3-dimethyl-5-nitro-2-trifluoromethylbenzimidazolium triflate as white crystals. Yield: 25%.

$^1$H-NMR (300 MHz, $CDCl_3$, relative to TMS) δ (ppm): 4.39 (s, 3H), 4.45 (s, 3H), 8.33 (d, J=9.4 Hz, 1H), 8.66 (d, J=9.4 Hz, 1H), 9.2 (s, 1H).

An isomer which could be understood as a tautomer was confirmed in $^1$H-NMR of the obtained compound.

$^1$H-NMR of the isomer (300 MHz, $CDCl_3$, relative to TMS) δ (ppm): 3.04 (s, 3H), 3.08 (s, 3H), 6.36 (d, J=12.5 Hz, 1H), 7.14 (d, J=1.1 Hz, 1H), 7.79 (dd, J=12.5 Hz, J=1.1 Hz, 1H).

Example 11

Production of 1-phenyl-2-trifluoromethylbenzimidazole

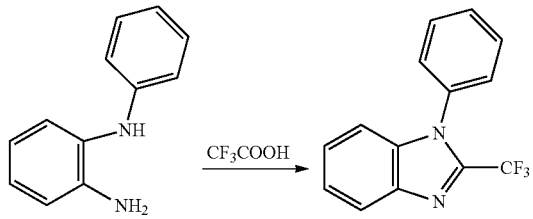 [SMILES: Nc1ccccc1Nc1ccccc1 ; "CF3COOH" ; FC(F)(F)c1nc2ccccc2n1-c1ccccc1]

To a 50 mL eggplant-shaped flask equipped with a magnetic stirrer, 3.7 g (20 mmol) of N-phenyl-1,2-phenylenediamine and 8.0 g (70 mmol) of trifluoroacetic acid were added, and the mixture was heated to reflux for 4 hours. After cooling, the reaction mixture was poured into an aqueous sodium hydrogen carbonate solution, and extracted with ethyl acetate. The ethyl acetate layer was washed with a saturated aqueous sodium chloride solution and dried over anhydrous magnesium sulfate, and then the solvent was distilled off under reduced pressure, and the resultant residue was purified by silica gel column chromatography to obtain 4.8 g of yellow oil. Yield: 92%.

$^1$H-NMR (400 MHz, $CDCl_3$, relative to TMS) δ (ppm): 7.15 (d, J=5.5 Hz, 1H), 7.37-7.45 (m, 4H), 7.59-7.60 (m, 3H), 7.94 (d, J=5.1 Hz, 1H).

Example 12

Production of 1-methyl-3-phenyl-2-trifluoromethylbenzimidazolium methyl sulfate

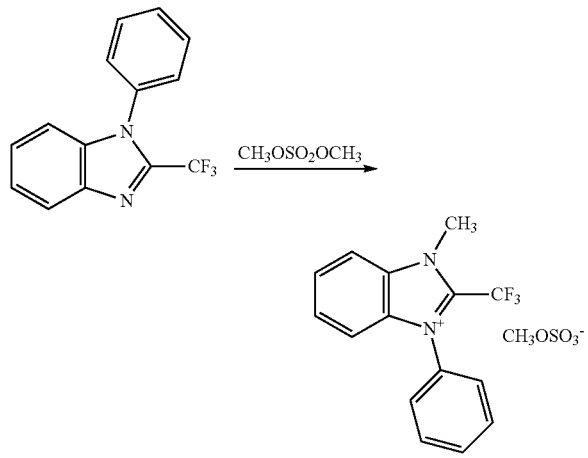

To a 100 mL eggplant-shaped flask equipped with a magnetic stirrer, 4.8 g (18 mmol) of 1-phenyl-2-trifluoromethylbenzimidazole, 3.5 g (28 mmol) of dimethyl sulfate and 30 mL of acetonitrile were added. The mixture was heated to reflux for 4 hours. After the reaction mixture was cooled, the solvent was distilled off under reduced pressure. The resultant residue was dissolved in dichloromethane, and then diethyl ether was added thereto. The precipitated crystals were collected by filtration and dried to obtain 6.4 g of pale yellow crystals. Yield: 89%.

$^1$H-NMR (400 MHz, CDCl$_3$, relative to TMS) δ (ppm): 3.13 (s, 3H), 4.50 (s, 3H), 7.30 (d, J=6.4 Hz, 1H), 7.67-7.74 (m, 4H), 7.78 (d, J=5.1 Hz, 2H), 7.84 (t, J=6.0 Hz, 1H), 8.06 (d, J=6.3 Hz, 1H).

Example 13

Production of 5-chloro-1,3-dimethyl-2-trifluoromethylbenzimidazolium triflate

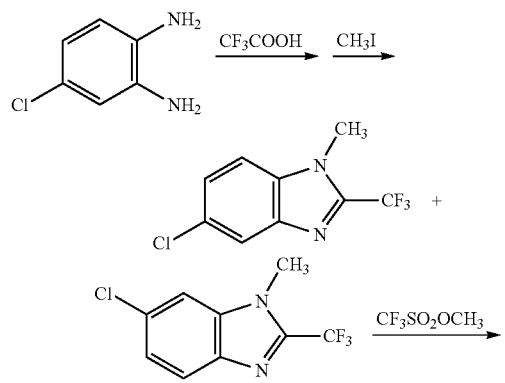

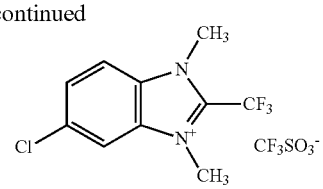

(1)
To a reaction vessel, 4.3 g (30 mmol) of 4-chloro-1,2-phenylenediamine and 10 mL (135 mmol) of trifluoroacetic acid were added. The mixture was heated to reflux for 5 hours. After cooling, the reaction mixture was poured into an aqueous sodium hydrogen carbonate solution, and extracted with ethyl acetate. The ethyl acetate layer was washed with a saturated aqueous sodium chloride solution and dried over anhydrous magnesium sulfate, and then the solvent was distilled off under reduced pressure to obtain 6.7 g of dark brown crystals.

(2)
To another reaction vessel, the crystals obtained in (1) above, 5.5 g (40 mmol) of potassium carbonate, 5.7 g (40 mmol) of methyl iodide and 80 mL of acetone were added. The mixture was heated to reflux for 4 hours. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure, and the residue was purified by silica gel column chromatography to obtain 7.0 g of white crystals as a mixture of 5-chloro-1-methyl-2-trifluoromethylbenzimidazole and 6-chloro-1-methyl-2-trifluoromethylbenzimidazole.

(3)
In still another reaction vessel, the crystals obtained in (2) above were dissolved in 100 mL of acetonitrile, and then 3.9 g (23.6 mmol) of methyl triflate (CF$_3$SO$_2$OCH$_3$) was added dropwise thereto. The mixture was stirred at room temperature for 3 hours. The solvent was distilled off under reduced pressure. The resultant residue was dissolved in dichloromethane and acetonitrile, and then diethyl ether was added thereto. The precipitated crystals were collected by filtration and dried to obtain 1.3 g of white crystals. The resultant filtrate was concentrated under reduced pressure, and the resultant residue was dissolved in dichloromethane, and then diethyl ether was added thereto. The precipitated crystals were collected by filtration and dried to obtain 10.5 g of 5-chloro-1,3-dimethyl-2-trifluoromethylbenzimidazolium triflate as white crystals. Yield: 88%.

$^1$H-NMR (300 MHz, CDCl$_3$, relative to TMS) δ (ppm): 4.24 (s, 3H), 4.27 (s, 3H), 7.75 (d, J=10.6 Hz, 1H), 7.85-7.88 (m, 2H).

Example 14

Production of 1-methyl-4,5,6,7-tetrachloro-2-trifluoromethylbenzimidazole

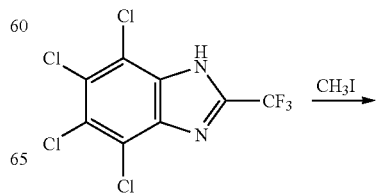

-continued

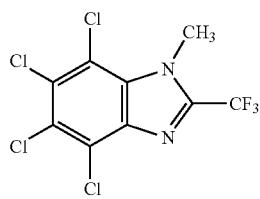

To a 50 mL eggplant-shaped flask equipped with a magnetic stirrer, 3.5 g (11 mmol) of 4,5,6,7-tetrachloro-2-trifluoromethylbenzimidazole, 1.8 g (13 mmol) of potassium carbonate, 1.7 g (12 mmol) of methyl iodide and 30 mL of acetone were added. The mixture was heated to reflux for 3 hours. 5.1 g (36 mmol) of methyl iodide was added thereto, and the mixture was heated to reflux for 1 hour. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure to obtain, 3.2 g of milky white crystals. Yield: 88%.

$^1$H-NMR (400 MHz, CDCl$_3$, relative to TMS) δ (ppm): 4.28 (s, 3H).

Example 15

Production of 1,3-dimethyl-4,5,6,7-tetrachloro-2-trifluoromethylbenzimidazolium methyl sulfate

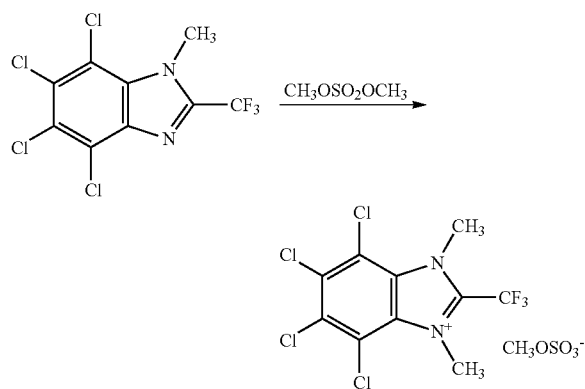

To a 50 mL eggplant-shaped flask equipped with a magnetic stirrer, 0.67 g (2 mmol) of 1-methyl-4,5,6,7-tetrachloro-2-trifluoromethylbenzimidazole and 2.8 g (22 mmol) of dimethyl sulfate were added. The mixture was stirred at 140° C. for 3 hours. The reaction mixture was cooled. Dichloromethane was added thereto, and then diisopropyl ether was added, and the precipitated crystals were collected by filtration and dried. The resultant filtrate was concentrated, and the resultant residue was dissolved in dichloromethane, and then diethyl ether was added thereto. The precipitated crystals were collected by filtration and dried. A total of 0.74 g of white crystals were obtained. Yield: 80%.

$^1$H-NMR (400 MHz, CDCl$_3$, relative to TMS) δ (ppm): 3.48 (s, 3H), 4.64 (s, 6H).

Example 16

Production of 1,3,5,7-tetramethyl-2,6-bis(trifluoromethyl)-3,5-dihydrobenzimidazolium bis methyl sulfate

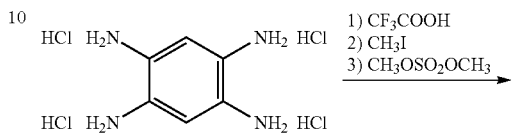

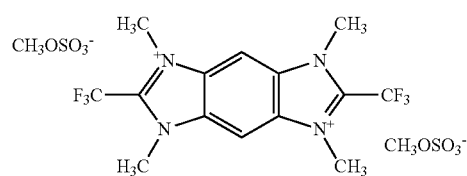

(1)
To a reaction vessel, 2.2 g (7.6 mmol)) of 1,2,4,5-benzenetetramine tetrahydrochloride and 7.0 g (61 mmol) of trifluoroacetic acid were added, and the mixture was heated to reflux for 3 hours, and then 1.6 g (16 mmol) of triethylamine was added thereto, and the mixture was heated to reflux for 2 hours. After cooling, the reaction mixture was poured into an aqueous sodium hydrogen carbonate solution, and extracted with ethyl acetate. The ethyl acetate layer was washed with a saturated aqueous sodium chloride solution and dried over anhydrous magnesium sulfate, and then the solvent was distilled off under reduced pressure to obtain 0.8 g of murky black crystals.

(2)
To another reaction vessel, the crystals obtained in (1) above, 0.9 g (6.5 mmol) of potassium carbonate, 3.9 g (27 mmol) of methyl iodide and 30 mL of acetone were added, and the mixture was heated to reflux for 3 hours. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure to obtain 0.3 g of murky black crystals.

(3)
To still another reaction vessel, the crystals obtained in (2) above and 5.8 g (46 mmol) of dimethyl sulfate were added. The mixture was stirred at 140° C. for 4 hours. To the reaction mixture, diisopropyl ether was added, and the precipitated crystals were collected by filtration and dried to obtain 0.51 g of 1,3,5,7-tetramethyl-2,6-bis(trifluoromethyl)-3,5-dihydrobenzimidazolium bis methyl sulfate as murky black crystals. Yield: 12%.

$^1$H-NMR (300 MHz, CDCl$_3$, relative to TMS) δ (ppm): 3.14 (s, 6H), 3.34 (s, 6H), 4.20 (s, 6H), 6.78 (s, 2H).

Example 17

Production of 1,3,5-trimethyl-2-trifluoromethylbenzimidazolium methyl sulfate

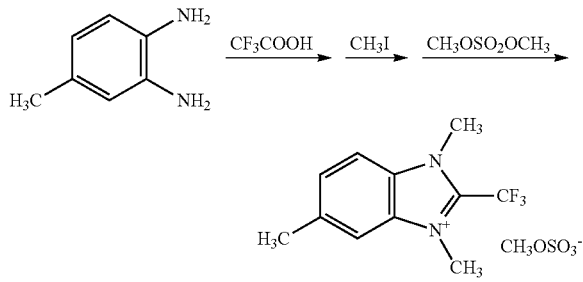

(1)

To a reaction vessel, 2.44 g (20 mmol) of 4-methyl-1,2-phenylenediamine and 10 g (88 mmol) of trifluoroacetic acid were added. The mixture was heated to reflux for 3 hours. After cooling, the reaction mixture was poured into an aqueous sodium hydrogen carbonate solution, and extracted with ethyl acetate. The ethyl acetate layer was washed with a saturated aqueous sodium chloride solution and dried over anhydrous magnesium sulfate, and then the solvent was distilled off under reduced pressure to obtain 4.08 g of light brown crystals.

(2)

To another reaction vessel, the crystals obtained in (1) above, 3.3 g (24 mmol) of potassium carbonate, 3.12 g (22 mmol) of methyl iodide and 30 mL of acetone were added. The mixture was heated to reflux for 2 hours. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure to obtain 4.26 g of brown crystals.

(3)

In still another reaction vessel, the crystals obtained in (2) above were dissolved in 30 mL of chloroform, and then 3.78 g (30 mmol) of dimethyl sulfate was added thereto. The mixture was heated to reflux for 5 hours. To the reaction mixture, diethyl ether was added, and the precipitated crystals were collected by filtration and dried to obtain 5.88 g of violet crystals. Yield: 87%.

$^1$H-NMR (300 MHz, CDCl$_3$, relative to TMS) δ (ppm): 2.60 (s, 3H), 3.38 (s, 3H), 4.25-4.28 (m, 6H), 7.58 (d, J=8.7 Hz, 1H), 7.71 (s, 1H), 7.83 (d, J=8.7 Hz, 1H).

Example 18

Production of 1,3,5,6-tetramethyl-2-trifluoromethylbenzimidazolium methyl sulfate

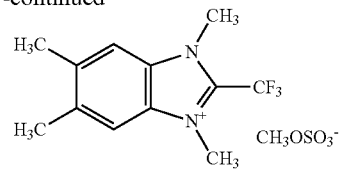

(1)

To a reaction vessel, 2.72 g (20 mmol) of 4,5-dimethyl-1,2-phenylenediamine and 6 g (53 mmol) of trifluoroacetic acid were added. The mixture was heated to reflux for 3 hours. After cooling, the reaction mixture was poured into an aqueous sodium hydrogen carbonate solution, and extracted with ethyl acetate. The ethyl acetate layer was washed with a saturated aqueous sodium chloride solution and dried over anhydrous magnesium sulfate, and then the solvent was distilled off under reduced pressure to obtain 4.08 g of light brown crystals.

(2)

To another reaction vessel, the crystals obtained in (1) above, 3.31 g (24 mmol) of potassium carbonate, 3.12 g (22 mmol) of methyl iodide and 30 mL of acetone were added. The mixture was heated to reflux for 2 hours. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure to obtain 4.35 g of brown crystals.

(3)

In still another reaction vessel, the crystals obtained in (2) above were dissolved in 30 mL of chloroform, and then 3.78 g (30 mmol) of dimethyl sulfate was added thereto. The mixture was heated to reflux for 5 hours. To the reaction mixture, diethyl ether was added, and the precipitated crystals were collected by filtration and dried to obtain 6.1 g of brown crystals. Yield: 86%.

$^1$H-NMR (300 MHz, CDCl$_3$, relative to TMS) δ (ppm): 2.49 (s, 6H), 3.42 (s, 3H), 4.258 (s, 3H), 4.263 (s, 3H), 7.68 (s, 2H).

Example 19

Production of 5,6-dichloro-1,3-dimethyl-2-trifluoromethylbenzimidazolium methyl sulfate

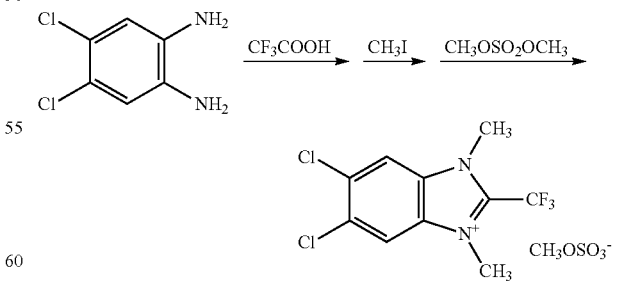

(1)

To a reaction vessel, 5.23 g (29.5 mmol) of 4,5-dichloro-1,2-phenylenediamine, 16.85 g (148 mmol) of trifluoroacetic acid and 30 mL of toluene were added. The mixture was heated to reflux for 3 hours. After cooling, the reaction mixture was poured into an aqueous sodium hydrogen carbonate solution, and extracted with ethyl acetate. The ethyl acetate layer was washed with a saturated aqueous sodium chloride solution and dried over anhydrous magnesium sulfate, and then the solvent was distilled off under reduced pressure. The resultant residue was washed with a mixed solvent of diisopropyl ether-hexane to obtain 6.75 g of light brown crystals.

(2)

To another reaction vessel, 2.55 g (10 mmol) of the crystals obtained in (1) above, 1.66 g (12 mmol) of potassium carbonate, 1.56 g (11 mmol) of methyl iodide and 30 mL of acetone were added. The mixture was heated to reflux for 2 hours. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure to obtain 2.65 g of brown crystals.

(3)

In still another reaction vessel, the crystals obtained in (2) above were dissolved in 20 mL of chloroform, and then 1.89 g (15 mmol) of dimethyl sulfate was added, and the mixture was heated to reflux for 4 hours. The chloroform was distilled off under reduced pressure, and then 3.17 g (25 mmol) of dimethyl sulfate was added thereto, and the mixture was stirred at 140° C. for 1 hour. To the reaction mixture, diethyl ether and dichloromethane were added, and the precipitated crystals were collected by filtration and dried to obtain 3.06 g of gray crystals. Yield: 79%.

$^1$H-NMR (400 MHz, CDCl$_3$, relative to TMS) δ (ppm): 3.47 (s, 3H), 4.31 (s, 3H), 4.32 (s, 3H) 8.55 (s, 2H).

Example 20

Production of 1-methyl-3-ethyl-2-trifluoromethylbenzimidazolium ethyl sulfate

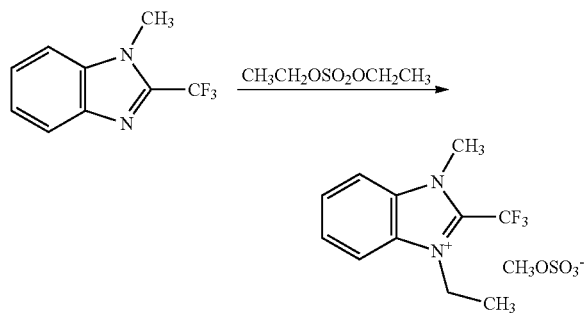

In a reaction vessel, 2.0 g (10 mmol) of 1-methyl-2-trifluoromethylbenzimidazole was dissolved in 10 mL of toluene, and then 2.8 g (18 mmol) of diethyl sulfate was added thereto. The mixture was heated to reflux for 2 hours. After cooling to room temperature, acetone and hexane were added to the reaction solution. The precipitated crystals were collected by filtration and dried to obtain 1.2 g of white crystals. Yield: 34%.

$^1$H-NMR (400 MHz, CDCl$_3$, relative to TMS) δ (ppm): 1.13 (t, J=7.1 Hz, 3H), 1.65 (t, J=7.3 Hz, 3H), 3.82 (q, J=7.1 Hz, 2H), 4.35 (s, 3H), 4.79 (q, J=7.3 Hz, 2H), 7.77-7.82 (m, 2H), 7.89-8.01 (m, 2H).

Example 21

Production of 1-N,N-dimethylaminocarbonylmethyl-3-methyl-2-trifluoromethylbenzimidazolium methyl sulfate

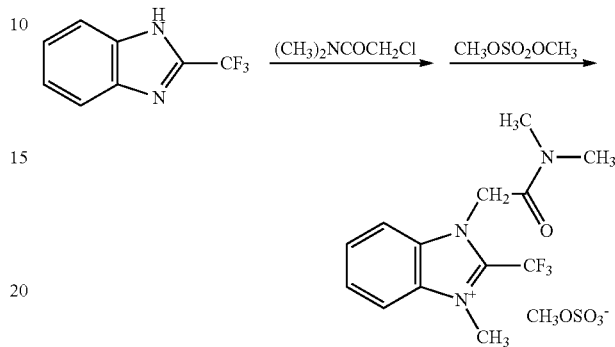

(1)

To a reaction vessel, 0.93 g (5 mmol) of 2-trifluoromethylbenzimidazole, 0.67 g (5.5 mmol) of α-chloro-N,N-dimethylacetamide, 1.08 g (7.8 mmol) of potassium carbonate and 10 mL of DMF were added. The mixture was stirred at 50° C. for 8 hours. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure, and the resultant residue was purified by silica gel column chromatography to obtain 0.84 g of oil.

(2)

In another reaction vessel, the oil obtained in (1) above was dissolved in 10 mL of acetonitrile, and then 0.59 g (4.7 mmol) of dimethyl sulfate was added. The mixture was heated to reflux for 4 hours. The acetonitrile was distilled off under reduced pressure, and then diethyl ether and dichloromethane were added to the residue. The precipitated crystals were collected by filtration and dried to obtain 0.47 g of white crystals. Yield: 24%.

$^1$H-NMR (400 MHz, CDCl$_3$, relative to TMS) δ (ppm): 3.00 (s, 3H), 3.26 (s, 3H), 3.52 (s, 3H) 4.27 (s, 3H), 5.89 (s, 2H), 7.72-7.76 (m, 2H), 7.80-7.83 (m, 1H), 8.16-8.18 (m, 1H).

Example 22

Production of 1,3-dimethyl-2-heptafluoropropylbenzimidazolium methyl sulfate

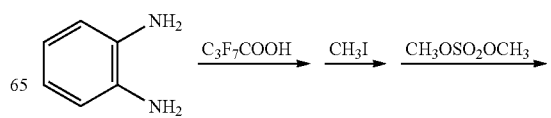

-continued

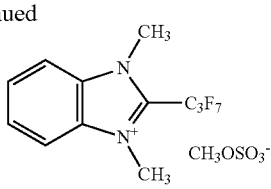

(1)

To a reaction vessel, 1.08 g (10 mmol) of 1,2-phenylenediamine and 4.28 g (20 mmol) of heptafluorobutanoic acid were added, and the mixture was heated to reflux for 4 hours. After cooling, the reaction mixture was poured into an aqueous sodium hydrogen carbonate solution, and extracted with ethyl acetate. The ethyl acetate layer was washed with a saturated aqueous sodium chloride solution and dried over anhydrous magnesium sulfate, and then the solvent was distilled off under reduced pressure to obtain 2.7 g of crystals.

(2)

To another reaction vessel, the crystals obtained in (1) above, 1.96 g (14 mmol) of potassium carbonate, 2.01 g (14 mmol) of methyl iodide and 30 mL of acetone were added. The mixture was heated to reflux for 3 hours. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure, and the resultant residue was purified by silica gel column chromatography to obtain 2.86 g of oil.

(3)

In still another reaction vessel, the oil obtained in (2) above was dissolved in 20 mL of acetonitrile, and then 1.8 g (14 mmol) of dimethyl sulfate was added. The mixture was heated to reflux for 15 hours. The acetonitrile was distilled off under reduced pressure. The operation of adding ethyl acetate to the resultant residue and removing the supernatant ethyl acetate solution was repeated for several times. The solvent was distilled off under reduced pressure from the resultant residue to obtain 2.0 g of sherbet-like solids. Yield: 49%.

$^1$H-NMR (400 MHz, CDCl$_3$, relative to TMS) δ (ppm): 3.48 (s, 3H), 4.32 (s, 6H), 7.81-7.84 (m, 2H), 7.98-8.00 (m, 2H).

Example 23

Production of 1,3-dimethyl-2-undecafluoropentylbenzimidazolium methyl sulfate

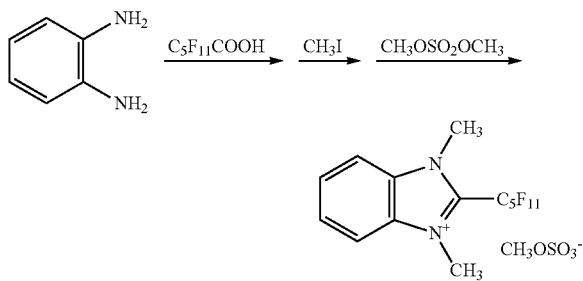

(1)

To a reaction vessel, 0.54 g (5 mmol) of 1,2-phenylenediamine and 3.14 g (10 mmol) of undecafluorohexanoic acid were added, and the mixture was heated to reflux for 5 hours. After cooling, the reaction mixture was poured into an aqueous sodium hydrogen carbonate solution, and extracted with ethyl acetate. The ethyl acetate layer was washed with a saturated aqueous sodium chloride solution and dried over anhydrous magnesium sulfate, and then the solvent was distilled off under reduced pressure to obtain crystals.

(2)

To another reaction vessel, the crystals obtained in (1) above, 1.04 g (7.5 mmol) of potassium carbonate, 1.06 g (7.5 mmol) of methyl iodide and 30 mL of acetone were added. The mixture was heated to reflux for 3 hours. After the reaction mixture was cooled, water was added thereto, and the mixture was extracted with ethyl acetate. The ethyl acetate layer was washed with a saturated aqueous sodium chloride solution and dried over anhydrous magnesium sulfate, and then the solvent was distilled off under reduced pressure. The resultant residue was purified by silica gel column chromatography to obtain 1.9 g of crystals.

(3)

In still another reaction vessel, the crystals obtained in (2) above were dissolved in 7.5 mL of acetonitrile, and then 0.95 g (7.5 mmol) of dimethyl sulfate was added thereto. The mixture was heated to reflux for 6 hours. The acetonitrile was distilled off under reduced pressure. The operation of adding ethyl acetate to the resultant residue and removing the supernatant ethyl acetate solution was repeated for several times. Ethyl acetate was added to the resultant residue, and the precipitated crystals were collected by filtration and dried to obtain 0.9 g of crystals. Yield: 36%.

$^1$H-NMR (400 MHz, CDCl$_3$, relative to TMS) δ (ppm): 3.40 (s, 3H), 4.33 (s, 6H), 7.81-7.84 (m, 2H), 7.94-7.96 (m, 2H).

Example 24

Production of 1,3-dimethyl-2-trifluoromethylbenzimidazolium trifluoroacetate

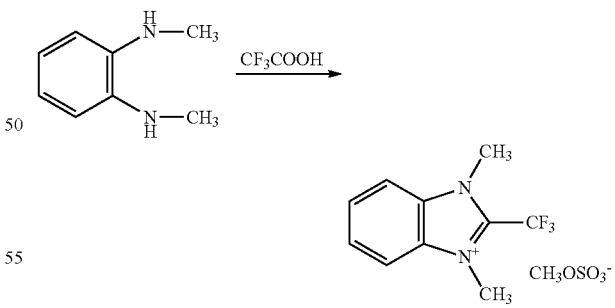

To a 50 mL eggplant-shaped flask equipped with a magnetic stirrer, 0.42 g (3.08 mmol) of N,N'-dimethyl-1,2-phenylenediamine and about 10 mL of trifluoroacetic acid were added. The mixture was heated to reflux for 4 hours. After the reaction mixture was cooled, the solvent was distilled off under reduced pressure to obtain 1.68 g of murky black oil. This oil was confirmed by NMR to contain 1,3-dimethyl-2-trifluoromethylbenzimidazolium trifluoroacetate as a main component.

$^1$H-NMR (400 MHz, CDCl$_3$, relative to TMS) δ (ppm): 4.33 (s, 6H), 7.85-7.92 (m, 4H).

Some of the compounds represented by the general formula (1) can also be produced by the same or similar method as Example 24.

Example 25

Production of (5-benzyloxypentyl) trifluoromethyl sulfide

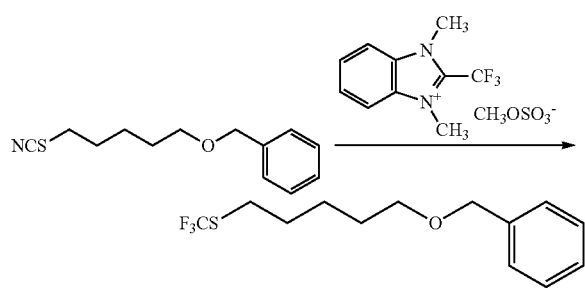

To a 6 mL vial equipped with a magnetic stirrer, 118 mg (0.5 mmol) of 1-benzyloxy-5-thiocyanatopentane, 300 mg of molecular sieve 4 A (manufactured by Sigma-Aldrich Co. LLC.; Molecular sieves, 4 A, powder, <5 micron, activated), 196 mg (0.6 mmol) of 1,3-dimethyl-2-trifluoromethylbenzimidazolium methyl sulfate and 1.5 mL of DMF were added. The mixture was stirred at −10° C. for 30 minutes, and then 52 mg (1.26 mmol) of sodium hydroxide was added thereto. The mixture was stirred at −10° C. for 16 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 58% of (5-benzyloxypentyl) trifluoromethyl sulfide (target compound), 3% of 1-benzyloxy-5-thiocyanatopentane (starting compound), 6% of 1,2-bis[5-(benzyloxy)pentyl]disulfide (by-product), 31% of 2,3-dihydro-1,3-dimethylbenzimidazole-2-one (compound derived from the fluoroalkylating agent) and 2% of 1,3-dimethyl-2,2-bis(trifluoromethyl)-2,3-dihydro-benzimidazole (compound derived from the fluoroalkylating agent). As a result of GC analysis using 1,4-diethylbenzene as the internal standard, the yield of (5-benzyloxypentyl) trifluoromethyl sulfide (target compound) was 87%.

Example 26

Production of (5-benzyloxypentyl) trifluoromethyl sulfide

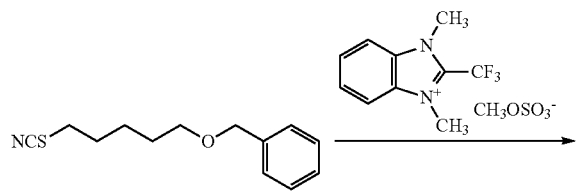
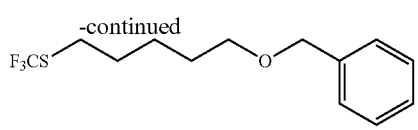

To a 20 mL vial equipped with a magnetic stirrer, 471 mg (2 mmol) of 1-benzyloxy-5-thiocyanatopentane, 1.2 g of molecular sieve 4 A (manufactured by Sigma-Aldrich Co. LLC.; Molecular sieves, 4 A, powder, <5 micron, activated), 783 mg (2.4 mmol) of 1,3-dimethyl-2-trifluoromethylbenzimidazolium methyl sulfate and 6 mL of DMF were added. The mixture was stirred at −10° C. for 30 minutes, and then 294 mg (5.04 mmol) of potassium hydroxide was added. The mixture was stirred at −10° C. for 16 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 59% of (5-benzyloxypentyl) trifluoromethyl sulfide (target compound), 5% of 1-benzyloxy-5-thiocyanatopentane (starting compound), 1% of 1,2-bis[5-(benzyloxy)pentyl]disulfide (by-product), 32% of 2,3-dihydro-1,3-dimethylbenzimidazole-2-one (compound derived from the fluoroalkylating agent) and 1% of 1,3-dimethyl-2,2-bis(trifluoromethyl)-2,3-dihydro-benzimidazole (compound derived from the fluoroalkylating agent). As a result of GC analysis using 1,4-diethylbenzene as the internal standard, the yield of (5-benzyloxypentyl) trifluoromethyl sulfide (target compound) was 90%.

Example 27

Production of (5-benzyloxypentyl) trifluoromethyl sulfide

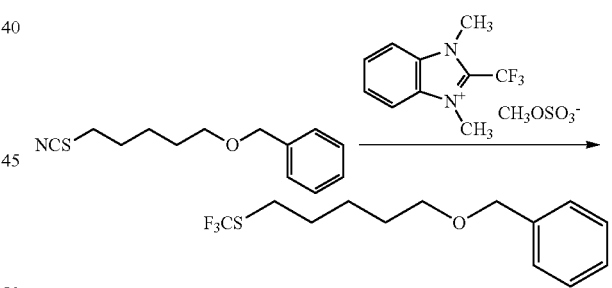

To a 6 mL vial equipped with a magnetic stirrer, 118 mg (0.5 mmol) of 1-benzyloxy-5-thiocyanatopentane, 300 mg of molecular sieve 4 A (manufactured by Sigma-Aldrich Co. LLC.; Molecular sieves, 4 A, powder, <5 micron, activated), 196 mg (0.6 mmol) of 1,3-dimethyl-2-trifluoromethylbenzimidazolium methyl sulfate and 1.5 mL of DMF were added. The mixture was stirred at −10° C. for 30 minutes, and then 31 mg (1.26 mmol) of lithium hydroxide was added thereto. The mixture was stirred at −10° C. for 16 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 59% of (5-benzyloxypentyl) trifluoromethyl sulfide (target compound), 5% of 1-benzyloxy-5-thiocyanatopentane (starting compound), 33% of 2,3-dihydro-1,3-dimethylbenzimidazole-2-one (compound derived from the fluoroalkylating agent) and 1% of 1,3-dimethyl-2,2-bis(trifluoromethyl)-2,3-dihydro-benzimidazole (compound derived from the fluoroalkylating agent). As a result of GC analysis using 1,4-diethylbenzene as the internal standard, the yield of (5-benzyloxypentyl) trifluoromethyl sulfide (target compound) was 96%.

Example 28

Production of (5-benzyloxypentyl) trifluoromethyl sulfide

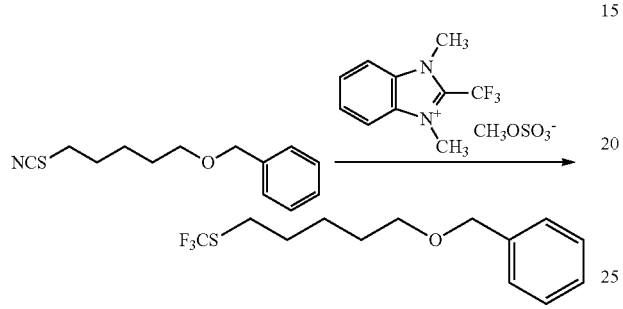

To a 6 mL vial equipped with a magnetic stirrer, 118 mg (0.5 mmol) of 1-benzyloxy-5-thiocyanatopentane, 196 mg (0.6 mmol) of 1,3-dimethyl-2-trifluoromethylbenzimidazolium methyl sulfate, 207 mg (1.5 mmol) of potassium carbonate, 161 mg (0.5 mmol) of tetrabutylammonium bromide and 1.5 mL of toluene were added. The mixture was stirred at room temperature for 15 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 19% of (5-benzyloxypentyl) trifluoromethyl sulfide (target compound), 35% of 1-benzyloxy-5-thiocyanatopentane (starting compound), 3% of 1,2-bis[5-(benzyloxy)pentyl]disulfide (by-product) and 42% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 44%.

Example 29

Production of (5-benzyloxypentyl) trifluoromethyl sulfide

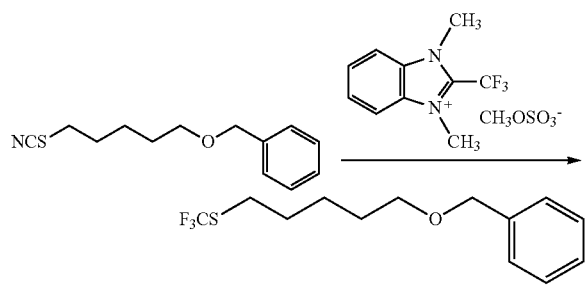

To a 6 mL vial equipped with a magnetic stirrer, 118 mg (0.5 mmol) of 1-benzyloxy-5-thiocyanatopentane, 196 mg (0.6 mmol) of 1,3-dimethyl-2-trifluoromethylbenzimidazolium methyl sulfate, 50 mg (1.26 mmol) of sodium hydroxide, 161 mg (0.5 mmol) of tetrabutylammonium bromide and 1.5 mL of toluene were added. The mixture was stirred at room temperature for 15 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 27% of (5-benzyloxypentyl) trifluoromethyl sulfide (target compound), 10% of 1-benzyloxy-5-thiocyanatopentane (starting compound), 18% of 1,2-bis[5-(benzyloxy)pentyl]disulfide (by-product) and 43% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 42%.

Example 30

Production of (5-benzyloxypentyl) trifluoromethyl sulfide

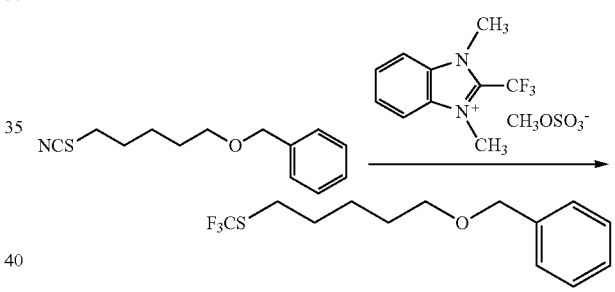

To a 6 mL vial equipped with a magnetic stirrer, 118 mg (0.5 mmol) of 1-benzyloxy-5-thiocyanatopentane, 196 mg (0.6 mmol) of 1,3-dimethyl-2-trifluoromethylbenzimidazolium methyl sulfate and 1.5 mL of DMF were added. The mixture was stirred at −10° C. for 30 minutes, and then 72 mg (1.8 mmol) of 60% sodium hydride was added thereto. The mixture was stirred at −10° C. for 30 minutes. Then, 37 mg (0.63 mmol) of potassium hydroxide was added thereto, and the mixture was stirred at −10° C. for 16 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 43% of (5-benzyloxypentyl) trifluoromethyl sulfide (target compound), 17% of 1-benzyloxy-5-thiocyanatopentane (starting compound), 38% of 2,3-dihydro-1,3-dimethylbenzimidazole-2-one (compound derived from the fluoroalkylating agent) and 2% of 1,3-dimethyl-2,2-bis(trifluoromethyl)-2,3-dihydro-benzimidazole (compound derived from the fluoroalkylating agent). As a result of GC analysis using 1,4-diethylbenzene as the internal standard, the yield of (5-benzyloxypentyl) trifluoromethyl sulfide (target compound) was 66%.

Example 31

Production of (5-acetyloxypentyl) trifluoromethyl sulfide

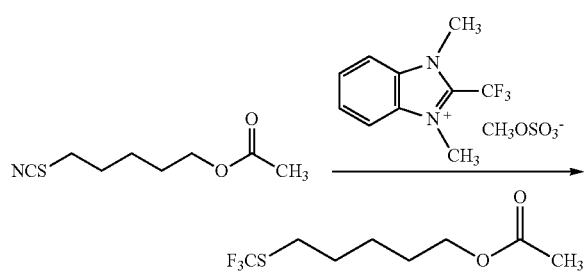

To a 6 mL vial equipped with a magnetic stirrer, 187 mg (1 mmol) of 1-acetyloxy-5-thiocyanatopentane, 300 mg of molecular sieve 4 A (manufactured by Sigma-Aldrich Co. LLC.; Molecular sieves, 4 A, powder, <5 micron, activated), 392 mg (1.2 mmol) of 1,3-dimethyl-2-trifluoromethylbenzimidazolium methyl sulfate and 0.5 mL of DMF were added. The mixture was stirred at −10° C. for 30 minutes, and then 148 mg (2.52 mmol) of potassium hydroxide was added thereto. The mixture was stirred at −10° C. for 1 hour. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 39% of (5-acetyloxypentyl) trifluoromethyl sulfide (target compound), 4% of 1-acetyloxy-5-thiocyanatopentane (starting compound), 1% of 1,2-bis[5-(acetyloxy)pentyl] disulfide (by-product) and 51% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 79%.

Example 32

Production of (5-acetyloxypentyl) trifluoromethyl sulfide

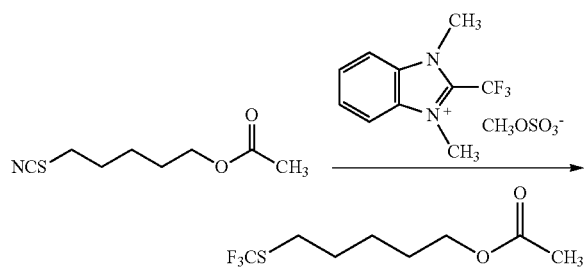

To a 6 mL vial equipped with a magnetic stirrer, 187 mg (1 mmol) of 1-acetyloxy-5-thiocyanatopentane, 392 mg (1.2 mmol) of 1,3-dimethyl-2-trifluoromethylbenzimidazolium methyl sulfate and 0.5 mL of DMF were added. The mixture was stirred at −10° C. for 30 minutes, and then 144 mg (3.6 mmol) of 60% sodium hydride was added thereto. The mixture was stirred at −10° C. for 30 minutes. Then, 74 mg (1.26 mmol) of potassium hydroxide was added thereto, and the mixture was stirred at −10° C. for 30 minutes. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 31% of (5-acetyloxypentyl) trifluoromethyl sulfide (target compound), 12% of 1-acetyloxy-5-thiocyanatopentane (starting compound), 1% of 1,2-bis(5-(acetyloxy)pentyl) disulfide (by-product), 49% of 2,3-dihydro-1,3-dimethylbenzimidazole-2-one (compound derived from the fluoroalkylating agent) and 2% of 1,3-dimethyl-2,2-bis(trifluoromethyl)-2,3-dihydro-benzimidazole (compound derived from the fluoroalkylating agent). As a result of GC analysis using 1,4-diethylbenzene as the internal standard, the yield of (5-acetyloxypentyl) trifluoromethyl sulfide (target compound) was 68%.

Example 33

Production of (5-benzyloxypentyl) trifluoromethyl sulfide

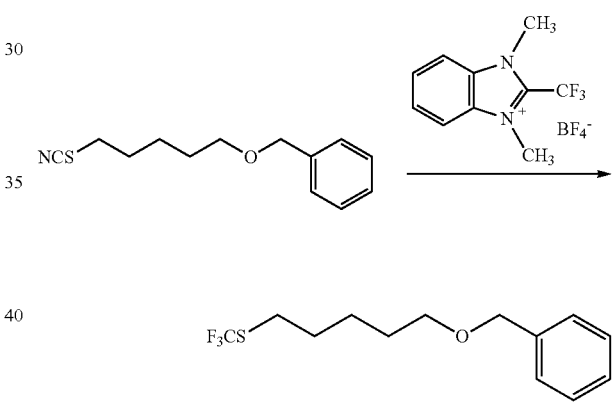

To a 10 mL eggplant-shaped flask equipped with a magnetic stirrer, 30 mg (0.125 mmol) of 1-benzyloxy-5-thiocyanatopentane, 35 mg (0.25 mmol) of potassium carbonate and 1 mL of DMF were added. While the mixture was stirred in an ice bath, 45 mg (0.15 mmol) of 1,3-dimethyl-2-trifluoromethylbenzimidazolium tetrafluoroborate was added thereto. While the temperature was raised to room temperature slowly, the mixture was stirred for 15 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 20% of (5-benzyloxypentyl) trifluoromethyl sulfide (target compound), 27% of 1-benzyloxy-5-thiocyanatopentane (starting compound) and 53% of 2,3-dihydro-1,3-dimethyl-benzimidazole-2-one (compound derived from the fluoroalkylating agent). The yield of (5-benzyloxypentyl) trifluoromethyl sulfide (target compound) was 43% in terms of GC area percentage.

Example 34

Production of (5-benzyloxypentyl) trifluoromethyl sulfide

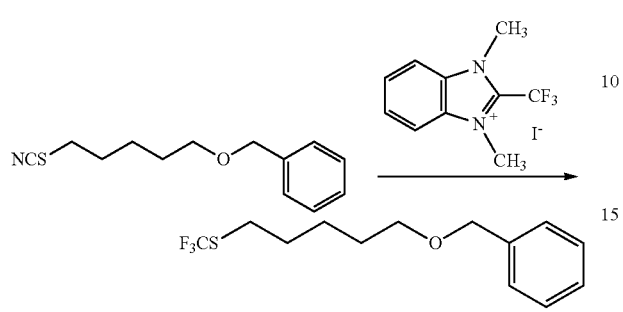

To a 10 mL eggplant-shaped flask equipped with a magnetic stirrer, 30 mg (0.125 mmol) of 1-benzyloxy-5-thiocyanatopentane, 35 mg (0.25 mmol) of potassium carbonate and 1 mL of DMF were added. While the mixture was stirred in an ice bath, 51 mg (0.15 mmol) of 1,3-dimethyl-2-trifluoromethylbenzimidazolium iodide was added thereto. While the temperature was raised to room temperature slowly, the mixture was stirred for 15 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 20% of (5-benzyloxypentyl) trifluoromethyl sulfide (target compound), 31% of 1-benzyloxy-5-thiocyanatopentane (starting compound) and 42% of 2,3-dihydro-1,3-dimethylbenzimidazole-2-one (compound derived from the fluoroalkylating agent). The yield of (5-benzyloxypentyl) trifluoromethyl sulfide (target compound) was 34% in terms of GC area percentage.

Example 35

Production of (5-benzyloxypentyl) trifluoromethyl sulfide

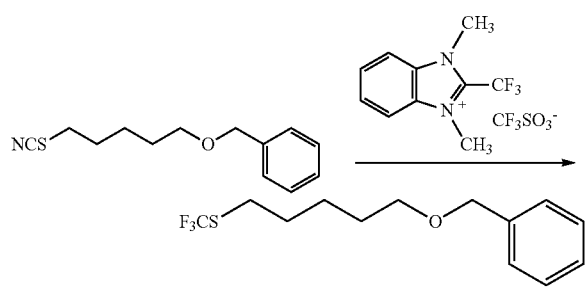

To a 10 mL eggplant-shaped flask equipped with a magnetic stirrer, 60 mg (0.25 mmol) of 1-benzyloxy-5-thiocyanatopentane, 70 mg (0.5 mmol) of potassium carbonate and 0.5 mL of DMF were added. While the mixture was stirred at room temperature, 110 mg (0.3 mmol) of 1,3-dimethyl-2-trifluoromethylbenzimidazolium triflate was added thereto. The mixture was stirred at room temperature for 2 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 24% of (5-benzyloxypentyl) trifluoromethyl sulfide (target compound), 31% of 1-benzyloxy-5-thiocyanatopentane (starting compound) and 45% of 2,3-dihydro-1,3-dimethylbenzimidazole-2-one (compound derived from the fluoroalkylating agent). The yield of (5-benzyloxypentyl) trifluoromethyl sulfide (target compound) was 44% in terms of GC area percentage.

Example 36

Production of (5-benzyloxypentyl) trifluoromethyl sulfide

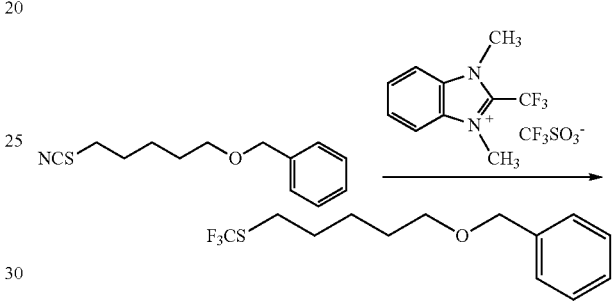

To a 10 mL eggplant-shaped flask equipped with a magnetic stirrer, 60 mg (0.25 mmol) of 1-benzyloxy-5-thiocyanatopentane, 70 mg (0.5 mmol) of potassium carbonate and 1 mL of DMSO were added. While the mixture was stirred at room temperature, 110 mg (0.3 mmol) of 1,3-dimethyl-2-trifluoromethylbenzimidazolium triflate was added thereto. The mixture was stirred at room temperature for 2 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 31% of (5-benzyloxypentyl) trifluoromethyl sulfide (target compound), 29% of 1-benzyloxy-5-thiocyanatopentane (starting compound) and 40% of 2,3-dihydro-1,3-dimethylbenzimidazole-2-one (compound derived from the fluoroalkylating agent). The yield of (5-benzyloxypentyl) trifluoromethyl sulfide (target compound) was 52% in terms of GC area percentage.

Example 37

Production of (5-benzyloxypentyl) trifluoromethyl sulfide

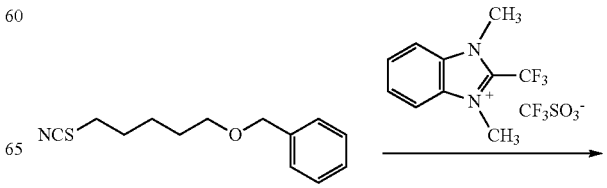

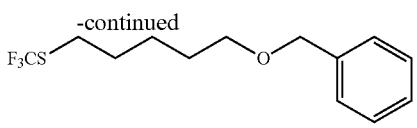

To a 10 mL eggplant-shaped flask equipped with a magnetic stirrer, 30 mg (0.125 mmol) of 1-benzyloxy-5-thiocyanatopentane, 98 mg (0.3 mmol) of cesium carbonate and 0.3 mL of DMF were added. While the mixture was stirred at −50° C. or lower, 55 mg (0.15 mmol) of 1,3-dimethyl-2-trifluoromethylbenzimidazolium triflate was added thereto. While the temperature was raised to room temperature slowly, the mixture was stirred for 15 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 42% of (5-benzyloxypentyl) trifluoromethyl sulfide (target compound), 14% of 1-benzyloxy-5-thiocyanatopentane (starting compound) and 44% of 1,3-dimethylbenzimidazole-2-one (compound derived from the fluoroalkylating agent). The yield of (5-benzyloxypentyl) trifluoromethyl sulfide (target compound) was 75% in terms of GC area percentage.

Example 38

Production of (5-benzyloxypentyl) trifluoromethyl sulfide

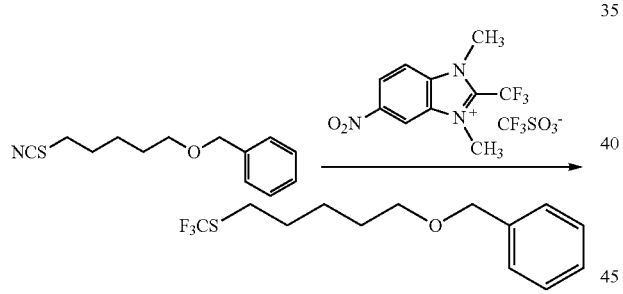

To a 50 mL eggplant-shaped flask equipped with a magnetic stirrer, 0.47 g (2 mmol) of 1-benzyloxy-5-thiocyanatopentane, 0.83 g (6 mmol) of potassium carbonate and 4 mL of DMF were added. A solution prepared by dissolving 1.64 g (4 mmol) of 1,3-dimethyl-5-nitro-2-trifluoromethylbenzimidazolium triflate in 4 mL of DMF was added dropwise thereto at room temperature over 2 hours. The mixture was stirred as it is for 15 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 41% of (5-benzyloxypentyl) trifluoromethyl sulfide (target compound), 12% of 1-benzyloxy-5-thiocyanatopentane (starting compound) and 47% of 2,3-dihydro-1,3-dimethyl-5-nitro-benzimidazole-2-one (compound derived from the fluoroalkylating agent). The yield of (5-benzyloxypentyl) trifluoromethyl sulfide (target compound) was 77% in terms of GC area percentage.

Example 39

Production of (5-benzyloxypentyl) trifluoromethyl sulfide

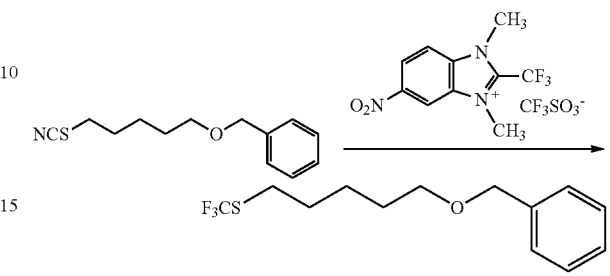

To a 50 mL eggplant-shaped flask equipped with a magnetic stirrer, 0.47 g (2 mmol) of 1-benzyloxy-5-thiocyanatopentane, 0.83 g (6 mmol) of potassium carbonate and 4 mL of DMF were added. A solution prepared by dissolving 1.6 g (4 mmol) of 5-chloro-1,3-dimethyl-2-trifluoromethylbenzimidazolium triflate in 4 mL of DMF was added dropwise thereto at room temperature over 2 hours. The mixture was stirred as it is for 15 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 28% of (5-benzyloxypentyl) trifluoromethyl sulfide (target compound), 6% of 1-benzyloxy-5-thiocyanatopentane (starting compound) and 66% of 2,3-dihydro-1,3-dimethyl-benzimidazole-2-one (compound derived from the fluoroalkylating agent). The yield of (5-benzyloxypentyl) trifluoromethyl sulfide (target compound) was 82% in terms of GC area percentage.

Example 40

Production of (5-benzyloxypentyl) pentafluoroethyl sulfide

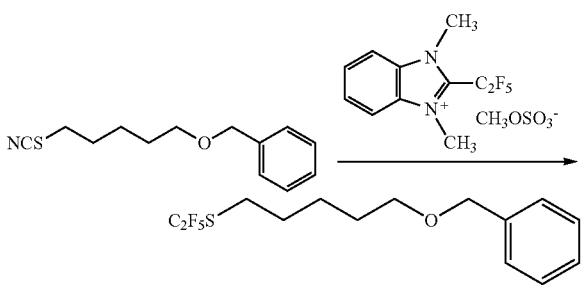

To a 10 mL eggplant-shaped flask equipped with a magnetic stirrer, 30 mg (0.125 mmol) of 1-benzyloxy-5-thiocyanatopentane, 35 mg (0.3 mmol) of potassium carbonate and 0.5 mL of DMF were added. While the mixture was stirred at room temperature, 56 mg (0.15 mmol) of 1,3-dimethyl-2-pentafluoroethylbenzimidazolium methyl sulfate was added thereto. The mixture was stirred at room temperature for 3 hours. The formation of (5-benzyloxypentyl) pentafluoroethyl sulfide (parent ion; 328) was confirmed by GC-MS analysis on the reaction mixture. As a result of GC analysis (area percentage) on the reaction mixture, the components in the reaction mixture excluding the solvents and the like were as follows: 18% of (5-benzyloxypentyl) pentafluoroethyl sulfide (target compound), 39% of 1-benzyloxy-5-thiocyanatopentane (starting compound) and 40% of 2,3-dihydro-1,3-dimethylbenzimidazole-2-one (compound derived from the fluoroalkylating agent). The yield of (5-benzyloxypentyl) pentafluoroethyl sulfide (target compound) was 30% in terms of GC area percentage.

Example 41

Production of (5-benzyloxypentyl) trifluoromethyl sulfide

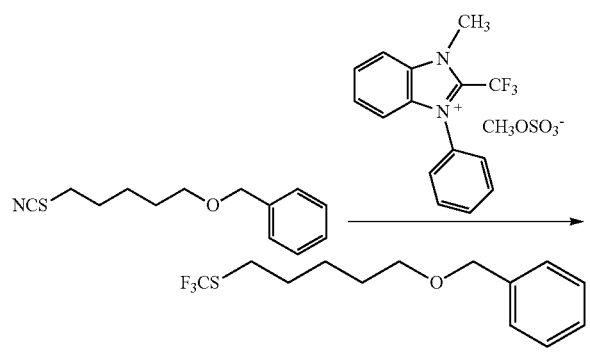

To a 10 mL eggplant-shaped flask equipped with a magnetic stirrer, 30 mg (0.125 mmol) of 1-benzyloxy-5-thiocyanatopentane, 35 mg (0.3 mmol) of potassium carbonate and 0.3 mL of DMF were added. While the mixture was stirred at room temperature, 58 mg (0.15 mmol) of 1-methyl-3-phenyl-2-trifluoromethylbenzimidazolium methyl sulfate was added thereto. The mixture was stirred at room temperature for 3 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 16% of (5-benzyloxypentyl) trifluoromethyl sulfide (target compound), 27% of 1-benzyloxy-5-thiocyanatopentane (starting compound) and 52% of 2,3-dihydro-1-methyl-3-phenylbenzimidazole-2-one (compound derived from the fluoroalkylating agent). The yield of (5-benzyloxypentyl) trifluoromethyl sulfide (target compound) was 33% in terms of GC area percentage.

Example 42

Production of (5-benzyloxypentyl) trifluoromethyl sulfide

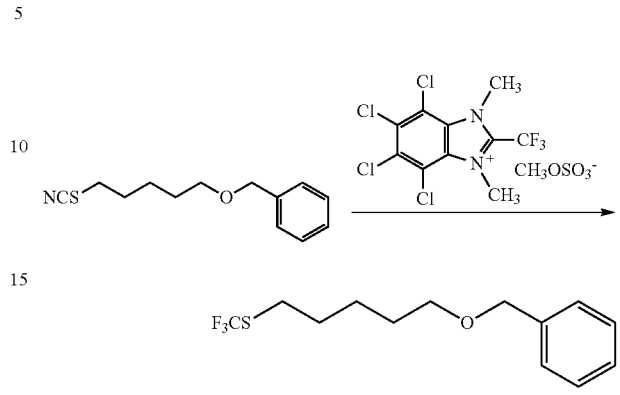

To a 10 mL eggplant-shaped flask equipped with a magnetic stirrer, 30 mg (0.125 mmol) of 1-benzyloxy-5-thiocyanatopentane, 35 mg (0.3 mmol) of potassium carbonate and 0.5 mL of DMF were added. While the mixture was stirred at room temperature, 70 mg (0.15 mmol) of 1,3-dimethyl-4,5,6,7-tetrachloro-2-trifluoromethylbenzimidazolium methyl sulfate was added thereto. The mixture was stirred at room temperature for 15 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 21% of (5-benzyloxypentyl) trifluoromethyl sulfide (target compound), 31% of 1-benzyloxy-5-thiocyanatopentane (starting compound) and 46% of 2,3-dihydro-1,3-dimethyl-4,5,6,7-tetrachloro-benzimidazole-2-one (compound derived from the fluoroalkylating agent). The yield of (5-benzyloxypentyl) trifluoromethyl sulfide (target compound) was 39% in terms of GC area percentage.

Example 43

Production of (5-benzyloxypentyl) trifluoromethyl sulfide

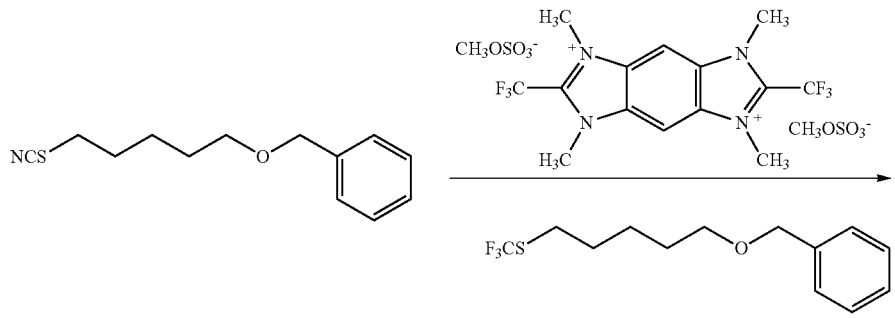

To a 10 mL eggplant-shaped flask equipped with a magnetic stirrer, 30 mg (0.125 mmol) of 1-benzyloxy-5-thiocyanatopentane, 35 mg (0.3 mmol) of potassium carbonate and 0.5 mL of DMF were added. While the mixture was stirred at room temperature, 43 mg (0.075 mmol) of 1,3,5,7-tetramethyl-2,6-bis(trifluoromethyl)-3,5-dihydrobenzodiimidazolium bis methyl sulfate was added thereto. The mixture was stirred at room temperature for 15 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 8% of (5-benzyloxypentyl) trifluoromethyl sulfide (target compound), 68% of 1-benzyloxy-5-thiocyanatopentane (starting compound), 3% of 1,3,5,7-tetramethyl-5,7-dihydrobenzodiimidazole-2,6-dione (compound derived from the fluoroalkylating agent) and 18% of 1,3,5,7-tetramethyl-6,6-bistrifluoromethyl-3,5,6,7-tetrahydrobenzodiimidazole-2-one (compound derived from the fluoroalkylating agent). The yield of (5-benzyloxypentyl) trifluoromethyl sulfide (target compound) was 10% in terms of GC area percentage.

Example 44

Production of 1-(2,4-difluorophenyl)-2,2,2-trifluoroethanol

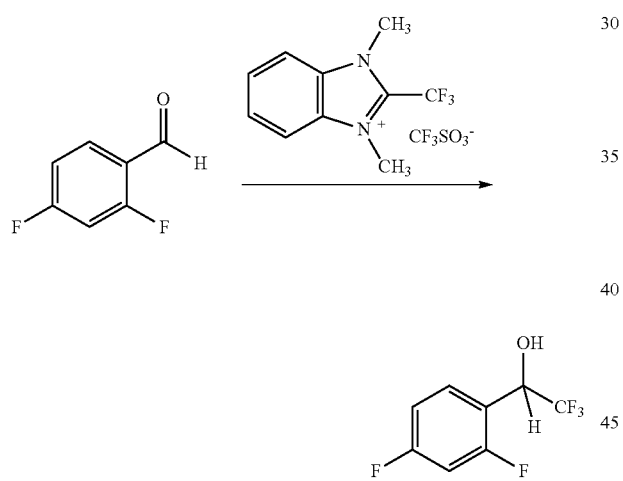

To a 10 mL eggplant-shaped flask equipped with a magnetic stirrer, 0.03 g (0.21 mmol) of 2,4-difluorobenzaldehyde, 0.06 g (0.42 mmol) of potassium carbonate and 1 mL of DMF were added. While the mixture was stirred at room temperature, 0.12 g (0.32 mmol) of 1,3-dimethyl-2-trifluoromethylbenzimidazolium triflate was added thereto. The mixture was stirred at room temperature for 2 hours. The formation of 1-(2,4-difluorophenyl)-2,2,2-trifluoroethanol (parent ion; 212) was confirmed by GC-MS analysis on the reaction mixture. As a result of GC analysis (area percentage) on the reaction mixture, the components in the reaction mixture excluding the solvents and the like were as follows: 15% of 1-(2,4-difluorophenyl)-2,2,2-trifluoroethanol (target compound), 13% of 2,4-difluorobenzaldehyde (starting compound) and 71% of 1,3-dimethylbenzimidazole-2-one (compound derived from the fluoroalkylating agent). The yield of 1-(2,4-difluorophenyl)-2,2,2-trifluoroethanol (target compound) was 52% in terms of GC area percentage.

Example 45

Production of 1-(4-methylphenyl)-2,2,2-trifluoroethanol

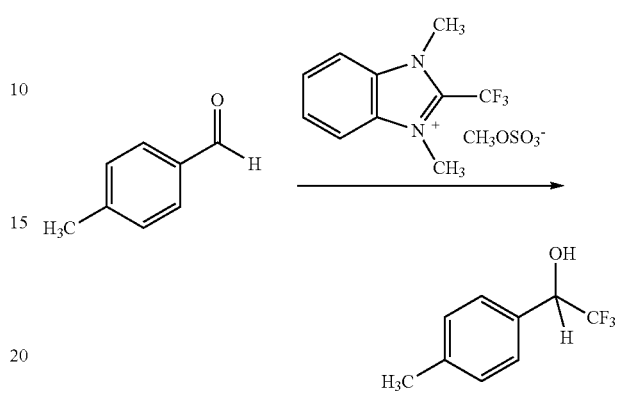

To a 10 mL eggplant-shaped flask equipped with a magnetic stirrer, 0.06 g (0.5 mmol) of 4-methylbenzaldehyde, 0.28 g (2 mmol) of potassium carbonate and 1 mL of DMF were added. While the mixture was stirred at room temperature, 0.33 g (1 mmol) of 1,3-dimethyl-2-trifluoromethylbenzimidazolium methyl sulfate was added thereto. The mixture was stirred at room temperature for 15 hours. The formation of 1-(4-methylphenyl)-2,2,2-trifluoroethanol (parent ion; 190) was confirmed by GC-MS analysis on the reaction mixture. As a result of GC analysis (area percentage) on the reaction mixture, the components in the reaction mixture excluding the solvents and the like were as follows: 6% of 1-(4-methylphenyl)-2,2,2-trifluoroethanol (target compound), 31% of 4-methylbenzaldehyde (starting compound) and 63% of 2,3-dihydro-1,3-dimethylbenzimidazole-2-one (compound derived from the fluoroalkylating agent). The yield of 1-(4-methylphenyl)-2,2,2-trifluoroethanol (target compound) was 16% in terms of GC area percentage.

Example 46

Production of 1-(3,4-difluorophenyl)-2,2,2-trifluoroethanol

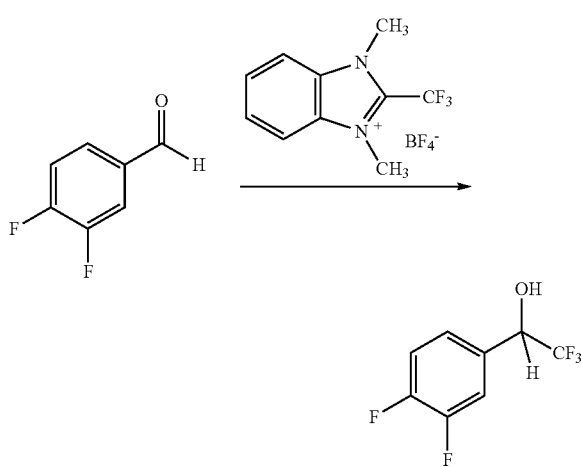

To a 10 mL eggplant-shaped flask equipped with a magnetic stirrer, 18 mg (0.125 mmol) of 3,4-difluorobenzaldehyde, 35 mg (0.25 mmol) of potassium carbonate and 1 mL of DMF were added. While the mixture was stirred at room temperature, 45 mg (0.15 mmol) of 1,3-dimethyl-2-trifluoromethylbenzimidazolium tetrafluoroborate was added thereto. The mixture was stirred at room temperature for 15 hours. The formation of 1-(3,4-difluorophenyl)-2,2,2-trifluoroethanol (parent ion; 212) was confirmed by GC-MS analysis on the reaction mixture. As a result of GC analysis (area percentage) on the reaction mixture, the components in the reaction mixture excluding the solvents and the like were as follows: 5% of 1-(3,4-difluorophenyl)-2,2,2-trifluoroethanol (target compound), 35% of 3,4-difluorobenzaldehyde (starting compound) and 59% of 1,3-dimethylbenzimidazole-2-one (compound derived from the fluoroalkylating agent). The yield of 1-(3,4-difluorophenyl)-2,2,2-trifluoroethanol (target compound) was 12% in terms of GC area percentage.

Example 47

Production of
1-(4-cyanophenyl)-2,2,2-trifluoroethanol

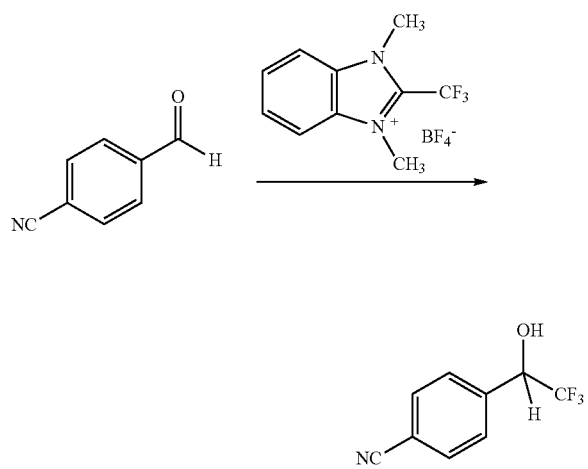

To a 10 mL eggplant-shaped flask equipped with a magnetic stirrer, 16 mg (0.125 mmol) of 4-cyanobenzaldehyde, 35 mg (0.25 mmol) of potassium carbonate and 1 mL of DMF were added. While the mixture was stirred at room temperature, 45 mg (0.15 mmol) of 1,3-dimethyl-2-trifluoromethylbenzimidazolium tetrafluoroborate was added thereto. The mixture was stirred at room temperature for 15 hours. The formation of 1-(4-cyanophenyl)-2,2,2-trifluoroethanol (parent ion; 201) was confirmed by GC-MS analysis on the reaction mixture. As a result of GC analysis (area percentage) on the reaction mixture, the components in the reaction mixture excluding the solvents and the like were as follows: 17% of 1-(4-cyanophenyl)-2,2,2-trifluoroethanol (target compound), 24% of 4-cyanobenzaldehyde (starting compound) and 59% of 2,3-dihydro-1,3-dimethylbenzimidazole-2-one (compound derived from the fluoroalkylating agent). The yield of 1-(4-cyanophenyl)-2,2,2-trifluoroethanol (target compound) was 41% in terms of GC area percentage.

Example 48

Production of
1-(4-nitrophenyl)-2,2,2-trifluoroethanol

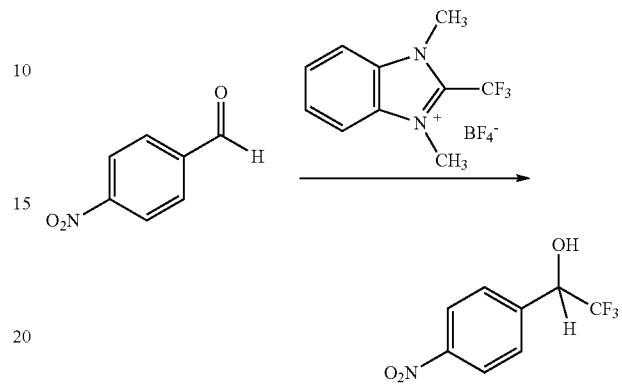

To a 10 mL eggplant-shaped flask equipped with a magnetic stirrer, 19 mg (0.125 mmol) of 4-nitrobenzaldehyde, 35 mg (0.25 mmol) of potassium carbonate and 1 mL of DMF were added. While the mixture was stirred at room temperature, 45 mg (0.15 mmol) of 1,3-dimethyl-2-trifluoromethylbenzimidazolium tetrafluoroborate was added thereto. The mixture was stirred at room temperature for 15 hours. The formation of 1-(4-nitrophenyl)-2,2,2-trifluoroethanol (parent ion; 221) was confirmed by GC-MS analysis on the reaction mixture. As a result of GC analysis (area percentage) on the reaction mixture, the components in the reaction mixture excluding the solvents and the like were as follows: 23% of 1-(4-nitrophenyl)-2,2,2-trifluoroethanol (target compound), 19% of 4-nitrobenzaldehyde (starting compound) and 58% of 2,3-dihydro-1,3-dimethylbenzimidazole-2-one (compound derived from the fluoroalkylating agent). The yield of 1-(4-nitrophenyl)-2,2,2-trifluoroethanol (target compound) was 55% in terms of GC area percentage.

Example 49

Production of 1-phenethyl-2,2,2-trifluoroethanol

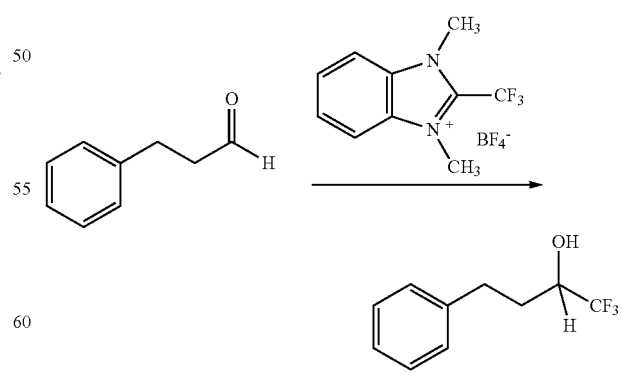

To a 10 mL eggplant-shaped flask equipped with a magnetic stirrer, 17 mg (0.125 mmol) of 3-phenylpropionaldehyde, 35 mg (0.25 mmol) of potassium carbonate and 0.5 mL of DMF were added. While the mixture was stirred at room temperature, 45 mg (0.15 mmol) of 1,3-dimethyl-2-trifluoromethylbenzimidazolium tetrafluoroborate was added thereto. The mixture was stirred at room temperature for 15 hours. The formation of 1-phenethyl-2,2,2-trifluoroethanol (parent ion; 204) was confirmed by GC-MS analysis on the reaction mixture. As a result of GC analysis (area percentage) on the reaction mixture, the components in the reaction mixture excluding the solvents and the like were as follows: 21% of 1-phenethyl-2,2,2-trifluoroethanol (target compound), 24% of 3-phenylpropionaldehyde (starting compound) and 46% of 2,3-dihydro-1,3-dimethylbenzimidazole-2-one (compound derived from the fluoroalkylating agent). The yield of 1-phenethyl-2,2,2-trifluoroethanol (target compound) was 39% in terms of GC area percentage.

Example 50

Production of 1-(3-pyridyl)-2,2,2-trifluoroethanol

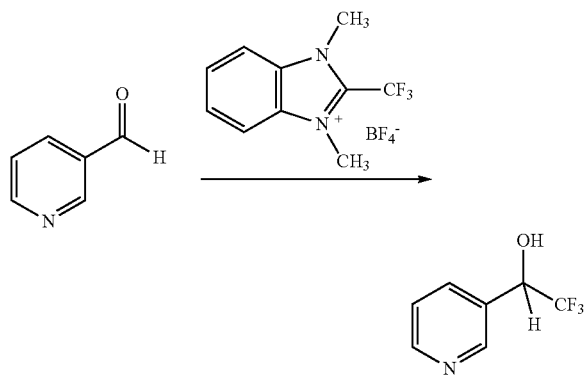

To a 10 mL eggplant-shaped flask equipped with a magnetic stirrer, 13 mg (0.125 mmol) of 3-pyridylcarboaldehyde, 35 mg (0.25 mmol) of potassium carbonate and 1 mL of DMF were added. While the mixture was stirred at room temperature, 45 mg (0.15 mmol) of 1,3-dimethyl-2-trifluoromethylbenzimidazolium tetrafluoroborate was added thereto. The mixture was stirred at room temperature for 15 hours. The formation of 1-(3-pyridyl)-2,2,2-trifluoroethanol (parent ion; 177) was confirmed by GC-MS analysis on the reaction mixture. As a result of GC analysis (area percentage) on the reaction mixture, the components in the reaction mixture excluding the solvents and the like were as follows: 19% of 1-(3-pyridyl)-2,2,2-trifluoroethanol (target compound), 11% of 3-pyridylcarboaldehyde (starting compound) and 70% of 2,3-dihydro-1,3-dimethylbenzimidazole-2-one (compound derived from the fluoroalkylating agent). The yield of 1-(3-pyridyl)-2,2,2-trifluoroethanol (target compound) was 63% in terms of GC area percentage.

Example 51

Production of 1-(5-phenyl-2-thienyl)-2,2,2-trifluoroethanol

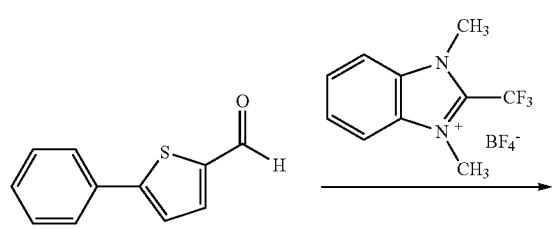

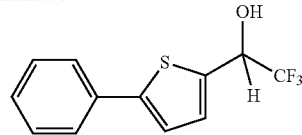

To a 10 mL eggplant-shaped flask equipped with a magnetic stirrer, 24 mg (0.125 mmol) of 5-phenyl-2-thienylcarboaldehyde, 35 mg (0.25 mmol) of potassium carbonate and 1 mL of DMF were added. While the mixture was stirred at room temperature, 45 mg (0.15 mmol) of 1,3-dimethyl-2-trifluoromethylbenzimidazolium tetrafluoroborate was added thereto. The mixture was stirred at room temperature for 15 hours. The formation of 1-(5-phenyl-2-thienyl)-2,2,2-trifluoroethanol (parent ion; 258) was confirmed by GC-MS analysis on the reaction mixture. As a result of GC analysis (area percentage) on the reaction mixture, the components in the reaction mixture excluding the solvents and the like were as follows: 9% of 1-(5-phenyl-2-thienyl)-2,2,2-trifluoroethanol (target compound), 40% of 5-phenyl-2-thienylcarboaldehyde (starting compound) and 50% of 2,3-dihydro-1,3-dimethylbenzimidazole-2-one (compound derived from the fluoroalkylating agent). The yield of 1-(5-phenyl-2-thienyl)-2,2,2-trifluoroethanol (target compound) was 18% in terms of GC area percentage.

Example 52

Production of methyl 4-(2,2,2-trifluoro-1-hydroxyethyl) benzoate

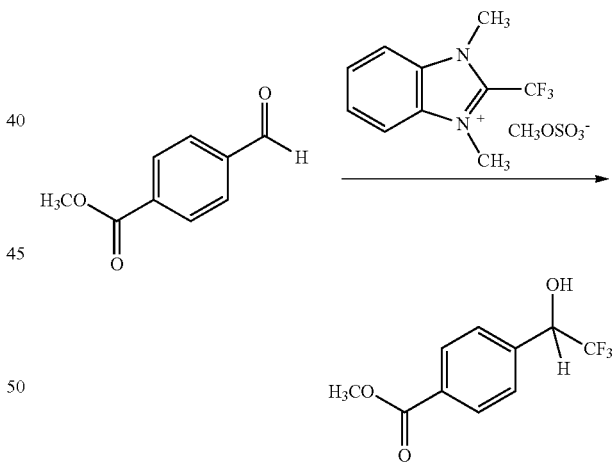

To a 10 mL eggplant-shaped flask equipped with a magnetic stirrer, 0.08 g (0.5 mmol) of methyl 4-formylbenzoate (starting compound), 0.14 g (1 mmol) of potassium carbonate and 1 mL of DMF were added. While the mixture was stirred under ice cooling, 0.2 g (0.6 mmol) of 1,3-dimethyl-2-trifluoromethylbenzimidazolium methyl sulfate (fluoroalkylating agent) was added thereto. While the temperature was raised to room temperature slowly, the mixture was stirred for 15 hours. The formation of methyl 4-(2,2,2-trifluoro-1-hydroxyethyl) benzoate (parent ion; 234) was confirmed by GC-MS analysis on the reaction mixture. As a result of GC analysis (area percentage) on the reaction mixture, the components in the reaction mixture excluding the solvents and the like were as follows: 21% of methyl 4-(2,2,2-trifluoro-1-hydroxyethyl)benzoate (target compound), 28% of methyl 4-formylbenzoate (starting compound), 44% of 2,3-dihydro-1,3-dimethylbenzimidazole-2-one (compound derived from the fluoroalkylating agent) and 6% of 1,3-dimethyl-2,2-bis(trifluoromethyl)-2,3-dihydrobenzimidazole (compound derived from the trifluoroalkylating agent). The yield of methyl 4-(2,2,2-trifluoro-1-hydroxyethyl) benzoate (target compound) was 43% in terms of GC area percentage.

Example 53

The reaction was carried out in the same manner as Example 52, except that the following compound was used instead of 1,3-dimethyl-2-trifluoromethylbenzimidazolium methyl sulfate as the fluoroalkylating agent and the amount of the solvent was changed from 2 L/mol to 5 L/mol based on the starting compound. The yield of the target compound was 41% in terms of GC area percentage.

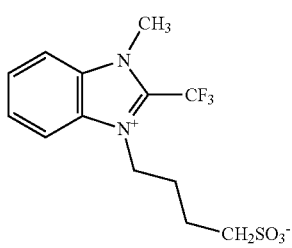

Example 54

The reaction was carried out in the same manner as Example 52, except that the following compound was used instead of 1,3-dimethyl-2-trifluoromethylbenzimidazolium methyl sulfate as the fluoroalkylating agent. The yield of the target compound was 33% in terms of GC area percentage.

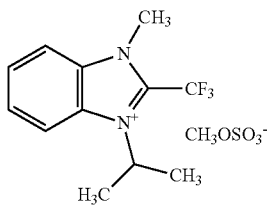

Example 55

The reaction was carried out in the same manner as Example 52, except that the following compound was used instead of 1,3-dimethyl-2-trifluoromethylbenzimidazolium methyl sulfate as the fluoroalkylating agent and the amount of the solvent was changed from 2 L/mol to 1 L/mol based on the starting compound. The yield of the target compound was 53% in terms of GC area percentage.

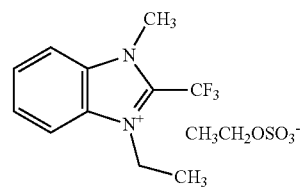

Example 56

The reaction was carried out in the same manner as Example 52, except that the following compound was used instead of 1,3-dimethyl-2-trifluoromethylbenzimidazolium methyl sulfate as the fluoroalkylating agent. The yield of the target compound was 58% in terms of GC area percentage.

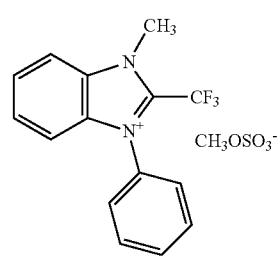

Example 57

The reaction was carried out in the same manner as Example 52, except that the following compound was used instead of 1,3-dimethyl-2-trifluoromethylbenzimidazolium methyl sulfate as the fluoroalkylating agent and the amount of the solvent was changed from 2 L/mol to 1 L/mol based on the starting compound. The yield of the target compound was 48% in terms of GC area percentage.

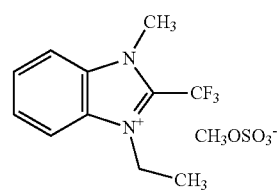

Example 58

The reaction was carried out in the same manner as Example 52, except that the following compound was used instead of 1,3-dimethyl-2-trifluoromethylbenzimidazolium methyl sulfate as the fluoroalkylating agent. The yield of the target compound was 74% in terms of GC area percentage.

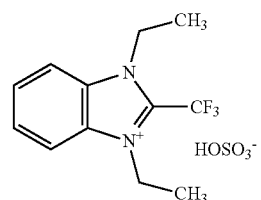

Example 59

Production of 1-phenyl-2,2,2-trifluoroethanol

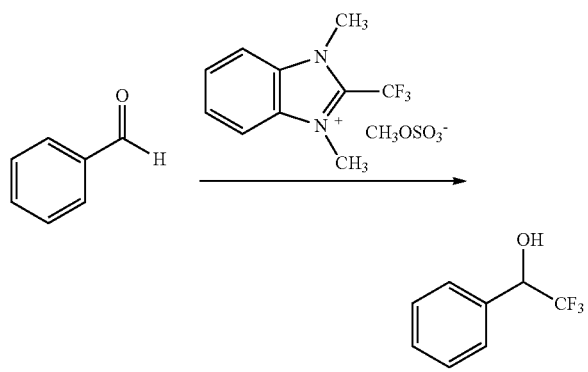

To a 6 mL vial equipped with a magnetic stirrer, 106 mg (1 mmol) of benzaldehyde, 300 mg of molecular sieve 4 A (manufactured by Tosoh Corporation; Zeolum (trade name); A-4; powder), 392 mg (1.2 mmol) of 1,3-dimethyl-2-trifluoromethylbenzimidazolium methyl sulfate and 1 mL of DMF were added. The mixture was stirred at −10° C. for 30 minutes, and then 148 mg (2.52 mmol) of potassium hydroxide was added thereto, and the mixture was stirred at −10° C. for 14 hours. Then, the mixture was stirred at 50° C. for 5 hours. The formation of 1-phenyl-2,2,2-trifluoroethanol (parent ion; 176) was confirmed by GC-MS analysis on the reaction mixture. As a result of GC analysis (area percentage) on the reaction mixture, the components in the reaction mixture excluding the solvents and the like were as follows: 35% of 1-phenyl-2,2,2-trifluoroethanol (target compound) and 54% of 2,3-dihydro-1,3-dimethylbenzimidazole-2-one (compound derived from the fluoroalkylating agent). As a result of GC analysis using 1,4-diethylbenzene as the internal standard, the yield of 1-phenyl-2,2,2-trifluoroethanol (target compound) was 59%.

Example 60

Production of 1,3-dimethyl-2-trifluoromethylbenzimidazolium iodide

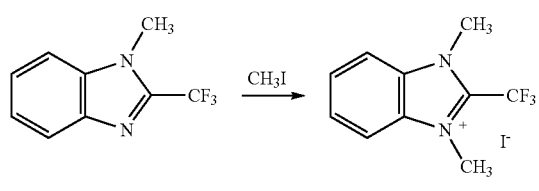

To a 50 mL eggplant-shaped flask equipped with a magnetic stirrer, 2.0 g (10 mmol) of 1-methyl-2-trifluoromethylbenzimidazole, 2.1 g (15 mmol) of methyl iodide and 10 mL of toluene were added. The mixture was stirred at 80° C. for 48 hours. After cooling to room temperature, the precipitated crystals were collected by filtration and dried to obtain 0.36 g of white crystals. Yield: 10%.

In Example 60, the fluoroalkylating agent wherein X⁻ was I⁻ was produced by using methyl iodide as the alkylating agent. However, the yield of Example 60 was lower as compared with the case where the fluoroalkylating agent wherein X⁻ was $CH_3OSO_3^-$ was produced by using dimethyl sulfate as the alkylating agent under the same reaction conditions.

Example 61

Production of (5-acetyloxypentyl) trifluoromethyl sulfide

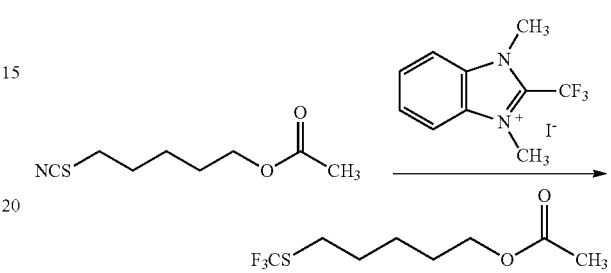

To a 6 mL vial equipped with a magnetic stirrer, 94 mg (0.5 mmol) of 1-acetyloxy-5-thiocyanatopentane, 150 mg of molecular sieve 4 A (manufactured by Tosoh Corporation; Zeolum (trade name); A-4; powder), 205 mg (0.6 mmol) of 1,3-dimethyl-2-trifluoromethylbenzimidazolium iodide and 0.5 mL of DMF were added. The mixture was stirred at −10° C. for 30 minutes, and then 74 mg (1.26 mmol) of potassium hydroxide was added thereto, and the mixture was stirred at −10° C. for 14 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 47% of (5-acetyloxypentyl) trifluoromethyl sulfide (target compound), 8% of 1-acetyloxy-5-thiocyanatopentane (starting compound) and 45% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 77%.

Example 62

Production of 1,3-diethyl-2-trifluoromethylbenzimidazolium ethyl sulfate

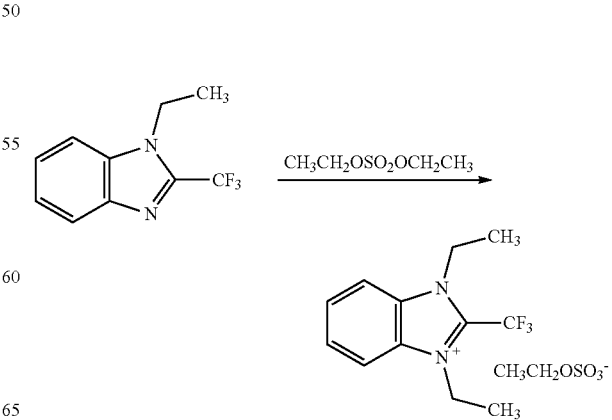

To a 50 mL eggplant-shaped flask equipped with a magnetic stirrer, 4.3 g (20 mmol) of 1-ethyl-2-trifluoromethylbenzimidazole, 4.7 g (30 mmol) of diethyl sulfate and 20 mL of toluene were added. The mixture was stirred at 80° C. for 24 hours. After cooling to room temperature, 20 mL of toluene was added thereto, and the mixture was vigorously stirred, and then the solvent was distilled off under reduced pressure. The resultant residue was dissolved in dichloromethane, and then diethyl ether was added thereto. The precipitated crystals were collected by filtration and dried to obtain 2.9 g of white crystals. Yield: 39%.

$^1$H-NMR (300 MHz, CDCl$_3$, relative to TMS) δ (ppm): 1.14 (t, J=7.2 Hz, 3H), 1.65 (t, J=7.4 Hz, 6H), 3.84 (q, J=7.1 Hz, 2H), 4.84 (q, J=7.4 Hz, 2H), 4.84 (q, J=7.4 Hz, 2H), 7.76-7.87 (m, 2H), 7.96-8.03 (m, 2H).

Example 63

Production of (5-acetyloxypentyl) trifluoromethyl sulfide

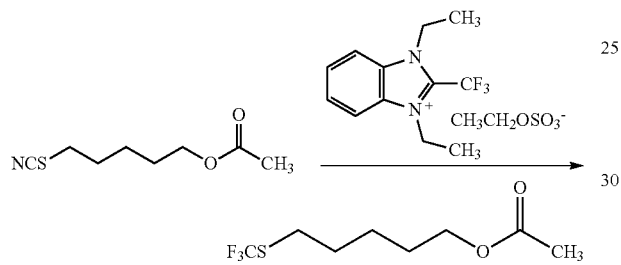

To a 6 mL vial equipped with a magnetic stirrer, 187 mg (1 mmol) of 1-acetyloxy-5-thiocyanatopentane, 442 mg (1.2 mmol) of 1,3-diethyl-2-trifluoromethylbenzimidazolium ethyl sulfate, 415 mg (3 mmol) of potassium carbonate and 1 mL of DMF were added. The mixture was stirred at room temperature for 14 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 11% of (5-acetyloxypentyl) trifluoromethyl sulfide (target compound), 20% of 1-acetyloxy-5-thiocyanatopentane (starting compound), 0.5% of 1,2-bis[5-(acetyloxy)pentyl]disulfide (by-product) and 68% of 2,3-dihydro-1,3-diethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 31%.

Example 64

Production of 1,3-dimethyl-5-nitro-2-trifluoromethylbenzimidazolium methyl sulfate

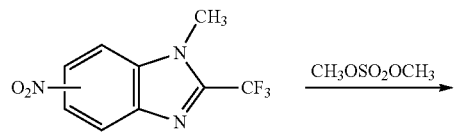

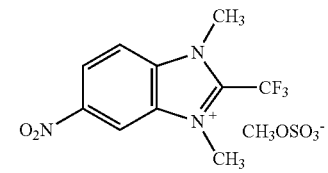

To a 50 mL eggplant-shaped flask equipped with a magnetic stirrer, 2.5 g (10 mmol) of a mixture of 1-methyl-5-nitro-2-trifluoromethylbenzimidazole and 1-methyl-6-nitro-2-trifluoromethylbenzimidazole prepared in the same manner as Examples 10(1) and 10(2), 1.9 g (15 mmol) of dimethyl sulfate and 20 mL of toluene were added. The mixture was heated to reflux for 24 hours. After cooling to room temperature, the solvent was distilled off under reduced pressure. The resultant residue was subjected to reslurry with dichloromethane, and crystals were collected by filtration and dried to obtain 3.0 g of white crystals. Yield: 81%.

$^1$H-NMR (300 MHz, D$_2$O, relative to D$_2$O) δ (ppm): 3.58 (s, 3H), 4.24 (q, J=1.6 Hz, 3H), 4.28 (q, J=1.6 Hz, 3H), 8.15 (dd, J=9.3, 0.6 Hz, 1H), 8.58 (dd, J=9.3, 2.1 Hz, 1H), 8.99 (dd, J=2.1, 0.6 Hz, 1H).

Example 65

Production of (5-acetyloxypentyl) trifluoromethyl sulfide

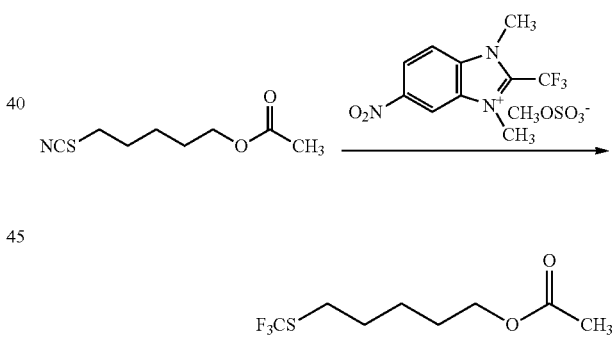

To a 6 mL vial equipped with a magnetic stirrer, 187 mg (1 mmol) of 1-acetyloxy-5-thiocyanatopentane, 415 mg (1.2 mmol) of 1,3-dimethyl-5-nitro-2-trifluoromethylbenzimidazolium methyl sulfate, 415 mg (3 mmol) of potassium carbonate and 1 mL of DMF were added. The mixture was stirred at room temperature for 24 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 24% of (5-acetyloxypentyl) trifluoromethyl sulfide (target compound) and 53% of 1-acetyloxy-5-thiocyanatopentane (starting compound). As a result of GC analysis using 1,4-diethylbenzene as the internal standard, the yield of (5-acetyloxypentyl) trifluoromethyl sulfide (target compound) was 27%.

Example 66

1,3-Dimethyl-5-methylthio-2-trifluoromethylbenzimidazolium methyl sulfate

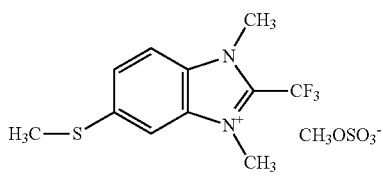

The above compound was synthesized by the same method as the Examples in the present specification and was identified by $^1$H-NMR analysis.

$^1$H-NMR (300 MHz, CDCl$_3$, relative to TMS) δ (ppm): 2.99 (s, 6H), 3.16 (s, 3H), 3.18 (s, 3H), 6.68 (d, J=7.8 Hz, 1H), 7.28 (d, J=7.8 Hz, 1H), 8.48 (s, 1H).

$^1$H-NMR of the isomer (300 MHz, CDCl3, relative to TMS) δ (ppm): 3.40 (s, 6H), 4.32 (s, 3H), 4.34 (s, 3H), 8.47 (d, J=8.8 Hz, 1H), 8.63 (d, J=8.8 Hz, 1H), 9.09 (s, 1H).

Example 67

1,3-Dimethyl-5-methylsulfinyl-2-trifluoromethyl-benzimidazolium methyl sulfate

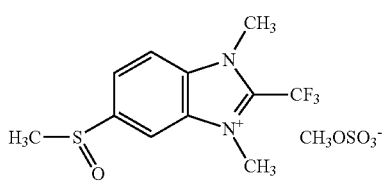

The above compound was synthesized by the same method as the Examples in the present specification and was identified by $^1$H-NMR analysis.

$^1$H-NMR (300 MHz, CDCl$_3$, relative to TMS) δ (ppm): 3.00 (s, 6H), 3.16 (s, 3H), 3.18 (s, 3H), 6.68 (d, J=8.0 Hz, 1H), 7.28 (d, J=8.0 Hz, 1H), 8.49 (s, 1H).

$^1$H-NMR of the isomer (300 MHz, CDCl3, relative to TMS) δ (ppm): 3.41 (s, 6H), 4.32 (s, 3H), 4.35 (s, 3H), 8.48 (d, J=8.8 Hz, 1H), 8.63 (d, J=8.8 Hz, 1H), 9.12 (s, 1H).

Example 68

1,3-Dimethyl-5-methylsulfonyl-2-trifluoro methyl sulfate

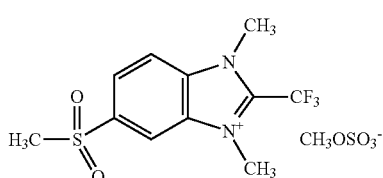

The above compound was synthesized by the same method as the Examples in the present specification and was identified by $^1$H-NMR analysis.

$^1$H-NMR (300 MHz, CDCl$_3$, relative to TMS) δ (ppm): 2.97 (m, 9H), 3.09 (s, 3H), 6.64 (d, J=7.6 Hz, 1H), 7.23 (d, J=7.6 Hz, 1H), 8.41 (s, 1H).

$^1$H-NMR of the isomer (300 MHz, CDCl3, relative to TMS) δ (ppm): 3.54 (s, 3H), 3.42 (s, 3H), 4.32 (s, 3H), 4.37 (s, 3H), 8.40 (d, J=8.8 Hz, 1H), 8.58 (d, J=8.8 Hz, 1H), 8.96 (s, 1H).

Example 69

1,3-Dimethyl-4-fluoro-2-trifluoromethylbenzimidazolium methyl sulfate

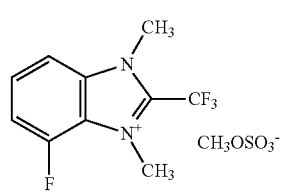

The above compound was synthesized by the same method as the Examples in the present specification and was identified by $^1$H-NMR analysis.

$^1$H-NMR (300 MHz, CDCl$_3$, relative to TMS) δ (ppm): 3.36 (s, 3H), 4.29 (s, 3H), 4.35 (s, 3H), 7.77-7.81 (m, 1H), 7.85-7.91 (m, 1H), 8.16 (d, J=8.8 Hz, 1H).

Example 70

Production of (6-acetyloxyhexyl) trifluoromethyl sulfide

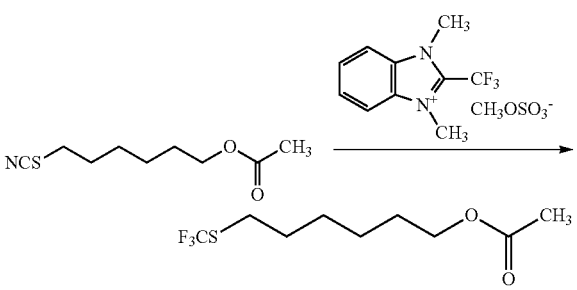

To a 50 mL three-necked flask equipped with a mechanical stirrer, 2 g (10 mmol) of 1-acetyloxy-6-thiocyanato-hexane, 3 g of molecular sieve 4 A (manufactured by Tosoh Corporation; Zeolum (trade name); A-4; powder), 3.9 g (12 mmol) of 1,3-dimethyl-2-trifluoromethylbenzimidazolium methyl sulfate and 5 mL of DMF were added. The mixture was stirred at −10° C. for 30 minutes, and then 1.5 g (25.2 mmol) of potassium hydroxide was added thereto in small portions over 1 hour, and the mixture was stirred at −10° C. for 2 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 41% of (6-acetyloxyhexyl) trifluoromethyl sulfide (target compound), 11% of 1-acetyloxy-6-thiocyanato-hexane (starting compound) and 47% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 75%.

Example 71

Production of (6-acetyloxyhexyl) trifluoromethyl sulfide

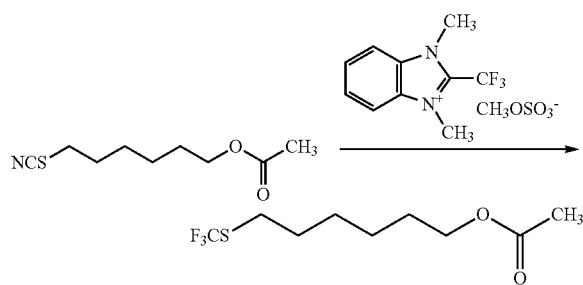

To a 50 mL three-necked flask equipped with a mechanical stirrer, 2 g (10 mmol) of 1-acetyloxy-6-thiocyanatohexane, 3 g of molecular sieve 4 A (manufactured by Tosoh Corporation; Zeolum (trade name); A-4; powder), 3.9 g (12 mmol) of 1,3-dimethyl-2-trifluoromethylbenzimidazolium methyl sulfate and 5 mL of DMF were added. The mixture was stirred at −20° C. for 30 minutes, and then 1.5 g (25.2 mmol) of potassium hydroxide was added thereto in small portions over 1 hour, and the mixture was stirred at −20° C. for 1 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 48% of (6-acetyloxyhexyl) trifluoromethyl sulfide (target compound), 3% of 1-acetyloxy-6-thiocyanatohexane (starting compound) and 47% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 89%.

Example 72

Production of (6-acetyloxyhexyl) trifluoromethyl sulfide

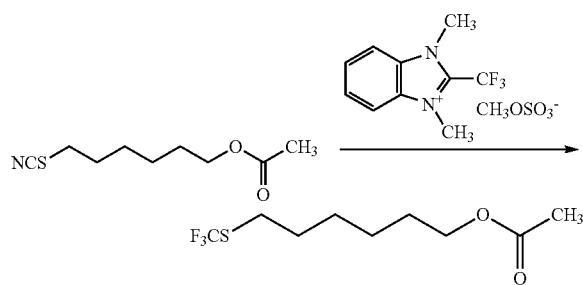

To a 50 mL three-necked flask equipped with a mechanical stirrer, 2 g (10 mmol) of 1-acetyloxy-6-thiocyanatohexane, 3 g of molecular sieve 4 A (manufactured by Tosoh Corporation; Zeolum (trade name); A-4; powder), 3.9 g (12 mmol) of 1,3-dimethyl-2-trifluoromethylbenzimidazolium methyl sulfate and 5 mL of DMF were added. The mixture was stirred at −30° C. for 30 minutes, and then 1.5 g (25.2 mmol) of potassium hydroxide was added thereto in small portions over 2 hour, and the mixture was stirred at −30° C. for 4 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 52% of (6-acetyloxyhexyl) trifluoromethyl sulfide (target compound) and 46% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 97%.

Example 73

Production of (6-acetyloxyhexyl) trifluoromethyl sulfide

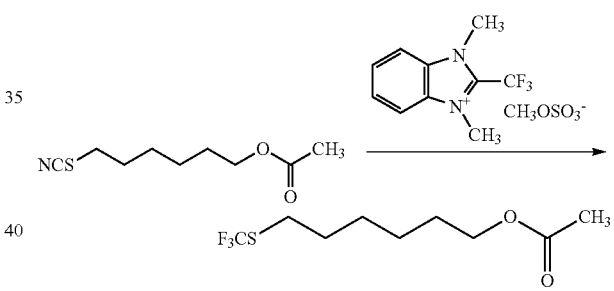

To a 6 mL vial equipped with a magnetic stirrer, 201 mg (1 mmol) of 1-acetyloxy-6-thiocyanatohexane, 300 mg of molecular sieve 4 A (manufactured by Tosoh Corporation; Zeolum (trade name); A-4; powder), 392 mg (1.2 mmol) of 1,3-dimethyl-2-trifluoromethylbenzimidazolium methyl sulfate and 1 mL of acetonitrile (MeCN) were added. The mixture was stirred at −10° C. for 30 minutes, and then 148 mg (2.52 mmol) of potassium hydroxide was added thereto, and the mixture was stirred at −10° C. for 14 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 25% of (6-acetyloxyhexyl) trifluoromethyl sulfide (target compound), 10% of 1-acetyloxy-6-thiocyanatohexane (starting compound), 5% of 1,2-bis[6-(acetyloxy)hexyl] disulfide (by-product) and 60% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 38%.

Example 74

Production of (6-acetyloxyhexyl) trifluoromethyl sulfide

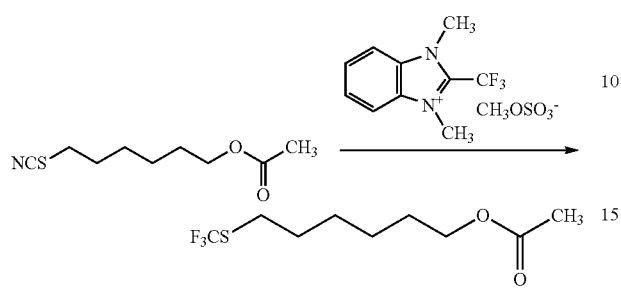

To a 6 mL vial equipped with a magnetic stirrer, 201 mg (1 mmol) of 1-acetyloxy-6-thiocyanatohexane, 300 mg of molecular sieve 4 A (manufactured by Tosoh Corporation; Zeolum (trade name); A-4; powder), 392 mg (1.2 mmol) of 1,3-dimethyl-2-trifluoromethylbenzimidazolium methyl sulfate and 0.5 mL of N,N-dimethylacetamide (DMAC) were added. The mixture was stirred at −10° C. for 30 minutes, and then 148 mg (2.52 mmol) of potassium hydroxide was added thereto, and the mixture was stirred at −10° C. for 14 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 45% of (6-acetyloxyhexyl) trifluoromethyl sulfide (target compound), 2% of 1-acetyloxy-6-thiocyanatohexane (starting compound) and 48% of 2,3-dihydro-1,3-dimethyl-benzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 81%.

Example 75

The reaction was carried out in the same manner as Example 74, except that 0.5 mL of N-methylpyrrolidone (NMP) was used instead of 0.5 mL of N,N-dimethylacetamide (DMAC) as the reaction solvent. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 48% of (6-acetyloxyhexyl) trifluoromethyl sulfide (target compound), 5% of 1-acetyloxy-6-thiocyanatohexane (starting compound), 2% of 1,2-bis[6-(acetyloxy)hexyl] disulfide (by-product) and 45% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 80%.

Example 76

The reaction was carried out in the same manner as Example 74, except that 1 mL of THF (tetrahydrofuran) was used instead of 0.5 mL of N,N-dimethylacetamide (DMAC) as the reaction solvent. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 24% of (6-acetyloxyhexyl) trifluoromethyl sulfide (target compound), 20% of 1-acetyloxy-6-thiocyanatohexane (starting compound), 4% of 1,2-bis[6-(acetyloxy)hexyl] disulfide (by-product) and 52% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 42%.

Example 77

Production of (6-acetyloxyhexyl) trifluoromethyl sulfide

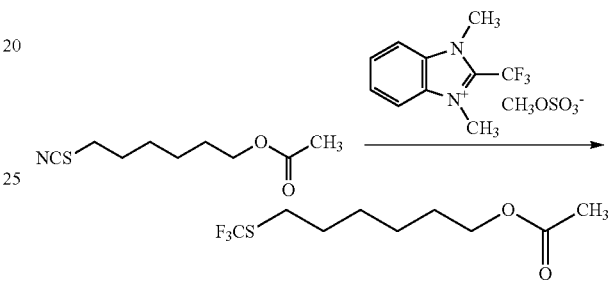

To a 100 ml four-neck flask equipped with a mechanical stirrer, 6 g (30 mmol) of 1-acetyloxy-6-thiocyanatohexane, 9 g of molecular sieve 4 A (manufactured by Tosoh Corporation; Zeolum (trade name); A-4; powder), 11.7 g (36 mmol) of 1,3-dimethyl-2-trifluoromethylbenzimidazolium methyl sulfate and 15 mL of DMF were added. The mixture was stirred at −30° C. for 30 minutes, and then a suspension prepared by dispersing 4.4 g (75.6 mmol) of potassium hydroxide in 15 mL of toluene was added dropwise thereto over 1 hour. After the completion of the dropwise addition, the mixture was stirred at −30° C. for 24 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 52% of (6-acetyloxyhexyl) trifluoromethyl sulfide (target compound) and 48% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 92%.

Example 78

Production of (6-acetyloxyhexyl) trifluoromethyl sulfide

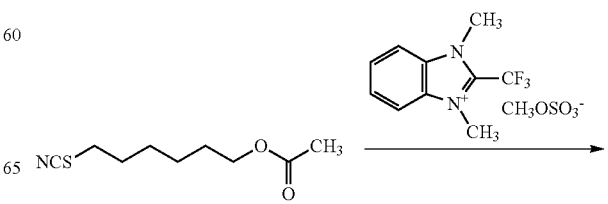

-continued

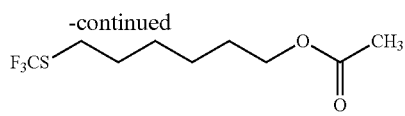

To a 50 ml three-neck flask equipped with a mechanical stirrer, 2 g (10 mmol) of 1-acetyloxy-6-thiocyanatohexane, 3 g of molecular sieve 4 A (manufactured by Tosoh Corporation; Zeolum (trade name); A-4; powder), 3.9 g (12 mmol) of 1,3-dimethyl-2-trifluoromethylbenzimidazolium methyl sulfate and 5 mL of DMF were added. The mixture was stirred at −30° C. for 30 minutes, and then a suspension prepared by dispersing 1.5 g (25.2 mmol) of potassium hydroxide in 7 mL of toluene was added dropwise thereto over 1 hour, and the mixture was stirred at −30° C. for 24 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 52% of (6-acetyloxyhexyl) trifluoromethyl sulfide (target compound) and 48% of 2,3-dihydro-1,3-dimethyl-benzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 99%.

Example 79

Production of (6-acetyloxyhexyl) trifluoromethyl sulfide

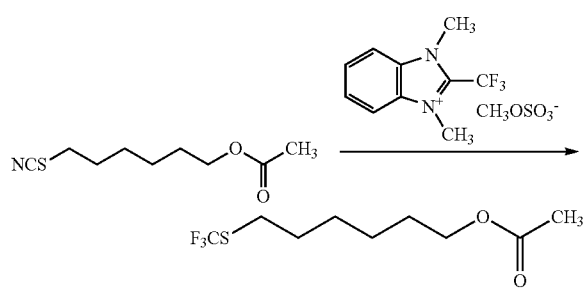

To a 6 mL vial equipped with a magnetic stirrer, 101 mg (0.5 mmol) of 1-acetyloxy-6-thiocyanatohexane, 203 mg (0.63 mmol) of tetrabutylammonium bromide, 196 mg (0.6 mmol) of 1,3-dimethyl-2-trifluoromethylbenzimidazolium methyl sulfate and 0.5 mL of toluene were added. The mixture was stirred at room temperature for 30 minutes, and then 74 mg (1.26 mmol) of potassium hydroxide was added thereto, and the mixture was stirred at room temperature for 24 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 24% of (6-acetyloxyhexyl) trifluoromethyl sulfide (target compound), 12% of 1-acetyloxy-6-thiocyanatohexane (starting compound), 9% of 1,2-bis[6-(acetyloxy)hexyl] disulfide (by-product) and 53% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 48%.

Example 80

Production of (6-acetyloxyhexyl) trifluoromethyl sulfide

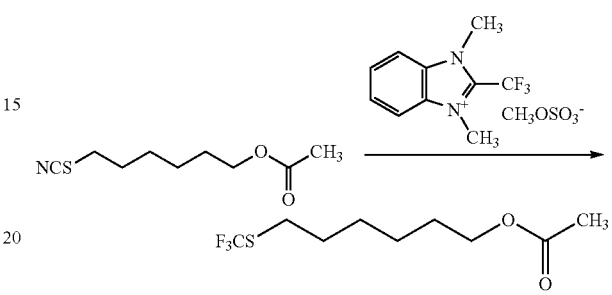

To a 6 mL vial equipped with a magnetic stirrer, 201 mg (1 mmol) of 1-acetyloxy-6-thiocyanatohexane, 32 mg (0.1 mmol) of tetrabutylammonium bromide, 392 mg (1.2 mmol) of 1,3-dimethyl-2-trifluoromethylbenzimidazolium methyl sulfate and 1 mL of toluene were added. The mixture was stirred at room temperature for 30 minutes, and then 415 mg (3 mmol) of potassium carbonate was added thereto, and the mixture was stirred at room temperature for 96 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 23% of (6-acetyloxyhexyl) trifluoromethyl sulfide (target compound), 27% of 1-acetyloxy-6-thiocyanatohexane (starting compound) and 50% of 2,3-dihydro-1,3-dimethyl-benzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 48%.

Example 81

Production of (6-acetyloxyhexyl) trifluoromethyl sulfide

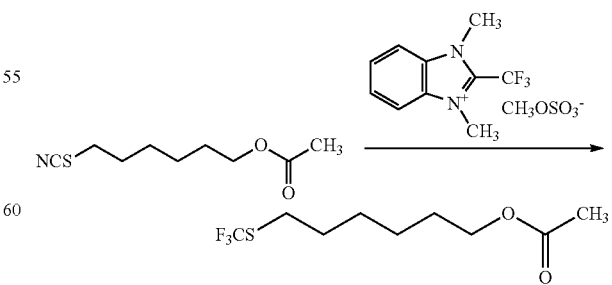

To a 6 mL vial equipped with a magnetic stirrer, 201 mg (1 mmol) of 1-acetyloxy-6-thiocyanatohexane, 32 mg (0.1 mmol) of tetrabutylammonium bromide, 392 mg (1.2 mmol)

of 1,3-dimethyl-2-trifluoromethylbenzimidazolium methyl sulfate and 1 mL of THF were added. The mixture was stirred at room temperature for 30 minutes, and then 174 mg (1.26 mmol) of potassium carbonate was added thereto, and the mixture was stirred at room temperature for 14 hours. Then, the mixture was stirred at 50° C. for 5 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 22% of (6-acetyloxyhexyl) trifluoromethyl sulfide (target compound), 27% of 1-acetyloxy-6-thiocyanatohexane (starting compound), 3% of 1,2-bis[6-(acetyloxy)hexyl] disulfide (by-product), 44% of 2,3-dihydro-1,3-dimethylbenzimidazole-2-one (compound derived from the fluoroalkylating agent) and 1% of 1,3-dimethyl-2,2-bis(trifluoromethyl)-2,3-dihydro-benzimidazole (compound derived from the fluoroalkylating agent). As a result of GC analysis using 1,4-diethylbenzene as the internal standard, the yield of (6-acetyloxyhexyl) trifluoromethyl sulfide (target compound) was 42%.

Example 82

The reaction was carried out in the same manner as Example 81, except that 36 mg (0.1 mmol) of benzyltributylammonium bromide was used instead of 32 mg (0.1 mmol) of tetrabutylammonium bromide as the phase transfer catalyst. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 23% of (6-acetyloxyhexyl) trifluoromethyl sulfide (target compound), 26% of 1-acetyloxy-6-thiocyanatohexane (starting compound), 4% of 1,2-bis[6-(acetyloxy)hexyl] disulfide (by-product), 44% of 2,3-dihydro-1,3-dimethylbenzimidazole-2-one (compound derived from the fluoroalkylating agent) and 1% of 1,3-dimethyl-2,2-bis(trifluoromethyl)-2,3-dihydro-benzimidazole (compound derived from the fluoroalkylating agent). As a result of GC analysis using 1,4-diethylbenzene as the internal standard, the yield of (6-acetyloxyhexyl) trifluoromethyl sulfide (target compound) was 45%.

Example 83

The reaction was carried out in the same manner as Example 81, except that 55 mg (0.1 mmol) of tetraoctylammonium bromide was used instead of 32 mg (0.1 mmol) of tetrabutylammonium bromide as the phase transfer catalyst. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 25% of (6-acetyloxyhexyl) trifluoromethyl sulfide (target compound), 26% of 1-acetyloxy-6-thiocyanatohexane (starting compound), 3% of 1,2-bis[6-(acetyloxy)hexyl] disulfide (by-product), 41% of 2,3-dihydro-1,3-dimethylbenzimidazole-2-one (compound derived from the fluoroalkylating agent) and 1% of 1,3-dimethyl-2,2-bis(trifluoromethyl)-2,3-dihydro-benzimidazole (compound derived from the fluoroalkylating agent). As a result of GC analysis using 1,4-diethylbenzene as the internal standard, the yield of (6-acetyloxyhexyl) trifluoromethyl sulfide (target compound) was 47%.

Example 84

Production of (5-acetyloxypentyl) trifluoromethyl sulfide

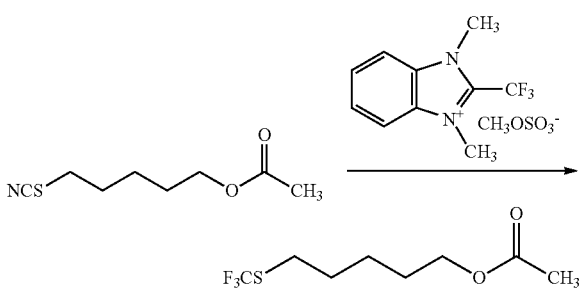

To a 9 mL vial equipped with a magnetic stirrer, 187 mg (1 mmol) of 1-acetyloxy-5-thiocyanatopentane, 1.6 g (5 mmol) of 1,3-dimethyl-2-trifluoromethylbenzimidazolium methyl sulfate and 5 mL of DMF were added. The mixture was stirred at room temperature for 30 minutes, and then 1.7 g (12.5 mmol) of potassium carbonate was added thereto, and the mixture was stirred at room temperature for 14 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 9% of (5-acetyloxypentyl) trifluoromethyl sulfide (target compound), 5% of 1-acetyloxy-5-thiocyanatopentane (starting compound) and 85% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 55%.

Example 85

Production of (5-benzyloxypentyl) trifluoromethyl sulfide

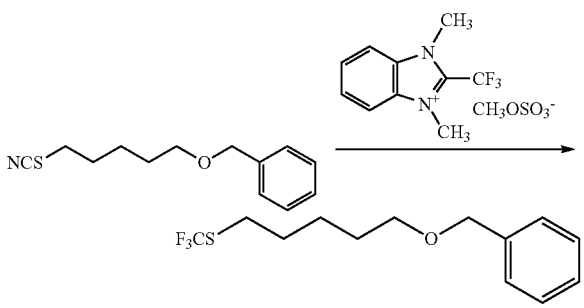

To a 6 mL vial equipped with a magnetic stirrer, 118 mg (0.5 mmol) of 1-benzyloxy-5-thiocyanatopentane, 300 mg of molecular sieve 4 A (manufactured by Tosoh Corporation;

Zeolum (trade name); A-4; powder), 196 mg (0.6 mmol) of 1,3-dimethyl-2-trifluoromethylbenzimidazolium methyl sulfate and 1.5 mL of DMF were added. The mixture was stirred at −10° C. for 30 minutes, and then 50 mg (1.26 mmol) of 60% sodium hydride was added thereto, and the mixture was stirred at −10° C. for 48 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 51% of (5-benzyloxypentyl) trifluoromethyl sulfide (target compound), 8% of 1-benzyloxy-5-thiocyanatopentane (starting compound) and 27% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 70%.

Example 86

Production of (5-benzyloxypentyl) trifluoromethyl sulfide

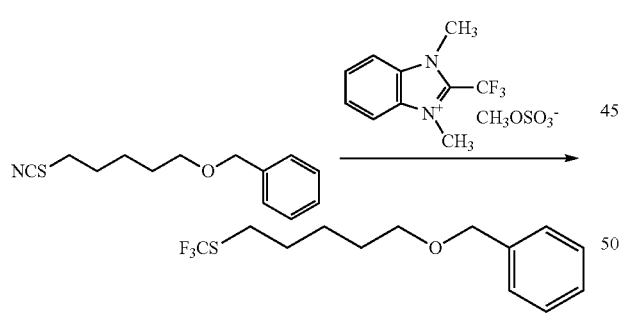

To a 6 mL vial equipped with a magnetic stirrer, 118 mg (0.5 mmol) of 1-benzyloxy-5-thiocyanatopentane, 196 mg (0.6 mmol) of 1,3-dimethyl-2-trifluoromethylbenzimidazolium methyl sulfate and 1.5 mL of DMF were added. The mixture was stirred at −10° C. for 30 minutes, and then 50 mg (1.26 mmol) of 60% sodium hydride was added thereto, and the mixture was stirred at −10° C. for 48 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 40% of (5-benzyloxypentyl) trifluoromethyl sulfide (target compound), 23% of 1-benzyloxy-5-thiocyanatopentane (starting compound) and 36% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 41%.

Example 87

Production of 5-trifluoromethylthiopentyl-[4-chloro-2-fluoro-5-(2,2,2-trifluoroethylthio)phenyl] ether

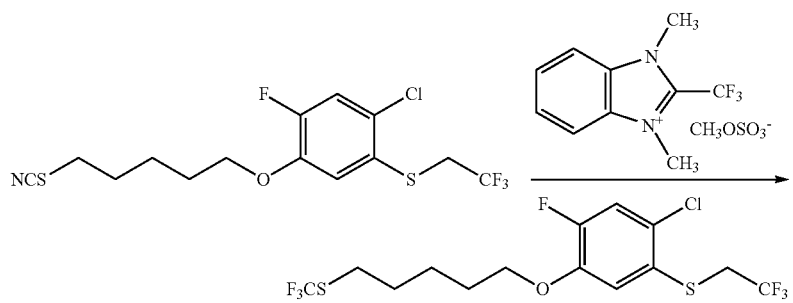

To a 6 mL vial equipped with a magnetic stirrer, 388 mg (1 mmol) of 5-thiocyanatopentyl-[4-chloro-2-fluoro-5-(2,2,2-trifluoroethylthio)phenyl] ether (starting compound), 300 mg of molecular sieve 4 A (manufactured by Tosoh Corporation; Zeolum (trade name); A-4; powder), 392 mg (1.2 mmol) of 1,3-dimethyl-2-trifluoromethylbenzimidazolium methyl sulfate and 1 mL of DMF were added. The mixture was stirred at −10° C. for 30 minutes, and then 148 mg (2.52 mmol) of potassium hydroxide was added thereto, and the mixture was stirred at −10° C. for 14 hours. The formation of the titled target compound (parent ion; 430) was confirmed by GC-MS analysis on the reaction mixture. As a result of GC analysis (area percentage) on the reaction mixture, the components in the reaction mixture excluding the solvents and the like were as follows:
61% of the target compound, 5% of the starting compound and 34% of 2,3-dihydro-1,3-dimethylbenzimidazole-2-one (compound derived from the fluoroalkylating agent).

The yield of the target compound was 92% in terms of GC area percentage.

Example 88

Production of (2,5-dichlorophenyl) trifluoromethyl sulfide

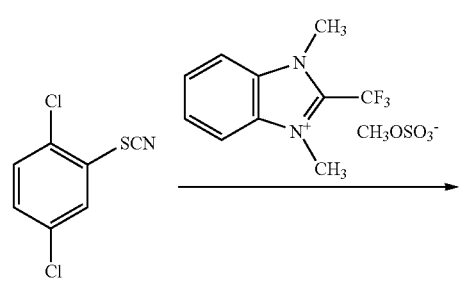

-continued

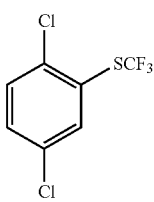

To a 10 mL eggplant-shaped flask equipped with a magnetic stirrer, 26 mg (0.125 mmol) of 1,4-dichloro-2-thiocyanatobenzene (starting compound), 35 mg (0.25 mmol) of potassium carbonate and 0.5 mL of DMF were added. While the mixture was stirred under ice cooling, 55 mg (0.17 mmol) of 1,3-dimethyl-2-trifluoromethylbenzimidazolium methyl sulfate was added thereto. While the temperature was raised to room temperature slowly, the mixture was stirred for 15 hours. The formation of (2,5-dichlorophenyl) trifluoromethyl sulfide (parent ion; 245) was confirmed by GC-MS analysis on the reaction mixture. As a result of GC analysis (area percentage) on the reaction mixture, the components in the reaction mixture excluding the solvents and the like were as follows: 5% of (2,5-dichlorophenyl) trifluoromethyl sulfide (target compound), 41% of 1,2-bis(2,5-dichlorophenyl) disulfide (by-product) and 54% of 2,3-dihydro-1,3-dimethylbenzimidazole-2-one (compound derived from the fluoroalkylating agent). The yield of (2,5-dichlorophenyl) trifluoromethyl sulfide (target compound) was 11% in terms of GC area percentage. The (2,5-dichlorophenyl) trifluoromethyl sulfide (target compound) is also referred to as (2,5-dichlorophenyl)(trifluoromethyl) sulfane.

Example 89

Production of (3-methoxyphenyl) trifluoromethyl sulfide

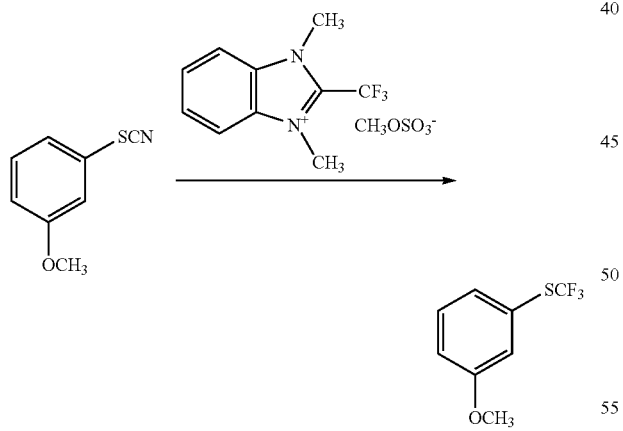

The reaction was carried out in the same manner as Example 88, except that 1-methoxy-3-thiocyanatobenzene was used instead of 1,4-dichloro-2-thiocyanatobenzene as the starting compound. As a result of GC analysis (area percentage) on the reaction mixture, the components in the reaction mixture excluding the solvents and the like were as follows: 19% of (3-methoxyphenyl) trifluoromethyl sulfide (target compound), 3% of 1,2-bis(3-methoxyphenyl) disulfide (by-product) and 64% of 2,3-dihydro-1,3-dimethylbenzimidazole-2-one (compound derived from the fluoroalkylating agent). The yield of (3-methoxyphenyl) trifluoromethyl sulfide (target compound) was 53% in terms of GC area percentage. The (3-methoxyphenyl) trifluoromethyl sulfide (target compound) is also referred to as (3-methoxyphenyl)(trifluoromethyl) sulfane.

Example 90

Production of (2,5-dichlorophenyl) trifluoromethyl sulfide

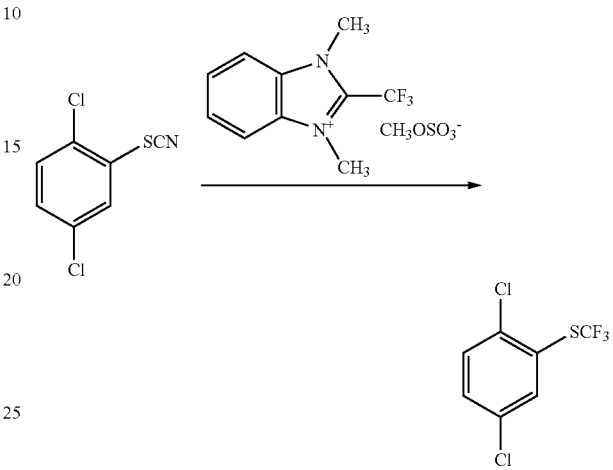

To a 10 mL eggplant-shaped flask equipped with a magnetic stirrer, 26 mg (0.125 mmol) of 1,4-dichloro-2-thiocyanatobenzene (starting compound), 55 mg (0.17 mmol) of 1,3-dimethyl-2-trifluoromethylbenzimidazolium methyl sulfate and 0.5 mL of DMF were added. While the mixture was stirred under ice cooling, 35 mg (0.25 mmol) of potassium carbonate was added thereto. While the temperature was raised to room temperature slowly, the mixture was stirred for 15 hours. The formation of (2,5-dichlorophenyl) trifluoromethyl sulfide (parent ion; 245) was confirmed by GC-MS analysis on the reaction mixture. As a result of GC analysis (area percentage) on the reaction mixture, the components in the reaction mixture excluding the solvents and the like were as follows: 8% of (2,5-dichlorophenyl) trifluoromethyl sulfide (target compound), 36% of 1,2-bis(2,5-dichlorophenyl) disulfide (by-product) and 57% of 2,3-dihydro-1,3-dimethylbenzimidazole-2-one (compound derived from the fluoroalkylating agent). The yield of (2,5-dichlorophenyl) trifluoromethyl sulfide (target compound) was 18% in terms of GC area percentage. As a result of GC analysis using chlorobenzene as the internal standard, the yield of the target compound was 25%.

Example 91

Production of (3-methoxyphenyl) trifluoromethyl sulfide

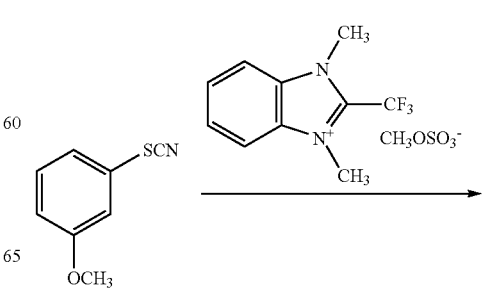

-continued

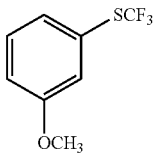

The reaction was carried out in the same manner as Example 90, except that 1-methoxy-3-thiocyanatobenzene was used instead of 1,4-dichloro-2-thiocyanatobenzene as the starting compound. The yield of (3-methoxyphenyl) trifluoromethyl sulfide as the target compound was 53% in terms of GC area percentage.

Example 92

The reaction was carried out in the same manner as Example 90, except that a mixture of 1-methyl-3-phenyl-4-thiocyanato-1H-pyrazole and 1-methyl-5-phenyl-4-thiocyanato-1H-pyrazole was used instead of 1,4-dichloro-2-thiocyanatobenzene as the starting compound. The yield of the mixture of 1-methyl-3-phenyl-4-trifluoromethylthio-1H-pyrazole and 1-methyl-5-phenyl-4-trifluoromethylthio-1H-pyrazole as the target compound was 40% in terms of GC area percentage.

Example 93

The reaction was carried out in the same manner as Example 90, except that 2-thiocyanatopyridine was used instead of 1,4-dichloro-2-thiocyanatobenzene as the starting compound. The yield of 2-trifluoromethylthiopyridine as the target compound was 35% in terms of GC area percentage.

Example 94

Production of (3-methoxyphenyl) trifluoromethyl sulfide

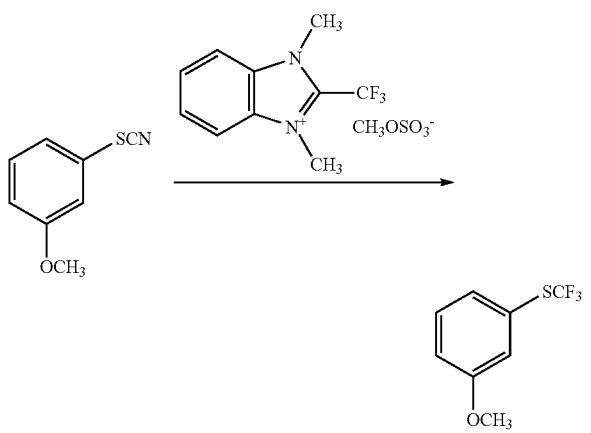

To a 6 mL vial equipped with a magnetic stirrer, 165 mg (1 mmol) of 1-methoxy-3-thiocyanatobenzene, 300 mg of molecular sieve 4 A (manufactured by Tosoh Corporation; Zeolum (trade name); A-4; powder), 392 mg (1.2 mmol) of 1,3-dimethyl-2-trifluoromethylbenzimidazolium methyl sulfate and 1 mL of DMF were added. The mixture was stirred at −10° C. for 30 minutes, and then 148 mg (2.52 mmol) of potassium hydroxide was added thereto, and the mixture was stirred at −10° C. for 40 hours. The formation of (3-methoxyphenyl) trifluoromethyl sulfide was confirmed by GC-MS analysis on the reaction mixture. As a result of GC analysis (area percentage) on the reaction mixture, the components in the reaction mixture excluding the solvents and the like were as follows: 39% of (3-methoxyphenyl) trifluoromethyl sulfide (target compound), 6% of 1,2-bis(3-(methyloxy)phenyl) disulfide (by-product) and 51% of 2,3-dihydro-1,3-dimethylbenzimidazole-2-one (compound derived from the fluoroalkylating agent). The yield of the target compound was 80% in terms of GC area percentage.

Example 95

Production of (5-acetyloxypentyl) trifluoromethyl sulfide

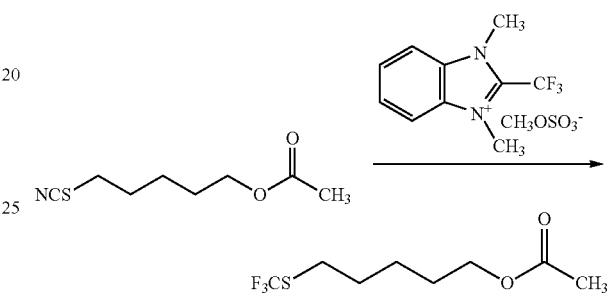

To a 6 mL vial equipped with a magnetic stirrer, 187 mg (1 mmol) of 1-acetyloxy-5-thiocyanatopentane, 300 mg of molecular sieve 3 A (manufactured by Tosoh Corporation; Zeolum (trade name); A-3; powder), 392 mg (1.2 mmol) of 1,3-dimethyl-2-trifluoromethylbenzimidazolium methyl sulfate and 1 mL of DMF were added. The mixture was stirred at −10° C. for 30 minutes, and then 148 mg (2.52 mmol) of potassium hydroxide was added thereto, and the mixture was stirred at −10° C. for 3 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 39% of (5-acetyloxypentyl) trifluoromethyl sulfide (target compound), 7% of 1-acetyloxy-5-thiocyanatopentane (starting compound), 1% of 1,2-bis[5-(acetyloxy)pentyl]disulfide (by-product) and 51% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 76%.

Example 96

Production of (5-acetyloxypentyl) trifluoromethyl sulfide

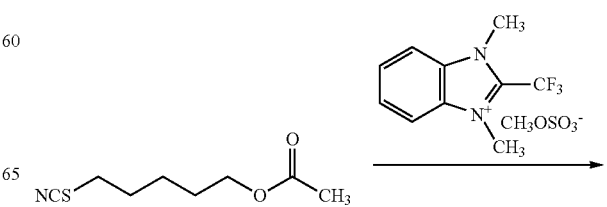

-continued

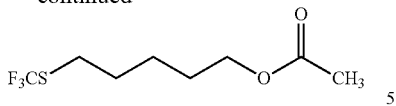

To a 6 mL vial equipped with a magnetic stirrer, 187 mg (1 mmol) of 1-acetyloxy-5-thiocyanatopentane, 300 mg of molecular sieve 5 A (manufactured by GL Sciences Inc.; powder), 392 mg (1.2 mmol) of 1,3-dimethyl-2-trifluoromethylbenzimidazolium methyl sulfate and 1 mL of DMF were added. The mixture was stirred at −10° C. for 30 minutes, and then 148 mg (2.52 mmol) of potassium hydroxide was added thereto, and the mixture was stirred at −10° C. for 12 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 52% of (5-acetyloxypentyl) trifluoromethyl sulfide (target compound), 1% of 1-acetyloxy-5-thiocyanatopentane (starting compound), 0.4% of 1,2-bis[5-(acetyloxy)pentyl]disulfide (by-product) and 47% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 76%.

Example 97

Production of (5-acetyloxypentyl) trifluoromethyl sulfide

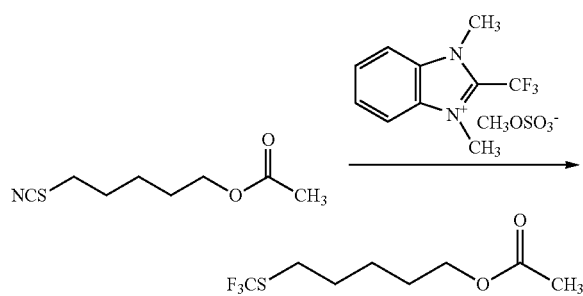

To a 6 mL vial equipped with a magnetic stirrer, 187 mg (1 mmol) of 1-acetyloxy-5-thiocyanatopentane, 300 mg of molecular sieve 13X (manufactured by GL Sciences Inc.; powder), 392 mg (1.2 mmol) of 1,3-dimethyl-2-trifluoromethylbenzimidazolium methyl sulfate and 1 mL of DMF were added. The mixture was stirred at −10° C. for 30 minutes, and then 148 mg (2.52 mmol) of potassium hydroxide was added thereto, and the mixture was stirred at −10° C. for 12 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 20% of (5-acetyloxypentyl) trifluoromethyl sulfide (target compound), 14% of 1-acetyloxy-5-thiocyanatopentane (starting compound), 4% of 1,2-bis[5-(acetyloxy)pentyl]disulfide (by-product) and 62% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 53%.

Example 98

Production of (5-acetyloxypentyl) trifluoromethyl sulfide

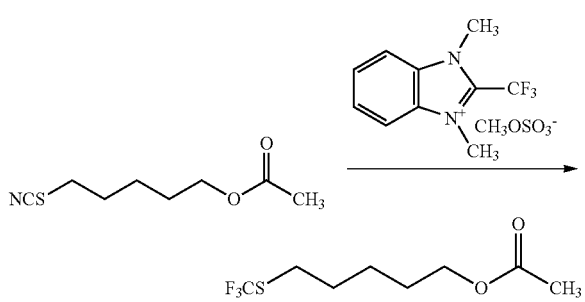

To a 6 mL vial equipped with a magnetic stirrer, 187 mg (1 mmol) of 1-acetyloxy-5-thiocyanatopentane, 392 mg (1.2 mmol) of 1,3-dimethyl-2-trifluoromethylbenzimidazolium methyl sulfate and 0.5 mL of DMF were added. The mixture was stirred at −10° C. for 30 minutes, and then 148 mg (2.52 mmol) of potassium hydroxide was added thereto, and the mixture was stirred at −10° C. for 14 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 10% of (5-acetyloxypentyl) trifluoromethyl sulfide (target compound), 7% of 1-acetyloxy-5-thiocyanatopentane (starting compound), 10% of 1,2-bis[5-(acetyloxy)pentyl]disulfide (by-product) and 64% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 21%.

Example 99

Production of (6-acetyloxyhexyl) trifluoromethyl sulfide

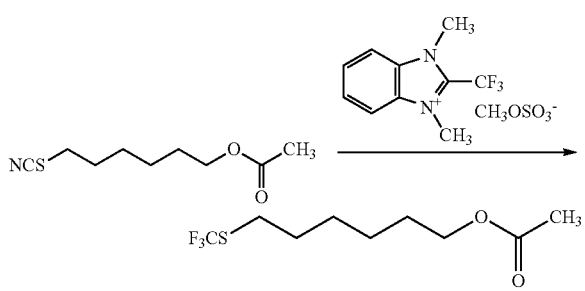

To a 50 mL three-necked flask equipped with a mechanical stirrer, 2 g (10 mmol) of 1-acetyloxy-6-thiocyanatohexane, 3 g of molecular sieve 4 A (manufactured by Tosoh Corporation; Zeolum (trade name); A-4; powder), 3.9 g (12 mmol) of 1,3-dimethyl-2-trifluoromethylbenzimidazolium methyl sulfate and 5 mL of DMF were added. The mixture was stirred at −30° C. for 30 minutes, and then a suspension prepared by dispersing 1.5 g (25.2 mmol) of potassium hydroxide in 7 mL of toluene was added dropwise thereto over 1 hour. The mixture was stirred at −30° C. for 24 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 52% of (6-acetyloxyhexyl) trifluoromethyl sulfide (target compound) and 48% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 99%.

Example 100

Production of (6-acetyloxyhexyl) trifluoromethyl sulfide

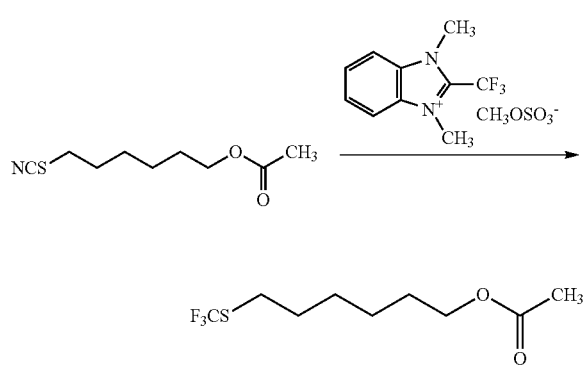

To a 50 mL three-necked flask equipped with a mechanical stirrer, 2 g (10 mmol) of 1-acetyloxy-6-thiocyanatohexane, 2 g of molecular sieve 4 A (manufactured by Tosoh Corporation; Zeolum (trade name); A-4; powder), 3.9 g (12 mmol) of 1,3-dimethyl-2-trifluoromethylbenzimidazolium methyl sulfate and 5 mL of DMF were added. The mixture was stirred at −30° C. for 30 minutes, and then a suspension prepared by dispersing 1.5 g (25.2 mmol) of potassium hydroxide in 7 mL of toluene was added dropwise thereto over 1 hour. The mixture was stirred at −30° C. for 14 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 52% of (6-acetyloxyhexyl) trifluoromethyl sulfide (target compound) and 48% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 93%.

Example 101

Production of (6-acetyloxyhexyl) trifluoromethyl sulfide

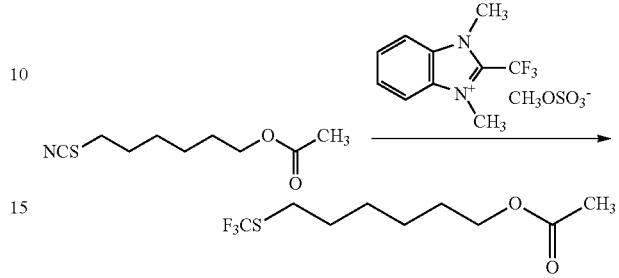

To a 50 mL three-necked flask equipped with a mechanical stirrer, 2 g (10 mmol) of 1-acetyloxy-6-thiocyanatohexane, 1.5 g of molecular sieve 4 A (manufactured by Tosoh Corporation; Zeolum (trade name); A-4; powder), 3.9 g (12 mmol) of 1,3-dimethyl-2-trifluoromethylbenzimidazolium methyl sulfate and 5 mL of DMF were added. The mixture was stirred at −30° C. for 30 minutes, and then a suspension prepared by dispersing 1.5 g (25.2 mmol) of potassium hydroxide in 7 mL of toluene was added dropwise thereto over 1 hour. The mixture was stirred at −30° C. for 16 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 26% of (6-acetyloxyhexyl) trifluoromethyl sulfide (target compound), 24% of 1-acetyloxy-6-thiocyanatohexane (starting compound) and 49% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 48%.

When the present invention was discussed after the present invention was completed, there was a possibility that a zeolite (for example, a molecular sieve) functions as a dehydrating agent. The results of a study on dehydrating agents other than a zeolite (for example, a molecular sieve) are shown in Examples 102 to 108.

Example 102

Production of (5-benzyloxypentyl) trifluoromethyl sulfide

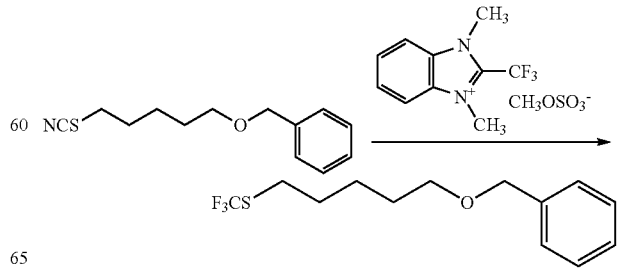

To a 6 mL vial equipped with a magnetic stirrer, 235 mg (1 mmol) of 1-benzyloxy-5-thiocyanatopentane, 300 mg of calcium chloride, 392 mg (1.2 mmol) of 1,3-dimethyl-2-trifluoromethylbenzimidazolium methyl sulfate and 1 mL of DMF were added. The mixture was stirred at −10° C. for 30 minutes, and then 148 mg (2.52 mmol) of potassium hydroxide was added thereto, and the mixture was stirred at −10° C. for 14 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 25% of (5-benzyloxypentyl) trifluoromethyl sulfide (target compound), 31% of 1-benzyloxy-5-thiocyanatopentane (starting compound), 2% of 1,2-bis[5-(benzyloxy)pentyl]disulfide (by-product) and 41% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 31%.

Example 103

The reaction was carried out in the same manner as Example 102, except that 300 mg of magnesium chloride was used instead of 300 mg of calcium chloride. The formation of the target compound was confirmed by GC-MS analysis on the reaction mixture. As a result of GC analysis (area percentage) on the reaction mixture, the components in the reaction mixture excluding the solvents and the like were as follows: 24% of (5-benzyloxypentyl) trifluoromethyl sulfide (target compound), 33% of 1-benzyloxy-5-thiocyanatopentane (starting compound) and 42% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 31%.

Example 104

The reaction was carried out in the same manner as Example 102, except that 300 mg of sodium sulfate was used instead of 300 mg of calcium chloride. The formation of the target compound was confirmed by GC-MS analysis on the reaction mixture. As a result of GC analysis (area percentage) on the reaction mixture, the components in the reaction mixture excluding the solvents and the like were as follows: 28% of (5-benzyloxypentyl) trifluoromethyl sulfide (target compound), 6% of 1-benzyloxy-5-thiocyanatopentane (starting compound), 22% of 1,2-bis[5-(benzyloxy)pentyl] disulfide (by-product) and 41% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 30%.

Example 105

The reaction was carried out in the same manner as Example 102, except that 300 mg of magnesium sulfate was used instead of 300 mg of calcium chloride. The formation of the target compound was confirmed by GC-MS analysis on the reaction mixture. As a result of GC analysis (area percentage) on the reaction mixture, the components in the reaction mixture excluding the solvents and the like were as follows: 26% of (5-benzyloxypentyl) trifluoromethyl sulfide (target compound), 16% of 1-benzyloxy-5-thiocyanatopentane (starting compound), 15% of 1,2-bis[5-(benzyloxy) pentyl] disulfide (by-product) and 40% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 30%.

Example 106

The reaction was carried out in the same manner as Example 102, except that 300 mg of silica gel was used instead of 300 mg of calcium chloride. The formation of the target compound was confirmed by GC-MS analysis on the reaction mixture. As a result of GC analysis (area percentage) on the reaction mixture, the components in the reaction mixture excluding the solvents and the like were as follows: 10% of (5-benzyloxypentyl) trifluoromethyl sulfide (target compound), 58% of 1-benzyloxy-5-thiocyanatopentane (starting compound) and 32% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 13%.

Example 107

The reaction was carried out in the same manner as Example 102, except that 134 mg (1.26 mmol) of trimethyl orthoformate was used instead of 300 mg of calcium chloride. The formation of the target compound was confirmed by GC-MS analysis on the reaction mixture. As a result of GC analysis (area percentage) on the reaction mixture, the components in the reaction mixture excluding the solvents and the like were as follows: 15% of (5-benzyloxypentyl) trifluoromethyl sulfide (target compound), 6% of 1-benzyloxy-5-thiocyanatopentane (starting compound), 42% of 1,2-bis[5-(benzyloxy)pentyl] disulfide (by-product) and 35% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 14%.

Example 108

The reaction was carried out in the same manner as Example 102, except that 300 mg of sodium sulfate was used instead of 300 mg of calcium chloride. The formation of the target compound was confirmed by GC-MS analysis on the reaction mixture. As a result of GC analysis (area percentage) on the reaction mixture, the components in the reaction mixture excluding the solvents and the like were as follows: 15% of (5-benzyloxypentyl) trifluoromethyl sulfide (target compound), 48% of 1-benzyloxy-5-thiocyanatopentane (starting compound) and 33% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 22%.

Example 109

Production of (5-acetyloxypentyl) trifluoromethyl sulfide

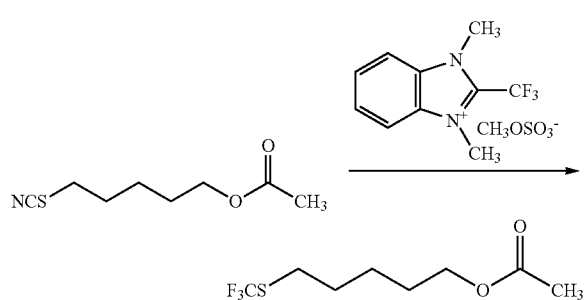

To a 6 mL vial equipped with a magnetic stirrer, 187 mg (1 mmol) of 1-acetyloxy-5-thiocyanatopentane, 300 mg of molecular sieve 4 A (manufactured by Tosoh Corporation; Zeolum (trade name); A-4; powder), 392 mg (1.2 mmol) of 1,3-dimethyl-2-trifluoromethylbenzimidazolium methyl sulfate and 0.5 mL of DMF were added. The mixture was stirred at 0° C. for 30 minutes, and then 148 mg (2.52 mmol) of potassium hydroxide was added thereto, and the mixture was stirred at 0° C. for 5 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 26% of (5-acetyloxypentyl) trifluoromethyl sulfide (target compound), 23% of 1-acetyloxy-5-thiocyanatopentane (starting compound) and 50% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 44%.

Example 110

Production of (5-acetyloxypentyl) trifluoromethyl sulfide

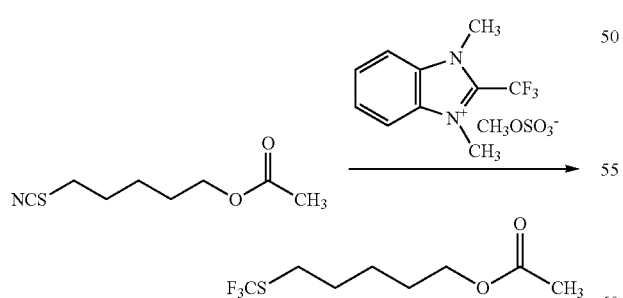

(1)
To a 100 mL four-necked flask equipped with a mechanical stirrer, 7.2 g (36 mmol) of 1-methyl-2-trifluoromethylbenzimidazole and 36 mL of toluene were added. The mixture was stirred at 80° C. for 30 minutes, and then 6.8 g (54 mmol) of dimethyl sulfate was added dropwise thereto over 1 hour. After the completion of the dropwise addition, the mixture was stirred at 80° C. for 42 hours. Then, 50 mL of toluene was added thereto, and the mixture was cooled to room temperature. The crystals of 1,3-dimethyl-2-trifluoromethylbenzimidazolium methyl sulfate were precipitated in the reaction system. After cooling, the stirring speed was decreased for decantation, and 50 mL of the toluene layer (supernatant liquid) was withdrawn from the reaction mixture with a pipette. Then, 50 mL of toluene was added to the remaining reaction mixture (suspension), followed by stirring for 5 minutes, and then the stirring speed was decreased, and subsequently 50 mL of the toluene layer (supernatant liquid) was withdrawn from the reaction mixture with a pipette. The same operation of adding toluene, followed by stirring, and then decreasing the stirring speed, followed by withdrawing the toluene layer with a pipette, was repeated another 4 times to prepare the mixture (suspension) of purified 1,3-dimethyl-2-trifluoromethylbenzimidazolium methyl sulfate and toluene.

(2)
To the mixture of 1,3-dimethyl-2-trifluoromethylbenzimidazolium methyl sulfate and toluene prepared in (1) above, 9 g of molecular sieve 4 A (manufactured by Tosoh Corporation; Zeolum (trade name); A-4; powder) and 10 mL of DMF were added, followed by cooling to −30° C., and then a solution prepared by diluting 5.6 g (30 mmol) of 1-acetyloxy-5-thiocyanatopentane with 5 mL of DMF was added, and the mixture was stirred at −30° C. for 30 minutes. Then, a suspension prepared by dispersing 4.4 g (75.6 mmol) of potassium hydroxide in 15 mL of toluene was added dropwise over 1 hour. After the completion of the dropwise addition, the mixture was stirred at −30° C. for 13 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 54% of (5-acetyloxypentyl) trifluoromethyl sulfide (target compound) and 46% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 96%.

Example 111

Production of (5-acetyloxypentyl) trifluoromethyl sulfide

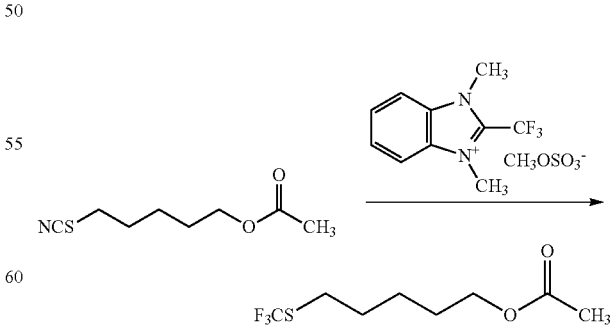

(1)
To a 100 mL four-necked flask equipped with a mechanical stirrer, 7.2 g (36 mmol) of 1-methyl-2-trifluoromethylbenzimidazole and 36 mL of toluene were added. The mixture was stirred at 80° C. for 30 minutes, and then 6.8 g (54 mmol) of dimethyl sulfate was added dropwise thereto over 1 hour. After the completion of the dropwise addition, the mixture was stirred at 80° C. for 42 hours. Then, 50 mL of toluene was added thereto, and the mixture was cooled to room temperature. The crystals of 1,3-dimethyl-2-trifluoromethylbenzimidazolium methyl sulfate were precipitated in the reaction system. After cooling, the stirring speed was decreased for decantation, and 50 mL of the toluene layer (supernatant liquid) was withdrawn from the reaction mixture with a pipette. Then, 50 mL of toluene was added to the remaining reaction mixture (suspension), followed by stirring for 5 minutes, and then the stirring speed was decreased, and subsequently 50 mL of the toluene layer (supernatant liquid) was withdrawn from the reaction mixture with a pipette. The same operation of adding toluene, followed by stirring, and then decreasing the stirring speed, followed by withdrawing the toluene layer with a pipette, was repeated another 4 times to prepare the mixture (suspension) of purified 1,3-dimethyl-2-trifluoromethylbenzimidazolium methyl sulfate and toluene.

(2)

To the mixture of 1,3-dimethyl-2-trifluoromethylbenzimidazolium methyl sulfate and toluene prepared in (1) above, 9 g of molecular sieve 4 A (manufactured by Tosoh Corporation; Zeolum (trade name); A-4; powder) and 10 mL of DMF were added, followed by cooling to −40° C., and then a solution prepared by diluting 5.6 g (30 mmol) of 1-acetyloxy-5-thiocyanatopentane with 5 mL of DMF was added, and the mixture was stirred at −40° C. for 30 minutes. Then, a suspension prepared by dispersing 4.4 g (75.6 mmol) of potassium hydroxide in 15 mL of toluene was added dropwise over 1 hour. After the completion of the dropwise addition, the mixture was stirred at −40° C. for 8 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 49% of (5-acetyloxypentyl) trifluoromethyl sulfide (target compound) and 51% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 96%.

Example 112

Production of 1-acetyloxy-5-thiotosylate pentane

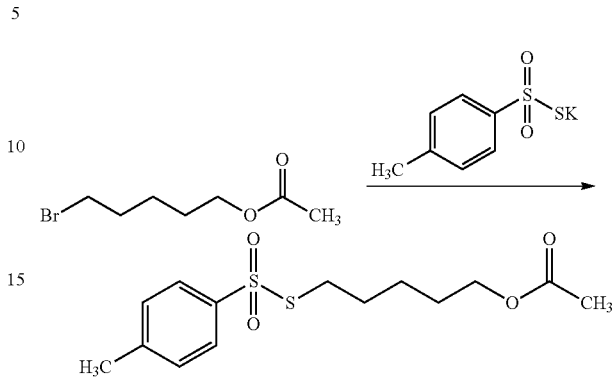

To a 100 mL eggplant-shaped flask equipped with a magnetic stirrer, 10.5 g (50 mmol) of 1-acetyloxy-5-bromopentane, 14.2 g (60 mmol) of potassium p-toluenethiosulfonate and 50 mL of acetonitrile were added. The mixture was heated to reflux for 5 hours. After cooling to room temperature, the solvent was distilled off under reduced pressure. Water was added thereto, and the mixture was extracted with toluene. The solvent was distilled off under reduced pressure to obtain 13.5 g of yellow oil. Yield: 85%.

$^1$H-NMR (300 MHz, CDCl$_3$) δ (ppm): 1.31-1.42 (m, 2H), 1.52-1.70 (m, 4H), 2.04 (s, 3H), 2.46 (s, 3H), 2.99 (t, J=7.2 Hz, 2H), 4.00 (t, J=6.5 Hz, 2H), 7.35 (d, J=8.1 Hz, 2H), 7.81 (d, J=8.1 Hz, 2H).

Example 113

Production of (5-acetyloxypentyl) trifluoromethyl sulfide

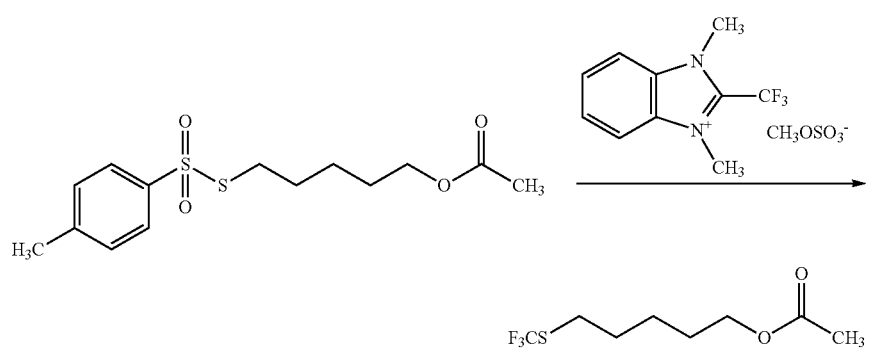

(1)

To a 100 mL four-necked flask equipped with a mechanical stirrer, 7.2 g (36 mmol) of 1-methyl-2-trifluoromethylbenzimidazole and 36 mL of toluene were added. The mixture was stirred at 80° C. for 30 minutes, and then 6.8 g (54 mmol) of dimethyl sulfate was added dropwise thereto over 1 hour. After the completion of the dropwise addition, the mixture was stirred at 80° C. for 42 hours. Then, 50 mL of toluene was added thereto, and the mixture was cooled to room temperature. The crystals of 1,3-dimethyl-2-trifluoromethylbenzimidazolium methyl sulfate were precipitated in the reaction system. After cooling, the stirring speed was decreased for decantation, and 50 mL of the toluene layer (supernatant liquid) was withdrawn from the reaction mixture with a pipette. Then, 50 mL of toluene was added to the remaining reaction mixture (suspension), followed by stirring for 5 minutes, and then the stirring speed was decreased, and subsequently 50 mL of the toluene layer (supernatant liquid) was withdrawn from the reaction mixture with a pipette. The same operation of adding toluene, followed by stirring, and then decreasing the stirring speed, followed by withdrawing the toluene layer with a pipette, was repeated another 4 times to prepare the mixture (suspension) of purified 1,3-dimethyl-2-trifluoromethylbenzimidazolium methyl sulfate and toluene.

(2)

To the mixture of 1,3-dimethyl-2-trifluoromethylbenzimidazolium methyl sulfate and toluene prepared in (1) above, 9 g of molecular sieve 4 A (manufactured by Tosoh Corporation; Zeolum (trade name); A-4; powder) and 10 mL of DMF were added, followed by cooling to −40° C., and then a solution prepared by diluting 9.5 g (30 mmol) of 1-acetyloxy-5-thiotosylate pentane with 5 mL of DMF was added, and the mixture was stirred at −30° C. for 30 minutes. Then, a suspension prepared by dispersing 4.4 g (75.6 mmol) of potassium hydroxide in 15 mL of toluene was added dropwise over 1 hour. After the completion of the dropwise addition, the mixture was stirred at −30° C. for 17 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 48% of (5-acetyloxypentyl) trifluoromethyl sulfide (target compound) and 52% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 90%.

Example 114

Production of 1-acetyloxy-6-thiotosylate hexane

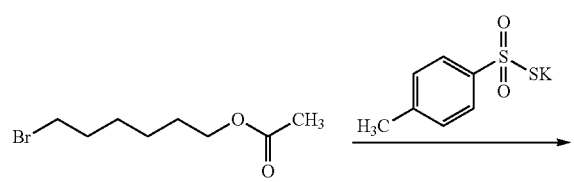

-continued

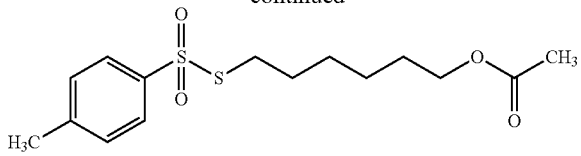

To a 50 mL eggplant-shaped flask equipped with a magnetic stirrer, 6.6 g (29.5 mmol) of 1-acetyloxy-6-bromohexane, 10.5 g (44.3 mmol) of potassium p-toluenethiosulfonate and 29.5 mL of acetonitrile were added. The mixture was heated to reflux for 5 hours. After cooling to room temperature, the solvent was distilled off under reduced pressure. Water was added thereto, and the mixture was extracted with toluene. The solvent was distilled off under reduced pressure to obtain 9.6 g of yellow oil. Yield: 98%.

$^1$H-NMR (300 MHz, CDCl$_3$) δ (ppm): 1.22-1.40 (m, 4H), 1.51-1.67 (m, 4H), 2.04 (s, 3H), 2.46 (s, 3H), 2.98 (t, J=7.4 Hz, 2H), 4.00 (t, J=6.5 Hz, 2H), 7.35 (d, J=8.4 Hz, 2H), 7.81 (d, J=8.4 Hz, 2H).

Example 115

Production of (6-acetyloxyhexyl) trifluoromethyl sulfide

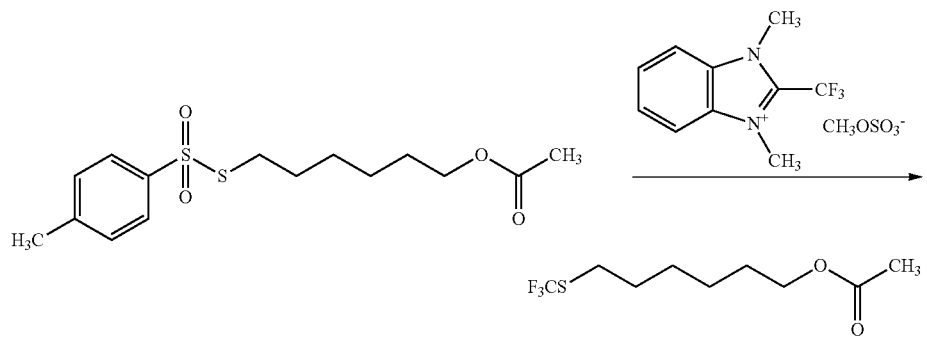

To a 6 mL vial equipped with a magnetic stirrer, 331 mg (1 mmol) of 1-acetyloxy-6-thiotosylate hexane, 300 mg of molecular sieve 4 A (manufactured by Tosoh Corporation; Zeolum (trade name); A-4; powder), 392 mg (1.2 mmol) of 1,3-dimethyl-2-trifluoromethylbenzimidazolium methyl sulfate and 2 mL of DMF were added. The mixture was stirred at −10° C. for 30 minutes, and then 148 mg (2.52 mmol) of potassium hydroxide was added thereto, and the mixture was stirred at −10° C. for 24 hours. The formation of (6-acetyloxyhexyl) trifluoromethyl sulfide (parent ion; 244) was confirmed by GC-MS analysis on the reaction mixture. As a result of GC analysis (area percentage) on the reaction mixture, the components in the reaction mixture excluding the solvents and the like were as follows: 42% of (6-acetyloxyhexyl) trifluoromethyl sulfide (target compound), 2% of 1-acetyloxy-6-thiotosylate hexane (starting compound) and 48% of 2,3-dihydro-1,3-dimethylbenzimidazole-2-one (compound derived from the fluoroalkylating agent). As a result of GC analysis using 1,4-diethylbenzene as the internal standard, the yield of (6-acetyloxyhexyl) trifluoromethyl sulfide (target compound) was 61%.

Example 116

Production of 1-benzyloxy-5-thiotosylate pentane

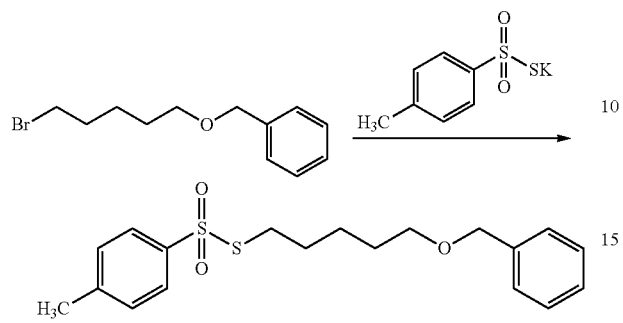

To a 50 mL eggplant-shaped flask equipped with a magnetic stirrer, 5.1 g (20 mmol) of 1-benzyloxy-5-bromopentane, 5.4 g (24 mmol) of potassium p-toluenethiosulfonate and 20 mL of acetonitrile were added. The mixture was stirred at 70° C. for 6 hours. After cooling to room temperature, the solvent was distilled off under reduced pressure. Water was added thereto, and the mixture was extracted with diethyl ether. The solvent was distilled off under reduced pressure. The resultant solids were dissolved in ethyl acetate, and then hexane was added thereto. The precipitated crystals were collected by filtration to obtain 5.5 g of yellow-white crystals. Yield: 75%.

$^1$H-NMR (400 MHz, CDCl$_3$, relative to TMS) δ (ppm): to be described.

$^1$H-NMR (300 MHz, CDCl$_3$) δ (ppm): 1.34-1.46 (m, 2H), 1.49-1.1.70 (m, 4H), 2.46 (s, 3H), 2.98 (t, J=7.4 Hz, 2H), 3.41 (t, J=6.3 Hz, 2H), 4.47 (s, 2H), 7.26-7.38 (m, 7H), 7.81 (t, J=8.4 Hz, 2H).

Example 117

Production of (5-benzyloxypentyl) trifluoromethyl sulfide

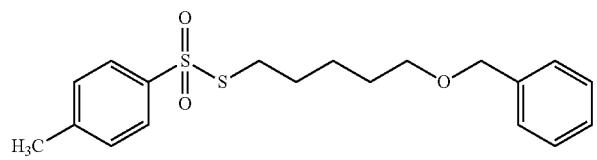

To a 6 mL vial equipped with a magnetic stirrer, 365 mg (1 mmol) of 1-benzyloxy-5-thiotosylate pentane, 300 mg of molecular sieve 4 A (manufactured by Tosoh Corporation; Zeolum (trade name); A-4; powder), 392 mg (1.2 mmol) of 1,3-dimethyl-2-trifluoromethylbenzimidazolium methyl sulfate and 2 mL of DMF were added. The mixture was stirred at −10° C. for 30 minutes, and then 148 mg (2.52 mmol) of potassium hydroxide was added thereto, and the mixture was stirred at −10° C. for 24 hours. The formation of (5-benzyloxypentyl) trifluoromethyl sulfide (parent ion; 278) was confirmed by GC-MS analysis on the reaction mixture. As a result of GC analysis (area percentage) on the reaction mixture, the components in the reaction mixture excluding the solvents and the like were as follows: 57% of (5-benzyloxypentyl) trifluoromethyl sulfide (target compound) and 41% of 2,3-dihydro-1,3-dimethylbenzimidazole-2-one (compound derived from the fluoroalkylating agent). As a result of GC analysis using 1,4-diethylbenzene as the internal standard, the yield of (5-benzyloxypentyl) trifluoromethyl sulfide (target compound) was 72%.

Example 118

Production of 5-(acetyloxypentyl) trifluoromethyl sulfide

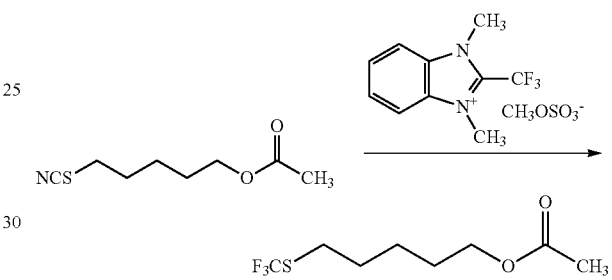

(1)

To a 100 mL four-necked flask equipped with a mechanical stirrer, 7.2 g (36 mmol) of 1-methyl-2-trifluoromethylbenzimidazole and 36 mL of toluene were added. The mixture was stirred at 80° C. for 30 minutes, and then 6.8 g (54 mmol) of dimethyl sulfate was added dropwise thereto over 1 hour. After the completion of the dropwise addition, the mixture was stirred at 80° C. for 42 hours. Then, 50 mL of toluene was added thereto, and the mixture was cooled to room temperature. The crystals of 1,3-dimethyl-2-trifluo-

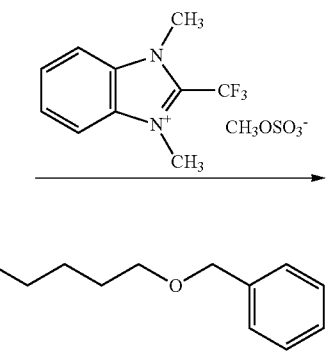

romethylbenzimidazolium methyl sulfate were precipitated in the reaction system. After cooling, the stirring speed was decreased for decantation, and 50 mL of the toluene layer (supernatant liquid) was withdrawn from the reaction mixture with a pipette. Then, 50 mL of toluene was added to the remaining reaction mixture (suspension), followed by stirring for 5 minutes, and then the stirring speed was decreased, and subsequently 50 mL of the toluene layer (supernatant liquid) was withdrawn from the reaction mixture with a pipette. The same operation of adding toluene, followed by stirring, and then decreasing the stirring speed, followed by withdrawing the toluene layer with a pipette, was repeated another 4 times to prepare the mixture (suspension) of purified 1,3-dimethyl-2-trifluoromethylbenzimidazolium methyl sulfate and toluene.

(2)

To the mixture of 1,3-dimethyl-2-trifluoromethylbenzimidazolium methyl sulfate and toluene prepared in (1) above, 9 g of molecular sieve 4 A (manufactured by Tosoh Corporation; Zeolum (trade name); A-4; powder) and 10 mL of DMF were added, followed by cooling to −30° C., and then a solution prepared by diluting 5.6 g (30 mmol) of 1-acetyloxy-5-thiocyanatopentane with 5 mL of DMF was added, and the mixture was stirred at −30° C. for 30 minutes. Then, a suspension prepared by dispersing 2.2 g (37.8 mmol) of potassium hydroxide in 15 mL of toluene was added dropwise over 1 hour. After the completion of the dropwise addition, 1.5 g (37.8 mmol) of 60% sodium hydride was added in small portions over 1 hour. Then, the mixture was stirred at −30° C. for 13 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 55% of (5-acetyloxypentyl) trifluoromethyl sulfide (target compound) and 45% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 99%.

Example 119

Production of (5-acetyloxypentyl) trifluoromethyl sulfide (supernatant liquid) was withdrawn from the reaction mixture with a pipette. Then, 50 mL of toluene was added to the remaining reaction mixture (suspension), followed by stirring for 5 minutes, and then the stirring speed was decreased, and subsequently 50 mL of the toluene layer (supernatant liquid) was withdrawn from the reaction mixture with a pipette. The same operation of adding toluene, followed by stirring, and then decreasing the stirring speed, followed by withdrawing the toluene layer with a pipette, was repeated another 4 times to prepare the mixture (suspension) of purified 1,3-dimethyl-2-trifluoromethylbenzimidazolium methyl sulfate and toluene.

(2)

To the mixture of 1,3-dimethyl-2-trifluoromethylbenzimidazolium methyl sulfate and toluene prepared in (1) above, 9 g of molecular sieve 4 A (manufactured by Tosoh Corporation; Zeolum (trade name); A-4; powder) and 10 mL of DMF were added, followed by cooling to −30° C., and then a solution prepared by diluting 9.5 g (30 mmol) of 1-acetyloxy-5-thiotosylate pentane with 5 mL of DMF was added, and the mixture was stirred at −30° C. for 30 minutes. Then, a suspension prepared by dispersing 2.2 g (37.8 mmol) of potassium hydroxide in 15 mL of toluene was added dropwise over 1 hour. After the completion of the dropwise addition, 1.5 g (37.8 mmol) of 60% sodium hydride was added in small portions over 1 hour. Then, the mixture was stirred at −30° C. for 36 hours. The formation of (5-acetyloxypentyl) trifluoromethyl sulfide (parent ion; 230) was confirmed by GC-MS analysis on the reaction mixture. As a result of GC analysis (area percentage) on the reaction mixture, the components in the reaction mixture excluding the solvents and the like were as follows: 43% of (5-acetyloxypentyl) trifluoromethyl sulfide (target compound) and 57% of 2,3-dihydro-1,3-dimethylbenzimidazole-2-one (compound derived from the fluoroalkylating agent). As a result of GC analysis using 1,4-diethylbenzene as the internal standard, the yield of (5-acetyloxypentyl) trifluoromethyl sulfide (target compound) was 83%.

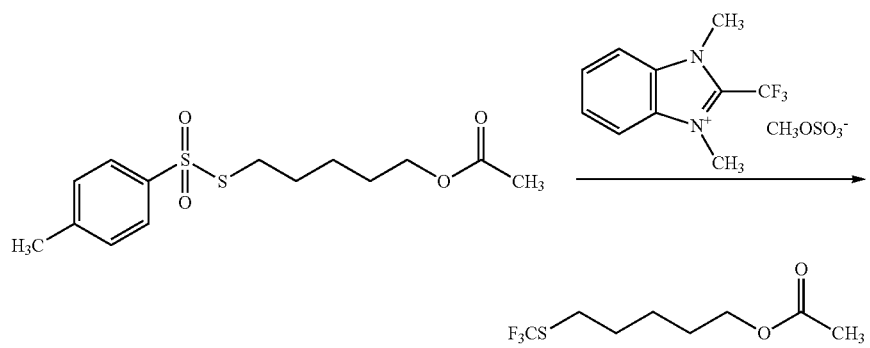

(1)

To a 100 mL four-necked flask equipped with a mechanical stirrer, 7.2 g (36 mmol) of 1-methyl-2-trifluoromethylbenzimidazole and 36 mL of toluene were added. The mixture was stirred at 80° C. for 30 minutes, and then 6.8 g (54 mmol) of dimethyl sulfate was added dropwise thereto over 1 hour. After the completion of the dropwise addition, the mixture was stirred at 80° C. for 42 hours. Then, 50 mL of toluene was added thereto, and the mixture was cooled to room temperature. The crystals of 1,3-dimethyl-2-trifluoromethylbenzimidazolium methyl sulfate were precipitated in the reaction system. After cooling, the stirring speed was decreased for decantation, and 50 mL of the toluene layer

Example 120

Production of 1-acetyloxy-6-thiocyanatohexane (1) Production of 6-bromohexyl acetate

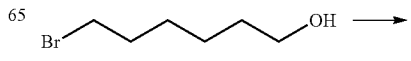

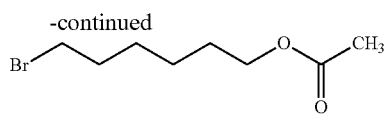

To a reaction flask, 93.3 g (515 mmol) of 6-bromo-1-hexanol, 65.5 g (618 mmol) of anhydrous sodium carbonate, 6.3 g (52 mmol) of N,N-dimethyl-4-aminopyridine and 515 mL of toluene were added. While the mixture was stirred under ice cooling, 59.6 g (584 mmol) of acetic anhydride was added dropwise thereto. After the completion of the dropwise addition, the mixture was stirred for 1 hour under ice cooling. The resultant reaction mixture was washed successively with water twice, with dilute hydrochloric acid and then with water. The toluene was distilled off under reduced pressure to obtain 114.9 g of 6-bromohexyl acetate. Yield: quantitative.

(2) Production of 1-acetyloxy-6-thiocyanatohexane

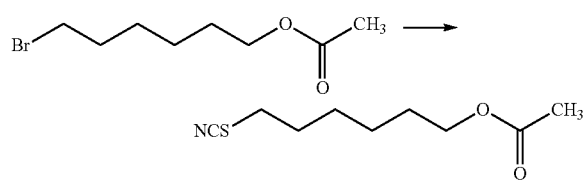

To a reaction flask, 114.9 g (515 mmol) of 6-bromohexyl acetate obtained in (1) above, 62.6 g (773 mmol) of sodium thiocyanate, 17 g (52 mmol) of tetrabutylammonium bromide, 515 mL of toluene and 515 mL of water were added. Then, the mixture was stirred at 50° C. for 24 hours. The resultant reaction mixture was partitioned between toluene and water, and the toluene layer was separated. The obtained toluene layer was washed 5 times with water. Subsequently, the toluene was distilled off under reduced pressure to obtain 90.0 g of 1-acetyloxy-6-thiocyanatohexane (purity: 94%). Yield in terms of purity: 82%.

$^1$H-NMR (300 MHz, CDCl$_3$) δ (ppm): 4.07 (t, J=6.6 Hz, 2H), 2.96 (t, J=6.9 Hz, 2H), 2.06 (s, 3H), 1.85 (quin, J=6.6 Hz, 2H), 1.66 (quin, J=6.9 Hz, 2H), 1.43 (m, 4H).

Example 121

Production of (6-acetyloxyhexyl) trifluoromethyl sulfide

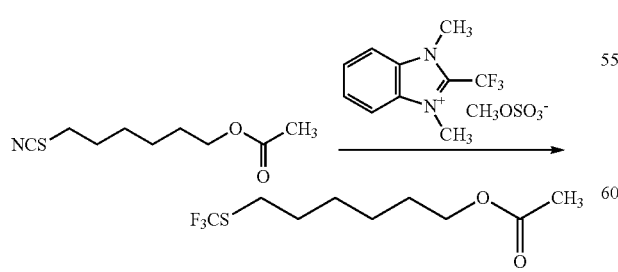

To a 500 mL four-necked flask equipped with a mechanical stirrer, 64 g (300 mmol) of 1-acetyloxy-6-thiocyanatohexane (purity: 94%) produced in Example 120, 90 g of molecular sieve 4 A (manufactured by Tosoh Corporation; Zeolum (trade name); A-4; powder), 118 g (360 mmol) of 1,3-dimethyl-2-trifluoromethylbenzimidazolium methyl sulfate and 150 mL of DMF were added. The mixture was stirred at −30° C. for 30 minutes, and then a suspension prepared by dispersing 44.4 g (756 mmol) of potassium hydroxide (purity: 95.5%) in 150 mL of toluene was added dropwise thereto over 3 hours. The mixture was stirred at −30° C. for 16 hours. Then, 90 mL of toluene was added, and the mixture was stirred at 0° C. for 30 minutes, and then the mixture was filtered. Water was added to the resultant filtrate, and the mixture was partitioned between toluene and water, and the toluene layer was separated. The resultant toluene layer was washed with water, and the toluene was distilled off under reduced pressure to obtain the crude product of the titled target compound. As a result of GC analysis by adding 1,4-diethylbenzene as the internal standard, the yield of (6-acetyloxyhexyl) trifluoromethyl sulfide (target compound) was 90%.

In addition, (6-acetyloxyhexyl) trifluoromethyl sulfide produced by the same method as Example 121 was purified and identified by the usual method.

$^1$H-NMR (300 MHz, CDCl$_3$) δ (ppm): 4.06 (t, J=6.6 Hz, 2H), 2.88 (t, J=7.2 Hz, 2H), 2.05 (s, 3H), 1.67 (m, 4H), 1.41 (m, 4H).

Example 122

Production of 1-acetyloxy-5-thiocyanatopentane (1) Production of 5-bromopentyl acetate

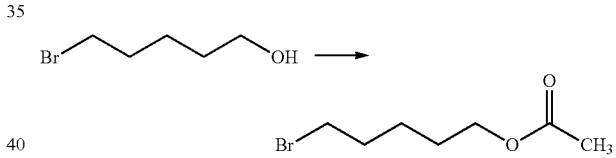

To a reaction flask, 33.4 g (200 mmol) of 5-bromo-1-pentanol, 25.4 g (240 mmol) of anhydrous sodium carbonate, 2.4 g (20 mmol) of N,N-dimethyl-4-aminopyridine and 200 mL of toluene were added. While the mixture was stirred under ice cooling, 22.5 g (220 mmol) of acetic anhydride was added dropwise thereto. After the completion of the dropwise addition, the mixture was stirred for 1 hour under ice cooling. The resultant reaction mixture was washed successively with water twice, with dilute hydrochloric acid and then with water. The toluene was distilled off under reduced pressure to obtain 41.8 g of 5-bromopentyl acetate. Yield: quantitative.

(2) Production of 1-acetyloxy-5-thiocyanatopentane

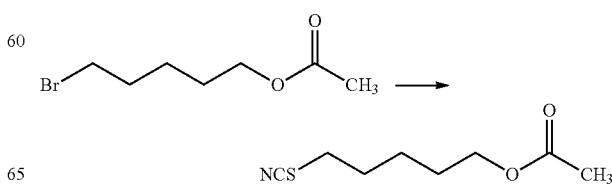

To a reaction flask, 41.8 g (200 mmol) of 5-bromopentyl acetate obtained in (1) above, 24.3 g (300 mmol) of sodium thiocyanate, 3.2 g (10 mmol) of tetrabutylammonium bromide, 100 mL of toluene and 100 mL of water were added. Then, the mixture was stirred at 50° C. for 24 hours. The resultant reaction mixture was partitioned between toluene and water, and the toluene layer was separated. The obtained toluene layer was washed 5 times with water. Subsequently, the toluene was distilled off under reduced pressure to obtain 35.1 g of 1-acetyloxy-5-thiocyanatopentane (purity: 92%). Yield in terms of purity: 86%.

$^1$H-NMR (300 MHz, CDCl$_3$) δ (ppm): 4.09 (t, J=6.3 Hz, 2H), 2.96 (t, J=7.2 Hz, 2H), 2.06 (s, 3H), 1.88 (m, 2H), 1.71 (m, 2H), 1.53 (m, 2H).

Example 123

Production of (5-acetyloxypentyl) trifluoromethyl sulfide

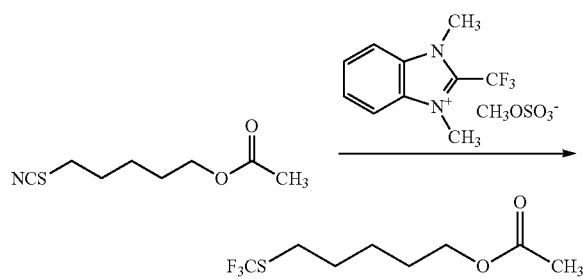

(1)

To a 100 mL four-necked flask equipped with a mechanical stirrer, 7.2 g (36 mmol) of 1-methyl-2-trifluoromethylbenzimidazole and 36 mL of toluene were added. The mixture was stirred at 80° C. for 30 minutes, and then 6.8 g (54 mmol) of dimethyl sulfate was added dropwise thereto over 1 hour. After the completion of the dropwise addition, the mixture was stirred at 80° C. for 40 hours. Then, 50 mL of toluene was added thereto, and the mixture was cooled to room temperature. The crystals of 1,3-dimethyl-2-trifluoromethylbenzimidazolium methyl sulfate were precipitated in the reaction system. After cooling, the stirring speed was decreased for decantation, and 50 mL of the toluene layer (supernatant liquid) was withdrawn from the reaction mixture with a pipette. Then, 50 mL of toluene was added to the remaining reaction mixture (suspension), followed by stirring for 5 minutes, and then the stirring speed was decreased, and subsequently 50 mL of the toluene layer (supernatant liquid) was withdrawn from the reaction mixture with a pipette. The same operation of adding toluene, followed by stirring, and then decreasing the stirring speed, followed by withdrawing the toluene layer with a pipette, was repeated another 4 times to prepare the mixture (suspension) of purified 1,3-dimethyl-2-trifluoromethylbenzimidazolium methyl sulfate and toluene.

(2)

To the mixture of 1,3-dimethyl-2-trifluoromethylbenzimidazolium methyl sulfate and toluene prepared in (1) above, 9 g of molecular sieve 4 A (manufactured by Tosoh Corporation; Zeolum (trade name); A-4; powder) and 10 mL of DMF were added, followed by cooling to −30° C., and then a solution prepared by diluting 5.6 g (30 mmol) of 1-acetyloxy-5-thiocyanatopentane with 5 mL of DMF was added, and the mixture was stirred at −30° C. for 30 minutes. Then, a suspension prepared by dispersing 4.4 g (75.6 mmol) of potassium hydroxide (purity: 95.5%) in 15 mL of toluene was added dropwise over 1 hour. After the completion of the dropwise addition, the mixture was stirred at −30° C. for 14 hours. Then, 9 mL of toluene was added, and the mixture was stirred at 0° C. for 30 minutes, and then the mixture was filtered. Water was added to the resultant filtrate, and the mixture was partitioned between toluene and water, and the toluene layer was separated. The resultant toluene layer was washed with water, and the toluene was distilled off under reduced pressure to obtain the crude product of the titled target compound. As a result of GC analysis by adding 1,4-diethylbenzene as the internal standard, the yield of (5-acetyloxypentyl) trifluoromethyl sulfide (target compound) was 90%.

In addition, (5-acetyloxypentyl) trifluoromethyl sulfide produced by the same method as Example 123 was purified and identified by the usual method.

$^1$H-NMR (300 MHz, CDCl$_3$) δ (ppm): 4.07 (t, J=6.3 Hz, 2H), 2.89 (t, J=7.5 Hz, 2H), 2.05 (s, 3H), 1.70 (m, 4H), 1.48 (m, 2H).

Example 124

Production of 1-benzyloxy-5-bromopentane

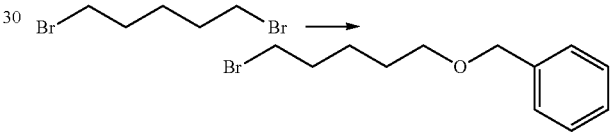

To a reaction flask, 49 g (1230 mmol) of sodium hydroxide and 196 mL of water were added. The mixture was stirred at room temperature for 30 minutes, and then 113 g (490 mmol) of 1,5-dibromopentane, 122 g (1130 mmol) of benzyl alcohol and 4 g (12.3 mmol) of tetrabutylammonium bromide were added. The mixture was stirred at 70° C. for 4 hours. Then, the mixture was partitioned between the organic layer and the aqueous layer, and the organic layer was separated. The obtained organic layer was purified by distillation under reduced pressure to obtain 79.6 g of 1-benzyloxy-5-bromopentane. Yield: 63%.

Example 125

Production of 1-benzyloxy-5-thiocyanatopentane

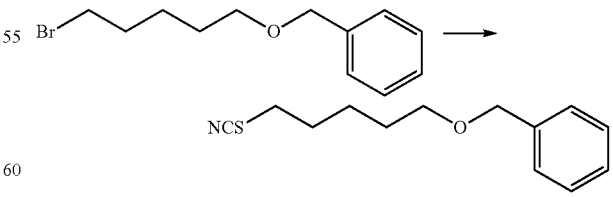

To a reaction flask, 25.7 g (100 mmol) of 1-benzyloxy-5-bromopentane, 12.2 g (150 mmol) of sodium thiocyanate and 100 mL of ethanol were added. The mixture was stirred at 80° C. for 4 hours. The ethanol was distilled off under reduced pressure from the resultant reaction mixture. Ethyl acetate and water were added to the resultant residue, and the mixture was partitioned between ethyl acetate and water, and the ethyl acetate layer was separated. Subsequently, the acetic acid was distilled off under reduced pressure. The resultant crude product was purified by silica gel column chromatography to obtain 17.1 g of 1-benzyloxy-5-thiocyanatopentane. Yield: 73%.

$^1$H-NMR (300 MHz, CDCl$_3$) δ (ppm): 1.48-1.70 (m, 4H), 1.84 (quin, J=7.4 Hz, 2H), 2.93 (t, J=7.4 Hz, 2H), 3.48 (t, J=6.3 Hz, 2H), 4.50 (s, 2H), 7.25-7.38 (m, 5H). GC-MS (m/z): M$^+$=235.

The physical property values of the compound represented by the general formula (1) and analogues thereof obtained in the Examples in the present specification are shown in Table 19. In addition, the physical property values (melting point or refractive index) of the compound represented by the general formula (1) and analogues thereof, which were produced by the same method as the Examples in the present specification are also shown in Table 19. The symbol * in Table 19 means the refractive index.

TABLE 19

| Compound No. | Melting point (° C.) or refractive index (n$_D^{20}$) |
|---|---|
| 1-4 | 214-217 |
| 1-5 | 211-213 |
| 1-14 | 160-161 |
| 1-19 | 211-213 |
| 1-31 | 110-113 |
| 1-32 | 116-118 |
| 1-38 | 185-186 |
| 1-41 | 247-250 |
| 1-48 | 183-185 |
| 1-62 | 192-195 |
| 1-69 | 140-143 |
| 1-76 | 171-174 |
| 1-91 | 150-153 |
| 1-98 | 105-108 |
| 1-109 | 1.457 * |
| 1-120 | 180-181 |
| 1-195 | 148-149 |
| 1-248 | 216-219 |
| 1-300 | 204-205 |
| 1-365 | 125-127 |
| 1-391 | 196-199 |
| 1-404 | 212-215 |
| 1-452 | 197-200 |
| 1-611 | 154-157 |
| 1-614 | 237-240 |
| 1-615 | unmeasurable (300° C. or more) |

Reference Example 1

Production of 1-bromo-6-trifluoromethylthiohexane (1) Production of 6-trifluoromethylthiohexan-1-ol

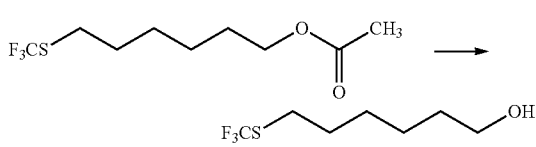

To a reaction flask, the total amount of (6-acetyloxyhexyl) trifluoromethyl sulfide obtained in Example 121, 46 g (333 mmol) of potassium carbonate and 269 mL of methanol were added. Then, the mixture was stirred at room temperature for 6 hours. Dilute hydrochloric acid was added dropwise to the resultant reaction mixture under ice cooling, and then toluene was added thereto. The mixture was partitioned between toluene and water, and the toluene layer was separated. Subsequently, the toluene was distilled off under reduced pressure to obtain the crude product of 6-trifluoromethylthiohexan-1-ol.

In addition, 6-trifluoromethylthiohexan-1-ol produced by the same method as Reference Example 1 was purified and identified by the usual manner.

$^1$H-NMR (300 MHz, CDCl$_3$) δ (ppm): 3.66 (t, J=6.6 Hz, 2H), 2.89 (t, J=7.5 Hz, 2H), 1.72 (quin, J=7.5 Hz, 2H), 1.59 (quin, J=6.6 Hz, 2H), 1.43 (m, 4H).

(2) Production of 1-bromo-6-trifluoromethylthiohexane

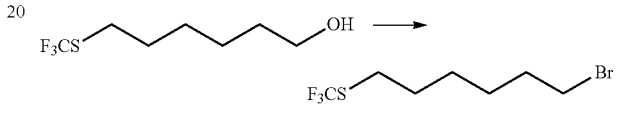

To a reaction flask, the total amount of 6-trifluoromethylthiohexan-1-ol obtained in (1) above, 90.7 g (538 mmol) of 48% hydrobromic acid and 8.7 g (27 mmol) of tetrabutylammonium bromide were added. Then, the mixture was heated to reflux for 13 hours. The resultant reaction mixture was cooled to room temperature, and toluene was added thereto, and the mixture was partitioned between toluene and water, and the toluene layer was separated. Subsequently, the toluene was distilled off under reduced pressure. The resultant residue was purified by distillation under reduced pressure, and heptane and water were added thereto, and the mixture was partitioned between heptane and water, and the heptane layer was obtained. Subsequently, the heptane was distilled off under reduced pressure to obtain 52.2 g of 1-bromo-6-trifluoromethylthiohexane. Yield: 74% (2 steps).

$^1$H-NMR (300 MHz, CDCl$_3$) δ (ppm): 3.41 (t, J=6.9 Hz, 2H), 2.89 (t, J=7.2 Hz, 2H), 1.87 (quin, J=7.2 Hz, 2H), 1.72 (quin, J=6.9 Hz, 2H), 1.47 (m, 4H).

Reference Example 2

Production of 1-bromo-5-trifluoromethylthiopentane (1) Production of 5-trifluoromethylthiopentane-1-ol

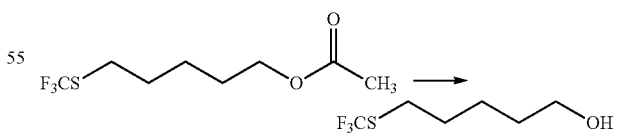

To a reaction flask, the total amount of (5-acetyloxypentyl) trifluoromethyl sulfide obtained in Example 123, 4.5 g (32.4 mmol) of potassium carbonate and 27 mL of methanol were added. Then, the mixture was stirred at room temperature for 6 hours. Dilute hydrochloric acid was added dropwise to the resultant reaction mixture under ice cooling, and then toluene was added thereto. The mixture was partitioned between toluene and water, and the toluene layer was separated. Subsequently, the toluene was distilled off under reduced pressure to obtain the crude product of 5-trifluoromethylthiopentan-1-ol.

In addition, 5-trifluoromethylthiopentan-1-ol produced by the same method as Reference Example 2 was purified and identified by the usual manner.

$^1$H-NMR (300 MHz, CDCl$_3$) δ (ppm): 3.67 (t, J=6.0 Hz, 2H), 2.90 (t, J=7.2 Hz, 2H), 1.74 (m, 2H), 1.54 (m, 4H).

(2) Production of 1-bromo-5-trifluoromethylthiopentane

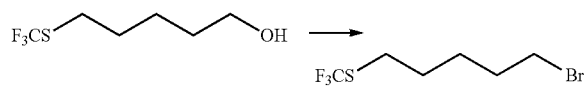

To a reaction flask, the total amount of 5-trifluoromethylthiopentan-1-ol obtained in (1) above, 9.1 g (54 mmol) of 48% hydrobromic acid and 0.87 g (2.7 mmol) of tetrabutylammonium bromide were added. Then, the mixture was heated to reflux for 14 hours. Toluene was added to the resultant reaction mixture, and the mixture was partitioned between toluene and water, and the toluene layer was separated. Subsequently, the toluene was distilled off under reduced pressure. The resultant residue was purified by distillation under reduced pressure to obtain 4.9 g of 1-bromo-5-trifluoromethylthiopentane. Yield: 72% (2 steps).

$^1$H-NMR (300 MHz, CDCl$_3$) δ (ppm): 3.42 (t, J=6.9 Hz, 2H), 2.90 (t, J=7.2 Hz, 2H), 1.90 (m, 2H), 1.74 (m, 2H), 1.57 (m, 2H).

Reference Example 3

Production of 5-mercapto-2,4-dimethylphenol (1) Production of 2,4-dimethylphenylmethanesulfonate

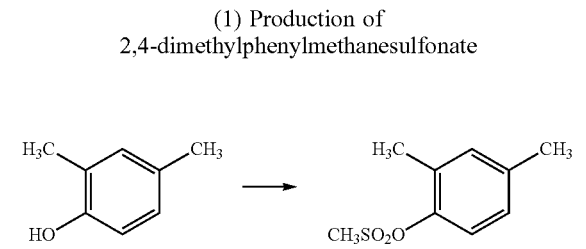

To a reaction flask, 12.22 g (100.0 mmol) of 2,4-dimethylphenol, 11.68 g (102.0 mmol) of methanesulfonylchloride and 100 mL of dichloromethane were added. Subsequently, while the mixture was stirred under ice cooling, a solution of 11.13 g (110.0 mmol) of triethylamine in 50 mL of dichloromethane was slowly added dropwise. After the completion of the dropwise addition, the mixture was stirred at room temperature for 1 hour. Water was added to the resultant reaction mixture, and the mixture was partitioned between dichloromethane and water, and the dichloromethane layer was separated. Subsequently, the dichloromethane layer was dried over anhydrous magnesium sulfate and filtered, and then the dichloromethane was distilled off under reduced pressure to obtain 19.78 g of 2,4-dimethylphenylmethanesulfonate with a yield of 99%.

$^1$H-NMR (300 MHz, CDCl$_3$) δ (ppm): 7.16 (d, J=8.1 Hz, 1H), 7.07 (d, J=0.6 Hz, 1H), 7.01 (dd, J=8.1, 0.6 Hz, 1H), 3.17 (s, 3H), 2.32 (s, 3H), 2.31 (s, 3H).

(2) Production of 5-chlorosulfonyl-2,4-dimethylphenylmethanesulfonate

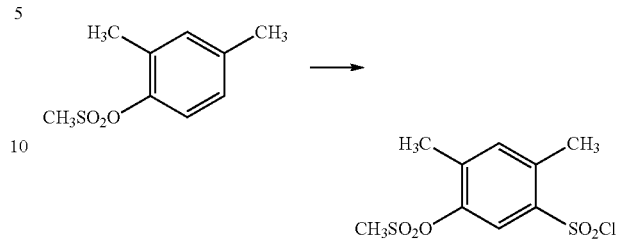

To a reaction flask, 5.91 g (22.2 mmol) of 30% fuming sulfuric acid and 10 mL of dichloromethane were added. Subsequently, while the mixture was stirred under ice cooling, a solution prepared by dissolving 4.35 g (21.7 mmol) of 2,4-dimethylphenylmethanesulfonate in 12 mL of dichloromethane was added dropwise. After the completion of the dropwise addition, the mixture was stirred under ice cooling for 1 hour. Then, 6.45 g (54.3 mmol) of thionyl chloride was added to the mixture. Subsequently, the mixture was stirred at 50° C. for 3 hours. The resultant reaction mixture was added dropwise to ice water, and then the mixture was partitioned between dichloromethane and water, and the dichloromethane layer was separated. Subsequently, the dichloromethane layer was dried over anhydrous magnesium sulfate and filtered, and then the dichloromethane was distilled off under reduced pressure. The resultant residue was purified by silica gel column chromatography to obtain 5.65 g of 5-chlorosulfonyl-2,4-dimethylphenylmethanesulfonate with a yield of 87%.

$^1$H-NMR (300 MHz, CDCl$_3$) δ (ppm): 7.93 (s, 1H), 7.35 (s, 1H), 3.30 (s, 3H), 2.75 (s, 3H), 2.45 (s, 3H).

(3) Production of 5-mercapto-2,4-dimethylphenylmethanesulfonate

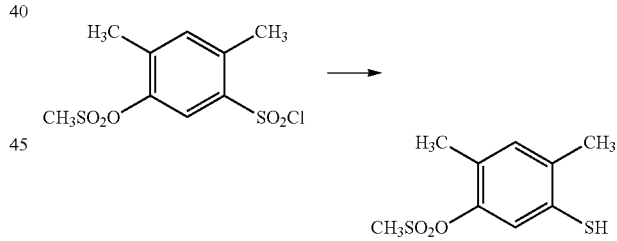

To a reaction flask, 610.0 mg (2.0 mmol) of 5-chlorosulfonyl-2,4-dimethylphenylmethanesulfonate, 2 mL of 18% hydrochloric acid and 2 mL of methanol were added. Subsequently, while the mixture was stirred at room temperature, 484.8 mg (4.1 mmol) of tin powder was added. Then, the mixture was stirred at 80° C. for 1 hour. The methanol was distilled off under reduced pressure from the resultant reaction mixture. Dichloromethane and water were added to the resultant residue, and the mixture was partitioned between dichloromethane and water, and the dichloromethane layer was separated. Subsequently, the dichloromethane layer was dried over anhydrous magnesium sulfate and filtered, and then the dichloromethane was distilled off under reduced pressure. The resultant residue was purified by silica gel column chromatography to obtain 400.0 mg of 5-mercapto-2,4-dimethylphenylmethanesulfonate with a yield of 84%.

$^1$H-NMR (300 MHz, CDCl$_3$) δ (ppm): 7.22 (s, 1H), 7.06 (s, 1H), 3.18 (s, 3H), 2.28 (s, 3H), 2.27 (s, 3H).

(4) Production of 5-mercapto-2,4-dimethylphenol

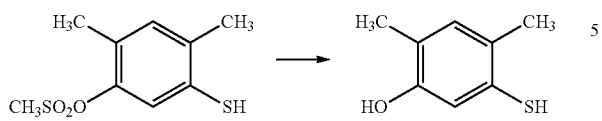

To a reaction flask, 2.32 g (10.0 mmol) of 5-mercapto-2,4-dimethylphenylmethanesulfonate, 4.00 g (100.0 mmol) of sodium hydroxide and 15 mL of water were added. Then, the mixture was stirred at 80° C. for 1 hour. Hydrochloric acid was added to the resultant reaction mixture to adjust the pH to about 1. Subsequently, dichloromethane was added thereto, and the mixture was partitioned between dichloromethane and water, and the dichloromethane layer was separated. Subsequently, the dichloromethane layer was dried over anhydrous magnesium sulfate and filtered, and then the dichloromethane was distilled off under reduced pressure. The resultant residue was purified by silica gel column chromatography to obtain 1.48 g of 5-mercapto-2,4-dimethylphenol with a yield of 96%.

$^1$H-NMR (300 MHz, CDCl$_3$) δ (ppm): 6.90 (s, 1H), 6.74 (s, 1H), 3.19 (s, 1H), 2.22 (s, 1H), 2.17 (s, 1H).

Reference Example 4

Production of bis(2,4-dimethyl-5-hydroxyphenyl) disulfide

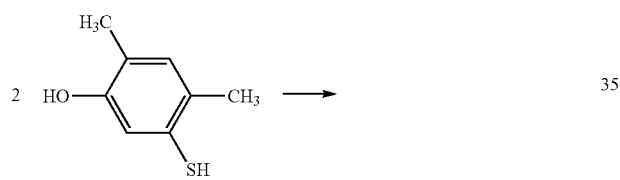

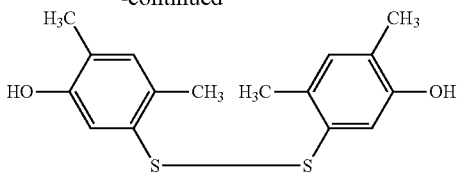

To a reaction flask, 4.32 g (28.0 mmol) of 5-mercapto-2,4-dimethylphenol, 42 mg (0.28 mmol) of sodium iodide and 80 mL of ethyl acetate were added. While the mixture was stirred at room temperature, 1.59 g (14 mmol) of 30% hydrogen peroxide aqueous solution was slowly added dropwise thereto. The mixture was stirred at room temperature for 1 hour. 5 mL of saturated aqueous sodium sulfite solution was added to the reaction mixture, and the mixture was stirred at room temperature for 10 minutes, and then the pH of the aqueous layer was adjusted to about 1 to 2 by adding concentrated hydrochloric acid thereto. The resultant mixture was partitioned between the organic layer and the aqueous layer, and the organic layer was separated. The organic layer was dried over anhydrous magnesium sulfate and filtered, and then the solvent was distilled off under reduced pressure. The resultant residue was purified by silica gel column chromatography to obtain 3.03 g of bis(2,4-dimethyl-5-hydroxyphenyl) disulfide with a yield of 71%.

$^1$H-NMR (300 MHz, CDCl$_3$) δ (ppm): 6.94 (s, 2H), 6.90 (s, 2H), 4.87 (s, 2H), 2.30 (s, 6H), 2.17 (s, 6H).

Melting point: 125 to 127° C.

Reference Example 5

Production of bis[2,4-dimethyl-5-(6-trifluoromethyl-thiohexyloxy)phenyl] disulfide

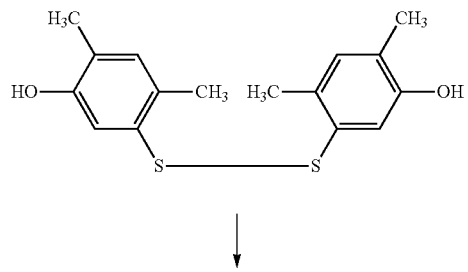

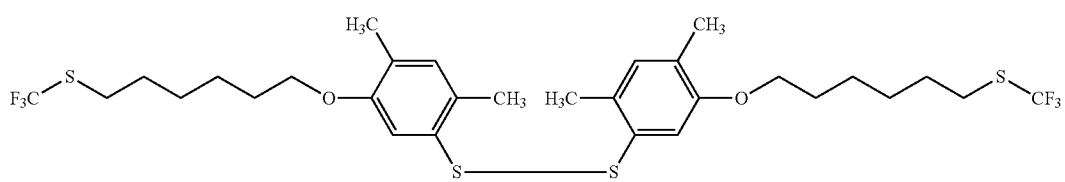

To a reaction flask, 2.60 g (8.5 mmol) of bis(2,4-dimethyl-5-hydroxyphenyl) disulfide, 4.73 g (17.9 mmol) of 1-bromo-6-trifluoromethylthiohexane, 2.58 g (18.7 mmol) of potassium carbonate, 0.63 g (1.7 mmol) of tetrabutylammonium iodide and 17 mL of N,N-dimethylformamide were added. The mixture was stirred at 80° C. for 20 hours under a nitrogen atmosphere. Dilute hydrochloric acid, water and diethyl ether were added to the reaction mixture, and the mixture was partitioned between the organic layer and the aqueous layer, and the organic layer was separated. The organic layer was dried over anhydrous magnesium sulfate and filtered, and then the solvent was distilled off under reduced pressure. The resultant residue was purified by silica gel column chromatography to obtain 4.95 g of bis[2,4-dimethyl-5-(6-trifluoromethylthiohexyloxy)phenyl] disulfide with a yield of 86%.

$^1$H-NMR (300 MHz, CDCl$_3$) δ (ppm): 6.92 (s, 2H), 6.90 (s, 2H), 3.78 (t, 4H), 2.88 (t, 4H), 2.30 (s, 6H), 2.14 (s, 6H), 1.72 (m, 8H), 1.45 (m, 8H).

Reference Example 6

Production of 6-trifluoromethylthiohexyl-[2,4-dimethyl-5-(2,2,2-trifluoroethylthio)phenyl] ether

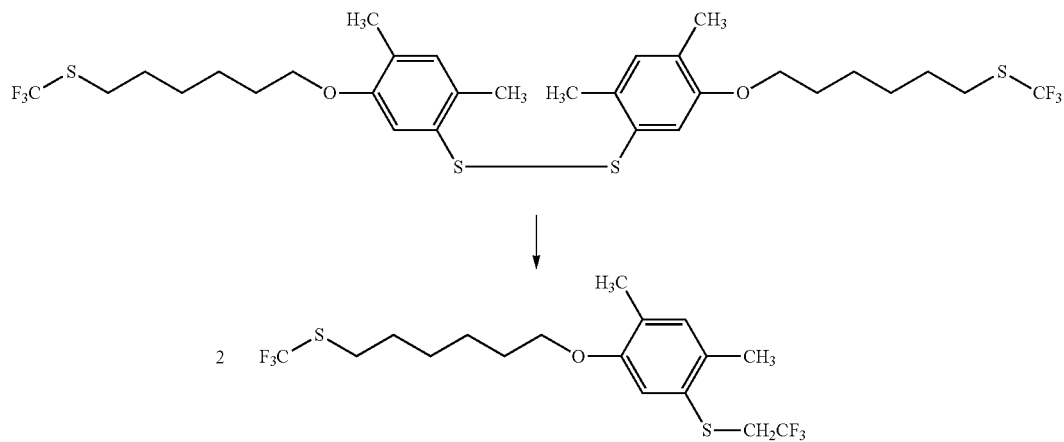

To a reaction flask, 337.4 mg (0.50 mmol) of bis[2,4-dimethyl-5-(6-trifluoromethylthiohexyloxy)phenyl] disulfide, 266.9 mg (1.05 mmol) of 2,2,2-trifluoroethyl p-toluenesulfonate, 152.0 mg (1.10 mmol) of potassium carbonate, 231.2 mg (1.50 mmol) of Rongalit (trade name) (sodium formaldehyde sulfoxylate dihydrate) and 2 mL of N,N-dimethylformamide were added. The mixture was stirred at 50° C. for 16 hours under a nitrogen atmosphere. Dilute hydrochloric acid, water and diethyl ether were added to the reaction mixture, and the mixture was partitioned between the organic layer and the aqueous layer, and the organic layer was separated. The organic layer was dried over anhydrous magnesium sulfate and filtered, and then the solvent was distilled off under reduced pressure. The resultant residue was purified by silica gel column chromatography to obtain 242.0 mg of 6-trifluoromethylthiohexyl-[2,4-dimethyl-5-(2,2,2-trifluoroethylthio)phenyl]ether with a yield of 58%.

$^1$H-NMR (300 MHz, CDCl$_3$) δ (ppm): 6.96 (s, 1H), 6.70 (s, 1H), 3.94 (t, 2H), 3.30 (q, 2H), 2.90 (t, 2H), 2.38 (s, 3H), 2.17 (s, 3H), 1.71-1.82 (m, 4H), 1.49-1.53 (m, 4H).

Reference Example 7

Production of 4-chloro-2-fluoro-5-mercaptophenol (1) Production of 4-chloro-5-chlorosulfonyl-2-fluorophenol

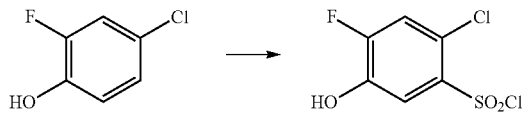 [SMILES: Oc1ccc(Cl)cc1F ; O=S(=O)(Cl)c1cc(O)c(F)cc1Cl]

To a reaction flask, 6.67 g (25.0 mmol) of 30% fuming sulfuric acid and 2.5 mL of dichloromethane were added. Subsequently, while the mixture was stirred at room temperature, a solution prepared by dissolving 732.8 mg (5.0 mmol) of 4-chloro-2-fluorophenol in 2.5 mL of dichloromethane was added dropwise. After the completion of the dropwise addition, the mixture was stirred at room temperature for 1 hour. Then, 5.95 g (50.0 mmol) of thionyl chloride was added to the mixture. Subsequently, the mixture was stirred at 50° C. for 1 hour. The resultant reaction mixture was added dropwise to ice water, and then the mixture was partitioned between dichloromethane and water, and the dichloromethane layer was separated. Subsequently, the dichloromethane layer was dried over anhydrous magnesium sulfate and filtered, and then the dichloromethane was distilled off under reduced pressure. The resultant residue was purified by silica gel column chromatography to obtain 941.0 mg of 4-chloro-5-chlorosulfonyl-2-fluorophenol with a yield of 77%.

$^1$H-NMR (300 MHz, CDCl$_3$) δ (ppm): 7.83 (d, J=8.4 Hz, 1H), 7.38 (d, J=9.9 Hz, 1H).

(2) Production of 4-chloro-2-fluoro-5-mercaptophenol

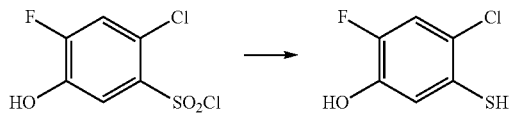 [SMILES: O=S(=O)(Cl)c1cc(O)c(F)cc1Cl ; Oc1cc(S)c(Cl)cc1F]

To a reaction flask, 245.1 mg (1.0 mmol) of 4-chloro-5-chlorosulfonyl-2-fluorophenol, 1 mL of 18% hydrochloric acid and 1 mL of methanol were added. Subsequently, while the mixture was stirred at room temperature, 237.4 mg (2.0 mmol) of tin powder was added. Then, the mixture was stirred at 80° C. for 1 hour. The methanol was distilled off under reduced pressure from the resultant reaction mixture. Dichloromethane and water were added to the resultant residue, and the mixture was partitioned between dichloromethane and water, and the dichloromethane layer was separated. Subsequently, the dichloromethane layer was dried over anhydrous magnesium sulfate and filtered, and then the dichloromethane was distilled off under reduced pressure. The resultant residue was purified by silica gel column chromatography to obtain 152.0 mg of 4-chloro-2-fluoro-5-mercaptophenol with a yield of 85%.

$^1$H-NMR (300 MHz, CDCl$_3$) δ (ppm): 7.14 (d, J=10.2 Hz, 1H), 7.01 (d, J=8.7 Hz, 1H), 3.82 (s, 1H).

Reference Example 8

Production of bis(2-chloro-4-fluoro-5-hydroxyphenyl) disulfide

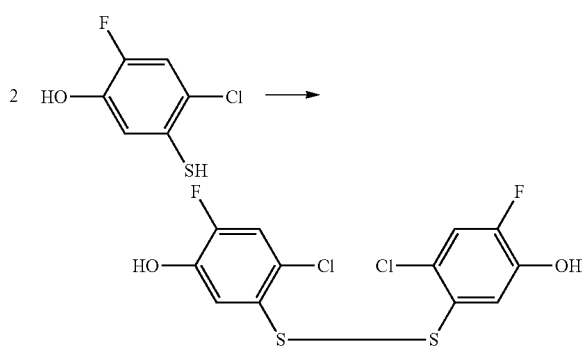

To a reaction flask, 44.7 mg (0.25 mmol) of 4-chloro-2-fluoro-5-mercaptophenol and 1 mL of water were added. While the mixture was stirred at room temperature, 26.7 mg (0.28 mmol) of 35% hydrogen peroxide aqueous solution was slowly added dropwise thereto. The mixture was stirred at room temperature for 1 hour. The reaction mixture was filtered, and then the filter cake was washed with water and dried to obtain 39.9 mg of bis(2-chloro-4-fluoro-5-hydroxyphenyl) disulfide with a yield of 90%.

$^1$H-NMR (300 MHz, CDCl$_3$) δ (ppm): 7.22 (d, J=8.7 Hz, 2H), 7.16 (d, J=9.6 Hz, 2H).

Melting point: 160° C.

Reference Example 9

Production of bis[2-chloro-4-fluoro-5-(5-trifluoromethylthiopentyloxy)phenyl]disulfide

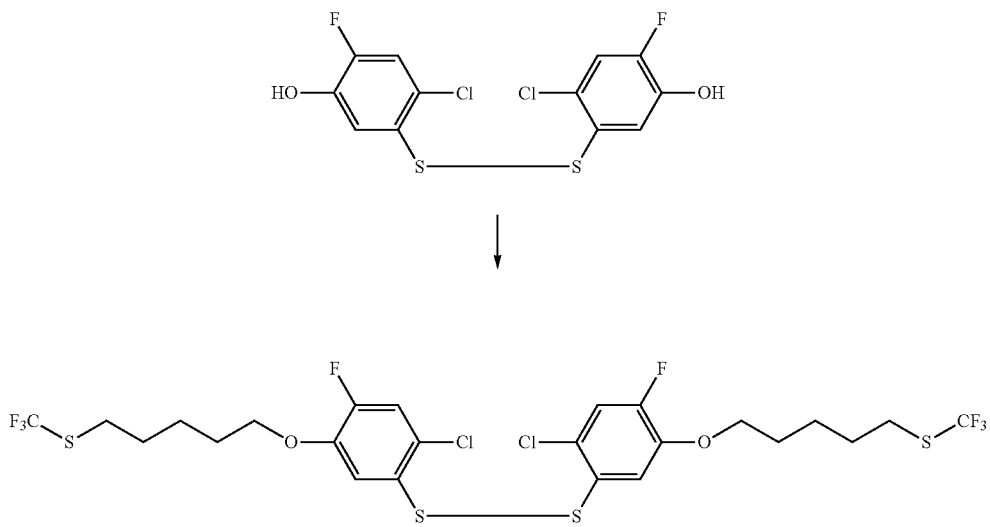

To a reaction flask, 177.6 mg (0.50 mmol) of bis(2-chloro-4-fluoro-5-hydroxyphenyl) disulfide, 263.7 mg (1.05 mmol) of 1-bromo-5-trifluoromethylthiopentane, 152.0 mg (1.10 mmol) of potassium carbonate, and 1 mL of N,N-dimethylformamide were added. The mixture was stirred at 50° C. for 15 hours under a nitrogen atmosphere. Dilute hydrochloric acid, water and diethyl ether were added to the reaction mixture, and the mixture was partitioned between the organic layer and the aqueous layer, and the organic layer was separated. The organic layer was dried over anhydrous magnesium sulfate and filtered, and then the solvent was distilled off under reduced pressure. The resultant residue was purified by silica gel column chromatography to obtain 277.0 mg of bis[2-chloro-4-fluoro-5-(5-trifluoromethylthiopentyloxy)phenyl] disulfide with a yield of 80%.

$^1$H-NMR (300 MHz, CDCl$_3$) δ (ppm): 7.21 (d, J=8.4 Hz, 2H), 7.12 (d, J=10.2 Hz, 2H), 3.97 (t, J=6.3 Hz, 4H), 2.90 (t, J=7.2 Hz, 4H), 1.78 (m, 8H), 1.56 (m, 4H).

Reference Example 10

Production of 5-trifluoromethylthiopentyl-[4-chloro-2-fluoro-5-(2,2,2-trifluoroethylthio)phenyl] ether

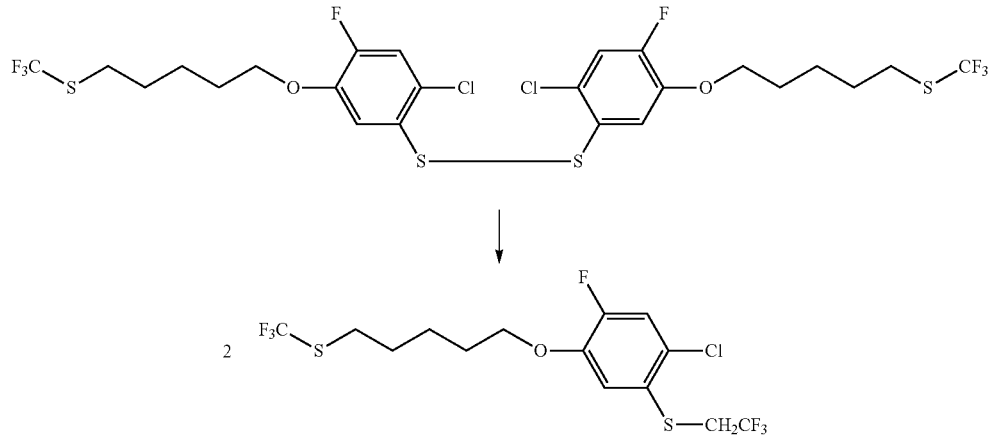

To a reaction flask, 277.0 mg (0.40 mmol) of bis[2-chloro-4-fluoro-5-(5-trifluoromethylthiopentyloxy)phenyl] disulfide, 213.5 mg (0.84 mmol) of 2,2,2-trifluoroethyl p-toluenesulfonate, 121.6 mg (0.88 mmol) of potassium carbonate, 184.9 mg (1.20 mmol) of Rongalit (trade name) (sodium formaldehyde sulfoxylate dihydrate), 72.0 mg (4.0 mmol) of water and 1 mL of N,N-dimethylformamide were added. The mixture was stirred at 50° C. for 12 hours under a nitrogen atmosphere. Dilute hydrochloric acid, water and diethyl ether were added to the reaction mixture, and the mixture was partitioned between the organic layer and the aqueous layer, and the organic layer was separated. The organic layer was dried over anhydrous magnesium sulfate and filtered, and then the solvent was distilled off under reduced pressure. The resultant residue was purified by silica gel column chromatography to obtain 306.0 mg of 5-trifluoromethylthiopentyl-[4-chloro-2-fluoro-5-(2,2,2-trifluoroethylthio)phenyl] ether with a yield of 89%.

$^1$H-NMR (300 MHz, CDCl$_3$) δ (ppm): 7.23 (d, J=8.4 Hz, 1H), 7.21 (d, J=10.8 Hz, 1H), 4.03 (t, J=6.3 Hz, 2H), 3.41 (d, J=9.6 Hz, 2H), 2.92 (t, J=7.5 Hz, 2H), 1.82 (m, 4H), 1.61 (m, 2H).

Reference Example 11

Production of 5-trifluoromethylthiopentyl-[4-chloro-2-fluoro-5-(2,2,2-trifluoroethylsulfinyl)phenyl] ether

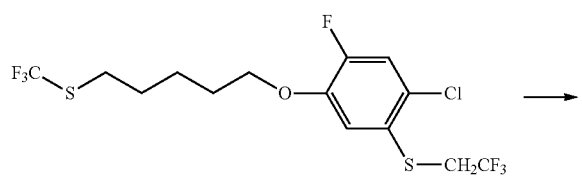

-continued

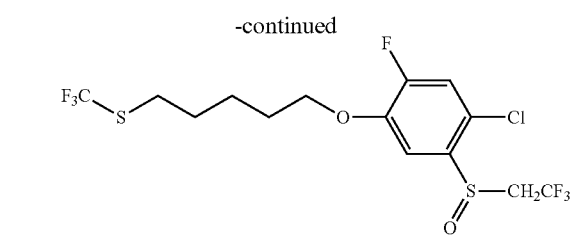

To a reaction flask, 86.2 mg (0.20 mmol) of 5-trifluoromethylthiopentyl-[4-chloro-2-fluoro-5-(2,2,2-trifluoroethylthio)phenyl] ether and 2 mL of dichloromethane were added. While the mixture was stirred at room temperature, 50.6 mg (0.22 mmol) of m-chloroperbenzoic acid was added thereto. The mixture was stirred at room temperature for 2 hours. An aqueous sodium sulfite solution, water and dichloromethane were added to the reaction mixture, and the mixture was partitioned between the organic layer and the aqueous layer, and the organic layer was separated. The organic layer was dried over anhydrous magnesium sulfate and filtered, and then the solvent was distilled off under reduced pressure. The resultant residue was purified by silica gel column chromatography to obtain 68.0 mg of 5-trifluoromethylthiopentyl-[4-chloro-2-fluoro-5-(2,2,2-trifluoroethylsulfinyl)phenyl]ether with a yield of 76%.

$^1$H-NMR (300 MHz, CDCl$_3$) δ (ppm): 7.54 (d, J=8.1 Hz, 1H), 7.21 (d, J=9.9 Hz, 1H), 4.13 (t, J=6.3 Hz, 2H), 3.72 (m, 1H), 3.37 (m, 1H), 2.92 (t, J=7.2 Hz, 2H), 1.84 (m, 4H), 1.62 (m, 2H).

By using the fluoroalkylating agent of the present invention, according to the method described in Examples and Reference Examples of the present specification, an industrially preferable method for the production of useful acaricides and/or useful insecticides (see Patent Document 2), and an industrially preferable method for the production of production intermediates thereof, can be provided.

INDUSTRIAL APPLICABILITY

The compounds having a fluoroalkyl group are useful as various chemical products (for example, pharmaceuticals, agricultural chemicals, electronic materials and so on) and production intermediates thereof.

For example, a variety of compounds having a trifluoromethyl group are widely known as useful compounds.

In particular, compounds having a trifluoromethylthio ($CF_3S$—) group are useful as insecticides and/or acaricides by themselves, and are also useful as intermediates for the production of another insecticide and/or another acaricide (for example, see Test Example 1 of Patent Document 1 and Test Example 1 of Patent Document 2).

The fluoroalkylating agent of the present invention is easy to handle and safe. Furthermore, the fluoroalkylation reaction of the present invention proceeds easily and safely, and highly selectively. In addition, the fluoroalkylating agent of the present invention can reduce the production cost in the production of the compound having a fluoroalkyl group.

The fluoroalkylating agent of the present invention can be produced from an easily available fluorocarboxylic acid derivative such as trifluoroacetic acid without using a greenhouse effect gas (for example, $CHF_3$) or Freon gas (for example, $CF_3I$ or $CBrF_3$). Furthermore, the fluoroalkylating agent of the present invention can be economically produced without requiring a special facility and technique. Therefore, a method for the production of the fluoroalkylating agent of the present invention solves the problems in the prior art, is industrially preferable, and can reduce the load on the environment.

The fluoroalkylating agent of the present invention has excellent reactivity. Therefore, the present invention can provide an option without using a strong base, if needed In other words, there is a possibility that the fluoroalkylating agent of the present invention can be applicable to a starting compound which is unstable against a strong base. Therefore, it is considered that the present invention has a broad range of application, i.e., wide versatility.

As described above, a novel fluoroalkylating agent of the present invention and use thereof (i.e., a method for the production of a compound having a fluoroalkyl group) have an industrially high value. Furthermore, a novel compound useful as the fluoroalkylating agent of the present invention also has an industrially high value. In short, the present invention has high industrial applicability.

The invention claimed is:

1. A fluoroalkylating agent represented by the general formula (1):

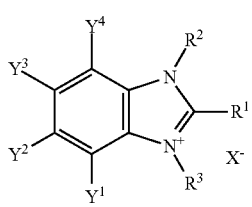

(1)

wherein $R^1$ is a C1 to C8 fluoroalkyl group;
$R^2$ and $R^3$ are each independently
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents, or
a C6 to C10 aryl group which may have one or more substituents;

$Y^1$, $Y^2$, $Y^3$ and $Y^4$ are each independently
a hydrogen atom, a halogen atom, a nitro group, a cyano group,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a hydroxy group,
a C1 to C6 alkoxy group,
a C1 to C6 alkylthio group, a C1 to C6 alkylsulfinyl group, a C1 to C6 alkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom, or two adjacent substituents of $Y^1$ and $Y^2$, $Y^2$ and $Y^3$, or $Y^3$ and $Y^4$, together with carbon atoms to which these substituents are attached, form a 4- to 8-membered carbocyclic ring or a 4- to 8-membered heterocyclic ring having 1 to 4 heteroatoms selected independently from an oxygen atom, a sulfur atom and a nitrogen atom, wherein the said formed ring may have one or more substituents; and $X^-$ is a monovalent anion;
wherein, the one or more substituents in each case is independently selected from the group consisting of
a halogen atom, a nitro group, a cyano group,
a C1 to C6 alkyl group,
a C2 to C6 alkenyl group,
a C2 to C6 alkynyl group,
a C3 to C8 cycloalkyl group,
a C1 to C6 haloalkyl group,
a hydroxy group,
a C1 to C6 alkoxy group,
a C1 to C6 haloalkoxy group,
a C1 to C6 alkylthio group, a C1 to C6 alkylsulfinyl group, a C1 to C6 alkylsulfonyl group,
a C1 to C6 haloalkylthio group, a C1 to C6 haloalkylsulfinyl group, a C1 to C6 haloalkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group,
a mono (C1 to C6 alkyl) aminocarbonyl group, a di (C1 to C6 alkyl) aminocarbonyl group,
a C6 to C10 aryl group,
a C6 to C10 aryloxy group,
a C6 to C10 aryl C1 to C4 alkyl group, and a heterocyclic group, wherein the heterocyclic group is a 5- to 10-membered heterocyclic group having 1 to 9 carbon atoms and 1 to 4 heteroatoms selected independently from a nitrogen atom,
an oxygen atom and a sulfur atom,
provided that the following cases of (i) to (x) are excluded:
(i) $R^1$ is a trifluoromethyl group,
  $R^2$ and $R^3$ are each a methyl group,
  $Y^1$, $Y^2$, $Y^3$ and $Y^4$ are each a hydrogen atom, and
  $X^-$ is $Br^-$;
(ii) $R^1$ is a trifluoromethyl group,
  $R^2$ and $R^3$ are each a methyl group,
  $Y^1$, $Y^2$, $Y^3$ and $Y^4$ are each a hydrogen atom, and
  $X^-$ is $I^-$;
(iii) $R^1$ is a trifluoromethyl group,
  $R^2$ and $R^3$ are each a methyl group,
  $Y^1$ is a hydrogen atom,
  $Y^2$ is a methyl group,
  $Y^3$ is a methyl group,
  $Y^4$ is a hydrogen atom, and
  $X^-$ is $I^-$;
(iv) $R^1$ is a trifluoromethyl group,
  $R^2$ and $R^3$ are each a methyl group,
  $Y^1$ is a hydrogen atom,
  $Y^2$ is a chlorine atom,
  $Y^3$ is a hydrogen atom,
  $Y^4$ is a hydrogen atom, and
  $X^-$ is $Br^-$;
(v) $R^1$ is a trifluoromethyl group,
  $R^2$ and $R^3$ are each a methyl group,
  $Y^1$, $Y^2$, $Y^3$ and $Y^4$ are each a bromine atom,
  $X^-$ is $Br^-$
(vi) $R^1$ is a trifluoromethyl group,
  $R^2$ is a butyl group,
  $R^3$ is a propyl substituted by a $SO_3H$ group,
  $Y^1$, $Y^2$, $Y^3$ and $Y^4$ are each a hydrogen atom and
  $X^-$ is $H_2PO_4^-$;
(vii) $R^1$ is a trifluoromethyl group,
  $R^2$ is a butyl group,
  $R^3$ is a propyl substituted by a $SO_3H$ group,
  $Y^1$, $Y^2$, $Y^3$ and $Y^4$ are each a hydrogen atom and
  $X^-$ is $HSO_4^-$;
(viii) $R^1$ is a trifluoromethyl group,
  $R^2$ is a butyl group,
  $R^3$ is a propyl substituted by a $SO_3H$ group,
  $Y^1$, $Y^2$, $Y^3$ and $Y^4$ are each a hydrogen atom and
  $X^-$ is p-tosylate;
(ix) $R^1$ is a trifluoromethyl group,
  $R^2$ is a methyl group,
  $R^3$ is a $CH=CH-COCF_3$,
  $Y^1$, $Y^2$, $Y^3$ and $Y^4$ are each a hydrogen atom and
  $X^-$ is triflate, and
(x) $R^1$ is $CH_2F$,
  $R^2$ is a methyl group,
  $R^3$ is an ethyl group,
  $Y^1$, $Y^3$ and $Y^4$ are each a hydrogen atom,
  $Y^2$ is $CF_3$ and
  $X^-$ is p-tosylate;
  wherein, the one or more substituents in each case is independently selected from the group consisting of
  a halogen atom, a nitro group, a cyano group,
  a C1 to C6 alkyl group,
  a C2 to C6 alkenyl group,
  a C2 to C6 alkynyl group,
  a C3 to C8 cycloalkyl group,
  a C1 to C6 haloalkyl group,
  a hydroxy group,
  a C1 to C6 alkoxy group,
  a C1 to C6 haloalkoxy group,
  a C1 to C6 alkylthio group, a C1 to C6 alkylsulfinyl group, a C1 to C6 alkylsulfonyl group,
  a C1 to C6 haloalkylthio group, a C1 to C6 haloalkylsulfinyl group, a C1 to C6 haloalkylsulfonyl group,
  an amino group, a mono (C1 to C6 alkyl) amino group, a di (C1 to C6 alkyl) amino group,
  a C1 to C6 acylamino group,
  a formyl group, a C2 to C6 acyl group,
  a C1 to C6 alkoxycarbonyl group,
  a mono (C1 to C6 alkyl) aminocarbonyl group, a di (C1 to C6 alkyl) aminocarbonyl group,
  a C6 to C10 aryl group,
  a C6 to C10 aryloxy group,
  a C6 to C10 aryl C1 to C4 alkyl group, and
  a heterocyclic group, wherein the heterocyclic group is a 5- to 10-membered heterocyclic group having 1 to 9 carbon atoms and 1 to 4 heteroatoms selected independently from a nitrogen atom,
  an oxygen atom and a sulfur atom.

2. The agent according to claim 1, wherein
$R^1$ is a C1 to C4 perfluoroalkyl group;
$R^2$ and $R^3$ are each independently a C1 to C4 alkyl group or a phenyl group;
$Y^1$, $Y^2$, $Y^3$ and $Y^4$ are each independently
a hydrogen atom, a halogen atom, a nitro group, a cyano group,
a C1 to C4 alkyl group or a C1 to C4 haloalkyl group; and
$X^-$ is $Cl^-$, $Br^-$, $I^-$,
$BF_4^-$,
$CF_3SO_3^-$,
$HOSO_3^-$, $CH_3OSO_3^-$ or $C_2H_5OSO_3^-$.

3. The agent according to claim 1, wherein
$R^1$ is a trifluoromethyl group or a pentafluoroethyl group;
$R^2$ and $R^3$ are each independently a methyl group, an ethyl group or a phenyl group;
$Y^1$, $Y^2$, $Y^3$ and $Y^4$ are each independently a hydrogen atom, a chlorine atom or a nitro group; and
$X^-$ is $Cl^-$, $Br^-$, $I^-$,
$BF_4^-$,
$CF_3SO_3^-$,
$HOSO_3^-$, $CH_3OSO_3^-$ or $C_2H_5OSO_3^-$.

4. The agent according to claim 1, wherein
$R^1$ is a trifluoromethyl group;
$R^2$ and $R^3$ are each a methyl group;
$Y^1$, $Y^2$, $Y^3$ and $Y^4$ are each a hydrogen atom; and
$X^-$ is $CH_3OSO_3-$.

5. A compound represented by the general formula (1A):

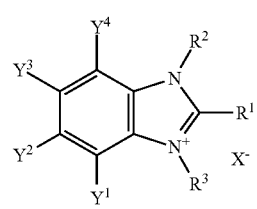

(1A)

wherein $R^1$ is a C1 to C8 fluoroalkyl group;
$R^2$ and $R^3$ are each independently
a C1 to C12 alkyl group which may have one or more substituents, a C2 to C6 alkenyl group which may have one or more substituents,
a C2 to C6 alkynyl group which may have one or more substituents,
a C3 to C8 cycloalkyl group which may have one or more substituents, or
a C6 to C10 aryl group which may have one or more substituents;
$Y^1$, $Y^2$, $Y^3$ and $Y^4$ are each independently
a hydrogen atom, a halogen atom, a nitro group, a cyano group,
a C1 to C12 alkyl group which may have one or more substituents,
a C2 to C6 alkenyl group which may have one or more substituents,
a C2 to C6 alkynyl group which may have one or more substituents,
a C3 to C8 cycloalkyl group which may have one or more substituents,
a hydroxy group,
a C1 to C6 alkoxy group,
a C1 to C6 alkylthio group, a C1 to C6 alkylsulfinyl group, a C1 to C6 alkylsulfonyl group,
an amino group, a mono (C1 to C6 alkyl) amino group, a di (C1 to C6 alkyl) amino group,
a C1 to C6 acylamino group,
a formyl group, a C2 to C6 acyl group,
a C1 to C6 alkoxycarbonyl group,
a C6 to C10 aryl group which may have one or more substituents, or
a heterocyclic group which may have one or more substituents, wherein the said heterocyclic group is a 5- to 10-membered heterocyclic group having 1 to 9 carbon atoms and 1 to 4 heteroatoms selected independently from a nitrogen atom, an oxygen atom and a sulfur atom, or two adjacent substituents of $Y^1$ and $Y^2$, $Y^2$ and $Y^3$, or $Y^3$ and $Y^4$, together with carbon atoms to which these substituents are attached, form a 4- to 8-membered carbocyclic ring or a 4- to 8-membered heterocyclic ring having 1 to 4 heteroatoms selected independently from an oxygen atom, a sulfur atom and a nitrogen atom, wherein the said formed ring may have one or more substituents; and
$X^-$ is a monovalent anion;
provided that the following cases of (i) to (x) are excluded:
(i) $R^1$ is a trifluoromethyl group,
  $R^2$ and $R^3$ are each a methyl group,
  $Y^1$, $Y^2$, $Y^3$ and $Y^4$ are each a hydrogen atom, and
  $X^-$ is $Br^-$;
(ii) $R^1$ is a trifluoromethyl group,
  $R^2$ and $R^3$ are each a methyl group,
  $Y^1$, $Y^2$, $Y^3$ and $Y^4$ are each a hydrogen atom, and
  $X^-$ is $I^-$;
(iii) $R^1$ is a trifluoromethyl group,
  $R^2$ and $R^3$ are each a methyl group,
  $Y^1$ is a hydrogen atom,
  $Y^2$ is a methyl group,
  $Y^3$ is a methyl group,
  $Y^4$ is a hydrogen atom, and
  $X^-$ is $I^-$;
(iv) $R^1$ is a trifluoromethyl group,
  $R^2$ and $R^3$ are each a methyl group,
  $Y^1$ is a hydrogen atom,
  $Y^2$ is a chlorine atom,
  $Y^3$ is a hydrogen atom,
  $Y^4$ is a hydrogen atom, and
  $X^-$ is $Br^-$;
(v) $R^1$ is a trifluoromethyl group,
  $R^2$ and $R^3$ are each a methyl group,
  $Y^1$, $Y^2$, $Y^3$ and $Y^4$ are each a bromine atom,
  $X^-$ is $Br^-$
(vi) $R^1$ is a trifluoromethyl group,
  $R^2$ is a butyl group,
  $R^3$ is a propyl substituted by a $SO_3H$ group,
  $Y^1$, $Y^2$, $Y^3$ and $Y^4$ are each a hydrogen atom and
  $X^-$ is $H_2PO_4^-$;
(vii) $R^1$ is a trifluoromethyl group,
  $R^2$ is a butyl group,
  $R^3$ is a propyl substituted by a $SO_3H$ group,
  $Y^1$, $Y^2$, $Y^3$ and $Y^4$ are each a hydrogen atom and
  $X^-$ is $HSO_4^-$;
(viii) $R^1$ is a trifluoromethyl group,
  $R^2$ is a butyl group,
  $R^3$ is a propyl substituted by a $SO_3H$ group,
  $Y^1$, $Y^2$, $Y^3$ and $Y^4$ are each a hydrogen atom and
  $X^-$ is p-tosylate;
(ix) $R^1$ is a trifluoromethyl group,
  $R^2$ is a methyl group,
  $R^3$ is a $CH=CH-COCF_3$,
  $Y^1$, $Y^2$, $Y^3$ and $Y^4$ are each a hydrogen atom and
  $X^-$ is triflate; and
(x) $R^1$ is $CH_2F$,
  $R^2$ is a methyl group,
  $R^3$ is an ethyl group,
  $Y^1$, $Y^3$ and $Y^4$ are each a hydrogen atom,
  $Y^2$ is $CF_3$ and
  $X^-$ is p-tosylate;
  wherein, the one or more substituents in each case is independently selected from the group consisting of
  a halogen atom, a nitro group, a cyano group,
  a C1 to C6 alkyl group,
  a C2 to C6 alkenyl group,
  a C2 to C6 alkynyl group,
  a C3 to C8 cycloalkyl group,
  a C1 to C6 haloalkyl group,
  a hydroxy group,
  a C1 to C6 alkoxy group,
  a C1 to C6 haloalkoxy group,
  a C1 to C6 alkylthio group, a C1 to C6 alkylsulfinyl group, a C1 to C6 alkylsulfonyl group,
  a C1 to C6 haloalkylthio group, a C1 to C6 haloalkylsulfinyl group, a C1 to C6 haloalkylsulfonyl group,
  an amino group, a mono (C1 to C6 alkyl) amino group, a di (C1 to C6 alkyl) amino group,
  a C1 to C6 acylamino group,
  a formyl group, a C2 to C6 acyl group,
  a C1 to C6 alkoxycarbonyl group,
  a mono (C1 to C6 alkyl) aminocarbonyl group, a di (C1 to C6 alkyl) aminocarbonyl group,
  a C6 to C10 aryl group,
  a C6 to C10 aryloxy group,
  a C6 to C10 aryl C1 to C4 alkyl group, and
  a heterocyclic group, wherein the heterocyclic group is a 5- to 10-membered heterocyclic group having 1 to 9 carbon atoms and 1 to 4 heteroatoms selected independently from a nitrogen atom,
  an oxygen atom and a sulfur atom.

6. The compound according to claim 5, wherein
$R^1$ is a C1 to C4 perfluoroalkyl group;
$R^2$ and $R^3$ are each independently a C1 to C4 alkyl group or a phenyl group;

$Y^1$, $Y^2$, $Y^3$ and $Y^4$ are each independently
a hydrogen atom, a halogen atom, a nitro group, a cyano group,
a C1 to C4 alkyl group or a C1 to C4 haloalkyl group; and
$X^-$ is $Cl^-$, $Br^-$, $I^-$,
$BF_4^-$,
$CF_3SO_3^-$,
$HOSO_3^-$, $CH_3OSO_3^-$ or $C_2H_5OSO_3^-$.

7. The compound according to claim 5, wherein
$R^1$ is a trifluoromethyl group or a pentafluoroethyl group;
$R^2$ and $R^3$ are each independently a methyl group, an ethyl group or a phenyl group;
$Y^1$, $Y^2$, $Y^3$ and $Y^4$ are each independently a hydrogen atom, a chlorine atom or a nitro group; and
$X^-$ is $Cl^-$, $Br^-$, $I^-$,
$BF_4^-$,
$CF_3SO_3^-$,
$HOSO_3^-$, $CH_3OSO_3^-$ or $C_2H_5OSO_3^-$.

8. The compound according to claim 5, wherein
$R^1$ is a trifluoromethyl group;
$R^2$ and $R^3$ are each a methyl group;
$Y^1$, $Y^2$, $Y^3$ and $Y^4$ are each a hydrogen atom; and
$X^-$ is $CH_3OSO_3^-$.

\* \* \* \* \*